US012799203B2

(12) United States Patent
Monga

(10) Patent No.: US 12,799,203 B2
(45) Date of Patent: Nov. 17, 2026

(54) METHOD OF TREATING UROTHELIAL CARCINOMA WITH ERDAFITINIB AND CETRELIMAB

(71) Applicant: Janssen Pharmaceutica NV, Beerse (BE)

(72) Inventor: Manish Monga, Raritan, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 859 days.

(21) Appl. No.: 17/904,129

(22) PCT Filed: Feb. 11, 2021

(86) PCT No.: PCT/EP2021/053384

§ 371 (c)(1),
(2) Date: Aug. 12, 2022

(87) PCT Pub. No.: WO2021/160763

PCT Pub. Date: Aug. 19, 2021

(65) Prior Publication Data

US 2023/0135136 A1 May 4, 2023

Related U.S. Application Data

(60) Provisional application No. 63/083,316, filed on Sep. 25, 2020, provisional application No. 63/078,736, filed on Sep. 15, 2020, provisional application No. 63/078,205, filed on Sep. 14, 2020, provisional application No. 63/055,187, filed on Jul. 22, 2020, provisional application No. 63/025,817, filed on May 15, 2020, provisional application No. 62/975,526, filed on Feb. 12, 2020.

(51) Int. Cl.

| | |
|---|---|
| ***C07K 16/28*** | (2006.01) |
| ***A61K 31/498*** | (2006.01) |
| ***A61K 31/555*** | (2006.01) |
| ***A61K 33/243*** | (2019.01) |
| ***A61K 45/06*** | (2006.01) |
| ***A61P 35/04*** | (2006.01) |

(52) U.S. Cl.

CPC ........ *C07K 16/2818* (2013.01); *A61K 31/498* (2013.01); *A61K 31/555* (2013.01); *A61K 33/243* (2019.01); *A61K 45/06* (2013.01); *A61P 35/04* (2018.01)

(58) Field of Classification Search

CPC ............ C07K 16/2818; C07K 2317/76; A61K 31/498; A61K 39/395

See application file for complete search history.

(56) References Cited

U.S. PATENT DOCUMENTS

| | | | |
|---|---|---|---|
| 4,666,828 | A | 5/1987 | Gusella |
| 4,683,202 | A | 7/1987 | Mullis |
| 4,801,531 | A | 1/1989 | Frossard |
| 5,033,252 | A | 7/1991 | Carter |
| 5,052,558 | A | 10/1991 | Carter |
| 5,192,659 | A | 3/1993 | Simons |
| 5,225,539 | A | 7/1993 | Winter |
| 5,272,057 | A | 12/1993 | Smulson et al. |
| 5,323,907 | A | 6/1994 | Kalvelage |
| 5,545,807 | A | 8/1996 | Surani et al. |
| 5,821,337 | A | 10/1998 | Carter et al. |
| 5,837,242 | A | 11/1998 | Holliger et al. |
| 5,882,864 | A | 3/1999 | An et al. |
| 6,150,584 | A | 11/2000 | Kucherlapati et al. |
| 6,218,529 | B1 | 4/2001 | An et al. |
| 6,255,458 | B1 | 7/2001 | Lonberg et al. |
| 6,818,749 | B1 | 11/2004 | Kashmiri et al. |
| 7,709,226 | B2 | 5/2010 | Foote |
| 8,748,356 | B2 | 6/2014 | Raghunathan |
| 2002/0018749 | A1 | 2/2002 | Hudson et al. |
| 2007/0148774 | A1 | 6/2007 | Mccafferty et al. |
| 2010/0261620 | A1 | 10/2010 | Almagro et al. |
| 2013/0072457 | A1 | 3/2013 | Saxty et al. |
| 2016/0287699 | A1 | 10/2016 | Karkera et al. |
| 2017/0121409 | A1 | 5/2017 | Verona et al. |
| 2017/0145102 | A1 | 5/2017 | Pierce et al. |
| 2017/0145103 | A1 | 5/2017 | Pierce et al. |
| 2018/0092901 | A1 | 4/2018 | Denker et al. |
| 2019/0225689 | A1 | 7/2019 | Attiyeh et al. |
| 2019/0256924 | A1 | 8/2019 | Vogelstein et al. |
| 2020/0208224 | A1 | 7/2020 | Platero et al. |
| 2022/0125793 | A1 | 4/2022 | Yonekura et al. |

FOREIGN PATENT DOCUMENTS

| | | | |
|---|---|---|---|
| CN | 107889462 | A | 4/2018 |
| CN | 108368174 | A | 8/2018 |
| EP | 0281604 | B1 | 3/1993 |
| EP | 0451216 | B1 | 1/1996 |

(Continued)

OTHER PUBLICATIONS

Clinical Trial NCT03473743 (20190131). (Year: 2019).*
Clinical Trial NCT03473743 (20180615). (Year: 2018).*
"A Study to Evaluate Safety, Efficacy, Pharmacokinetics, and Pharmacodynamics of Erdafitinib Plus JNJ-63723283 (Cetrelimab), an Anti-PD-1 Monoclonal Antibody, in Participants With Metastatic or Locally Advanced Urothelial Cancer With Selected FGFR Gene Alterations", Jan. 2, 2024, pp. 1-20.
Casadei et al., "Targeted therapies for advanced bladder cancer: new strategies with FGFR inhibitors", Therapeutic Advances in Medical Oncology, Oct. 29, 2019, vol. 11, pp. 1-14.
Angerer et al., "Tissue-Specific Gene Expression: Demonstration of Tissue-Specific Expression by in Situ Hybridization", Meth. Enzymol., 1987, vol. 152, p. 649.

(Continued)

*Primary Examiner* — Elly-Gerald Stoica
(74) *Attorney, Agent, or Firm* — BakerHostetler

(57) ABSTRACT

Disclosed herein are methods of treating urothelial carcinoma. In particular, the disclosed methods include combination therapies for the treatment of urothelial carcinoma comprising administering a fibroblast growth factor receptor (FGFR) inhibitor and an anti-PD1 antibody or antigen binding fragment thereof.

36 Claims, 19 Drawing Sheets

Specification includes a Sequence Listing.

(56) References Cited

FOREIGN PATENT DOCUMENTS

| | | | |
|---|---|---|---|
| WO | 88/01649 | A1 | 3/1988 |
| WO | 90/04036 | A1 | 4/1990 |
| WO | 90/07861 | A1 | 7/1990 |
| WO | 92/01047 | A1 | 1/1992 |
| WO | 92/22653 | A1 | 12/1992 |
| WO | 94/13804 | A1 | 6/1994 |
| WO | 98/44001 | A1 | 10/1998 |
| WO | 99/45962 | A1 | 9/1999 |
| WO | 02/43478 | A2 | 6/2002 |
| WO | 02/66630 | A1 | 8/2002 |
| WO | 2006/000420 | A1 | 1/2006 |
| WO | 2006/127926 | A2 | 11/2006 |
| WO | 2008/112408 | A1 | 9/2008 |
| WO | 2009/085462 | A1 | 7/2009 |
| WO | 2016/048833 | A2 | 3/2016 |
| WO | 2016/134234 | A1 | 8/2016 |
| WO | 2016/140717 | A1 | 9/2016 |
| WO | 2016/161239 | A1 | 10/2016 |
| WO | 2018/141921 | A1 | 8/2018 |
| WO | 2019/142149 | A2 | 7/2019 |
| WO | 2020/131627 | A1 | 6/2020 |
| WO | 2020/165181 | A1 | 8/2020 |
| WO | 2020/201138 | A1 | 10/2020 |
| WO | 2020/205493 | A1 | 10/2020 |
| WO | 2021/058798 | A1 | 4/2021 |

OTHER PUBLICATIONS

Ausubel et al., "Informatics for Molecular Biologists", Current Protocols in Molecular Biology, John Wiley & Sons Inc, 2004, Suppl. 68, pp. 1-2.

Bartlett et al., "Technical Overview, Molecular Diagnosis of Cancer, Methods and Protocols", Second Edition, Series: Methods in Molecular Medicine, ISBN: 1-59259-760-2; Mar. 2004, pp. 77-88.

Bello et al., "E-3810 Is a Potent Dual Inhibitor of VEG FR and FGFR that Exerts Antitumor Activity in Multiple Preclinical Models", Cancer Res., 2011, vol. 71, No. 4, pp. 1396-1405.

Cancer Genome Atlas Research Network, "Comprehensive molecular characterization of urothelial bladder carcinoma", Nature, 2014, vol. 507, No. 7492, pp. 315-322.

Chothia et al., "Canonical Structures for the Hypervariable Regions of Immunoglobulins", J. Mol. Biol., 1987, vol. 196, pp. 901-917.

Deprimo et al., "Expression profiling of blood samples from an SU5416 Phase III metastatic colorectal cancer clinical trial: a novel strategy for biomarker identification", BMC Cancer, 2003, vol. 3, No. 3, pp. 1-12.

Gavine et al., "An Orally Bioavailable, Potent and Selective Inhibitor of the Fibroblast Growth Factor Receptor Tyrosine Kinase Family", Cancer Res, 2012, vol. 72, pp. 2045-2056.

Haugsten et al., "Roles of Fibroblast Growth Factor Receptors in Carcinogenesis", Mol. Cancer, 2010, vol. 8, pp. 1439-1452.

Honegger et al., "Yet Another Numbering Scheme for Immunoglobulin Variable Domains: An Automatic Modeling and Analysis Tool", J. Mol. Biol., 2001, vol. 309, pp. 657-670.

Innis et al., "PCR Protocols: A Guide to Methods and Applications", Academic Press, Inc., 1990, p. 1.

Kabat et al., "Sequences in Proteins of immunological interest", 5th Ed. Public Health Service, National Institutes of Health, Bethesda, MD, 1991, pp. 1-2.

Knappik et al., "Fully Synthetic Human Combinatorial Antibody Libraries (HuCAL) Based on Modular Consensus Frameworks and CDRs Randomized with Trinucleotides", J. Mol. Biol., 2000, vol. 296, pp. 57-86.

Knights et al., "De-regulated FGF receptors as therapeutic targets in cancer", Pharmacology and Therapeutics, 2010, vol. 125, No. 1, pp. 105-117.

Knowles et al., "Molecular biology of bladder cancer: New Insights into Pathogenesis and Clinical Diversity", Nat. Rev. Cancer, 2015, vol. 15, pp. 25-41.

Korc et al., "The Role of Fibroblast Growth Factors in Tumor Growth", Current Cancer Drug Targets, 2009, vol. 9 No. 5, pp. 639-651.

Lefranc et al., "IMGT unique numbering for immunoglobulin and T cell receptor variable domains and Ig superfamily V-like domains", Dev. Comp. Immunol., 2003, vol. 27, pp. 55-77.

Li et al., "Prognostic genetic signatures in upper tract urothelial carcinoma", Curr. Urol. Rep., 2016, vol. 17, No. 12, pp. 1-14.

Loriot et al., "Erdafitinib in Locally Advanced or Metastatic Urothelial Carcinoma," N. Engl. J. Med., 2019, vol. 381, No. 4, pp. 338-348.

Marandino et al., "Erdafitinib for the treatment of urothelial cancer," Expert Review of Anticancer Therapy, Oct. 2019, vol. 19, No. 10, pp. 835-846.

Martin et al., "Structural Families in Loops of Homologous Proteins: Automatic Classification, Modelling and Application to Antibodies", J. Bmol. Biol., 1996, vol. 263, pp. 800-815.

Moreno et al., "Does escalation results from phase lb/II Norse study of erdafitinib (ERDA) + PD-1 inhibitor JNJ-63723283 (Cetrelimab [CET]) in patients (pts) with metastatic or locally advanced urothelial carcinoma (mUC) and selected fibroblast growth factor receptor (FGFR) gene alterations", Journal of Clinical Oncology, Feb. 2020, vol. 38, Suppl. 6, pp. 1-4.

Orre et al., "VEGF, VEGFR-1, VEGFR-2, Microvessel Density And Endothelial Cell Proliferation In Tumours Of The Ovary", Int. J. Cancer, 1999, vol. 84, No. 2, 101-108.

Padlan, "A Possible Procedure For Reducing The Immunogenicity of Antibody Variable Domains While Preserving Their Ligand-Binding Properties", Mol. Immunol., 1991, vol. 28, pp. 489-499.

Rutkowski et al., "Anti-PD-1 antibody cetrelimab (JNJ-63723283) in patients with advanced cancers: Updated phase I/II study results", Journal of clinical oncology, 2019, vol. 37, Issue 8, pp. 1-18.

Sambrook et al., "Molecular Cloning: A Laboratory Manual", 3rd Ed., Cold Spring Harbor Laboratory Press, 2001, pp. 1-21.

Shi et al., "De Novo Selection of High-Affinity Antibodies from Synthetic Fab Libraries Displayed on Phage as pIX Fusion Proteins", J. Mol. Biol., 2010, vol. 397, pp. 385-396.

Siefker-Radtke et al., "Efficacy of programmed death 1 (PD-1) and programmed death 1 ligand (PD-L1) inhibitors in patients with FGFR mutations and gene fusions: Results from a data analysis of an ongoing phase 2 study of erdafitinib (JNJ-42756493) in patients (pts) with advanced urothelial cancer (UC)", ASCO-GU, 2018, Abstract 450, pp. 1-4.

Soria et al., "Safety And Activity Of The Pan-Fibroblast Growth Factor Receptor (FGFR) Inhibitor Erdafitinib In Phase 1 Study Patients With Advanced Urothelial Carcinoma", Annals of Oncology, 2016, vol. 27, Suppl. 6, pp. vi269-vi295.

Tabernero et al., "Phase I Dose-Escalation Study of JNJ-42756493, an Oral Pan-Fibroblast Growth Factor Receptor Inhibitor, in Patients With Advanced Solid Tumors", J. Clin. Oncol., 2015, vol. 33, pp. 3401-3408.

Wu et al., "Complementarity their Implications for Antibody Proteins and Myeloma Light Chains and of the Variable Regions of Bence Jones Pillars Article: A", J. Exp. Med., 1970, vol. 132, pp. 211-250.

Yafi et al., "First- and second-line therapy for metastatic urothelial carcinoma of the bladder", Curr. Oncol., 2011, vol. 18, pp. e25-e34.

Katsumi et al., "Urothelial Carcinoma", Journal of the Showa Academy of Sciences, 2016, vol. 76, No. 2, pp. 108-115.

Montazeri et al., "Erdafitinib for the treatment of metastatic bladder cancer", Expert Review of Clinical Pharmacology, Dec. 6, 2019, 16 Pages.

Katoh et al., "FGFR inhibitors: Effects on Cancer Cells, Tumor Microenvironment and Whole-Body Homeostasis (Review)," International Journal of Molecular Medicine, 2016, vol. 38, No. 1, pp. 3-15.

Palakurthi et al., "The Combined Effect of FGFR Inhibition and PD-1 Blockade Promotes Tumor-Intrinsic Induction of Antitumor Immunity," Cancer Immunology Research, Jul. 22, 2019, vol. 7, Issue 9, pp. 1457-1471.

(56) References Cited

OTHER PUBLICATIONS

Rodriguez-Vida et al., "Complexity of FGFR signaling in metastatic urothelial cancer", Journal of Hematology & Oncology, 2015, vol. 8, No. 119, pp. 1-8.

* cited by examiner

CD38+ CD4 T cells/Lymphocytes (%) Fold Induction vs. C1D1

| | E8J | | | | E8RJ | | | | EJ | | | | |
|---|---|---|---|---|---|---|---|---|---|---|---|---|---|
| | C1D1 | C1D15 | C2D1 | C3D1 | C1D1 | C1D15 | C2D1 | C3D1 | C1D1 | C1D15 | C2D1 | C3D1 | C3D15 |
| Count | 4 | 4 | 3 | 4 | 4 | 4 | 4 | 4 | 9 | 8 | 8 | 7 | 1 |
| Avg | 1 | 1.25019 | 1.11506 | 1.07722 | 1 | 1.06039 | 1.19307 | 1.26397 | 1 | 1.10671 | 0.980112 | 1.02568 | 0.724271 |
| Median | 1 | 1.1859 | 0.987302 | 1.0734 | 1 | 1.04772 | 1.11428 | 1.26334 | 1 | 1.08526 | 0.993197 | 0.998307 | 0.724271 |
| Outliers | 0 | 0 | 0 | 0 | 0 | 0 | 0 | 0 | 0 | 0 | 0 | 0 | 0 |
| StdDev | 0 | 0.486729 | 0.261848 | 0.24613 | 0 | 0.23714 | 0.283358 | 0.551591 | 0 | 0.186154 | 0.0720083 | 0.223122 | (Empty) |

CD38+ CD8 T cells/Lymphocytes (%) Fold Induction vs. C1D1

CD38+/CD3+ T Cells (%) Fold Induction vs. C1D1

| | E8J | | | | E8RJ | | | | EJ | | | | |
|---|---|---|---|---|---|---|---|---|---|---|---|---|---|
| | C1D1 | C1D15 | C2D1 | C3D1 | C1D1 | C1D15 | C2D1 | C3D1 | C1D1 | C1D15 | C2D1 | C3D1 | C3D15 |
| Count | 4 | 4 | 3 | 4 | 4 | 4 | 4 | 4 | 9 | 8 | 8 | 7 | 1 |
| Avg | 1 | 1.13545 | 1.00814 | 1.00811 | 1 | 1.34097 | 1.31641 | 1.52063 | 1 | 1.21715 | 1.09191 | 1.10572 | 0.760428 |
| Median | 1 | 1.03501 | 0.928786 | 1.04686 | 1 | 1.20823 | 1.11224 | 1.33319 | 1 | 1.05262 | 1.10378 | 1.0113 | 0.760428 |
| Outliers | 0 | 0 | 0 | 0 | 0 | 0 | 1 | 0 | 0 | 0 | 0 | 0 | 0 |
| StdDev | 0 | 0.376396 | 0.256952 | 0.328069 | 0 | 0.429092 | 0.473045 | 0.56597 | 0 | 0.337691 | 0.144205 | 0.32843 | (Empty) |

CD38+ CD4 T cells /CD3+ T Cells (%) Fold Induction vs. C1D1

| | E8J | | | | E8RJ | | | | EJ | | | | |
|---|---|---|---|---|---|---|---|---|---|---|---|---|---|
| | C1D1 | C1D15 | C2D1 | C3D1 | C1D1 | C1D15 | C2D1 | C3D1 | C1D1 | C1D15 | C2D1 | C3D1 | C3D15 |
| Count | 4 | 4 | 3 | 4 | 4 | 4 | 4 | 4 | 9 | 8 | 8 | 7 | 1 |
| Avg | 1 | 1.26166 | 1.08633 | 1.02369 | 1 | 1.10941 | 1.18632 | 1.3552 | 1 | 1.09191 | 0.991352 | 1.02168 | 0.737596 |
| Median | 1 | 1.1856 | 1.02634 | 1.00696 | 1 | 1.0923 | 1.07574 | 1.21768 | 1 | 1.09568 | 0.997239 | 1.07197 | 0.737596 |
| Outliers | 0 | 0 | 0 | 0 | 0 | 0 | 0 | 1 | 0 | 0 | 2 | 0 | 0 |
| StdDev | 0 | 0.452239 | 0.193472 | 0.144858 | 0 | 0.268493 | 0.295914 | 0.413192 | 0 | 0.172279 | 0.064571 | 0.219621 | (Empty) |

CD38+ CD8 T cells/CD3+ T Cells (%) Fold Induction vs. C1D1

| | E8J | | | | E8RJ | | | | EJ | | | | |
|---|---|---|---|---|---|---|---|---|---|---|---|---|---|
| | C1D1 | C1D15 | C2D1 | C3D1 | C1D1 | C1D15 | C2D1 | C3D1 | C1D1 | C1D15 | C2D1 | C3D1 | C3D15 |
| Count | 4 | 4 | 3 | 4 | 4 | 4 | 4 | 4 | 9 | 8 | 8 | 7 | 1 |
| Avg | 1 | 1.51217 | 1.27102 | 1.07892 | 1 | 4.01756 | 1.93676 | 5.23462 | 1 | 1.42781 | 1.22821 | 1.09063 | 0.953996 |
| Median | 1 | 1.41565 | 1.21102 | 1.17173 | 1 | 2.34138 | 1.68648 | 2.69677 | 1 | 1.31206 | 1.1927 | 1.0644 | 0.953996 |
| Outliers | 0 | 0 | 0 | 0 | 0 | 0 | 0 | 0 | 0 | 0 | 0 | 2 | 0 |
| StdDev | 0 | 0.418207 | 0.351664 | 0.446695 | 0 | 4.38527 | 0.911142 | 6.28436 | 0 | 0.43875 | 0.260563 | 0.267552 | (Empty) |

CD38+/CD4+ T Cells (%) Fold Induction vs. C1D1

| | E8J | | | | E8RJ | | | | EJ | | | | |
|---|---|---|---|---|---|---|---|---|---|---|---|---|---|
| | C1D1 | C1D15 | C2D1 | C3D1 | C1D1 | C1D15 | C2D1 | C3D1 | C1D1 | C1D15 | C2D1 | C3D1 | C3D15 |
| Count | 4 | 4 | 3 | 4 | 4 | 4 | 4 | 4 | 9 | 8 | 8 | 7 | 1 |
| Avg | 1 | 1.35245 | 1.14567 | 1.05152 | 1 | 1.12623 | 1.17613 | 1.36761 | 1 | 1.06561 | 0.99476 | 0.996436 | 0.726629 |
| Median | 1 | 1.28658 | 1.01494 | 0.995485 | 1 | 1.10186 | 1.09569 | 1.24861 | 1 | 1.05389 | 1.00241 | 1.05362 | 0.726629 |
| Outliers | 0 | 0 | 0 | 1 | 0 | 0 | 0 | 0 | 0 | 2 | 0 | 0 | 0 |
| StdDev | 0 | 0.514278 | 0.287171 | 0.165898 | 0 | 0.290439 | 0.26705 | 0.395787 | 0 | 0.140468 | 0.0783405 | 0.186033 | (Empty) |

CD38+/CD8+ T Cells (%) Fold Induction vs. C1D1

| | E8J | | | | E8RJ | | | | EJ | | | | |
|---|---|---|---|---|---|---|---|---|---|---|---|---|---|
| | C1D1 | C1D15 | C2D1 | C3D1 | C1D1 | C1D15 | C2D1 | C3D1 | C1D1 | C1D15 | C2D1 | C3D1 | C3D15 |
| Count | 4 | 4 | 3 | 4 | 4 | 4 | 4 | 4 | 9 | 8 | 8 | 7 | 1 |
| Avg | 1 | 1.30227 | 1.19479 | 0.985858 | 1 | 3.87809 | 1.95303 | 4.85506 | 1 | 1.45635 | 1.27591 | 1.14353 | 0.943125 |
| Median | 1 | 1.25626 | 1.0037 | 1.09644 | 1 | 2.31357 | 1.63714 | 2.81194 | 1 | 1.35881 | 1.26626 | 1.09306 | 0.943125 |
| Outliers | 0 | 0 | 0 | 0 | 0 | 0 | 0 | 0 | 0 | 1 | 0 | 2 | 0 |
| StdDev | 0 | 0.211268 | 0.348311 | 0.325888 | 0 | 4.16131 | 0.96701 | 5.41056 | 0 | 0.440079 | 0.272439 | 0.329036 | (Empty) |

CD3+CD38+/Lymphocytes (%) Fold Induction vs. C1D1

| | ARM A | | | | | | ARM B | | | | | |
|---|---|---|---|---|---|---|---|---|---|---|---|---|
| | C1D1 | C1D15 | C2D1 | C2D15 | C3D1 | C3D15 | C1D1 | C1D15 | C2D1 | C2D15 | C3D1 | C3D15 |
| Count | 8 | 5 | 7 | 3 | 2 | 2 | 9 | 8 | 8 | 8 | 5 | 5 |
| Avg | 1 | 1.13356 | 1.07362 | 1.16001 | 1.12486 | 1.01317 | 1 | 1.43767 | 1.22422 | 1.33537 | 1.6291 | 1.4055 |
| Median | 1 | 1.16513 | 0.966448 | 1.17459 | 1.12486 | 1.01317 | 1 | 1.34059 | 1.09761 | 1.2422 | 1.62506 | 1.25517 |
| Outliers | 0 | 0 | 0 | 0 | 0 | 0 | 0 | 1 | 0 | 1 | 0 | 1 |
| StdDev | 0 | 0.283798 | 0.263554 | 0.36423 | 0.0866871 | 0.642843 | 0 | 0.457884 | 0.321367 | 0.543389 | 0.74178 | 0.536945 |

CD38+ CD4 T cells/Lymphocytes (%) Fold Induction vs. C1D1

| | ARM A | | | | | | ARM B | | | | | |
|---|---|---|---|---|---|---|---|---|---|---|---|---|
| | C1D1 | C1D15 | C2D1 | C2D15 | C3D1 | C3D15 | C1D1 | C1D15 | C2D1 | C2D15 | C3D1 | C3D15 |
| Count | 8 | 5 | 7 | 3 | 2 | 2 | 9 | 8 | 8 | 8 | 5 | 5 |
| Avg | 1 | 1.31432 | 1.07863 | 1.2675 | 1.09176 | 0.8649 | 1 | 1.17278 | 1.01209 | 1.08995 | 1.18832 | 1.17536 |
| Median | 1 | 1.07115 | 1.15539 | 0.932765 | 1.09176 | 0.8649 | 1 | 0.986158 | 0.994272 | 0.97418 | 1.02478 | 1.09318 |
| Outliers | 0 | 2 | 0 | 0 | 0 | 0 | 0 | 1 | 0 | 1 | 0 | 1 |
| StdDev | 0 | 0.650918 | 0.191892 | 0.624191 | 0.336632 | 0.0763441 | 0 | 0.411277 | 0.331069 | 0.409095 | 0.358774 | 0.47381 |

CD38+ CD8 T cells/Lymphocytes (%) Fold Induction vs. C1D1

| | ARM A | | | | | | ARM B | | | | | |
|---|---|---|---|---|---|---|---|---|---|---|---|---|
| | C1D1 | C1D15 | C2D1 | C2D15 | C3D1 | C3D15 | C1D1 | C1D15 | C2D1 | C2D15 | C3D1 | C3D15 |
| Count | 8 | 5 | 7 | 3 | 2 | 2 | 9 | 8 | 8 | 8 | 5 | 5 |
| Avg | 1 | 1.12588 | 1.20073 | 1.22064 | 1.63074 | 1.55457 | 1 | 1.66203 | 1.77935 | 1.77853 | 2.11198 | 1.85318 |
| Median | 1 | 1.1173 | 1.086 | 1.2677 | 1.63074 | 1.55457 | 1 | 1.56178 | 1.86243 | 1.75699 | 1.74497 | 1.77043 |
| Outliers | 0 | 0 | 0 | 0 | 0 | 0 | 0 | 1 | 0 | 0 | 0 | 2 |
| StdDev | 0 | 0.294706 | 0.2267 | 0.205018 | 0.468293 | 1.4428 | 0 | 0.537765 | 0.44641 | 0.912287 | 1.42107 | 0.419222 |

CD38+/CD3+ T Cells (%) Fold Induction vs. C1D1

| | ARM A C1D1 | ARM A C1D15 | ARM A C2D1 | ARM A C2D15 | ARM A C3D1 | ARM A C3D15 | ARM B C1D1 | ARM B C1D15 | ARM B C2D1 | ARM B C2D15 | ARM B C3D1 | ARM B C3D15 |
|---|---|---|---|---|---|---|---|---|---|---|---|---|
| Count | 8 | 5 | 7 | 3 | 2 | 2 | 9 | 8 | 8 | 8 | 5 | 5 |
| Avg | 1 | 1.11614 | 1.08798 | 1.2115 | 1.10783 | 0.998985 | 1 | 1.43474 | 1.29772 | 1.37742 | 1.63279 | 1.3213 |
| Median | 1 | 1.10776 | 1.04312 | 1.19129 | 1.10783 | 0.998985 | 1 | 1.41582 | 1.24079 | 1.44506 | 1.57546 | 1.25237 |
| Outliers | 0 | 0 | 0 | 0 | 0 | 0 | 0 | 0 | 1 | 1 | 0 | 0 |
| StdDev | 0 | 0.207323 | 0.21699 | 0.306344 | 0.0748106 | 0.551622 | 0 | 0.450336 | 0.320882 | 0.517012 | 0.799276 | 0.408041 |

CD38+ CD4 T cells /CD3+ T Cells (%) Fold Induction vs. C1D1

| | ARM A | | | | | | ARM B | | | | | |
|---|---|---|---|---|---|---|---|---|---|---|---|---|
| | C1D1 | C1D15 | C2D1 | C2D15 | C3D1 | C3D15 | C1D1 | C1D15 | C2D1 | C2D15 | C3D1 | C3D15 |
| Count | 8 | 5 | 7 | 3 | 2 | 2 | 9 | 8 | 8 | 8 | 5 | 5 |
| Avg | 1 | 1.29165 | 1.09253 | 1.32414 | 1.07741 | 0.876886 | 1 | 1.16764 | 1.06425 | 1.12708 | 1.17971 | 1.10134 |
| Median | 1 | 1.07742 | 1.11486 | 1.02431 | 1.07741 | 0.876886 | 1 | 0.964318 | 1.04473 | 1.01066 | 1.06472 | 1.03441 |
| Outliers | 0 | 1 | 0 | 0 | 0 | 0 | 0 | 1 | 2 | 1 | 0 | 0 |
| StdDev | 0 | 0.588112 | 0.126756 | 0.588682 | 0.340907 | 0.0112439 | 0 | 0.389399 | 0.321688 | 0.405676 | 0.374278 | 0.35907 |

CD38+ CD8 T cells/CD3+ T Cells (%) Fold Induction vs. C1D1

| | ARM A | | | | | | ARM B | | | | | |
|---|---|---|---|---|---|---|---|---|---|---|---|---|
| | C1D1 | C1D15 | C2D1 | C2D15 | C3D1 | C3D15 | C1D1 | C1D15 | C2D1 | C2D15 | C3D1 | C3D15 |
| Count | 8 | 5 | 7 | 3 | 2 | 2 | 9 | 8 | 8 | 8 | 5 | 5 |
| Avg | 1 | 1.10562 | 1.22397 | 1.28324 | 1.60621 | 1.50961 | 1 | 1.65815 | 1.92317 | 1.857 | 2.13089 | 1.74946 |
| Median | 1 | 1.0623 | 1.28198 | 1.28582 | 1.60621 | 1.50961 | 1 | 1.56565 | 2.01498 | 1.93199 | 1.68925 | 1.72664 |
| Outliers | 0 | 0 | 0 | 0 | 0 | 0 | 0 | 0 | 0 | 0 | 0 | 2 |
| StdDev | 0 | 0.209553 | 0.20182 | 0.125743 | 0.446204 | 1.31025 | 0 | 0.531558 | 0.61148 | 0.951109 | 1.50356 | 0.260941 |

CD38+/CD4+ T Cells (%) Fold Induction vs. C1D1

| | ARM A | | | | | ARM B | | | | |
|---|---|---|---|---|---|---|---|---|---|---|
| | C1D1 | C1D15 | C2D1 | C2D15 | C3D1 | C3D15 | C1D1 | C1D15 | C2D1 | C2D15 | C3D1 | C3D15 |
| Count | 8 | 5 | 7 | 3 | 2 | 2 | 9 | 8 | 8 | 8 | 5 | 5 |
| Avg | 1 | 1.29909 | 1.1121 | 1.33669 | 1.17095 | 0.944235 | 1 | 1.21884 | 1.20331 | 1.19506 | 1.24756 | 1.07276 |
| Median | 1 | 1.04974 | 1.1068 | 1.0356 | 1.17095 | 0.944235 | 1 | 1.1726 | 1.14765 | 1.12046 | 1.30802 | 1.02936 |
| Outliers | 0 | 1 | 0 | 0 | 0 | 0 | 0 | 1 | 0 | 1 | 0 | 0 |
| StdDev | 0 | 0.553217 | 0.130125 | 0.527397 | 0.224822 | 0.207552 | 0 | 0.342103 | 0.253161 | 0.400226 | 0.416696 | 0.339557 |

| | ARM A C1D1 | ARM A C1D15 | ARM A C2D1 | ARM A C2D15 | ARM A C3D1 | ARM A C3D15 | ARM B C1D1 | ARM B C1D15 | ARM B C2D1 | ARM B C2D15 | ARM B C3D1 | ARM B C3D15 |
|---|---|---|---|---|---|---|---|---|---|---|---|---|
| Count | 8 | 5 | 7 | 3 | 2 | 2 | 9 | 8 | 8 | 8 | 5 | 5 |
| Avg | 1 | 1.08417 | 1.18268 | 1.27431 | 1.35205 | 1.19793 | 1 | 1.51796 | 1.56822 | 1.63921 | 1.88813 | 1.88741 |
| Median | 1 | 1.05979 | 1.19205 | 1.23248 | 1.35205 | 1.19793 | 1 | 1.63153 | 1.56389 | 1.60186 | 1.77255 | 1.73514 |
| Outliers | 0 | 0 | 0 | 0 | 0 | 0 | 0 | 0 | 1 | 0 | 0 | 0 |
| StdDev | 0 | 0.244571 | 0.193329 | 0.160896 | 0.11565 | 0.724201 | 0 | 0.340418 | 0.319777 | 0.724881 | 1.12831 | 0.464311 |

SEQUENCE LISTING

<160> NUMBER OF SEQ ID NOS: 49

<210> SEQ ID NO 1
<211> LENGTH: 268
<212> TYPE: DNA
<213> ORGANISM: Homo sapiens

<400> SEQUENCE: 1
tcggaccgcg gcaactacac ctgcgtcgtg gagaacaagt ttggcagcat ccggcagacg 60
tacacgctgg acgtgctgga gtgctccccg caccggccca tcctgcaggc ggggctgccg 120
gccaaccaga cggcggtgct gggcagcgac gtggagttcc actgcaaggt gtacagtgac 180
gcacagcccc acatccagtg gctcaagcac gtggaggtga atggcagcaa ggtgggcccg 240
gacggcacac cctacgttac cgtgctca 268

<210> SEQ ID NO 2
<211> LENGTH: 378
<212> TYPE: DNA
<213> ORGANISM: Homo sapiens

<400> SEQUENCE: 2
gaccgcggca actacacctg cgtcgtggag aacaagtttg gcagcatccg gcagacgtac 60
acgctggacg tgctgggtga gggccctggg gcggcgcggg ggtgggggcg gcagtggcgg 120
tggtggtgag ggagggggtg gcccctgagc gtcatctgcc cccacagagc gctgcccgca 180
ccggcccatc ctgcaggcgg ggctgccggc caaccagacg gcggtgctgg gcagcgacgt 240
ggagttccac tgcaaggtgt acagtgacgc acagccccac atccagtggc tcaagcacgt 300
ggaggtgaat ggcagcaagg tgggcccgga cggcacaccc tacgttaccg tgctcaaggt 360
gggccaccgt gtgcacgt 378

<210> SEQ ID NO 3
<211> LENGTH: 234
<212> TYPE: DNA
<213> ORGANISM: Homo sapiens

<400> SEQUENCE: 3
gcgggcaatt ctattgggtt ttctcatcac tctgcgtggc tggtggtgct gccagccgag 60
gaggagctgg tggaggctga cgaggcgtgc agtgtgtatg caggcatcct cagctacggg 120
gtgggcttct tcctgttcat cctggtggtg gcggctgtga cgctctgccg cctgcgcagc 180
ccccccaaga aaggcctggg ctcccccacc gtgcacaaga tctcccgctt cccg 234

<210> SEQ ID NO 4
<211> LENGTH: 301
<212> TYPE: DNA
<213> ORGANISM: Homo sapiens

<400> SEQUENCE: 4
ctagaggttc tctccttgca caacgtcacc tttgaggacg ccggggagta cacctgcctg 60
gcgggcaatt ctattgggtt ttctcatcac tctgcgtggc tggtggtgct gccagccgag 120
gaggagctgg tggaggctga cgaggcgggc agtgtgtgtg caggcatcct cagctacggg 180
gtgggcttct tcctgttcat cctggtggtg gcggctgtga cgctctgccg cctgcgcagc 240
ccccccaaga aaggcctggg ctcccccacc gtgcacaaga tctcccgctt cccgctcaag 300
c 301

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
gacctggacc gtgtccttac c 21

<210> SEQ ID NO 6
<211> LENGTH: 21
<212> TYPE: DNA
<213> ORGANISM: Artificial Sequence
<220> FEATURE:
<223> OTHER INFORMATION: Synthetic primer -continued

<400> SEQUENCE: 6
cttccccagt tccaggttct t 21

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
aggacctgga ccgtgtcctt 20

<210> SEQ ID NO 8
<211> LENGTH: 20
<212> TYPE: DNA
<213> ORGANISM: Artificial Sequence
<220> FEATURE:
<223> OTHER INFORMATION: synthetic primer

<400> SEQUENCE: 8
tataggtccg gtggacaggg 20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
ctggaccgtg tccttaccgt 20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
gcagcccagg attgaactgt 20

<210> SEQ ID NO 11
<211> LENGTH: 23
<212> TYPE: DNA
<213> ORGANISM: Artificial Sequence
<220> FEATURE:
<223> OTHER INFORMATION: Synthetic primer

<400> SEQUENCE: 11
tggatcgaat tctcactctc aca 23

<210> SEQ ID NO 12
<211> LENGTH: 21
<212> TYPE: DNA
<213> ORGANISM: Artificial Sequence
<220> FEATURE:
<223> OTHER INFORMATION: Synthetic primer

<400> SEQUENCE: 12
gccaagcaat ctgcgtattt g 21

<210> SEQ ID NO 13

<211> LENGTH: 23
<212> TYPE: DNA
<213> ORGANISM: Artificial Sequence
<220> FEATURE:
<223> OTHER INFORMATION: Synthetic primer

<400> SEQUENCE: 13
gctcttcaat acagccctga tca 23

<210> SEQ ID NO 14
<211> LENGTH: 24
<212> TYPE: DNA
<213> ORGANISM: Artificial Sequence
<220> FEATURE:
<223> OTHER INFORMATION: Synthetic primer

<400> SEQUENCE: 14
acttggatcg aattctcact ctca 24

<210> SEQ ID NO 15
<211> LENGTH: 23
<212> TYPE: DNA
<213> ORGANISM: Artificial Sequence
<220> FEATURE:
<223> OTHER INFORMATION: Synthetic primer

<400> SEQUENCE: 15
tggatcgaat tctcactctc aca 23

<210> SEQ ID NO 16
<211> LENGTH: 25
<212> TYPE: DNA
<213> ORGANISM: Artificial Sequence
<220> FEATURE:
<223> OTHER INFORMATION: Synthetic primer

<400> SEQUENCE: 16
gcaaagcctg aattttcttg aataa 25

<210> SEQ ID NO 17
<211> LENGTH: 18
<212> TYPE: DNA
<213> ORGANISM: Artificial Sequence
<220> FEATURE:
<223> OTHER INFORMATION: Synthetic primer

<400> SEQUENCE: 17
gcatccggca gacgtaca 18

<210> SEQ ID NO 18
<211> LENGTH: 15
<212> TYPE: DNA
<213> ORGANISM: Artificial Sequence
<220> FEATURE:
<223> OTHER INFORMATION: Synthetic primer

<400> SEQUENCE: 18
ccccgcctgc aggat 15

<210> SEQ ID NO 19
<211> LENGTH: 18
<212> TYPE: DNA
<213> ORGANISM: Artificial Sequence
<220> FEATURE:
<223> OTHER INFORMATION: Synthetic primer

<400> SEQUENCE: 19
gcatccggca gacgtaca 18

<210> SEQ ID NO 20
<211> LENGTH: 15
<212> TYPE: DNA
<213> ORGANISM: Artificial Sequence
<220> FEATURE:
<223> OTHER INFORMATION: Synthetic primer

<400> SEQUENCE: 20
ccccgcctgc aggat 15

<210> SEQ ID NO 21
<211> LENGTH: 19
<212> TYPE: DNA
<213> ORGANISM: Artificial Sequence
<220> FEATURE:
<223> OTHER INFORMATION: Synthetic primer

<400> SEQUENCE: 21
aggagctggt ggaggctga 19

<210> SEQ ID NO 22
<211> LENGTH: 19
<212> TYPE: DNA
<213> ORGANISM: Artificial Sequence
<220> FEATURE:
<223> OTHER INFORMATION: Synthetic primer

<400> SEQUENCE: 22
ccgtagctga ggatgcctg 19

<210> SEQ ID NO 23
<211> LENGTH: 18
<212> TYPE: DNA
<213> ORGANISM: Artificial Sequence
<220> FEATURE:
<223> OTHER INFORMATION: Synthetic primer

<400> SEQUENCE: 23
ctggtggagg ctgacgag 18

<210> SEQ ID NO 24
<211> LENGTH: 16
<212> TYPE: DNA
<213> ORGANISM: Artificial Sequence
<220> FEATURE:
<223> OTHER INFORMATION: Synthetic primer

<400> SEQUENCE: 24
agcccacccc gtagct 16

<210> SEQ ID NO 25
<211> LENGTH: 21
<212> TYPE: DNA
<213> ORGANISM: Artificial Sequence
<220> FEATURE:
<223> OTHER INFORMATION: Synthetic primer

<400> SEQUENCE: 25
gtcgtggaga acaagtttgg c 21

<210> SEQ ID NO 26
<211> LENGTH: 17
<212> TYPE: DNA

<213> ORGANISM: Artificial Sequence
<220> FEATURE:
<223> OTHER INFORMATION: Synthetic primer

<400> SEQUENCE: 26
gtctggttgg ccggcag 17

<210> SEQ ID NO 27
<211> LENGTH: 21
<212> TYPE: DNA
<213> ORGANISM: Artificial Sequence
<220> FEATURE:
<223> OTHER INFORMATION: Synthetic primer

<400> SEQUENCE: 27
gtcgtggaga acaagtttgg c 21

<210> SEQ ID NO 28
<211> LENGTH: 17
<212> TYPE: DNA
<213> ORGANISM: Artificial Sequence
<220> FEATURE:
<223> OTHER INFORMATION: Synthetic primer

<400> SEQUENCE: 28
gtctggttgg ccggcag 17

<210> SEQ ID NO 29
<211> LENGTH: 19
<212> TYPE: DNA
<213> ORGANISM: Artificial Sequence
<220> FEATURE:
<223> OTHER INFORMATION: synthetic primer

<400> SEQUENCE: 29
aggagctggt ggaggctga 19

<210> SEQ ID NO 30
<211> LENGTH: 19
<212> TYPE: DNA
<213> ORGANISM: Artificial Sequence
<220> FEATURE:
<223> OTHER INFORMATION: Synthetic primer

<400> SEQUENCE: 30
ccgtagctga ggatgcctg 19

<210> SEQ ID NO 31
<211> LENGTH: 16
<212> TYPE: DNA
<213> ORGANISM: Artificial Sequence
<220> FEATURE:
<223> OTHER INFORMATION: Synthetic primer

<400> SEQUENCE: 31
gacgaggcgg gcagtg 16

<210> SEQ ID NO 32
<211> LENGTH: 19
<212> TYPE: DNA
<213> ORGANISM: Artificial Sequence
<220> FEATURE:
<223> OTHER INFORMATION: Synthetic primer

<400> SEQUENCE: 32
gaagaagccc accccgtag 19

<210> SEQ ID NO 33
<211> LENGTH: 2850
<212> TYPE: DNA
<213> ORGANISM: Artificial Sequence
<220> FEATURE:
<223> OTHER INFORMATION: Synthetic polynucleotide

<400> SEQUENCE: 33
atgggcgccc ctgcctgcgc cctcgcgctc tgcgtggccg tggccatcgt ggccggcgcc 60
tcctcggagt ccttggggac ggagcagcgc gtcgtggggc gagcggcaga agtcccgggc 120
ccagagcccg gccagcagga gcagttggtc ttcggcagcg gggatgctgt ggagctgagc 180
tgtcccccgc ccgggggtgg tcccatgggg cccactgtct gggtcaagga tggcacaggg 240
ctggtgccct cggagcgtgt cctggtgggg ccccagcggc tgcaggtgct gaatgcctcc 300
cacgaggact ccggggccta cagctgccgg cagcggctca cgcagcgcgt actgtgccac 360
ttcagtgtgc gggtgacaga cgctccatcc tcgggagatg acgaagacgg ggaggacgag 420
gctgaggaca caggtgtgga cacaggggcc ccttactgga cacggcccga gcggatggac 480
aagaagctgc tggccgtgcc ggccgccaac accgtccgct tccgctgccc agccgctggc 540
aaccccactc cctccatctc ctggctgaag aacggcaggg agttccgcgg cgagcaccgc 600
attggaggca tcaagctgcg gcatcagcag tggagcctgg tcatggaaag cgtggtgccc 660
tcggaccgcg gcaactacac ctgcgtcgtg gagaacaagt ttggcagcat ccggcagacg 720
tacacgctgg acgtgctgga gcgctccccg caccggccca tcctgcaggc ggggctgccg 780
gccaaccaga cggcggtgct gggcagcgac gtggagttcc actgcaaggt gtacagtgac 840
gcacagcccc acatccagtg gctcaagcac gtggaggtga atggcagcaa ggtgggcccg 900
gacggcacac cctacgttac cgtgctcaag acggcgggcg ctaacaccac cgacaaggag 960
ctagaggttc tctccttgca caacgtcacc tttgaggacg ccggggagta cacctgcctg 1020
gcgggcaatt ctattgggtt ttctcatcac tctgcgtggc tggtggtgct gccagccgag 1080
gaggagctgg tggaggctga cgaggcgggc agtgtgtatg caggcatcct cagctacggg 1140
gtgggcttct tcctgttcat cctggtggtg gcggctgtga cgctctgccg cctgcgcagc 1200
ccccccaaga aaggcctggg ctcccccacc gtgcacaaga tctcccgctt cccgctcaag 1260
cgacaggtgt ccctggagtc caacgcgtcc atgagctcca acacaccact ggtgcgcatc 1320
gcaaggctgt cctcagggga gggccccacg ctggccaatg tctccgagct cgagctgcct 1380
gccgacccca aatgggagct gtctcgggcc cggctgaccc tgggcaagcc ccttggggag 1440
ggctgcttcg gccaggtggt catggcggag gccatcggca ttgacaagga ccgggccgcc 1500
aagcctgtca ccgtagccgt gaagatgctg aaagacgatg ccactgacaa ggacctgtcg 1560
gacctggtgt ctgagatgga gatgatgaag atgatcggga aacacaaaaa catcatcaac 1620
ctgctgggcg cctgcacgca gggcgggccc ctgtacgtgc tggtggagta cgcggccaag 1680
ggtaacctgc gggagtttct gcgggcgcgg cggcccccgg gcctggacta ctccttcgac 1740
acctgcaagc cgcccgagga gcagctcacc ttcaaggacc tggtgtcctg tgcctaccag 1800
gtggcccggg gcatggagta cttggcctcc cagaagtgca tccacaggga cctggctgcc 1860
cgcaatgtgc tggtgaccga ggacaacgtg atgaagatcg cagacttcgg gctggcccgg 1920
gacgtgcaca acctcgacta ctacaagaag acgaccaacg gccggctgcc cgtgaagtgg 1980
atggcgcctg aggccttgtt tgaccgagtc tacactcacc agagtgacgt ctggtccttt 2040

-continued

```
ggggtcctgc tctgggagat cttcacgctg gggggctccc cgtaccccgg catccctgtg   2100

gaggagctct tcaagctgct gaaggagggc caccgcatgg acaagcccgc caactgcaca   2160

cacgacctgt acatgatcat gcgggagtgc tggcatgccg cgccctccca gaggcccacc   2220

ttcaagcagc tggtggagga cctggaccgt gtccttaccg tgacgtccac cgacgtaaag   2280

gcgacacagg aggagaaccg ggagctgagg agcaggtgtg aggagctcca cgggaagaac   2340

ctggaactgg ggaagatcat ggacaggttc gaagaggttg tgtaccaggc catggaggaa   2400

gttcagaagc agaaggaact ttccaaagct gaaatccaga aagttctaaa agaaaaagac   2460

caacttacca cagatctgaa ctccatggag aagtccttct ccgacctctt caagcgtttt   2520

gagaaacaga aagaggtgat cgagggctac cgcaagaacg aagagtcact gaagaagtgc   2580

gtggaggatt acctggcaag gatcacccag gagggccaga ggtaccaagc cctgaaggcc   2640

cacgcggagg agaagctgca gctggcaaac gaggagatcg cccaggtccg gagcaaggcc   2700

caggcggaag cgttggccct ccaggccagc ctgaggaagg agcagatgcg catccagtcg   2760

ctggagaaga cagtggagca gaagactaaa gagaacgagg agctgaccag gatctgcgac   2820

gacctcatct ccaagatgga gaagatctga                                    2850
```

<210> SEQ ID NO 34
<211> LENGTH: 2955
<212> TYPE: DNA
<213> ORGANISM: Artificial Sequence
<220> FEATURE:
<223> OTHER INFORMATION: Synthetic polynucleotide

<400> SEQUENCE: 34

```
atgggcgccc ctgcctgcgc cctcgcgctc tgcgtggccg tggccatcgt ggccggcgcc     60

tcctcggagt ccttggggac ggagcagcgc gtcgtggggc gagcggcaga agtcccgggc    120

ccagagcccg gccagcagga gcagttggtc ttcggcagcg gggatgctgt ggagctgagc    180

tgtcccccgc ccgggggtgg tcccatgggg cccactgtct gggtcaagga tggcacaggg    240

ctggtgccct cggagcgtgt cctggtgggg ccccagcggc tgcaggtgct gaatgcctcc    300

cacgaggact ccggggccta cagctgccgg cagcggctca cgcagcgcgt actgtgccac    360

ttcagtgtgc gggtgacaga cgctccatcc tcgggagatg acgaagacgg ggaggacgag    420

gctgaggaca caggtgtgga cacaggggcc ccttactgga cacggcccga gcggatggac    480

aagaagctgc tggccgtgcc ggccgccaac accgtccgct tccgctgccc agccgctggc    540

aaccccactc cctccatctc ctggctgaag aacggcaggg agttccgcgg cgagcaccgc    600

attggaggca tcaagctgcg gcatcagcag tggagcctgg tcatggaaag cgtggtgccc    660

tcggaccgcg gcaactacac ctgcgtcgtg gagaacaagt ttggcagcat ccggcagacg    720

tacacgctgg acgtgctgga gcgctccccg caccggccca tcctgcaggc ggggctgccg    780

gccaaccaga cggcggtgct gggcagcgac gtggagttcc actgcaaggt gtacagtgac    840

gcacagcccc acatccagtg gctcaagcac gtggaggtga atggcagcaa ggtgggcccg    900

gacggcacac cctacgttac cgtgctcaag acggcgggcg ctaacaccac cgacaaggag    960

ctagaggttc tctccttgca caacgtcacc tttgaggacg ccggggagta cacctgcctg   1020

gcgggcaatt ctattgggtt ttctcatcac tctgcgtggc tggtggtgct gccagccgag   1080

gaggagctgg tggaggctga cgaggcgggc agtgtgtatg caggcatcct cagctacggg   1140

gtgggcttct tcctgttcat cctggtggtg gcggctgtga cgctctgccg cctgcgcagc   1200

ccccccaaga aaggcctggg ctcccccacc gtgcacaaga tctcccgctt cccgctcaag   1260
```

cgacaggtgt ccctggagtc caacgcgtcc atgagctcca acacaccact ggtgcgcatc 1320
gcaaggctgt cctcagggga gggccccacg ctggccaatg tctccgagct cgagctgcct 1380
gccgacccca aatgggagct gtctcgggcc cggctgaccc tgggcaagcc ccttggggag 1440
ggctgcttcg gccaggtggt catggcggag gccatcggca ttgacaagga ccgggccgcc 1500
aagcctgtca ccgtagccgt gaagatgctg aaagacgatg ccactgacaa ggacctgtcg 1560
gacctggtgt ctgagatgga gatgatgaag atgatcggga aacacaaaaa catcatcaac 1620
ctgctgggcg cctgcacgca gggcgggccc ctgtacgtgc tggtggagta cgcggccaag 1680
ggtaacctgc gggagtttct gcgggcgcgg cggcccccgg gcctggacta ctccttcgac 1740
acctgcaagc cgcccgagga gcagctcacc ttcaaggacc tggtgtcctg tgcctaccag 1800
gtggcccggg gcatggagta cttggcctcc cagaagtgca tccacaggga cctggctgcc 1860
cgcaatgtgc tggtgaccga ggacaacgtg atgaagatcg cagacttcgg gctggcccgg 1920
gacgtgcaca acctcgacta ctacaagaag acgaccaacg gccggctgcc cgtgaagtgg 1980
atggcgcctg aggccttgtt tgaccgagtc tacactcacc agagtgacgt ctggtccttt 2040
ggggtcctgc tctgggagat cttcacgctg gggggctccc cgtaccccgg catccctgtg 2100
gaggagctct tcaagctgct gaaggagggc caccgcatgg acaagcccgc caactgcaca 2160
cacgacctgt acatgatcat gcgggagtgc tggcatgccg cgccctccca gaggcccacc 2220
ttcaagcagc tggtggagga cctggaccgt gtccttaccg tgacgtccac cgacgtgcca 2280
ggcccacccc caggtgttcc cgcgcctggg ggcccacccc tgtccaccgg acctatagtg 2340
gacctgctcc agtacagcca gaaggacctg gatgcagtgg taaaggcgac acaggaggag 2400
aaccgggagc tgaggagcag gtgtgaggag ctccacggga agaacctgga actggggaag 2460
atcatggaca ggttcgaaga ggttgtgtac caggccatgg aggaagttca gaagcagaag 2520
gaactttcca aagctgaaat ccagaaagtt ctaaaagaaa aagaccaact taccacagat 2580
ctgaactcca tggagaagtc cttctccgac ctcttcaagc gttttgagaa acagaaagag 2640
gtgatcgagg gctaccgcaa gaacgaagag tcactgaaga agtgcgtgga ggattacctg 2700
gcaaggatca cccaggaggg ccagaggtac caagccctga aggcccacgc ggaggagaag 2760
ctgcagctgg caaacgagga gatcgcccag gtccggagca aggcccaggc ggaagcgttg 2820
gccctccagg ccagcctgag gaaggagcag atgcgcatcc agtcgctgga gaagacagtg 2880
gagcagaaga ctaaagagaa cgaggagctg accaggatct gcgacgacct catctccaag 2940
atggagaaga tctga 2955

<210> SEQ ID NO 35
<211> LENGTH: 3765
<212> TYPE: DNA
<213> ORGANISM: Artificial Sequence
<220> FEATURE:
<223> OTHER INFORMATION: Synthetic polynucleotide

<400> SEQUENCE: 35
atgggcgccc ctgcctgcgc cctcgcgctc tgcgtggccg tggccatcgt ggccggcgcc 60
tcctcggagt ccttggggac ggagcagcgc gtcgtggggc gagcggcaga agtcccgggc 120
ccagagcccg gccagcagga gcagttggtc ttcggcagcg gggatgctgt ggagctgagc 180
tgtcccccgc ccgggggtgg tcccatgggg cccactgtct gggtcaagga tggcacaggg 240
ctggtgccct cggagcgtgt cctggtgggg ccccagcggc tgcaggtgct gaatgcctcc 300

-continued

```
cacgaggact ccggggccta cagctgccgg cagcggctca cgcagcgcgt actgtgccac    360
ttcagtgtgc gggtgacaga cgctccatcc tcgggagatg acgaagacgg ggaggacgag    420
gctgaggaca caggtgtgga cacaggggcc ccttactgga cacggcccga gcggatggac    480
aagaagctgc tggccgtgcc ggccgccaac accgtccgct tccgctgccc agccgctggc    540
aaccccactc cctccatctc ctggctgaag aacggcaggg agttccgcgg cgagcaccgc    600
attggaggca tcaagctgcg gcatcagcag tggagcctgg tcatggaaag cgtggtgccc    660
tcggaccgcg gcaactacac ctgcgtcgtg gagaacaagt ttggcagcat ccggcagacg    720
tacacgctgg acgtgctgga gcgctccccg caccggccca tcctgcaggc ggggctgccg    780
gccaaccaga cggcggtgct gggcagcgac gtggagttcc actgcaaggt gtacagtgac    840
gcacagcccc acatccagtg gctcaagcac gtggaggtga atggcagcaa ggtgggcccg    900
gacggcacac cctacgttac cgtgctcaag tcctggatca gtgagagtgt ggaggccgac    960
gtgcgcctcc gcctggccaa tgtgtcggag cgggacgggg gcgagtacct ctgtcgagcc   1020
accaatttca taggcgtggc cgagaaggcc ttttggctga gcgttcacgg gccccgagca   1080
gccgaggagg agctggtgga ggctgacgag gcgggcagtg tgtatgcagg catcctcagc   1140
tacggggtgg gcttcttcct gttcatcctg gtggtggcgg ctgtgacgct ctgccgcctg   1200
cgcagccccc ccaagaaagg cctgggctcc cccaccgtgc acaagatctc ccgcttcccg   1260
ctcaagcgac aggtgtccct ggagtccaac gcgtccatga gctccaacac accactggtg   1320
cgcatcgcaa ggctgtcctc aggggagggc cccacgctgg ccaatgtctc cgagctcgag   1380
ctgcctgccg accccaaatg ggagctgtct cgggcccggc tgaccctggg caagcccctt   1440
ggggagggct gcttcggcca ggtggtcatg gcggaggcca tcggcattga caaggaccgg   1500
gccgccaagc ctgtcaccgt agccgtgaag atgctgaaag acgatgccac tgacaaggac   1560
ctgtcggacc tggtgtctga gatggagatg atgaagatga tcgggaaaca caaaaacatc   1620
atcaacctgc tgggcgcctg cacgcagggc gggcccctgt acgtgctggt ggagtacgcg   1680
gccaagggta acctgcggga gtttctgcgg gcgcggcggc ccccgggcct ggactactcc   1740
ttcgacacct gcaagccgcc cgaggagcag ctcaccttca aggacctggt gtcctgtgcc   1800
taccaggtgg cccggggcat ggagtacttg gcctcccaga agtgcatcca cagggacctg   1860
gctgcccgca atgtgctggt gaccgaggac aacgtgatga agatcgcaga cttcgggctg   1920
gcccgggacg tgcacaacct cgactactac aagaagacga ccaacggccg gctgcccgtg   1980
aagtggatgg cgcctgaggc cttgtttgac cgagtctaca ctcaccagag tgacgtctgg   2040
tcctttgggg tcctgctctg ggagatcttc acgctggggg gctccccgta ccccggcatc   2100
cctgtggagg agctcttcaa gctgctgaag gagggccacc gcatggacaa gcccgccaac   2160
tgcacacacg acctgtacat gatcatgcgg gagtgctggc atgccgcgcc ctcccagagg   2220
cccaccttca agcagctggt ggaggacctg gaccgtgtcc ttaccgtgac gtccaccgac   2280
aatgttatgg aacagttcaa tcctgggctg cgaaatttaa taaacctggg gaaaaattat   2340
gagaaagctg taaacgctat gatcctggca ggaaaagcct actacgatgg agtggccaag   2400
atcggtgaga ttgccactgg gtcccccgtg tcaactgaac tgggacatgt cctcatagag   2460
atttcaagta cccacaagaa actcaacgag agtcttgatg aaaattttaa aaaattccac   2520
aaagagatta tccatgagct ggagaagaag atagaacttg acgtgaaata tatgaacgca   2580
actctaaaaa gataccaaac agaacacaag aataaattag agtctttgga gaaatcccaa   2640
gctgagttga agaagatcag aaggaaaagc caaggaagcc gaaacgcact caaatatgaa   2700
```

cacaaagaaa ttgagtatgt ggagaccgtt acttctcgtc agagtgaaat ccagaaattc 2760
attgcagatg gttgcaaaga ggctctgctt gaagagaaga ggcgcttctg ctttctggtt 2820
gataagcact gtggctttgc aaaccacata cattattatc acttacagtc tgcagaacta 2880
ctgaattcca agctgcctcg gtggcaggag acctgtgttg atgccatcaa agtgccagag 2940
aaaatcatga atatgatcga agaaataaag accccagcct ctacccccgt gtctggaact 3000
cctcaggctt cacccatgat cgagagaagc aatgtggtta ggaaagatta cgacaccctt 3060
tctaaatgct caccaaagat gccccccgct ccttcaggca gagcatatac cagtcccttg 3120
atcgatatgt ttaataaccc agccacggct gccccgaatt cacaaagggt aaataattca 3180
acaggtactt ccgaagatcc cagtttacag cgatcagttt cggttgcaac gggactgaac 3240
atgatgaaga agcagaaagt gaagaccatc ttcccgcaca ctgcgggctc caacaagacc 3300
ttactcagct ttgcacaggg agatgtcatc acgctgctca tccccgagga gaaggatggc 3360
tggctctatg gagaacacga cgtgtccaag gcgaggggtt ggttcccgtc gtcgtacacg 3420
aagttgctgg aagaaaatga gacagaagca gtgaccgtgc ccacgccaag ccccacacca 3480
gtgagaagca tcagcaccgt gaacttgtct gagaatagca gtgttgtcat ccccccaccc 3540
gactacttgg aatgcttgtc catgggggca gctgccgaca ggagagcaga ttcggccagg 3600
acgacatcca cctttaaggc cccagcgtcc aagcccgaga ccgcggctcc taacgatgcc 3660
aacgggactg caaagccgcc ttttctcagc ggagaaaacc cctttgccac tgtgaaactc 3720
cgcccgactg tgacgaatga tcgctcggca cccatcattc gatga 3765

<210> SEQ ID NO 36
<211> LENGTH: 4989
<212> TYPE: DNA
<213> ORGANISM: Artificial Sequence
<220> FEATURE:
<223> OTHER INFORMATION: Synthetic polynucleotide

<400> SEQUENCE: 36
atggtcagct ggggtcgttt catctgcctg gtcgtggtca ccatggcaac cttgtccctg 60
gcccggccct ccttcagttt agttgaggat accacattag agccagaaga gccaccaacc 120
aaataccaaa tctctcaacc agaagtgtac gtggctgcgc caggggagtc gctagaggtg 180
cgctgcctgt tgaaagatgc cgccgtgatc agttggacta aggatggggt gcacttgggg 240
cccaacaata ggacagtgct tattggggag tacttgcaga taaagggcgc cacgcctaga 300
gactccggcc tctatgcttg tactgccagt aggactgtag acagtgaaac ttggtacttc 360
atggtgaatg tcacagatgc catctcatcc ggagatgatg aggatgacac cgatggtgcg 420
gaagattttg tcagtgagaa cagtaacaac aagagagcac catactggac caacacagaa 480
aagatggaaa agcggctcca tgctgtgcct gcggccaaca ctgtcaagtt tcgctgccca 540
gccgggggga acccaatgcc aaccatgcgg tggctgaaaa acgggaagga gtttaagcag 600
gagcatcgca ttggaggcta caaggtacga aaccagcact ggagcctcat tatggaaagt 660
gtggtcccat ctgacaaggg aaattatacc tgtgtagtgg agaatgaata cgggtccatc 720
aatcacacgt accacctgga tgttgtggag cgatcgcctc accggcccat cctccaagcc 780
ggactgccgg caaatgcctc cacagtggtc ggaggagacg tagagtttgt ctgcaaggtt 840
tacagtgatg cccagcccca catccagtgg atcaagcacg tggaaaagaa cggcagtaaa 900
tacgggcccg acgggctgcc ctacctcaag gttctcaagg ccgccggtgt taacaccacg 960

-continued

```
gacaaagaga ttgaggttct ctatattcgg aatgtaactt ttgaggacgc tggggaatat   1020
acgtgcttgg cgggtaattc tattgggata tcctttcact ctgcatggtt gacagttctg   1080
ccagcgcctg gaagagaaaa ggagattaca gcttccccag actacctgga gatagccatt   1140
tactgcatag ggtcttcttt aatcgcctgt atggtggtaa cagtcatcct gtgccgaatg   1200
aagaacacga ccaagaagcc agacttcagc agccagccgg ctgtgcacaa gctgaccaaa   1260
cgtatccccc tgcggagaca ggtaacagtt tcggctgagt ccagctcctc catgaactcc   1320
aacaccccgc tggtgaggat aacaacacgc ctctcttcaa cggcagacac ccccatgctg   1380
gcaggggtct ccgagtatga acttccagag gacccaaaat gggagtttcc aagagataag   1440
ctgacactgg gcaagcccct gggagaaggt tgctttgggc aagtggtcat ggcggaagca   1500
gtgggaattg acaaagacaa gcccaaggag gcggtcaccg tggccgtgaa gatgttgaaa   1560
gatgatgcca cagagaaaga cctttctgat ctggtgtcag agatggagat gatgaagatg   1620
attgggaaac acaagaatat cataaatctt cttggagcct gcacacagga tgggcctctc   1680
tatgtcatag ttgagtatgc ctctaaaggc aacctccgag aatacctccg agcccggagg   1740
ccacccggga tggagtactc ctatgacatt aaccgtgttc ctgaggagca gatgaccttc   1800
aaggacttgg tgtcatgcac ctaccagctg gccagaggca tggagtactt ggcttcccaa   1860
aaatgtattc atcgagattt agcagccaga aatgttttgg taacagaaaa caatgtgatg   1920
aaaatagcag actttggact cgccagagat atcaacaata tagactatta caaaaagacc   1980
accaatgggc ggcttccagt caagtggatg gctccagaag ccctgtttga tagagtatac   2040
actcatcaga gtgatgtctg gtccttcggg gtgttaatgt gggagatctt cactttaggg   2100
ggctcgccct acccagggat tcccgtggag gaacttttta agctgctgaa ggaaggacac   2160
agaatggata agccagccaa ctgcaccaac gaactgtaca tgatgatgag ggactgttgg   2220
catgcagtgc cctcccagag accaacgttc aagcagttgg tagaagactt ggatcgaatt   2280
ctcactctca caaccaatga gatcatggag gaaacaaata cgcagattgc ttggccatca   2340
aaactgaaga tcggagccaa atccaagaaa gatccccata ttaaggtttc tggaaagaaa   2400
gaagatgtta aagaagccaa ggaaatgatc atgtctgtct tagacacaaa aagcaatcga   2460
gtcacactga agatggatgt ttcacataca gaacattcac atgtaatcgg caaaggtggc   2520
aacaatatta aaaaagtgat ggaagaaacc ggatgccata tccactttcc agattccaac   2580
aggaataacc aagcagaaaa aagcaaccag gtatctatag cgggacaacc agcaggagta   2640
gaatctgccc gagttagaat tcgggagctg cttcctttgg tgctgatgtt tgagctacca   2700
attgctggaa ttcttcaacc ggttcctgat cctaattccc cctctattca gcatatatca   2760
caaacgtaca atatttcagt atcatttaaa cagcgttccc gaatgtatgg tgctactgtc   2820
atagtacgag ggtctcagaa taacactagt gctgtgaagg aaggaactgc catgctgtta   2880
gaacatcttg ctgggagctt agcatcagct attcctgtga gcacacaact agatattgca   2940
gctcaacatc atctctttat gatgggtcga aatgggagca acatcaaaca tatcatgcag   3000
agaacaggtg ctcagatcca ctttcctgat cccagtaatc cacaaaagaa atctaccgtc   3060
tacctccagg gcaccattga gtctgtctgt cttgcaaggc aatatctcat gggttgtctt   3120
cctcttgtgt tgatgtttga tatgaaggaa gaaattgaag tagatccaca attcattgcg   3180
cagttgatgg aacagcttga tgtcttcatc agtattaaac caaagcccaa acagccaagc   3240
aagtctgtga ttgtgaaaag tgttgagcga aatgccttaa atatgtatga agcaaggaaa   3300
tgtctcctcg gacttgaaag cagtggggtt accatagcaa ccagtccatc cccagcatcc   3360
```

```
tgccctgccg gcctggcatg tcccagcctg gatatcttag cttcagcagg ccttggactc   3420

actggactag gtcttttggg acccaccacc ttatctctga acacttcaac aaccccaaac   3480

tcactcttga atgctcttaa tagctcagtc agtcctttgc aaagtccaag ttctggtaca   3540

cccagcccca cattatgggc acccccactt gctaatactt caagtgccac aggtttttct   3600

gctataccac accttatgat tccatctact gcccaagcca cattaactaa tattttgttg   3660

tctggagtgc ccacctatgg gcacacagct ccatctcccc ctcctggctt gactcctgtt   3720

gatgtccata tcaacagtat gcagaccgaa ggcaaaaaaa tctctgctgc tttaaatgga   3780

catgcacagt ctccagatat aaaatatggt gcaatatcca cttcatcact tggagaaaaa   3840

gtgctgagtg caaatcacgg ggatccgtcc atccagacaa gtgggtctga gcagacatct   3900

cccaaatcaa gccccactga aggttgtaat gatgcttttg ttgaagtagg catgcctcga   3960

agtccttccc attctgggaa tgctggtgac ttgaaacaga tgatgtgtcc ctccaaggtt   4020

tcctgtgcca aaaggcagac agtggaacta ttgcaaggca cgaaaaactc acacttacac   4080

agcactgaca ggttgctctc agaccctgaa ctgagtgcta ccgaaagccc tttggctgac   4140

aagaaggctc cagggagtga gcgcgctgca gagagggcag cagctgccca gcaaaactcc   4200

gaaagggccc accttgctcc acggtcatca tatgtcaaca tgcaggcatt tgactatgaa   4260

cagaagaagc tattagccac caaagctatg ttaaagaaac cagtggtgac ggaggtcaga   4320

acgcccacaa atacctggag tggcctgggt ttttctaaat ccatgccagc tgaaactatc   4380

aaggagttga gaagggccaa tcatgtgtcc tataagccca caatgacaac cacttatgag   4440

ggctcatcca tgtccctttc acggtccaac agtcgtgagc acttgggagg tggaagcgaa   4500

tctgataact ggagagaccg aaatggaatt ggacctggaa gtcatagtga atttgcagct   4560

tctattggca gccctaagcg taaacaaaac aaatcaacgg aacactatct cagcagtagc   4620

aattacatgg actgcatttc ctcgctgaca ggaagcaatg gctgtaactt aaatagctct   4680

ttcaaaggtt ctgacctccc tgagctcttc agcaaactgg gcctgggcaa atacacagat   4740

gttttccagc aacaagagat cgatcttcag acattcctca ctctcacaga tcaggatctg   4800

aaggagctgg gaataactac ttttggtgcc aggaggaaaa tgctgcttgc aatttcagaa   4860

ctaaataaaa accgaagaaa gctttttgaa tcgccaaatg cacgcacctc tttcctggaa   4920

ggtggagcga gtggaaggct accccgtcag tatcactcag acattgctag tgtcagtggc   4980

cgctggtag                                                           4989
```

<210> SEQ ID NO 37
<211> LENGTH: 3213
<212> TYPE: DNA
<213> ORGANISM: Artificial Sequence
<220> FEATURE:
<223> OTHER INFORMATION: Synthetic polynucleotide

<400> SEQUENCE: 37

```
atggtcagct ggggtcgttt catctgcctg gtcgtggtca ccatggcaac cttgtccctg     60

gcccggccct ccttcagttt agttgaggat accacattag agccagaaga gccaccaacc    120

aaataccaaa tctctcaacc agaagtgtac gtggctgcgc caggggagtc gctagaggtg    180

cgctgcctgt tgaaagatgc cgccgtgatc agttggacta aggatggggt gcacttgggg    240

cccaacaata ggacagtgct tattggggag tacttgcaga taaagggcgc cacgcctaga    300

gactccggcc tctatgcttg tactgccagt aggactgtag acagtgaaac ttggtacttc    360
```

-continued

```
atggtgaatg tcacagatgc catctcatcc ggagatgatg aggatgacac cgatggtgcg    420
gaagattttg tcagtgagaa cagtaacaac aagagagcac catactggac caacacagaa    480
aagatggaaa agcggctcca tgctgtgcct gcggccaaca ctgtcaagtt tcgctgccca    540
gccgggggga acccaatgcc aaccatgcgg tggctgaaaa acgggaagga gtttaagcag    600
gagcatcgca ttggaggcta caaggtacga aaccagcact ggagcctcat tatggaaagt    660
gtggtcccat ctgacaaggg aaattatacc tgtgtagtgg agaatgaata cgggtccatc    720
aatcacacgt accacctgga tgttgtggag cgatcgcctc accggcccat cctccaagcc    780
ggactgccgg caaatgcctc cacagtggtc ggaggagacg tagagtttgt ctgcaaggtt    840
tacagtgatg cccagcccca catccagtgg atcaagcacg tggaaaagaa cggcagtaaa    900
tacgggcccg acgggctgcc ctacctcaag gttctcaagg ccgccggtgt taacaccacg    960
gacaaagaga ttgaggttct ctatattcgg aatgtaactt ttgaggacgc tggggaatat   1020
acgtgcttgg cgggtaattc tattgggata tcctttcact ctgcatggtt gacagttctg   1080
ccagcgcctg gaagagaaaa ggagattaca gcttccccag actacctgga gatagccatt   1140
tactgcatag ggtcttcttt aatcgcctgt atggtggtaa cagtcatcct gtgccgaatg   1200
aagaacacga ccaagaagcc agacttcagc agccagccgg ctgtgcacaa gctgaccaaa   1260
cgtatccccc tgcggagaca ggtaacagtt tcggctgagt ccagctcctc catgaactcc   1320
aacaccccgc tggtgaggat aacaacacgc ctctcttcaa cggcagacac ccccatgctg   1380
gcaggggtct ccgagtatga acttccagag gacccaaaat gggagtttcc aagagataag   1440
ctgacactgg gcaagcccct gggagaaggt tgctttgggc aagtggtcat ggcggaagca   1500
gtgggaattg acaaagacaa gcccaaggag gcggtcaccg tggccgtgaa gatgttgaaa   1560
gatgatgcca cagagaaaga cctttctgat ctggtgtcag agatggagat gatgaagatg   1620
attgggaaac acaagaatat cataaatctt cttggagcct gcacacagga tgggcctctc   1680
tatgtcatag ttgagtatgc ctctaaaggc aacctccgag aatacctccg agcccggagg   1740
ccacccggga tggagtactc ctatgacatt aaccgtgttc ctgaggagca gatgaccttc   1800
aaggacttgg tgtcatgcac ctaccagctg gccagaggca tggagtactt ggcttcccaa   1860
aaatgtattc atcgagattt agcagccaga aatgttttgg taacagaaaa caatgtgatg   1920
aaaatagcag actttggact cgccagagat atcaacaata tagactatta caaaaagacc   1980
accaatgggc ggcttccagt caagtggatg gctccagaag ccctgtttga tagagtatac   2040
actcatcaga gtgatgtctg gtccttcggg gtgttaatgt gggagatctt cactttaggg   2100
ggctcgccct acccagggat tcccgtggag gaacttttta agctgctgaa ggaaggacac   2160
agaatggata agccagccaa ctgcaccaac gaactgtaca tgatgatgag ggactgttgg   2220
catgcagtgc cctcccagag accaacgttc aagcagttgg tagaagactt ggatcgaatt   2280
ctcactctca caaccaatga gatggcagat gatcagggct gtattgaaga gcagggggtt   2340
gaggattcag caaatgaaga ttcagtggat gctaagccag accggtcctc gtttgtaccg   2400
tccctcttca gtaagaagaa gaaaaatgtc accatgcgat ccatcaagac cacccgggac   2460
cgagtgccta catatcagta caacatgaat tttgaaaagc tgggcaaatg catcataata   2520
aacaacaaga actttgataa agtgacaggt atgggcgttc gaaacggaac agacaaagat   2580
gccgaggcgc tcttcaagtg cttccgaagc ctgggttttg acgtgattgt ctataatgac   2640
tgctcttgtg ccaagatgca agatctgctt aaaaaagctt ctgaagagga ccatacaaat   2700
gccgcctgct tcgcctgcat cctcttaagc catggagaag aaaatgtaat ttatgggaaa   2760
```

-continued

```
gatggtgtca caccaataaa ggatttgaca gcccacttta ggggggatag atgcaaaacc   2820

cttttagaga aacccaaact cttcttcatt caggcttgcc gagggaccga gcttgatgat   2880

ggcatccagg ccgactcggg gcccatcaat gacacagatg ctaatcctcg atacaagatc   2940

ccagtggaag ctgacttcct cttcgcctat tccacggttc caggctatta ctcgtggagg   3000

agcccaggaa gaggctcctg gtttgtgcaa gccctctgct ccatcctgga ggagcacgga   3060

aaagacctgg aaatcatgca gatcctcacc agggtgaatg acagagttgc caggcacttt   3120

gagtctcagt ctgatgaccc acacttccat gagaagaagc agatcccctg tgtggtctcc   3180

atgctcacca aggaactcta cttcagtcaa tag                                3213


<210> SEQ ID NO 38
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 38

tttttttttt tttttttttt tttt                                            24


<210> SEQ ID NO 39
<211> LENGTH: 268
<212> TYPE: PRT
<213> ORGANISM: Homo sapiens

<400> SEQUENCE: 39

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Leu Lys Glu Asp
            180                 185                 190

Pro Ser Ala Val Pro Val Phe Ser Val Asp Tyr Gly Glu Leu Asp Phe
        195                 200                 205

Gln Trp Arg Glu Lys Thr Pro Glu Pro Pro Val Pro Cys Val Pro Glu
    210                 215                 220
```

-continued

```
Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
                245                 250                 255

Leu Arg Pro Glu Asp Gly His Cys Ser Trp Pro Leu
            260                 265


<210> SEQ ID NO 40
<211> LENGTH: 5
<212> TYPE: PRT
<213> ORGANISM: Artificial Sequence
<220> FEATURE:
<223> OTHER INFORMATION: antibody HCDR1

<400> SEQUENCE: 40

Ser Tyr Ala Ile Ser
1               5


<210> SEQ ID NO 41
<211> LENGTH: 17
<212> TYPE: PRT
<213> ORGANISM: Artificial Sequence
<220> FEATURE:
<223> OTHER INFORMATION: Antibody HCDR2

<400> SEQUENCE: 41

Gly Ile Ile Pro Ile Phe Asp Thr Ala Asn Tyr Ala Gln Lys Phe Gln
1               5                   10                  15

Gly


<210> SEQ ID NO 42
<211> LENGTH: 14
<212> TYPE: PRT
<213> ORGANISM: Artificial Sequence
<220> FEATURE:
<223> OTHER INFORMATION: Antibody HDR3

<400> SEQUENCE: 42

Pro Gly Leu Ala Ala Ala Tyr Asp Thr Gly Ser Leu Asp Tyr
1               5                   10


<210> SEQ ID NO 43
<211> LENGTH: 11
<212> TYPE: PRT
<213> ORGANISM: Artificial Sequence
<220> FEATURE:
<223> OTHER INFORMATION: Antibody LCDR1

<400> SEQUENCE: 43

Arg Ala Ser Gln Ser Val Arg Ser Tyr Leu Ala
1               5                   10


<210> SEQ ID NO 44
<211> LENGTH: 7
<212> TYPE: PRT
<213> ORGANISM: Artificial Sequence
<220> FEATURE:
<223> OTHER INFORMATION: Antibody LCDR2

<400> SEQUENCE: 44

Asp Ala Ser Asn Arg Ala Thr
1               5


<210> SEQ ID NO 45
<211> LENGTH: 9
```

<212> TYPE: PRT
<213> ORGANISM: Artificial Sequence
<220> FEATURE:
<223> OTHER INFORMATION: Antibody LCDR3

<400> SEQUENCE: 45

Gln Gln Arg Asn Tyr Trp Pro Leu Thr
1 5

<210> SEQ ID NO 46
<211> LENGTH: 123
<212> TYPE: PRT
<213> ORGANISM: Artificial Sequence
<220> FEATURE:
<223> OTHER INFORMATION: Antibody VH

<400> SEQUENCE: 46

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Asp Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Pro Gly Leu Ala Ala Ala Tyr Asp Thr Gly Ser Leu Asp Tyr
100 105 110

Trp Gly Gln Gly Thr Leu Val Thr Val Ser Ser
115 120

<210> SEQ ID NO 47
<211> LENGTH: 107
<212> TYPE: PRT
<213> ORGANISM: Artificial Sequence
<220> FEATURE:
<223> OTHER INFORMATION: Antibody VL

<400> SEQUENCE: 47

Glu Ile Val Leu Thr Gln Ser Pro Ala Thr Leu Ser Leu Ser Pro Gly
1 5 10 15

Glu Arg Ala Thr Leu Ser Cys Arg Ala Ser Gln Ser Val Arg Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Asn Tyr Trp Pro Leu
85 90 95

Thr Phe Gly Gln Gly Thr Lys Val Glu Ile Lys
100 105

<210> SEQ ID NO 48
<211> LENGTH: 450
<212> TYPE: PRT

<213> ORGANISM: Artificial Sequence
<220> FEATURE:
<223> OTHER INFORMATION: Antibody HC

<400> SEQUENCE: 48

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Asp Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Pro Gly Leu Ala Ala Ala Tyr Asp Thr Gly Ser Leu Asp Tyr
100 105 110

Trp Gly Gln Gly Thr Leu Val Thr Val Ser Ser Ala Ser Thr Lys Gly
115 120 125

Pro Ser Val Phe Pro Leu Ala Pro Cys Ser Arg Ser Thr Ser Glu Ser
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Lys Thr Tyr Thr Cys Asn Val
195 200 205

Asp His Lys Pro Ser Asn Thr Lys Val Asp Lys Arg Val Glu Ser Lys
210 215 220

Tyr Gly Pro Pro Cys Pro Pro Cys Pro Ala Pro Glu Phe Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser Gln Glu
260 265 270

Asp Pro Glu Val Gln Phe Asn Trp Tyr Val Asp Gly Val Glu Val His
275 280 285

Asn Ala Lys Thr Lys Pro Arg Glu Glu Gln Phe Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Gly Leu Pro Ser Ser Ile Glu
325 330 335

Lys Thr Ile Ser Lys Ala Lys Gly Gln Pro Arg Glu Pro Gln Val Tyr
340 345 350

Thr Leu Pro Pro Ser Gln Glu Glu Met Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val

-continued

```
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450


<210> SEQ ID NO 49
<211> LENGTH: 214
<212> TYPE: PRT
<213> ORGANISM: Artificial Sequence
<220> FEATURE:
<223> OTHER INFORMATION: Antibody LC

<400> SEQUENCE: 49

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Tyr Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

METHOD OF TREATING UROTHELIAL CARCINOMA WITH ERDAFITINIB AND CETRELIMAB

CROSS-REFERENCE TO RELATED APPLICATIONS

This application is the National Stage of International Patent Application No. PCT/EP2021/053384, filed Feb. 11, 2021, which claims the benefit of U.S. Provisional Ser. No. 62/975,526, filed Feb. 12, 2020, U.S. Provisional Ser. No. 63/025,817, filed May 15, 2020, U.S. Provisional Ser. No. 63/055,187, filed Jul. 22, 2020, U.S. Provisional Ser. No. 63/078,205, filed Sep. 14, 2020, U.S. Provisional Ser. No. 63/078,736, filed Sep. 15, 2020 and U.S. Provisional Ser. No. 63/083,316, filed Sep. 25, 2020, the disclosures of which are incorporated herein by reference in their entireties.

SEQUENCE LISTING

The instant application contains a Sequence Listing which is being submitted herewith electronically in ASCII format and is hereby incorporated by reference in its entirety. Said ASCII copy, created on Aug. 12, 2022, is named 103693_003701_SL.txt and is 42,831 bytes in size.

TECHNICAL FIELD

Disclosed herein are methods of treating urothelial carcinoma. In particular, the disclosed methods include combination therapies for the treatment of urothelial carcinoma comprising administering a fibroblast growth factor receptor (FGFR) inhibitor and an anti-PD1 antibody or antigen binding fragment thereof.

BACKGROUND

Bladder cancer is the most common malignancy involving the urinary system. Urothelial carcinoma (UC) is the predominant histologic type and the fourth most common cancer in men and eleventh most common in women. Cancer Genome Atlas Research Network. *Nature.* 2014 Mar. 20; 507(7492):315-322. Patients with locally advanced UC or metastatic or surgically unresectable UC (mUC) have poor outcomes with second-line therapies following relapse on cisplatin-based chemotherapy. Yafi F A, et al. *Curr Oncol.* 2011; 18:e25-e34.

FGFR alterations are common in patients with mUC, particularly in the luminal I subtype, and can cause constitutive FGFR signaling that may contribute to carcinogenesis. Haugsten E M, et al. *Mol Cancer.* 2018; 8:1439-1452. As many as 20% of patients with mUC have FGFR alterations, and FGFR mutations are even more frequent (37%) in patients with upper tract UC. Knowles M A, et al. *Nat Rev Cancer.* 2015; 15:25-41. Li Q, et al. *Curr Urol Rep.* 2016; 17:12; 7.

New cancer treatment methods are needed for FGFR mutation or fusion positive patients with urothelial carcinoma.

SUMMARY

Described herein are methods of treating urothelial carcinoma comprising, for example, administering a FGFR inhibitor, in particular at a dose of about 8 mg per day, in particular erdafitinib, more in particular erdafitinib at a dose of about 8 mg per day, in combination with an anti-PD1 antibody or antigen binding fragment thereof, in particular at a dose of about 240 mg every two weeks, in particular cetrelimab, to a patient that has been diagnosed with urothelial carcinoma who harbors at least one FGFR2 genetic alteration and/or FGFR3 genetic alteration. In certain embodiments, the urothelial carcinoma is locally advanced or metastatic.

Described herein is a combination of a FGFR inhibitor at a dose of about 8 mg per day and an anti-PD1 antibody or antigen binding fragment thereof at a dose of about 240 mg every two weeks, in particular for use in the treatment of urothelial carcinoma in a patient who harbors at least one FGFR2 genetic alteration and/or FGFR3 genetic alteration. In certain embodiments, the urothelial carcinoma is locally advanced or metastatic.

Described herein is a FGFR inhibitor for use in combination with an anti-PD1 antibody or antigen binding fragment thereof for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 240 mg every two weeks. In certain embodiments, the urothelial carcinoma is locally advanced or metastatic.

Described herein is an anti-PD1 antibody or antigen binding fragment thereof for use in combination with a FGFR inhibitor for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 240 mg every two weeks. In certain embodiments, the urothelial carcinoma is locally advanced or metastatic.

Described herein is the use of a FGFR inhibitor at a dose of about 8 mg per day for the manufacture of a medicament for the treatment of urothelial carcinoma in a patient who harbors at least one FGFR2 genetic alteration and/or FGFR3 genetic alteration wherein the FGFR inhibitor is used or is to be used in combination with an anti-PD1 antibody or antigen binding fragment thereof at a dose of about 240 mg every two weeks. In certain embodiments, the urothelial carcinoma is locally advanced or metastatic.

Described herein is the use of an anti-PD1 antibody or antigen binding fragment thereof at a dose of about 240 mg every two weeks for the manufacture of a medicament for the treatment of urothelial carcinoma in a patient who harbors at least one FGFR2 genetic alteration and/or FGFR3 genetic alteration wherein the anti-PD1 antibody or antigen binding fragment thereof is used or is to be used in combination with a FGFR inhibitor at a dose of about 8 mg per day. In certain embodiments, the urothelial carcinoma is locally advanced or metastatic.

Described herein are methods of treating urothelial carcinoma comprising, for example, administering erdafitinib at a dose of about 8 mg per day, in particular orally, in combination with an anti-PD1 antibody or antigen binding fragment thereof, in particular cetrelimab, in particular cetrelimab at a dose of about 240 mg every two weeks, in particular cetrelimab at a dose of about 240 mg every two weeks IV, to a patient that has been diagnosed with urothelial carcinoma who harbors at least one FGFR2 genetic alteration and/or FGFR3 genetic alteration. In certain embodiments, the urothelial carcinoma is locally advanced or metastatic.

Described herein is a combination of erdafitinib at a dose of about 8 mg per day, in particular orally, and an anti-PD1 antibody or antigen binding fragment thereof, in particular cetrelimab, in particular cetrelimab at a dose of about 240 mg every two weeks, in particular cetrelimab at a dose of about 240 mg every two weeks IV, in particular for use in the treatment of urothelial carcinoma in a patient who harbors at least one FGFR2 genetic alteration and/or FGFR3 genetic alteration. In certain embodiments, the urothelial carcinoma is locally advanced or metastatic.

Described herein is erdafitinib for use in combination with an anti-PD1 antibody or antigen binding fragment thereof for use in the treatment of urothelial carcinoma in a patient who harbors at least one FGFR2 genetic alteration and/or FGFR3 genetic alteration, wherein erdafitinib is administered or is to be administered at a dose of about 8 mg per day, in particular orally, and wherein in a particular embodiment the anti-PD1 antibody or antigen binding fragment thereof is cetrelimab, and wherein in a particular embodiment cetrelimab is administered or is to be administered at a dose of about 240 mg every two weeks IV. In certain embodiments, the urothelial carcinoma is locally advanced or metastatic.

Described herein is an anti-PD1 antibody or antigen binding fragment thereof for use in combination with erdafitinib for use in the treatment of urothelial carcinoma in a patient who harbors at least one FGFR2 genetic alteration and/or FGFR3 genetic alteration, wherein erdafitinib is administered or is to be administered at a dose of about 8 mg per day, in particular orally, and wherein in a particular embodiment, the anti-PD1 antibody or antigen binding fragment thereof is cetrelimab, and wherein in a particular embodiment cetrelimab is administered or is to be administered at a dose of about 240 mg every two weeks IV. In certain embodiments, the urothelial carcinoma is locally advanced or metastatic.

Described herein is the use of erdafitinib at a dose of about 8 mg per day, in particular orally, for the manufacture of a medicament for the treatment of urothelial carcinoma in a patient who harbors at least one FGFR2 genetic alteration and/or FGFR3 genetic alteration wherein erdafitinib is used or is to be used in combination with an anti-PD1 antibody or antigen binding fragment thereof, in particular cetrelimab, in particular cetrelimab at a dose of about 240 mg every two weeks IV. In certain embodiments, the urothelial carcinoma is locally advanced or metastatic.

Described herein is the use of an anti-PD1 antibody or antigen binding fragment thereof, in particular cetrelimab, in particular cetrelimab at a dose of about 240 mg every two weeks IV for the manufacture of a medicament for the treatment of urothelial carcinoma in a patient who harbors at least one FGFR2 genetic alteration and/or FGFR3 genetic alteration wherein the anti-PD1 antibody or antigen binding fragment thereof is used or is to be used in combination with erdafitinib at a dose of about 8 mg per day, in particular orally. In certain embodiments, the urothelial carcinoma is locally advanced or metastatic. In further embodiments, administration of the FGFR inhibitor in combination with the anti-PD1 antibody or antigen binding fragment thereof provides improved anti-tumor activity as measured by objective response rate relative to a patient that has been diagnosed with urothelial carcinoma that has not received treatment with an FGFR inhibitor and an anti-PD1 antibody or antigen binding fragment thereof. In some embodiments, administration of the FGFR inhibitor in combination with the anti-PD1 antibody or antigen binding fragment thereof does not result in hematological toxicity, in particular does not result in hematological toxicity of Grade 3 or higher. In still further embodiments, administration of the FGFR inhibitor in combination with the anti-PD1 antibody or antigen binding fragment thereof does not result in non-hematological toxicity of Grade 3 or higher.

In certain embodiments, the patient received at least one systemic therapy for the treatment of urothelial carcinoma prior to administration of said FGFR inhibitor and said anti-PD1 antibody or antigen binding fragment thereof. In some embodiments, the at least one systemic therapy for the treatment of urothelial carcinoma is platinum-containing chemotherapy. In further embodiments, the urothelial carcinoma progressed during or following at least one line of the platinum-containing chemotherapy. In still further embodiments, the platinum-containing chemotherapy is neoadjuvant platinum-containing chemotherapy or adjuvant platinum-containing chemotherapy. In even further embodiments, the urothelial carcinoma progressed within 12 months following at least one line of the neoadjuvant platinum-containing chemotherapy or adjuvant platinum-containing chemotherapy.

In some embodiments, the patient did not receive systemic therapy for the treatment of urothelial carcinoma prior to said administration of said FGFR inhibitor and said anti-PD1 antibody or antigen binding fragment thereof. In certain embodiments, the patient is cisplatin-ineligible. In further embodiments, the patient has an ECOG performance status of less than or equal to 2.

In certain embodiments, the FGFR2 genetic alteration and/or FGFR3 genetic alteration is an FGFR3 gene mutation, FGFR2 gene fusion, or FGFR3 gene fusion. In some embodiments, the FGFR3 gene mutation is R248C, S249C, G370C, Y373C, or any combination thereof. In still further embodiments, the FGFR2 or FGFR3 gene fusion is FGFR3-TACC3, FGFR3-BAIAP2L1, FGFR2-BICC1, FGFR2-CASP7, or any combination thereof.

In some embodiments, said methods or uses further comprise evaluating a biological sample from the patient for the presence of one or more FGFR2 or FGFR3 genetic alterations prior to administration of said FGFR inhibitor and said anti-PD1 antibody or antigen binding fragment thereof. In certain embodiments, the biological sample is blood, lymph fluid, bone marrow, a solid tumor sample, or any combination thereof.

In further embodiments, the FGFR inhibitor is erdafitinib. In further embodiments, erdafitinib is administered daily, in particular once daily. In still further embodiments, erdafitinib is administered orally. In certain embodiments, erdafitinib is administered orally on a continuous daily dosing schedule. In some embodiments, erdafitinib is administered orally at a dose of about 8 mg once daily. In some embodiments, erdafitinib is administered orally at a dose of about 8 mg once daily on a continuous daily dosing schedule. In further embodiments, the dose of erdafitinib is increased from 8 mg per day to 9 mg per day after initiating treatment if the patient exhibits a serum phosphate ($PO_4$) level that is less than about 5.5 mg/dL. In certain embodiments, erdafitinib is present in a solid dosage form. In further embodiments, the solid dosage form is a tablet.

In certain embodiments, the anti-PD1 antibody or antigen binding fragment thereof is cetrelimab. In further embodiments, the cetrelimab is administered by intravenous infusion. In still further embodiments, the cetrelimab is administered at a dose of about 240 mg: (a) once every two weeks, once every three weeks, once every four weeks, once every five weeks or once every six weeks; (b) once every two weeks; (c) once every three weeks; (d) once every four weeks; (e) once every five weeks; or (f) once every six weeks. In further embodiments, the cetrelimab is administered at a dose of about 240 mg, in particular 240 mg once every two weeks in cycle 1 to 4 of treatment. In further embodiments, the cetrelimab is administered at a dose of about 480 mg, in particular 480 mg once every 4 weeks. In further embodiments, the cetrelimab is administered at a dose of about 480 mg, in particular 480 mg once every 4 weeks, as of cycle 5 of treatment and beyond. In further embodiments, the cetrelimab is administered at a dose of about 360 mg, in particular 360 mg once every three weeks.

Also described herein are methods of improving objective response rate in a patient with urothelial carcinoma relative to a patient that has been diagnosed with urothelial carcinoma that has not received treatment with an FGFR inhibitor and an anti-PD1 antibody or antigen binding fragment thereof, said method comprising administering a FGFR inhibitor at a dose of about 8 mg per day in combination with an anti-PD1 antibody or antigen binding fragment thereof at a dose of about 240 mg (e.g. every two weeks) to a patient that has been diagnosed with urothelial carcinoma who harbors at least one FGFR2 genetic alteration and/or FGFR3 genetic alteration. In an embodiment, the anti-PD1 antibody or antigen binding fragment thereof is administered or is to be administered at a dose of about 240 mg (e.g. every two weeks) in cycle 1 to 4 of treatment.

Further provided herein are methods of treating urothelial carcinoma comprising: (a) evaluating a biological sample from a patient with urothelial carcinoma for the presence of one or more FGFR gene alterations, in particular FGFR2 or 3 gene alterations; and (b) administering a FGFR inhibitor at a dose of about 8 mg per day in combination with an anti-PD1 antibody or antigen binding fragment thereof at a dose of about 240 mg (e.g. every two weeks) to the patient if one or more FGFR gene alterations, in particular FGFR2 or 3 gene alterations, is present in the sample. In an embodiment, the anti-PD1 antibody or antigen binding fragment thereof is administered or is to be administered at a dose of about 240 mg (e.g. every two weeks) in cycle 1 to 4 of treatment.

Further provided herein is a combination of a FGFR inhibitor at a dose of about 8 mg per day and an anti-PD1 antibody or antigen binding fragment thereof at a dose of about 240 mg (e.g. every two weeks), in particular for use in the treatment of urothelial carcinoma in a patient who harbors at least one FGFR2 genetic alteration and/or FGFR3 genetic alteration, and wherein the combination is administered or is to be administered after evaluation of a biological sample from the patient for the presence of one or more FGFR2 or 3 gene alterations and if one or more FGFR2 or 3 gene alterations is present in the sample. In an embodiment, the anti-PD1 antibody or antigen binding fragment thereof is administered or is to be administered at a dose of about 240 mg (e.g. every two weeks) in cycle 1 to 4 of treatment.

Further provided herein is a FGFR inhibitor for use in combination with an anti-PD1 antibody or antigen binding fragment thereof for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 240 mg (e.g. every two weeks), and wherein the combination is administered or is to be administered after evaluation of a biological sample from the patient for the presence of one or more FGFR2 or 3 gene alterations and if one or more FGFR2 or 3 gene alterations is present in the sample. In an embodiment, the anti-PD1 antibody or antigen binding fragment thereof is administered or is to be administered at a dose of about 240 mg (e.g. every two weeks) in cycle 1 to 4 of treatment.

Further provided herein is an anti-PD1 antibody or antigen binding fragment thereof for use in combination with a FGFR inhibitor for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 240 mg (e.g. every two weeks), and wherein the combination is administered or is to be administered after evaluation of a biological sample from the patient for the presence of one or more FGFR2 or 3 gene alterations and if one or more FGFR2 or 3 gene alterations is present in the sample. In an embodiment, the anti-PD1 antibody or antigen binding fragment thereof is administered or is to be administered at a dose of about 240 mg (e.g. every two weeks) in cycle 1 to 4 of treatment.

Further provided herein is the use of a FGFR inhibitor at a dose of about 8 mg per day for the manufacture of a medicament for the treatment of urothelial carcinoma in a patient who harbors at least one FGFR2 genetic alteration and/or FGFR3 genetic alteration wherein the FGFR inhibitor is used or is to be used in combination with an anti-PD1 antibody or antigen binding fragment thereof at a dose of about 240 mg (e.g. every two weeks), and wherein the combination is administered or is to be administered after evaluation of a biological sample from the patient for the presence of one or more FGFR2 or 3 gene alterations and if one or more FGFR2 or 3 gene alterations is present in the sample. In an embodiment, the anti-PD1 antibody or antigen binding fragment thereof is administered or is to be administered at a dose of about 240 mg (e.g. every two weeks) in cycle 1 to 4 of treatment.

Further provided herein is the use of an anti-PD1 antibody or antigen binding fragment thereof at a dose of about 240 mg (e.g. every two weeks) for the manufacture of a medicament for the treatment of urothelial carcinoma in a patient who harbors at least one FGFR2 genetic alteration and/or FGFR3 genetic alteration wherein the anti-PD1 antibody or antigen binding fragment thereof is used or is to be used in combination with a FGFR inhibitor at a dose of about 8 mg per day, and wherein the combination is administered or is to be administered after evaluation of a biological sample from the patient for the presence of one or more FGFR2 or 3 gene alterations and if one or more FGFR2 or 3 gene alterations is present in the sample. In an embodiment, the anti-PD1 antibody or antigen binding fragment thereof is administered or is to be administered at a dose of about 240 mg (e.g. every two weeks) in cycle 1 to 4 of treatment.

Also described herein are methods of improving objective response rate in a patient with urothelial carcinoma relative to a patient that has been diagnosed with urothelial carcinoma that has not received treatment with an FGFR inhibitor and an anti-PD1 antibody or antigen binding fragment thereof, said method comprising administering a FGFR inhibitor at a dose of about 8 mg per day in combination with an anti-PD1 antibody or antigen binding fragment thereof at a dose of about 480 mg (e.g. every four weeks) to a patient that has been diagnosed with urothelial carcinoma who harbors at least one FGFR2 genetic alteration and/or FGFR3 genetic alteration. In an embodiment, the anti-PD1 antibody or antigen binding fragment thereof is administered or is to be administered at a dose of about 480 mg (e.g. every four weeks) as of cycle 5 of treatment and beyond.

Further provided herein are methods of treating urothelial carcinoma comprising: (a) evaluating a biological sample from a patient with urothelial carcinoma for the presence of one or more FGFR gene alterations, in particular FGFR2 or 3 gene alterations; and (b) administering a FGFR inhibitor at a dose of about 8 mg per day in combination with an anti-PD1 antibody or antigen binding fragment thereof at a dose of about 480 mg (e.g. every four weeks) to the patient if one or more FGFR gene alterations, in particular FGFR2 or 3 gene alterations, is present in the sample. In an embodiment, the anti-PD1 antibody or antigen binding fragment thereof is administered or is to be administered at a dose of about 480 mg (e.g. every four weeks) as of cycle 5 of treatment and beyond.

Further provided herein is a combination of a FGFR inhibitor at a dose of about 8 mg per day and an anti-PD1 antibody or antigen binding fragment thereof at a dose of about 480 mg (e.g. every four weeks), in particular for use in the treatment of urothelial carcinoma in a patient who harbors at least one FGFR2 genetic alteration and/or FGFR3 genetic alteration, and wherein the combination is administered or is to be administered after evaluation of a biological sample from the patient for the presence of one or more FGFR2 or 3 gene alterations and if one or more FGFR2 or 3 gene alterations is present in the sample. In an embodiment, the anti-PD1 antibody or antigen binding fragment thereof is administered or is to be administered at a dose of about 480 mg (e.g. every four weeks) as of cycle 5 of treatment and beyond.

Further provided herein is a FGFR inhibitor for use in combination with an anti-PD1 antibody or antigen binding fragment thereof for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 480 mg (e.g. every four weeks), and wherein the combination is administered or is to be administered after evaluation of a biological sample from the patient for the presence of one or more FGFR2 or 3 gene alterations and if one or more FGFR2 or 3 gene alterations is present in the sample. In an embodiment, the anti-PD1 antibody or antigen binding fragment thereof is administered or is to be administered at a dose of about 480 mg (e.g. every four weeks) as of cycle 5 of treatment and beyond.

Further provided herein is an anti-PD1 antibody or antigen binding fragment thereof for use in combination with a FGFR inhibitor for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 480 mg (e.g. every four weeks), and wherein the combination is administered or is to be administered after evaluation of a biological sample from the patient for the presence of one or more FGFR2 or 3 gene alterations and if one or more FGFR2 or 3 gene alterations is present in the sample. In an embodiment, the anti-PD1 antibody or antigen binding fragment thereof is administered or is to be administered at a dose of about 480 mg (e.g. every four weeks) as of cycle 5 of treatment and beyond.

Further provided herein is the use of a FGFR inhibitor at a dose of about 8 mg per day for the manufacture of a medicament for the treatment of urothelial carcinoma in a patient who harbors at least one FGFR2 genetic alteration and/or FGFR3 genetic alteration wherein the FGFR inhibitor is used or is to be used in combination with an anti-PD1 antibody or antigen binding fragment thereof at a dose of about 480 mg (e.g. every four weeks), and wherein the combination is administered or is to be administered after evaluation of a biological sample from the patient for the presence of one or more FGFR2 or 3 gene alterations and if one or more FGFR2 or 3 gene alterations is present in the sample. In an embodiment, the anti-PD1 antibody or antigen binding fragment thereof is administered or is to be administered at a dose of about 480 mg (e.g. every four weeks) as of cycle 5 of treatment and beyond.

Further provided herein is the use of an anti-PD1 antibody or antigen binding fragment thereof at a dose of about 480 mg (e.g. every four weeks) for the manufacture of a medicament for the treatment of urothelial carcinoma in a patient who harbors at least one FGFR2 genetic alteration and/or FGFR3 genetic alteration wherein the anti-PD1 antibody or antigen binding fragment thereof is used or is to be used in combination with a FGFR inhibitor at a dose of about 8 mg per day, and wherein the combination is administered or is to be administered after evaluation of a biological sample from the patient for the presence of one or more FGFR2 or 3 gene alterations and if one or more FGFR2 or 3 gene alterations is present in the sample. In an embodiment, the anti-PD1 antibody or antigen binding fragment thereof is administered or is to be administered at a dose of about 480 mg (e.g. every four weeks) as of cycle 5 of treatment and beyond.

As described herein, a cycle is defined as a 4 week period; or a cycle is defined as a 28 day period.

Also described herein are methods of improving objective response rate in a patient with urothelial carcinoma relative to a patient that has been diagnosed with urothelial carcinoma that has not received treatment with an FGFR inhibitor and an anti-PD1 antibody or antigen binding fragment thereof, said method comprising administering a FGFR inhibitor at a dose of about 8 mg per day in combination with an anti-PD1 antibody or antigen binding fragment thereof at a dose of about 360 mg (e.g. every three weeks) to a patient that has been diagnosed with urothelial carcinoma who harbors at least one FGFR2 genetic alteration and/or FGFR3 genetic alteration. In an embodiment, the treatment further comprises a platinum chemotherapy, in particular cisplatin or carboplatin. In an embodiment the platinum chemotherapy is administered or is to be administered every three weeks. In an embodiment, the platinum chemotherapy is administered or is to be administered at a dose of 50 $mg/m^2$, or 60 $mg/m^2$, or at a dose for a AUC of 4 mg/mL*min, or at a dose for a AUC of 5 mg/mL*min. In an embodiment, cisplatin is administered or is to be administered at a dose of 50 $mg/m^2$ or 60 $mg/m^2$. In an embodiment, carboplatin is administered or is to be administered at a dose for an AUC of 4 mg/mL*min or at a dose for an AUC of 5 mg/mL*min.

Further provided herein are methods of treating urothelial carcinoma comprising: (a) evaluating a biological sample from a patient with urothelial carcinoma for the presence of one or more FGFR gene alterations, in particular FGFR2 or 3 gene alterations; and (b) administering a FGFR inhibitor at a dose of about 8 mg per day in combination with an anti-PD1 antibody or antigen binding fragment thereof at a dose of about 360 mg (e.g. every three weeks) to the patient if one or more FGFR gene alterations, in particular FGFR2 or 3 gene alterations, is present in the sample. In an embodiment, the treatment further comprises a platinum chemotherapy, in particular cisplatin or carboplatin. In an embodiment the platinum chemotherapy is administered or is to be administered every three weeks. In an embodiment, the platinum chemotherapy is administered or is to be administered at a dose of 50 $mg/m^2$, or 60 $mg/m^2$, or at a dose for a AUC of 4 mg/mL*min, or at a dose for a AUC of 5 mg/mL*min. In an embodiment, cisplatin is administered or is to be administered at a dose of 50 $mg/m^2$ or 60 $mg/m^2$. In an embodiment, carboplatin is administered or is to be administered at a dose for an AUC of 4 mg/mL*min or at a dose for an AUC of 5 mg/mL*min.

Further provided herein is a combination of a FGFR inhibitor at a dose of about 8 mg per day and an anti-PD1 antibody or antigen binding fragment thereof at a dose of about 360 mg (e.g. every three weeks), in particular for use in the treatment of urothelial carcinoma in a patient who harbors at least one FGFR2 genetic alteration and/or FGFR3 genetic alteration, and wherein the combination is administered or is to be administered after evaluation of a biological sample from the patient for the presence of one or more FGFR2 or 3 gene alterations and if one or more FGFR2 or 3 gene alterations is present in the sample. In an embodiment, the treatment further comprises a platinum chemotherapy, in particular cisplatin or carboplatin. In an embodiment the platinum chemotherapy is administered or is to be administered every three weeks. In an embodiment, the platinum chemotherapy is administered or is to be administered at a dose of 50 $mg/m^2$, or 60 $mg/m^2$, or at a dose for a AUC of 4 mg/mL*min, or at a dose for a AUC of 5 mg/mL*min. In an embodiment, cisplatin is administered or is to be administered at a dose of 50 $mg/m^2$ or 60 $mg/m^2$. In an embodiment, carboplatin is administered or is to be administered at a dose for an AUC of 4 mg/mL*min or at a dose for an AUC of 5 mg/mL*min.

Further provided herein is a FGFR inhibitor for use in combination with an anti-PD1 antibody or antigen binding fragment thereof for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 360 mg (e.g. every three weeks), and wherein the combination is administered or is to be administered after evaluation of a biological sample from the patient for the presence of one or more FGFR2 or 3 gene alterations and if one or more FGFR2 or 3 gene alterations is present in the sample. In an embodiment, the treatment further comprises a platinum chemotherapy, in particular cisplatin or carboplatin. In an embodiment the platinum chemotherapy is administered or is to be administered every three weeks. In an embodiment, the platinum chemotherapy is administered or is to be administered at a dose of 50 $mg/m^2$, or 60 $mg/m^2$, or at a dose for a AUC of 4 mg/mL*min, or at a dose for a AUC of 5 mg/mL*min. In an embodiment, cisplatin is administered or is to be administered at a dose of 50 $mg/m^2$ or 60 $mg/m^2$. In an embodiment, carboplatin is administered or is to be administered at a dose for an AUC of 4 mg/mL*min or at a dose for an AUC of 5 mg/mL*min.

Further provided herein is an anti-PD1 antibody or antigen binding fragment thereof for use in combination with a FGFR inhibitor for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 360 mg (e.g. every three weeks), and wherein the combination is administered or is to be administered after evaluation of a biological sample from the patient for the presence of one or more FGFR2 or 3 gene alterations and if one or more FGFR2 or 3 gene alterations is present in the sample. In an embodiment, the treatment further comprises a platinum chemotherapy, in particular cisplatin or carboplatin. In an embodiment the platinum chemotherapy is administered or is to be administered every three weeks. In an embodiment, the platinum chemotherapy is administered or is to be administered at a dose of 50 $mg/m^2$, or 60 $mg/m^2$, or at a dose for a AUC of 4 mg/mL*min, or at a dose for a AUC of 5 mg/mL*min. In an embodiment, cisplatin is administered or is to be administered at a dose of 50 $mg/m^2$ or 60 $mg/m^2$. In an embodiment, carboplatin is administered or is to be administered at a dose for an AUC of 4 mg/mL*min or at a dose for an AUC of 5 mg/mL*min.

Further provided herein is the use of a FGFR inhibitor at a dose of about 8 mg per day for the manufacture of a medicament for the treatment of urothelial carcinoma in a patient who harbors at least one FGFR2 genetic alteration and/or FGFR3 genetic alteration wherein the FGFR inhibitor is used or is to be used in combination with an anti-PD1 antibody or antigen binding fragment thereof at a dose of about 360 mg (e.g. every three weeks), and wherein the combination is administered or is to be administered after evaluation of a biological sample from the patient for the presence of one or more FGFR2 or 3 gene alterations and if one or more FGFR2 or 3 gene alterations is present in the sample. In an embodiment, the treatment further comprises a platinum chemotherapy, in particular cisplatin or carboplatin. In an embodiment the platinum chemotherapy is administered or is to be administered every three weeks. In an embodiment, the platinum chemotherapy is administered or is to be administered at a dose of 50 $mg/m^2$, or 60 $mg/m^2$, or at a dose for a AUC of 4 mg/mL*min, or at a dose for a AUC of 5 mg/mL*min. In an embodiment, cisplatin is administered or is to be administered at a dose of 50 $mg/m^2$ or 60 $mg/m^2$. In an embodiment, carboplatin is administered or is to be administered at a dose for an AUC of 4 mg/mL*min or at a dose for an AUC of 5 mg/mL*min.

Further provided herein is the use of an anti-PD1 antibody or antigen binding fragment thereof at a dose of about 360 mg (e.g. every three weeks) for the manufacture of a medicament for the treatment of urothelial carcinoma in a patient who harbors at least one FGFR2 genetic alteration and/or FGFR3 genetic alteration wherein the anti-PD1 antibody or antigen binding fragment thereof is used or is to be used in combination with a FGFR inhibitor at a dose of about 8 mg per day, and wherein the combination is administered or is to be administered after evaluation of a biological sample from the patient for the presence of one or more FGFR2 or 3 gene alterations and if one or more FGFR2 or 3 gene alterations is present in the sample. In an embodiment, the treatment further comprises a platinum chemotherapy, in particular cisplatin or carboplatin. In an embodiment the platinum chemotherapy is administered or is to be administered every three weeks. In an embodiment, the platinum chemotherapy is administered or is to be administered at a dose of 50 $mg/m^2$, or 60 $mg/m^2$, or at a dose for a AUC of 4 mg/mL*min, or at a dose for a AUC of 5 mg/mL*min. In an embodiment, cisplatin is administered or is to be administered at a dose of 50 $mg/m^2$ or 60 $mg/m^2$. In an embodiment, carboplatin is administered or is to be administered at a dose for an AUC of 4 mg/mL*min or at a dose for an AUC of 5 mg/mL*min.

BRIEF DESCRIPTION OF THE DRAWINGS

The summary, as well as the following detailed description, is further understood when read in conjunction with the appended drawings. For the purpose of illustrating the disclosed methods and uses, the drawings show exemplary embodiments of the methods and uses; however, the methods and uses are not limited to the specific embodiments disclosed. In the drawings.

DETAILED DESCRIPTION OF ILLUSTRATIVE EMBODIMENTS

Figure 1:
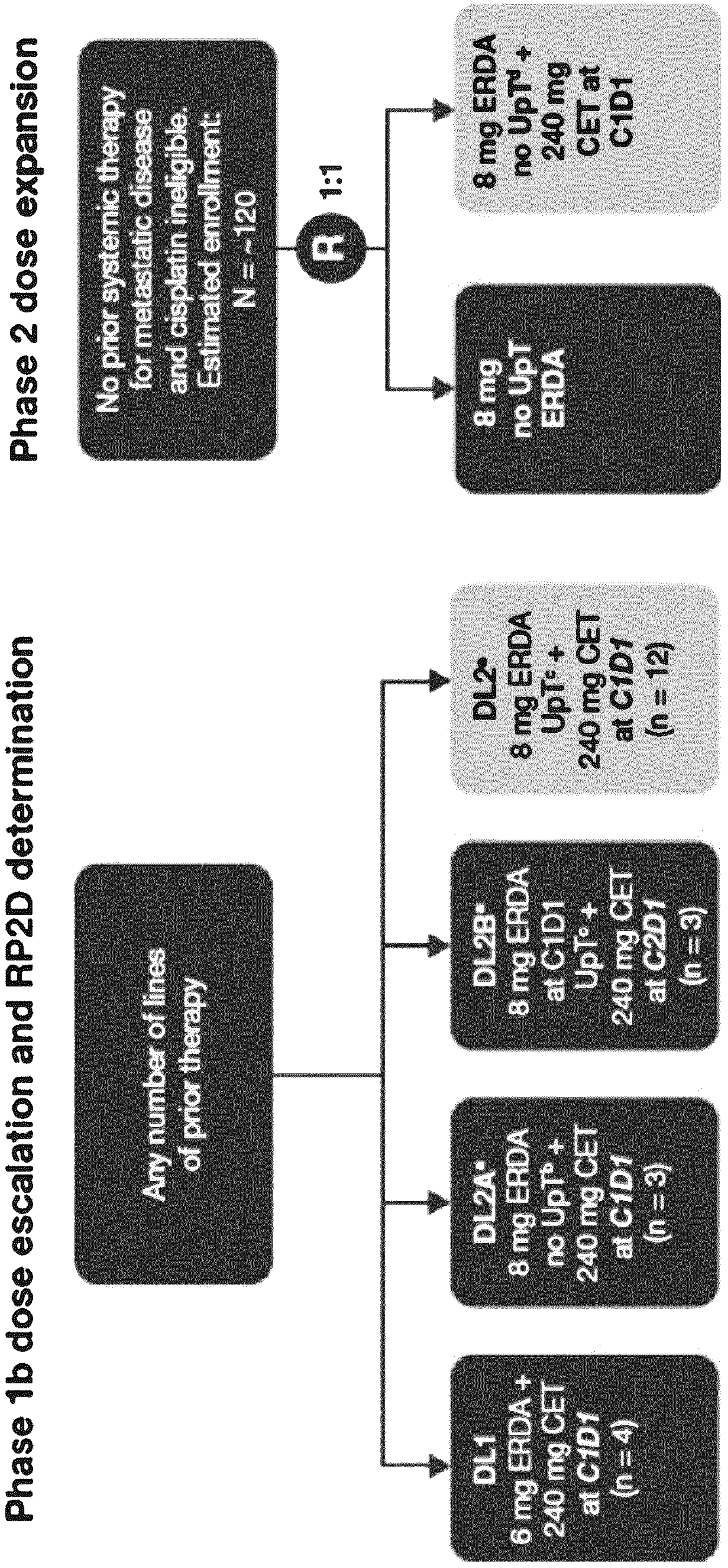
FIG. 1 is a study schematic for the phase 1b/2, multicenter, open-label dose escalation study to evaluate erdafitinib plus cetrelimab. ERDA stands for erdafitinib, CET stands for cetrelimab, UpT stands for uptitration, C1D1 stands for Cycle 1 Day 1, C2D2 stands for Cycle 2 Day 2, R stands for randomized, and DL stands for dose level. Footnote (a): 8 mg with or without uptitration (DL2 and DL2A) may be considered as the same dose level. Footnote (b): No UpT=no uptitration allowed. Footnote (c): UpT=uptitration of ERDA (after RP2D, uptitration of ERDA dose from 8 mg to 9 mg on C1D15 based on phosphate [$PO_4$] level) was permitted. Footnote (d): The RP2D was originally determined to be 8 mg ERDA UpT+CET, but after an amendment to the protocol, this was revised to 8 mg ERDA no UpT for phase 2 of the study.

It is to be appreciated that certain features of the invention which are, for clarity, described herein in the context of separate embodiments may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, although an embodiment may be described as part of a series of steps or part of a more general structure, each said step may also be considered an independent embodiment in itself, combinable with others.

Certain Terminology

The transitional terms "comprising", "consisting essentially of", and "consisting" are intended to connote their generally in accepted meanings in the patent vernacular; that is, (i) "comprising", which is synonymous with "including", "containing", or "characterized by", is inclusive or open-ended and does not exclude additional, unrecited elements or method steps; (ii) "consisting of" excludes any element, step, or ingredient not specified in the claim or embodiment; and (iii) "consisting essentially of" limits the scope of a claim or embodiment to the specified materials or steps "and those that do not materially affect the basic and novel characteristic(s)" of the claimed invention or embodiment. More specifically, the basic and novel characteristics relates to the ability of the method to provide at least one of the benefits described herein, including but not limited to the ability to improve the survivability of the human population relative to the survivability of the comparative human population described elsewhere herein. Embodiments described in terms of the phrase "comprising" (or its equivalents), also provide, as embodiments, those which are independently described in terms of "consisting of" and "consisting essentially of".

When a value is expressed as an approximation by use of the descriptor "about", it will be understood that the particular value forms another embodiment. If not otherwise specified, the term "about" signifies a variance of 10% of the associated value, but additional embodiments include those where the variance may be ±5%, ±15%, ±20%, ±25%, or ±50%, in particular the term "about" signifies a variance of ±5% or ±10% of the associated value, more in particular ±5%.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

As used herein, the singular forms "a," "an," and "the" include the plural.

The following abbreviations are used throughout the disclosure: FGFR (fibroblast growth factor receptor); FGFR3-TACC3 V1 (fusion between genes encoding FGFR3 and transforming acidic coiled-coil containing protein 3 variant 1); FGFR3-TACC3 V3 (fusion between genes encoding FGFR3 and transforming acidic coiled-coil containing protein 3 variant 3); FGFR3-BAIAP2L1 (fusion between genes encoding FGFR3 and brain-specific angiogenesis inhibitor 1-associated protein 2-like protein 1); FGFR2-BICC1 (fusion between genes encoding FGFR2 and bicaudal C homolog 1); FGFR2-CASP7 (fusion between genes encoding FGFR2 and caspase 7).

As used herein, "patient" is intended to mean any animal, in particular, mammals. Thus, the methods are applicable to human and nonhuman animals, although most preferably with humans. The terms "patient" and "subject" and "human" may be used interchangeably.

The terms "treat" and "treatment" refer to the treatment of a patient afflicted with a pathological condition and refers to an effect that alleviates the condition by killing the cancerous cells, but also to an effect that results in the inhibition of the progress of the condition, and includes a reduction in the rate of progress, a halt in the rate of progress, amelioration of the condition, and cure of the condition. Treatment as a prophylactic measure (i.e., prophylaxis) is also included.

"Therapeutically effective amount" refers to an amount effective, at doses and for periods of time necessary, to achieve a desired therapeutic result. A therapeutically effective amount may vary depending on factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the patient.

The term "dosage" refers to the information of the amount of the therapeutic to be taken by the subject and the frequency of the number of times the therapeutic is to be taken by the subject.

The term "dose" refers to the amount or quantity of the therapeutic to be taken each time.

The term "cancer" as used herein refers to an abnormal growth of cells which tend to proliferate in an uncontrolled way and, in some cases, to metastasize (spread).

The terms "co-administration" or the like, as used herein, encompass administration of the selected therapeutic agents to a single patient, and are intended to include treatment regimens in which the agents are administered by the same or different route of administration or at the same or different time.

The term "pharmaceutical combination" as used herein, means a product that results from the mixing or combining of more than one active ingredient and includes both fixed and non-fixed combinations of the active ingredients. The term "fixed combination" means that the active ingredients, e.g., erdafitinib and a co-agent, are both administered to a patient simultaneously in the form of a single unit or single dosage form. The term "non-fixed combination" means that the active ingredients, e.g., erdafitinib and a co-agent, are administered to a patient as separate units or separate dosage forms, either simultaneously, concurrently or sequentially with no specific intervening time limits, wherein such administration provides therapeutically effective levels of the two active ingredients in the body of the human. The latter also applies to cocktail therapy, e.g., the administration of three or more active ingredients.

The term "continuous daily dosing schedule" refers to the administration of a particular therapeutic agent without any drug holidays from the particular therapeutic agent. In some embodiments, a continuous daily dosing schedule of a particular therapeutic agent comprises administration of a particular therapeutic agent every day at roughly the same time each day.

The term "objective response rate" or "overall response rate" (ORR), which are used interchangeably herein, is defined as the percentage of participants with PR or CR as defined by RECIST 1.1, as assessed by the investigator The term "disease control rate" (DCR) is defined as the percentage of participants who have achieved SD and confirmed and unconfirmed CR and PR.

The term "dose limiting toxicities" (DLT) is defined as hematological/non hematological toxicity of Grade 3 or higher. Toxicities described herein are graded for severity according to the National Cancer Institute Common Terminology Criteria for Adverse Events (NCI-CTCAE), version 4.03. The criteria for non-hematological toxicities, as described herein, are provided in the Table 1:

TABLE 1

| Criteria for non-hematological toxicity | |
|---|---|
| | Exceptions |
| Any Grade 3 | Asthenia, anorexia, fever, or constipation<br>Fatigue that improves to Grade ≤2 in ≤7 days<br>Nausea lasting for ≤7 days responding to BSC[a]<br>Vomiting and diarrhea that resolves in ≤3 with BSC[a]<br>Laboratory abnormalities that do not require hospitalization and are not felt to be clinically significant by the investigator<br>Tumor flare (defined as local pain, irritation, or rash localized at sites of known or suspected tumor) that improves to Grade ≤2 in ≤7 days<br>Elevation in AST or ALT for ≤7 days |
| Any Grade 4 | None |
| Any Grade 5 | None |
| Elevation in AST or ALT >3x ULN meeting criteria for Hy's law[b] | |

Abbreviations: ALT = alanine aminotransferase; AST = aspartate aminotransferase; BSC = best supportive care; ULN = upper limit of normal.
[a]Best supportive care (including electrolyte and hormone supplementation where clinically applicable) according to institutional standards.
[b]Concurrent elevation of bilimbin >2 times institutional ULN without initial evidence of cholestasis and no alternative etiology for AST/ALT elevation.

The criteria for hematological toxicities, as described herein, are provided in Table 2:

TABLE 2

| Criteria for Hematological Toxicity |
|---|
| Neutrophil count decreased: Grade 4 for >7 days |
| Febrile neutropenia: Grace ≥3 or 4 |
| Platelet count decreased: Grade 3 with clinically significant bleeding or Grade 4 |
| Any Grade 5 toxicity |

The term "adverse event" is any untoward medical event that occurs in a participant administered an investigational product, and it does not necessarily indicate only events with clear causal relationship with the relevant investigational product.

The term "complete response" (CR) is defined in the Response Evaluation Criteria in Solid Tumors (RECIST) Version 1.1, i.e., disappearance of all target lesions, with no remnant present and no viable tumor seen on histopathological examination.

The term "partial response" (PR) is defined in the RECIST Version 1.1, i.e. at least a 30% decrease in the sum of diameters of target lesions, taking as reference the baseline sum diameters.

The term "stable disease" (SD) is defined in the RECIST Version 1.1, i.e. neither sufficient shrinkage to qualify for PR nor sufficient increase to qualify for PD, taking as reference the smallest sum diameters while on study.

The term "progressive disease" (PD) is defined in the RECIST Version 1.1, i.e. at least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm. The appearance of one or more new lesions is also considered progression.

The term "duration of response" (DoR) is defined as the time from the date of initial documentation of a response (CR or PR) to the date of first documented evidence of progressive disease (or relapse for participants who experience CR during the study) or death.

The term "time to response" (TTR) is defined as the time from the date of randomization to the date of initial documentation of a response (CR or PR).

The term "overall survival" (OS) is defined as the time from the date of randomization to the date of the participant's death resulting from any cause.

The term "progression-free survival" (PFS) is defined as the duration from the date of randomization until the date of first documented evidence of progressive disease (or relapse for participants who experience CR during the study) or death, whichever comes first.

The term "Maximum Observed Analyte Concentration" (Cmax) is defined as is the maximum observed analyte concentration.

The term "placebo" as used herein means administration of a pharmaceutical composition that does not include an FGFR inhibitor, in particular erdafitinib, andanti-PD1 antibody or antigen binding fragment thereof, in particular, cetrelimab.

The term "randomization" as it refers to a clinical trial refers to the time when the patient is confirmed eligible for the clinical trial and gets assigned to a treatment arm.

The terms "kit" and "article of manufacture" are used as synonyms.

The term "biological sample" refers to any sample from a patient in which cancerous cells can be obtained and detection of a FGFR genetic alteration is possible. Suitable biological samples include, but are not limited to, blood, lymph fluid, bone marrow, a solid tumor sample, or any combination thereof. In some embodiments, the biological sample can be formalin-fixed paraffin-embedded tissue (FFPET).

The term "antagonist" or "antagonistic" refers to an anti-PD1 antibody which upon binding to PD-1 suppresses at least one biological activity mediated by PD-1 ligand PD-L1 or PD-L2. The anti-PD-1 antibody is an antagonist when the at least one biological activity mediated by PD-L1 or PD-L2 is suppressed by at least about 20%, 30%, 40%, 45%, 50%, 55%, 60%, 65%, 70%, 75%, 80%, 85%, 90%, 95%, or 100% greater than in the absence of the antagonist (e.g., negative control), or when the suppression is statistically significant when compared to the suppression in the absence of the antagonist. A typical biological activity that is mediated by PD-L1 or PD-L2 binding to PD-1 is inhibition of antigen-specific CD4+ and/or CD8+ T cells. Therefore, antagonistic antibody relieves PD-L1 mediated suppression resulting in enhancement of immune responses.

The term "anti-PD-1 antibody" refers to an antibody that blocks the interaction between PD-1 and PD-L1, e.g., by specifically binding to PD-1. As used here, "block(s) the interaction" refers to the ability of an anti-PD-1 antibody to inhibit or reduce binding of PD-L1 to PD-1, such that signaling/functioning through PD-1 is abolished or diminished.

The term "specifically binds", "specific binding" or "binds" refer to antibody binding to an antigen (e.g. PD-1) or an epitope within the antigen with greater affinity than for other antigens. Typically, the antibody binds to the antigen or the epitope within the antigen with an equilibrium dissociation constant (KD) of about $1\times10^{-8}$ M or less, for example about $1\times10^{-9}$ M or less, about $1\times10^{-10}$ M or less, about $1\times10^{-11}$ M or less, or about $1\times10^{-12}$ M or less, typically with a KD that is at least one hundred-fold less than its KD for binding to a non-specific antigen (e.g., BSA, casein). The KD may be measured using standard procedures. Antibodies that specifically bind to the antigen or the epitope within the antigen may, however, have cross-reactivity to other related antigens, for example to the same antigen from other species (homologs), such as human or monkey, for example *Macaca fascicularis* (cynomolgus, cyno), Pan troglodytes (chimpanzee, chimp) or *Callithrix jacchus* (common marmoset, marmoset).

The term "PD-1" refers to human programmed cell death protein 1, PD-1. PD-1 is also known as CD279 or PDCD1. The amino acid sequence of the mature human PD-1 (without signal sequence) is shown in SEQ ID NO: 39. The extracellular domain spans residues 1-150, the transmembrane domain spans residues 151-171 and the cytoplasmic domain spans residues 172-268 of SEQ ID NO: 39 (Table 3)

TABLE 3

| | |
|---|---|
| Mature human PD-1 (without signal sequence) (SEQ ID NO: 39) | PGWFLDSPDRPWNPPTFSPALLVVT EGDNATFTCSFSNTSESFVLNWYRM SPSNQTDKLAAFPEDRSQPGQDCRF RVTQLPNGRDFHMSVVRARRNDSGT YLCGAISLAPKAQIKESLRAELRVT ERRAEVPTAHPSPSPRPAGQFQTLV VGVVGGLLGSLVLLVWVLAVICSRA ARGTIGARRTGQPLKEDPSAVPVFS VDYGELDFQWREKTPEPPVPCVPEQ TEYATIVFPSGMGTSSPARRGSADG PRSAQPLRPEDGHCSWPL |

"Antibodies" is meant in a broad sense and includes immunoglobulin molecules belonging to any class, IgA, IgD, IgE, IgG and IgM, or sub-class IgA1, IgA2, IgG1, IgG2, IgG3 and IgG4 and including either kappa (κ) and lambda (λ) light chain. Antibodies include monoclonal antibodies, full length antibodies, antigen binding fragments, bispecific or multispecific antibodies, dimeric, tetrameric or multimeric antibodies, single chain antibodies, domain antibodies and any other modified configuration of the immunoglobulin molecule that comprises an antigen binding fragment of the required specificity. "Full length antibodies" are comprised of two heavy chains (HC) and two light chains (LC) inter-connected by disulfide bonds. Each heavy chain is comprised of a heavy chain variable region (VH) and a heavy chain constant region (comprised of domains CH1, hinge, CH2 and CH3). Each light chain is comprised of a light chain variable region (VL) and a light chain constant region (CL). The VH and the VL may be further subdivided into regions of hypervariability, termed complementarity determining regions (CDR), interspersed with framework regions (FR). Each VH and VL is composed of three CDRs and four FR segments, arranged from amino-terminus to carboxy-terminus in the following order: FR1, CDR1, FR2, CDR2, FR3, CDR3, and FR4. Antibodies include antibodies generated using various technologies, including antibodies generated from immunized mice or rat or identified from phage or mammalian display libraries as described herein.

"Complementarity determining regions (CDR)" are antibody regions that bind an antigen. There are three CDRs in the VH (HCDR1, HCDR2, HCDR3) and three CDRs in the VL (LCDR1, LCDR2, LCDR3). CDRs may be defined using various delineations such as Kabat (Wu et al. (1970) *J Exp Med* 132: 211-50) (Kabat et al., Sequences of Proteins of Immunological Interest, 5th Ed. Public Health Service, National Institutes of Health, Bethesda, Md., 1991), Chothia (Chothia et al. (1987) J Mol Biol 196: 901-17), IMGT (Lefranc et al. (2003) Dev Comp Immunol 27: 55-77) and AbM (Martin and Thornton (1996) J Bmol Biol 263: 800-15). The correspondence between the various delineations and variable region numbering are described (see e.g. Lefranc et al. (2003) Dev Comp Immunol 27: 55-77; Honegger and Pluckthun, (2001) J Mol Biol 309:657-70; International ImMunoGeneTics (IMGT) database; Web resources, http://www_imgt_org). Available programs such as abYsis by UCL Business PLC may be used to delineate the CDRs. The term "CDR", "HCDR1", "HCDR2", "HCDR3", "LCDR1", "LCDR2" and "LCDR3" as used herein includes CDRs defined by any of the methods described supra, Kabat, Chothia, IMGT or AbM, unless otherwise explicitly stated in the specification.

"Antigen binding fragment" refers to a portion of an immunoglobulin molecule that retains the antigen binding properties of the parental full-length antibody. Exemplary antigen binding fragments are heavy chain complementarity determining regions (HCDR) 1, 2 and/or 3, light chain complementarity determining regions (LCDR) 1, 2 and/or 3, the VH, the VL, the VH and the VL, Fab, F(ab')2, Fd and Fv fragments as well as domain antibodies (dAb) consisting of either one VH domain or one VL domain. The VH and the VL domains may be linked together via a synthetic linker to form various types of single chain antibody designs in which the VH/VL domains pair intramolecularly, or intermolecularly in those cases when the VH and VL domains are expressed by separate chains, to form a monovalent antigen binding site, such as single chain Fv (scFv) or diabody; described for example in Int. Pat. Publ. No. WO1998/44001, Int. Pat. Publ. No. WO1988/01649; Int. Pat. Publ. No. WO1994/13804; Int. Pat. Publ. No. WO1992/01047.

"Humanized antibody" refers to an antibody in which CDR sequences are derived from non-human species and the frameworks are derived from human immunoglobulin sequences. Humanized antibody may include substitutions in the framework so that the framework may not be an exact copy of expressed human immunoglobulin or human immunoglobulin germline gene sequences. Antibodies in which at least one CDR is derived from non-human species and at least one framework is derived from human immunoglobulin sequences are humanized antibodies. Humanized antibody may include substitutions in the frameworks so that the frameworks may not be exact copies of expressed human immunoglobulin or human immunoglobulin germline gene sequences.

"Human antibody" refers to an antibody that is optimized to have minimal immune response when administered to a human subject. Variable regions of human antibody are derived from human germline immunoglobulin sequences. If the antibody contains a constant region or a portion of the constant region, the constant region is also derived from human germline immunoglobulin sequences.

Human antibody comprises heavy or light chain variable regions that are "derived from" human germline immunoglobulin sequences if the variable regions of the antibody are obtained from a system that uses human germline immunoglobulin genes. Such exemplary systems are human immunoglobulin gene libraries displayed on phage or mammalian cells, and transgenic non-human animals such as mice, rats or chicken carrying human immunoglobulin loci. "Human antibody" typically contains amino acid differences when compared to the immunoglobulins expressed in humans due to differences between the systems used to obtain the antibody and human immunoglobulin loci, introduction of naturally occurring somatic mutations, intentional introduction of substitutions into the framework or the CDRs. "Human antibody" is typically about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin sequences. In some cases, "human antibody" may contain consensus framework sequences derived from human framework sequence analyses, for example as described in (Knappik et al. (2000) J Mol Biol 296: 57-86), or synthetic HCDR3 incorporated into human immunoglobulin gene libraries displayed on phage, for example as described in (Shi et al. (2010) *J Mol Biol* 397: 385-96), and in Int. Patent Publ. No. WO2009/085462. Antibodies in which CDRs are derived from a non-human species are not included in the definition of "human antibody".

"Monoclonal antibody" refers to an antibody population with single amino acid composition in each antibody chain except for possible well-known alterations such as removal of C-terminal lysine from the antibody heavy chain or alterations due to post-translational modification(s) of amino acids, such as methionine oxidation or asparagine or glutamine deamidation. Monoclonal antibodies typically specifically bind one antigenic epitope, except that bispecific or multispecific monoclonal antibodies specifically bind two or more distinct antigenic epitopes. Monoclonal antibodies may have heterogeneous glycosylation within the antibody population. Monoclonal antibody may be monospecific or multispecific, or monovalent, bivalent or multivalent. A bispecific antibody is included in the term monoclonal antibody.

"Isolated" refers to a homogenous population of molecules (such as synthetic polynucleotides or a protein such as an antibody) which have been substantially separated and/or purified away from other components of the system the molecules are produced in, such as a recombinant cell, as well as a protein that has been subjected to at least one purification or isolation step. "Isolated antibody" refers to an antibody that is substantially free of other cellular material and/or chemicals and encompasses antibodies that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

FGFR Genetic Alterations

Described herein are methods of or uses for treating urothelial carcinoma comprising, consisting of, or consisting essentially of administering a FGFR inhibitor at a dose of about 8 mg per day in combination with an anti-PD1 antibody or antigen binding fragment thereof at a dose of about 240 mg every two weeks to a patient that has been diagnosed with urothelial carcinoma and harbors at least one FGFR2 genetic alteration and/or FGFR3 genetic alteration (i.e., one or more FGFR2 genetic alteration, one or more FGFR3 genetic alteration, or a combination thereof). Described herein are methods of or uses for treating urothelial carcinoma comprising, consisting of, or consisting essentially of administering at least one FGFR inhibitor at a dose of about 8 mg per day in combination with an anti-PD1 antibody or antigen binding fragment thereof at a dose of about 240 mg every two weeks to a patient that has been diagnosed with urothelial carcinoma and harbors at least one FGFR2 genetic alteration and/or FGFR3 genetic alteration. Described herein are methods of or uses for treating urothelial carcinoma comprising, consisting of, or consisting essentially of administering two or more FGFR inhibitors at a dose of about 8 mg per day in combination with an anti-PD1 antibody or antigen binding fragment thereof at a dose of about 240 mg every two weeks to a patient that has been diagnosed with urothelial carcinoma and harbors at least one FGFR2 genetic alteration and/or FGFR3 genetic alteration.

Described herein are methods of or uses for treating urothelial carcinoma comprising, consisting of, or consisting essentially of administering a FGFR inhibitor at a dose of about 8 mg per day in combination with an anti-PD1 antibody or antigen binding fragment thereof at a dose of about 480 mg every four weeks to a patient that has been diagnosed with urothelial carcinoma and harbors at least one FGFR2 genetic alteration and/or FGFR3 genetic alteration (i.e., one or more FGFR2 genetic alteration, one or more FGFR3 genetic alteration, or a combination thereof). Described herein are methods of or uses for treating urothelial carcinoma comprising, consisting of, or consisting essentially of administering at least one FGFR inhibitor at a dose of about 8 mg per day in combination with an anti-PD1 antibody or antigen binding fragment thereof at a dose of about 480 mg every four weeks to a patient that has been diagnosed with urothelial carcinoma and harbors at least one FGFR2 genetic alteration and/or FGFR3 genetic alteration. Described herein are methods of or uses for treating urothelial carcinoma comprising, consisting of, or consisting essentially of administering two or more FGFR inhibitors at a dose of about 8 mg per day in combination with an anti-PD1 antibody or antigen binding fragment thereof at a dose of about 480 mg every four weeks to a patient that has been diagnosed with urothelial carcinoma and harbors at least one FGFR2 genetic alteration and/or FGFR3 genetic alteration.

Described herein are methods of or uses for treating urothelial carcinoma comprising, consisting of, or consisting essentially of administering a FGFR inhibitor at a dose of about 8 mg per day in combination with an anti-PD1 antibody or antigen binding fragment thereof at a dose of about 360 mg every three weeks to a patient that has been diagnosed with urothelial carcinoma and harbors at least one FGFR2 genetic alteration and/or FGFR3 genetic alteration (i.e., one or more FGFR2 genetic alteration, one or more FGFR3 genetic alteration, or a combination thereof). Described herein are methods of or uses for treating urothelial carcinoma comprising, consisting of, or consisting essentially of administering at least one FGFR inhibitor at a dose of about 8 mg per day in combination with an anti-PD1 antibody or antigen binding fragment thereof at a dose of about 360 mg every three weeks to a patient that has been diagnosed with urothelial carcinoma and harbors at least one FGFR2 genetic alteration and/or FGFR3 genetic alteration. Described herein are methods of or uses for treating urothelial carcinoma comprising, consisting of, or consisting essentially of administering two or more FGFR inhibitors at a dose of about 8 mg per day in combination with an anti-PD1 antibody or antigen binding fragment thereof at a dose of about 360 mg every three weeks to a patient that has been diagnosed with urothelial carcinoma and harbors at least one FGFR2 genetic alteration and/or FGFR3 genetic alteration. In an embodiment, the treatment further comprises a platinum chemotherapy, in particular cisplatin or carboplatin. In an embodiment the platinum chemotherapy is administered or is to be administered every three weeks. In an embodiment, the platinum chemotherapy is administered or is to be administered at a dose of 50 mg/m$^2$, or 60 mg/m$^2$, or at a dose for a AUC of 4 mg/mL*min, or at a dose for a AUC of 5 mg/mL*min. In an embodiment, cisplatin is administered or is to be administered at a dose of 50 mg/m$^2$ or 60 mg/m$^2$. In an embodiment, carboplatin is administered or is to be administered at a dose for an AUC of 4 mg/mL*min or at a dose for an AUC of 5 mg/mL*min.

The fibroblast growth factor (FGF) family of protein tyrosine kinase (PTK) receptors regulates a diverse array of physiologic functions including mitogenesis, wound healing, cell differentiation and angiogenesis, and development. Both normal and malignant cell growth as well as proliferation are affected by changes in local concentration of FGFs, extracellular signaling molecules which act as autocrine as well as paracrine factors. Autocrine FGF signaling may be particularly important in the progression of steroid hormone-dependent cancers to a hormone independent state.

FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signaling in human pancreatic cancer (Knights et al., *Pharmacology and Therapeutics* 2010 125:1 (105-117); Korc M. et al *Current Cancer Drug Targets* 2009 9:5 (639-651)).

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase FGFR numbered 1 to 4 (FGFR1 to FGFR4).

In certain embodiments, the urothelial carcinoma is susceptible to an FGFR2 genetic alteration and/or an FGFR3 genetic alteration.

As used herein, "FGFR genetic alteration" refers to an alteration in the wild type FGFR gene, including, but not limited to, FGFR fusion genes, FGFR mutations, FGFR amplifications, or any combination thereof. The terms "variant" and "alteration" are used interchangeably herein.

In certain embodiments, the FGFR2 or FGFR3 genetic alteration is an FGFR gene fusion. "FGFR fusion" or "FGFR gene fusion" refers to a gene encoding a portion of FGFR (e.g., FGRF2 or FGFR3) and one of the herein disclosed fusion partners, or a portion thereof, created by a translocation between the two genes. The terms "fusion" and "translocation" are used interchangeable herein. The presence of one or more of the following FGFR fusion genes in a biological sample from a patient can be determined using the disclosed methods or uses or by methods known to those of ordinary skill in the art: FGFR3-TACC3, FGFR3-BAIAP2L1, FGFR2-BICC1, FGFR2-CASP7, or any combination thereof. In certain embodiments, FGFR3-TACC3 is FGFR3-TACC3 variant 1 (FGFR3-TACC3 V1) or FGFR3-TACC3 variant 3 (FGFR3-TACC3 V3). Table 4 provides the FGFR fusion genes and the FGFR and fusion partner exons that are fused. The sequences of the individual FGFR fusion genes are disclosed in Table 7.

TABLE 4

| Fusion Gene | FGFR Exon | Partner Exon |
|---|---|---|
| FGFR2 | | |
| FGFR2-BICC1 | 19 | 3 |
| FGFR2-CASP7 | 19 | 4 |
| FGFR3 | | |
| FGFR3-BAIAP2L1 | 18 | 2 |
| FGFR3-TACC3 V1 | 18 | 11 |
| FGFR3-TACC3 V3 | 18 | 10 |

FGFR genetic alterations include FGFR single nucleotide polymorphism (SNP). "FGFR single nucleotide polymorphism" (SNP) refers to a FGFR2 or FGFR3 gene in which a single nucleotide differs among individuals. In certain embodiments, the FGFR2 or FGFR3 genetic alteration is an FGFR3 gene mutation. In particular, FGFR single nucleotide polymorphism" (SNP) refers to a FGFR3 gene in which a single nucleotide differs among individuals. The presence of one or more of the following FGFR SNPs in a biological sample from a patient can be determined by methods known to those of ordinary skill in the art or methods disclosed in WO 2016/048833, FGFR3 R248C, FGFR3 S249C, FGFR3 G370C, FGFR3 Y373C, or any combination thereof. The sequences of the FGFR SNPs are provided in Table 5.

TABLE 5

| FGFR3 mutant | Sequence |
|---|---|
| FGFR3 R248C | TCGGACCGCGGCAACTACACCTGCG<br>TCGTGGAGAACAAGTTTGGCAGCAT<br>CCGGCAGACGTACACGCTGGACGTG<br>CTGGAG(**T**)GCTCCCCGCACCGGCC<br>CATCCTGCAGGCGGGGCTGCCGGCC<br>AACCAGACGGCGGTGCTGGGCAGCG<br>ACGTGGAGTTCCACTGCAAGGTGTA<br>CAGTGACGCACAGCCCCACATCCAG<br>TGGCTCAAGCACGTGGAGGTGAATG<br>GCAGCAAGGTGGGCCCGGACGGCAC<br>ACCCTACGTTACCGTGCTCA<br>(SEQ ID NO: 1) |
| FGFR3 S249C | GACCGCGGCAACTACACCTGCGTCG<br>TGGAGAACAAGTTTGGCAGCATCCG<br>GCAGACGTACACGCTGGACGTGCTG<br>GGTGAGGGCCCTGGGGCGGCGCGGG<br>GGTGGGGGCGGCAGTGGCGGTGGTG<br>GTGAGGGAGGGGGTGGCCCCTGAGC<br>GTCATCTGCCCCCACAGAGCGCT(**G**<br>)CCCGCACCGGCCCATCCTGCAGGC<br>GGGGCTGCCGGCCAACCAGACGGCG<br>GTGCTGGGCAGCGACGTGGAGTTCC<br>ACTGCAAGGTGTACAGTGACGCACA<br>GCCCCACATCCAGTGGCTCAAGCAC<br>GTGGAGGTGAATGGCAGCAAGGTGG<br>GCCCGGACGGCACACCCTACGTTAC<br>CGTGCTCAAGGTGGGCCACCGTGTG<br>CACGT<br>(SEQ ID NO: 2) |
| FGFR3 G370C | GCGGGCAATTCTATTGGGTTTTCTC<br>ATCACTCTGCGTGGCTGGTGGTGCT<br>GCCAGCCGAGGAGGAGCTGGTGGAG<br>GCTGACGAGGCG(**T**)GCAGTGTGTA<br>TGCAGGCATCCTCAGCTACGGGGTG<br>GGCTTCTTCCTGTTCATCCTGGTGG<br>TGGCGGCTGTGACGCTCTGCCGCCT<br>GCGCAGCCCCCCCAAGAAAGGCCTG<br>GGCTCCCCCACCGTGCACAAGATCT<br>CCCGCTTCCCG<br>(SEQ ID NO: 3) |
| FGFR3 Y373C* | CTAGAGGTTCTCTCCTTGCACAACG<br>TCACCTTTGAGGACGCCGGGGAGTA<br>CACCTGCCTGGCGGGCAATTCTATT<br>GGGTTTTCTCATCACTCTGCGTGGC<br>TGGTGGTGCTGCCAGCCGAGGAGGA<br>GCTGGTGGAGGCTGACGAGGCGGGC<br>AGTGTGT(**G**)TGCAGGCATCCTCAG<br>CTACGGGGTGGGCTTCTTCCTGTTC<br>ATCCTGGTGGTGGCGGCTGTGACGC<br>TCTGCCGCCTGCGCAGCCCCCCCAA<br>GAAAGGCCTGGGCTCCCCCACCGTG<br>CACAAGATCTCCCGCTTCCCGCTCA<br>AGC<br>(SEQ ID NO: 4) |

Sequences correspond to nucleotides 920-1510 of FGFR3 (Genebank ID # NM_000142.4).

Nucleotides in bold underline represent the SNP.

*Sometimes mistakenly referred to as Y375C in the literature.

As used herein, "FGFR genetic alteration gene panel" includes one or more of the above listed FGFR genetic alterations. In some embodiments, the FGFR genetic alteration gene panel is dependent upon the patient's cancer type.

The FGFR genetic alteration gene panel that is used in the evaluating step of the disclosed methods is based, in part, on the patient's cancer type. For patients with urothelial carcinoma, in particular locally advanced or metastatic UC, a suitable FGFR genetic alteration gene panel can comprise FGFR3-TACC3 V1, FGFR3-TACC3 V3, FGFR3-BAIAP2L1, FGFR2-BICC1, FGFR2-CASP7, FGFR3 R248C, FGFR3 S249C, FGFR3 G370C, or FGFR3 Y373C, or any combination thereof.

FGFR Inhibitors for Use in the Disclosed Methods or Uses

Suitable FGFR inhibitors for use in the disclosed methods are provided herein. The FGFR inhibitors may be used alone or in combination with one or more additional FGFR inhibitors in the treatment methods described herein.

In some embodiments, if one or more FGFR genetic alterations are present in the sample, the urothelial carcinoma can be treated with a FGFR inhibitor disclosed in U.S. Publication No. 2013/0072457 A1 (incorporated herein by reference), including any tautomeric or stereochemically isomeric form thereof, and a N-oxide thereof, a pharmaceutically acceptable salt thereof, or a solvate thereof.

In some aspects, for example, the urothelial carcinoma may be treated with N-(3,5-dimethoxyphenyl)-N'-(1-methylethyl)-N-[3-(1-methyl-1H-pyrazol-4-yl)quinoxalin-6-yl]ethane-1,2-diamine (referred to herein as "JNJ-42756493" or "JNJ493" or erdafitinib), including any tautomeric form thereof, N-oxides thereof, pharmaceutically acceptable salts thereof, or solvates thereof. In some embodiments, the FGFR inhibitor can be the compound of formula (I), also referred to as erdafitinib:

(I)

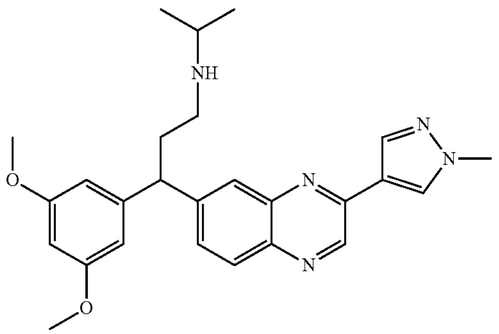

or a pharmaceutically acceptable salt thereof. In some aspects, the pharmaceutically acceptable salt is a HCl salt. In preferred aspects, erdafitinib base is used.

Erdafitinib (also referred to as ERDA), a once-daily oral pan-FGFR kinase inhibitor, has been approved by the U.S. Food and Drug Administration (FDA) for the treatment of adult patients who have locally advanced UC or mUC which has susceptible FGFR3 or FGFR2 genetic alterations and who have progressed during or following at least one line of prior platinum-containing chemotherapy, including within 12 months of neoadjuvant or adjuvant platinum-containing chemotherapy. Loriot Y et al. *NEJM.* 2019; 381:338-48. Erdafitinib has shown clinical benefits and tolerability in patients with mUC and alteration in FGFR expressions. Tabernero J, et al. *J Clin Oncol.* 2015; 33:3401-3408; Soria J-C, et al. *Ann Oncol.* 2016; 27(Suppl 6):vi266-vi295. Abstract 781PD; Siefker-Radtke A O, et al. ASCO 2018. Abstract 4503; Siefker-Radtke A, et al. ASCO-GU 2018. Abstract 450.

In some embodiments, the urothelial carcinoma can be treated with a FGFR inhibitor wherein the FGFR inhibitor is N-[5-[2-(3,5-Dimethoxyphenyl)ethyl]-2H-pyrazol-3-yl]-4-(3,5-diemthylpiperazin-1-yl)benzamide (AZD4547), as described in Gavine, P. R., et al., AZD4547: An Orally Bioavailable, Potent, and Selective Inhibitor of the Fibroblast Growth Factor Receptor Tyrosine Kinase Family, Cancer Res. Apr. 15, 2012 72; 2045:

(II)

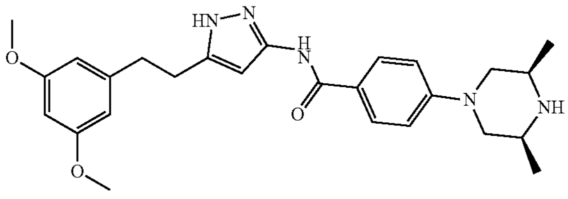

including, when chemically possible, any tautomeric or stereochemically isomeric form thereof, and a N-oxide thereof, a pharmaceutically acceptable salt thereof, or a solvate thereof.

In some embodiments, the urothelial carcinoma can be treated with a FGFR inhibitor wherein the FGFR inhibitor is 3-(2,6-Dichloro-3,5-dimethoxy-phenyl)-1-{6-[4-(4 ethyl-piperazin-1-yl)-phenylamino]-pyrimid-4-yl}-methyl-urea (NVP-BGJ398) as described in Int'l Publ. No. WO2006/000420:

(III)

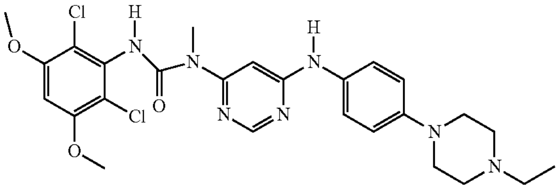

including, when chemically possible, any tautomeric or stereochemically isomeric form thereof, and a N-oxide thereof, a pharmaceutically acceptable salt thereof, or a solvate thereof.

In some embodiments, the urothelial carcinoma can be treated with a FGFR inhibitor wherein the FGFR inhibitor is 4-amino-5-fluoro-3-[6-(4-methylpiperazin-1-yl)-1H-benzimidazol-2-yl]-1H-quinolin-2-one (dovitinib) as described in Int't Publ. No. WO2006/127926:

(IV)

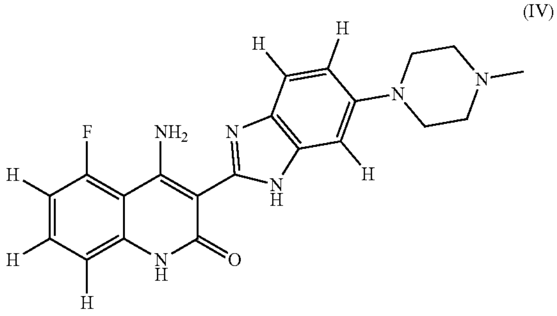 [SMILES: CN1CCN(c2ccc3nc(-c4c(N)c5c(F)cccc5[nH]c4=O)[nH]c3c2)CC1]

including, when chemically possible, any tautomeric or stereochemically isomeric form thereof, and a N-oxide thereof, a pharmaceutically acceptable salt thereof, or a solvate thereof.

In some embodiments, the urothelial carcinoma can be treated with a FGFR inhibitor wherein the FGFR inhibitor is 6-(7-((1-Aminocyclopropyl)-methoxy)-6-methoxyquinolin-4-yloxy)-N-methyl-1-naphthamide (AL3810) (lucitanib; E-3810), as described in Bello, E. et al., E-3810 Is a Potent Dual Inhibitor of VEGFR and FGFR that Exerts Antitumor Activity in Multiple Preclinical Models, Cancer Res Feb. 15, 2011 71(A)1396-1405 and Int'l Publ. No. WO2008/112408:

(V)

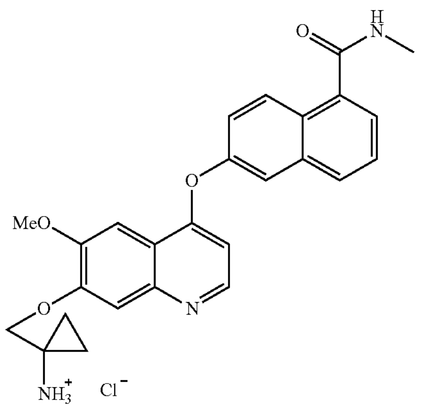

including, when chemically possible, any tautomeric or stereochemically isomeric form thereof, and a N-oxide thereof, a pharmaceutically acceptable salt thereof, or a solvate thereof.

In some embodiments, the urothelial carcinoma can be treated with a FGFR inhibitor wherein the FGFR inhibitor is pemigatinib (11-(2,6-difluoro-3,5-dimethoxyphenyl)-13-ethyl-4-(morpholin-4-ylmethyl)-5,7,11,13-tetrazatricyclo[7.4.0.0$^{2,6}$]trideca-1,3,6,8-tetraen-12-one:

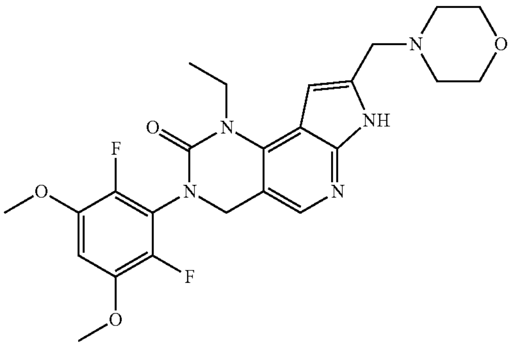 [SMILES: CCN1C(=O)N(c2c(F)c(OC)cc(OC)c2F)Cc2cnc3[nH]c(CN4CCOCC4)cc3c21]

including, when chemically possible, any tautomeric or stereochemically isomeric form thereof, and a N-oxide thereof, a pharmaceutically acceptable salt thereof, or a solvate thereof.

Additional suitable FGFR inhibitors include BAY1163877 (Bayer), BAY1179470 (Bayer), TAS-120 (Taiho), ARQ087 (ArQule), ASP5878 (Astellas), FF284 (Chugai), FP-1039 (GSK/FivePrime), Blueprint, LY-2874455 (Lilly), RG-7444 (Roche), or any combination thereof, including, when chemically possible, any tautomeric or stereochemical isomeric forms thereof, N-oxides thereof, pharmaceutically acceptable salts thereof, or solvates thereof.

In an embodiment the FGFR inhibitor generally, and erdafitinib more specifically, is administered as a pharmaceutically acceptable salt. In a preferred embodiment the FGFR inhibitor generally, and erdafitinib more specifically, is administered in base form. In an embodiment the FGFR inhibitor generally, and erdafitinib more specifically, is administered as a pharmaceutically acceptable salt in an amount corresponding to 8 mg base equivalent or corresponding to 9 mg base equivalent. In an embodiment the FGFR inhibitor generally, and erdafitinib more specifically, is administered in base form in an amount of 8 mg or 9 mg. In an embodiment the FGFR inhibitor generally, and erdafitinib more specifically, is administered in base form in an amount of 8 mg.

The salts can be prepared by for instance reacting the FGFR inhibitor generally, and erdafitinib more specifically, with an appropriate acid in an appropriate solvent.

Acid addition salts may be formed with acids, both inorganic and organic. Examples of acid addition salts include salts formed with an acid selected from the group consisting of acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids. Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

In an embodiment, the FGFR inhibitor generally, and erdafitinib more specifically, is administered in the form of a solvate. As used herein, the term "solvate" means a physical association of erdafitinib with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. The term "solvate" is intended to encompass both solution-phase and isolatable solvates. Non-limiting examples of solvents that may form solvates include water, isopropanol, ethanol, methanol, DMSO, ethyl acetate, acetic acid or ethanolamine and the like.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid-State NMR (SS-NMR, also known as Magic Angle Spinning NMR or MAS-NMR). Such techniques are as much a part of the standard analytical toolkit of the skilled chemist as NMR, IR, HPLC and MS. Alternatively the skilled person can deliberately form a solvate using crystallization conditions that include an amount of the solvent required for the particular solvate. Thereafter the standard methods described above, can be used to establish whether solvates had formed. Also encompassed are any complexes (e.g. inclusion complexes or clathrates with compounds such as cyclodextrins, or complexes with metals).

Furthermore, the compound may have one or more polymorph (crystalline) or amorphous forms.

The compounds include compounds with one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$. The isotopes may be radioactive or nonradioactive. In one embodiment, the compounds contain no radioactive isotopes. Such compounds are preferred for therapeutic use. In another embodiment, however, the compound may contain one or more radioisotopes. Compounds containing such radioisotopes may be useful in a diagnostic context.

Anti-PD1 Antibodies for Use in the Disclosed Methods or Uses

Suitable anti-PD1 antibodies or antigen fragments thereof for use in the disclosed methods are provided herein. The anti-PD1 antibodies or antigen fragments thereof may be used alone or in combination for the treatment methods described herein.

In some embodiments, if one or more FGFR genetic alterations are present in the sample, the urothelial carcinoma can be treated with an anti-PD1 antibody or antigen fragment thereof disclosed in U.S. Publication No. 2019/

0225689 or U.S. Publication No. 2017/0121409 (incorporated herein by reference in their entireties), such as cetrelimab.

In some embodiments, the antagonistic anti-PD1 antibody or an antigen binding fragment thereof comprises a heavy chain complementarity determining region 1 (HCDR1) of SEQ ID NO: 40, a HCDR2 of SEQ ID NO: 41, a HCDR3 of SEQ ID NO: 42, a light chain complementarity determining region 1 (LCDR1) of SEQ ID NO: 43, a LCDR2 of SEQ ID NO: 44 and a LCDR3 of SEQ ID NO: 45.

In some embodiments, the anti-PD-1 antibody or the antigen binding fragment thereof comprises a heavy chain variable region (VH) of SEQ ID NO: 46 and a light chain variable region (VL) or SEQ ID NO: 47.

In some embodiments, the anti-PD-1 antibody or the antigen binding fragment thereof is an IgG1, an IgG2, and IgG3 or an IgG4 isotype. In some embodiments, the antagonistic anti-PD-1 antibody or the antigen binding fragment thereof is an IgG4 isotype. In some embodiments, the anti-PD-1 antibody or the antigen binding fragment thereof is an IgG4 isotype and comprises proline at position 228, residue numbering according to the EU Index.

In some embodiments, the anti-PD-1 antibody is a nG4m (a) allotype.

In some embodiments, the anti-PD-1 antibody or an antigen binding fragment thereof has at least one substitution in an Fc region to modulate antibody effector functions or antibody half-life.

In some embodiments, the anti-PD-1 antibody comprises a heavy chain of SEQ ID NO: 48 and a light chain of SEQ ID NO: 49.

In some embodiments, the anti-PD-1 antibody is cetrelimab. Cetrelimab is an IgG4/x antibody characterized by following amino acid sequences: the HCDR1 of SEQ ID NO: 40, the HCDR2 of SEQ ID NO: 41, the HCDR3 of SEQ ID NO: 42, the LCDR1 of SEQ ID NO: 43, the LCDR2 of SEQ ID NO: 44, the LCDR3 of SEQ ID NO: 45, the VH of SEQ ID NO: 46, the VL of SEQ ID NO: 47, the HC of SEQ ID NO: 48 and the LC of SEQ ID NO: 49.

Cetrelimab (JNJ-63723283, CET) is a fully human immunoglobulin (Ig) G4 kappa monoclonal antibody that binds to programmed death receptor-1 (PD-1) with high affinity and specificity. Cetrelimab has shown activity in solid tumors. Rutkowski P, et al. *Journal of Clinical Oncology*. 2019; 37(8):31.

Chemotherapeutic Agents for Use in the Disclosed Methods or Uses

Suitable chemotherapeutic agents for use in the disclosed methods are provided herein. In some embodiments the urothelial carcinoma is treated with the disclosed FGFR inhibitors and anti-PD-1 antibodies in further combination with chemotherapy. In certain embodiments, the chemotherapy is platinum chemotherapy.

Platinum-based chemotherapies and PD-1 therapies in eligible patients remain the mainstay of systemic therapy in metastatic or locally advanced urothelial cancer; however, long-term outcomes are often not adequate. Thus, there remains a need for new combination regimens, such as regimens that include the disclosed FGFR inhibitors with platinum-based chemotherapies and PD-1 therapies.

In certain embodiments, the platinum chemotherapy is cisplatin. Cisplatin is a chemotherapeutic agent that cross-links with DNA to trigger apoptosis by interfering with mitosis and breakdown of DNA damage repair.

In certain embodiments, the platinum chemotherapy is carboplatin. Carboplatin is an alternate chemotherapeutic agent that inhibits the synthesis of RNA, DNA, and proteins in cells.

Generation of the Anti-PD1 Antibodies for Use in the Disclosed Methods or Uses

Antagonistic anti-PD-1 antibodies or antigen-binding fragments thereof used in the methods of the invention may be generated using various technologies. For example, the hybridoma method of Kohler and Milstein may be used to generate monoclonal antibodies. In the hybridoma method, a mouse or other host animal, such as a hamster, rat or monkey, is immunized with human and/or cyno PD-1 antigens, such as the extracellular domain of PD-1, followed by fusion of spleen cells from immunized animals with myeloma cells using standard methods to form hybridoma cells. Colonies arising from single immortalized hybridoma cells may be screened for production of antibodies with desired properties, such as specificity of binding, cross-reactivity or lack thereof, affinity for the antigen, and functionality such as antagonistic activity.

Exemplary humanization techniques including selection of human acceptor frameworks include CDR grafting (U.S. Pat. No. 5,225,539), SDR grafting (U.S. Pat. No. 6,818,749), Resurfacing (Padlan, (1991) Mol Immunol 28:489-499), Specificity Determining Residues Resurfacing (U.S. Patent Publ. No. 2010/0261620), human framework adaptation (U.S. Pat. No. 8,748,356) or superhumanization (U.S. Pat. No. 7,709,226). In these methods, CDRs or a subset of CDR residues of parental antibodies are transferred onto human frameworks that may be selected based on their overall homology to the parental frameworks, based on similarity in CDR length, or canonical structure identity, or a combination thereof.

Humanized antibodies may be further optimized to improve their selectivity or affinity to a desired antigen by incorporating altered framework support residues to preserve binding affinity (backmutations) by techniques such as those described in Int. Patent Publ. Nos. WO1990/007861 and WO 1992/22653, or by introducing variation at any of the CDRs for example to improve affinity of the antibody.

Transgenic animals, such as mice or rat carrying human immunoglobulin (Ig) loci in their genome may be used to generate antibodies against PD-1, and are described in for example U.S. Pat. No. 6,150,584, Int. Patent Publ. No. WO1999/45962, Int. Patent Publ. Nos. WO2002/066630, WO2002/43478, WO2002/043478 and WO1990/04036. The endogenous immunoglobulin loci in such animal may be disrupted or deleted, and at least one complete or partial human immunoglobulin locus may be inserted into the genome of the animal using homologous or non-homologous recombination, using transchromosomes, or using minigenes. Companies such as Regeneron (http://_www_regeneron_com), Harbour Antibodies (http://_www_harbourantibodies_com), Open Monoclonal Technology, Inc. (OMT) (http://_www_omtinc_net), KyMab (http://_www-_kymab_com), Trianni (http://_www.trianni_com) and Ablexis (http://_www_ablexis_com) may be engaged to provide human antibodies directed against a selected antigen using technologies as described above.

Antibodies may be selected from a phage display library, where the phage is engineered to express human immunoglobulins or portions thereof such as Fabs, single chain antibodies (scFv), or unpaired or paired antibody variable regions. The antibodies of the invention may be isolated for example from phage display library expressing antibody heavy and light chain variable regions as fusion proteins with bacteriophage pIX coat protein as described in Shi et al., (2010) J Mol Biol 397:385-96, and Int. Patent Publ. No. WO09/085462). The libraries may be screened for phage binding to human and/or cyno PD-1 and the obtained positive clones may be further characterized, the Fabs isolated from the clone lysates, and expressed as full length IgGs.

The CDRs of an antibody may be grafted on any human framework and the functionality of the resulting antibody may be tested. For example, antibody JNJ-63723283 comprises frameworks derived from human germline genes IGHV1-69 and IGKV3-11. Alternatively, JNJ-63723283 HCDRs may be grafted to other IGHV1 germline gene subgroup frameworks and the LCDRs may be grafted to other IGKV3 germline gene subgroup frameworks and the resulting antibodies are tested for desired functionality. The human germline gene sequences are well known and can be retrieved for example from ImMunoGeneTics Information System®.

Preparation of immunogenic antigens and monoclonal antibody production may be performed using any suitable technique, such as recombinant protein production. The immunogenic antigens may be administered to an animal in the form of purified protein, or protein mixtures including whole cells or cell or tissue extracts, or the antigen may be formed de novo in the animal's body from nucleic acids encoding said antigen or a portion thereof.

Methods of producing antibodies at large scales are known. Antibodies may be produced for example in CHO cells cultured using known methods. The antibody may be isolated and/or purified from culture medium by removing solids by centrifugation or filtering as a first step in the purification process. The antibody may be further purified by standard methods including chromatography (e.g., ion exchange, affinity, size exclusion, and hydroxyapatite chromatography), gel filtration, centrifugation, or differential solubility, ethanol precipitation or by any other available technique for the purification of antibodies. Protease inhibitors such as phenyl methyl sulfonyl fluoride (PMSF), leupeptin, pepstatin or aprotinin can be added at any or all stages to reduce or eliminate degradation of the antibody during the purification process. One of ordinary skill in the art will appreciate that the exact purification technique will vary depending on the character of the polypeptide or protein to be purified, the character of the cells from which the polypeptide or protein is expressed, and the composition of the medium in which the cells were grown.

Methods of Treatment and Uses

Described herein are methods of treating urothelial carcinoma comprising, consisting of, or consisting essential of, administering a FGFR inhibitor at a dose of about 8 mg per day in combination with an anti-PD1 antibody or antigen binding fragment thereof at a dose of about 240 mg every two weeks to a patient that has been diagnosed with urothelial carcinoma who harbors at least one FGFR2 genetic alteration and/or FGFR3 genetic alteration. In an embodiment, the anti-PD1 antibody or antigen binding fragment thereof is administered or is to be administered at a dose of about 240 mg every two weeks in cycle 1 to 4 of treatment. According to particular embodiments, the dose of about 240 mg every two weeks of the anti-PD1 antibody or antigen binding fragment thereof refers to a single intravenous (IV) infusion once every two weeks. According to particular embodiments, on days in which both the FGFR inhibitor (e.g., erdafitinib) and the anti-PD1 antibody (e.g., cetrelimab) are administered, the FGFR inhibitor is administered within about 60 minutes, or about 60 minutes±about 15 minutes before the start of the anti-PD1 antibody IV infusion, e.g., between about 45 minutes to about 75 minutes, before the start of the IV infusion. According to alternative embodiments, the FGFR inhibitor is administered within about 1 hour, or about 2 hours, or about 3 hours, or about 4 hours, or about 5 hours before or after the start of the anti-PD1 antibody IV infusion.

Described herein is a combination of a FGFR inhibitor at a dose of about 8 mg per day and an anti-PD1 antibody or antigen binding fragment thereof at a dose of about 240 mg every two weeks, in particular for use in the treatment of urothelial carcinoma in a patient who harbors at least one FGFR2 genetic alteration and/or FGFR3 genetic alteration. In an embodiment, the anti-PD1 antibody or antigen binding fragment thereof is administered or is to be administered at a dose of about 240 mg every two weeks in cycle 1 to 4 of treatment.

Described herein is a combination of a FGFR inhibitor at a dose of about 8 mg per day and an anti-PD1 antibody or antigen binding fragment thereof at a dose of about 360 mg every three weeks, in particular for use in the treatment of urothelial carcinoma in a patient who harbors at least one FGFR2 genetic alteration and/or FGFR3 genetic alteration. In an embodiment, the treatment further comprises a platinum chemotherapy, in particular cisplatin or carboplatin. In an embodiment the platinum chemotherapy is administered or is to be administered every three weeks. In an embodiment, the platinum chemotherapy is administered or is to be administered at a dose of 50 $mg/m^2$, or 60 $mg/m^2$, or at a dose for a AUC of 4 mg/mL*min, or at a dose for a AUC of 5 mg/mL*min. In an embodiment, cisplatin is administered or is to be administered at a dose of 50 $mg/m^2$ or 60 $mg/m^2$. In an embodiment, carboplatin is administered or is to be administered at a dose for an AUC of 4 mg/mL*min or at a dose for an AUC of 5 mg/mL*min.

Described herein is a combination of a FGFR inhibitor at a dose of about 8 mg per day and an anti-PD1 antibody or antigen binding fragment thereof at a dose of about 480 mg every four weeks, in particular for use in the treatment of urothelial carcinoma in a patient who harbors at least one FGFR2 genetic alteration and/or FGFR3 genetic alteration. In an embodiment, the anti-PD1 antibody or antigen binding fragment thereof is administered or is to be administered at a dose of about 480 mg every four weeks as of cycle 5 of treatment and beyond.

Described herein is a FGFR inhibitor for use in combination with an anti-PD1 antibody or antigen binding fragment thereof for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 240 mg every two weeks. In an embodiment, the anti-PD1 antibody or antigen binding fragment thereof is administered or is to be administered at a dose of about 240 mg every two weeks in cycle 1 to 4 of treatment.

Described herein is a FGFR inhibitor for use in combination with an anti-PD1 antibody or antigen binding fragment thereof for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 360 mg every three weeks.

In an embodiment, the treatment further comprises a platinum chemotherapy, in particular cisplatin or carboplatin. In an embodiment the platinum chemotherapy is administered or is to be administered every three weeks. In an embodiment, the platinum chemotherapy is administered or is to be administered at a dose of 50 $mg/m^2$, or 60 $mg/m^2$, or at a dose for a AUC of 4 mg/mL*min, or at a dose for a AUC of 5 mg/mL*min. In an embodiment, cisplatin is administered or is to be administered at a dose of 50 $mg/m^2$ or 60 $mg/m^2$. In an embodiment, carboplatin is administered or is to be administered at a dose for an AUC of 4 mg/mL*min or at a dose for an AUC of 5 mg/mL*min.

Described herein is a FGFR inhibitor for use in combination with an anti-PD1 antibody or antigen binding fragment thereof for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 480 mg every four weeks. In an embodiment, the anti-PD1 antibody or antigen binding fragment thereof is administered or is to be administered at a dose of about 480 mg every four weeks as of cycle 5 of treatment and beyond.

Described herein is an anti-PD1 antibody or antigen binding fragment thereof for use in combination with a FGFR inhibitor for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 240 mg every two weeks. In an embodiment, the anti-PD1 antibody or antigen binding fragment thereof is administered or is to be administered at a dose of about 240 mg every two weeks in cycle 1 to 4 of treatment.

Described herein is an anti-PD1 antibody or antigen binding fragment thereof for use in combination with a FGFR inhibitor for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 360 mg every three weeks. In an embodiment, the treatment further comprises a platinum chemotherapy, in particular cisplatin or carboplatin. In an embodiment the platinum chemotherapy is administered or is to be administered every three weeks. In an embodiment, the platinum chemotherapy is administered or is to be administered at a dose of 50 $mg/m^2$, or 60 $mg/m^2$, or at a dose for a AUC of 4 mg/mL*min, or at a dose for a AUC of 5 mg/mL*min. In an embodiment, cisplatin is administered or is to be administered at a dose of 50 $mg/m^2$ or 60 $mg/m^2$. In an embodiment, carboplatin is administered or is to be administered at a dose for an AUC of 4 mg/mL*min or at a dose for an AUC of 5 mg/mL*min.

Described herein is an anti-PD1 antibody or antigen binding fragment thereof for use in combination with a FGFR inhibitor for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 480 mg every four weeks. In an embodiment, the anti-PD1 antibody or antigen binding fragment thereof is administered or is to be administered at a dose of about 480 mg every four weeks as of cycle 5 of treatment and beyond.

Described herein is the use of a FGFR inhibitor at a dose of about 8 mg per day for the manufacture of a medicament for the treatment of urothelial carcinoma in a patient who harbors at least one FGFR2 genetic alteration and/or FGFR3 genetic alteration wherein the FGFR inhibitor is used or is to be used in combination with an anti-PD1 antibody or antigen binding fragment thereof at a dose of about 240 mg every two weeks. In an embodiment, the anti-PD1 antibody or antigen binding fragment thereof is administered or is to be administered at a dose of about 240 mg every two weeks in cycle 1 to 4 of treatment.

Described herein is the use of a FGFR inhibitor at a dose of about 8 mg per day for the manufacture of a medicament for the treatment of urothelial carcinoma in a patient who harbors at least one FGFR2 genetic alteration and/or FGFR3 genetic alteration wherein the FGFR inhibitor is used or is to be used in combination with an anti-PD1 antibody or antigen binding fragment thereof at a dose of about 360 mg every three weeks. In an embodiment, the treatment further comprises a platinum chemotherapy, in particular cisplatin or carboplatin. In an embodiment the platinum chemotherapy is administered or is to be administered every three weeks. In an embodiment, the platinum chemotherapy is administered or is to be administered at a dose of 50 $mg/m^2$, or 60 $mg/m^2$, or at a dose for a AUC of 4 mg/mL*min, or at a dose for a AUC of 5 mg/mL*min. In an embodiment, cisplatin is administered or is to be administered at a dose of 50 $mg/m^2$ or 60 $mg/m^2$. In an embodiment, carboplatin is administered or is to be administered at a dose for an AUC of 4 mg/mL*min or at a dose for an AUC of 5 mg/mL*min.

Described herein is the use of a FGFR inhibitor at a dose of about 8 mg per day for the manufacture of a medicament for the treatment of urothelial carcinoma in a patient who harbors at least one FGFR2 genetic alteration and/or FGFR3 genetic alteration wherein the FGFR inhibitor is used or is to be used in combination with an anti-PD1 antibody or antigen binding fragment thereof at a dose of about 480 mg every four weeks. In an embodiment, the anti-PD1 antibody or antigen binding fragment thereof is administered or is to be administered at a dose of about 480 mg every four weeks as of cycle 5 of treatment and beyond.

Described herein is the use of an anti-PD1 antibody or antigen binding fragment thereof at a dose of about 240 mg every two weeks for the manufacture of a medicament for the treatment of urothelial carcinoma in a patient who harbors at least one FGFR2 genetic alteration and/or FGFR3 genetic alteration wherein the anti-PD1 antibody or antigen binding fragment thereof is used or is to be used in combination with a FGFR inhibitor at a dose of about 8 mg per day. In an embodiment, the anti-PD1 antibody or antigen binding fragment thereof is administered or is to be administered at a dose of about 240 mg every two weeks in cycle 1 to 4 of treatment.

Described herein is the use of an anti-PD1 antibody or antigen binding fragment thereof at a dose of about 360 mg every three weeks for the manufacture of a medicament for the treatment of urothelial carcinoma in a patient who harbors at least one FGFR2 genetic alteration and/or FGFR3 genetic alteration wherein the anti-PD1 antibody or antigen binding fragment thereof is used or is to be used in combination with a FGFR inhibitor at a dose of about 8 mg per day. In an embodiment, the treatment further comprises a platinum chemotherapy, in particular cisplatin or carboplatin. In an embodiment the platinum chemotherapy is administered or is to be administered every three weeks. In an embodiment, the platinum chemotherapy is administered or is to be administered at a dose of 50 mg/m$^2$, or 60 mg/m$^2$, or at a dose for a AUC of 4 mg/mL*min, or at a dose for a AUC of 5 mg/mL*min. In an embodiment, cisplatin is administered or is to be administered at a dose of 50 mg/m$^2$ or 60 mg/m$^2$. In an embodiment, carboplatin is administered or is to be administered at a dose for an AUC of 4 mg/mL*min or at a dose for an AUC of 5 mg/mL*min.

Described herein is the use of an anti-PD1 antibody or antigen binding fragment thereof at a dose of about 480 mg every four weeks for the manufacture of a medicament for the treatment of urothelial carcinoma in a patient who harbors at least one FGFR2 genetic alteration and/or FGFR3 genetic alteration wherein the anti-PD1 antibody or antigen binding fragment thereof is used or is to be used in combination with a FGFR inhibitor at a dose of about 8 mg per day. In an embodiment, the anti-PD1 antibody or antigen binding fragment thereof is administered or is to be administered at a dose of about 480 mg every four weeks as of cycle 5 of treatment and beyond.

Further provided herein is a combination of a FGFR inhibitor at a dose of about 8 mg per day and an anti-PD1 antibody or antigen binding fragment thereof at a dose of about 240 mg every two weeks, in particular for use in the treatment of urothelial carcinoma in a patient who harbors at least one FGFR2 genetic alteration and/or FGFR3 genetic alteration, and wherein the combination is administered or is to be administered after evaluation of a biological sample from the patient for the presence of one or more FGFR2 or 3 gene alterations and if one or more FGFR2 or 3 gene alterations is present in the sample. In an embodiment, the anti-PD1 antibody or antigen binding fragment thereof is administered or is to be administered at a dose of about 240 mg every two weeks in cycle 1 to 4 of treatment.

Further provided herein is a combination of a FGFR inhibitor at a dose of about 8 mg per day and an anti-PD1 antibody or antigen binding fragment thereof at a dose of about 360 mg every three weeks, in particular for use in the treatment of urothelial carcinoma in a patient who harbors at least one FGFR2 genetic alteration and/or FGFR3 genetic alteration, and wherein the combination is administered or is to be administered after evaluation of a biological sample from the patient for the presence of one or more FGFR2 or 3 gene alterations and if one or more FGFR2 or 3 gene alterations is present in the sample. In an embodiment, the treatment further comprises a platinum chemotherapy, in particular cisplatin or carboplatin. In an embodiment the platinum chemotherapy is administered or is to be administered every three weeks. In an embodiment, the platinum chemotherapy is administered or is to be administered at a dose of 50 mg/m$^2$, or 60 mg/m$^2$, or at a dose for a AUC of 4 mg/mL*min, or at a dose for a AUC of 5 mg/mL*min. In an embodiment, cisplatin is administered or is to be administered at a dose of 50 mg/m$^2$ or 60 mg/m$^2$. In an embodiment, carboplatin is administered or is to be administered at a dose for an AUC of 4 mg/mL*min or at a dose for an AUC of 5 mg/mL*min.

Further provided herein is a combination of a FGFR inhibitor at a dose of about 8 mg per day and an anti-PD1 antibody or antigen binding fragment thereof at a dose of about 480 mg every four weeks, in particular for use in the treatment of urothelial carcinoma in a patient who harbors at least one FGFR2 genetic alteration and/or FGFR3 genetic alteration, and wherein the combination is administered or is to be administered after evaluation of a biological sample from the patient for the presence of one or more FGFR2 or 3 gene alterations and if one or more FGFR2 or 3 gene alterations is present in the sample. In an embodiment, the anti-PD1 antibody or antigen binding fragment thereof is administered or is to be administered at a dose of about 480 mg every four weeks as of cycle 5 of treatment and beyond.

Further provided herein is a FGFR inhibitor for use in combination with an anti-PD1 antibody or antigen binding fragment thereof for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 240 mg every two weeks, and wherein the combination is administered or is to be administered after evaluation of a biological sample from the patient for the presence of one or more FGFR2 or 3 gene alterations and if one or more FGFR2 or 3 gene alterations is present in the sample. In an embodiment, the anti-PD1 antibody or antigen binding fragment thereof is administered or is to be administered at a dose of about 240 mg every two weeks in cycle 1 to 4 of treatment.

Further provided herein is a FGFR inhibitor for use in combination with an anti-PD1 antibody or antigen binding fragment thereof for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 360 mg every three weeks, and wherein the combination is administered or is to be administered after evaluation of a biological sample from the patient for the presence of one or more FGFR2 or 3 gene alterations and if one or more FGFR2 or 3 gene alterations is present in the sample. In an embodiment, the treatment further comprises a platinum chemotherapy, in particular cisplatin or carboplatin. In an embodiment the platinum chemotherapy is administered or is to be administered every three weeks. In an embodiment, the platinum chemotherapy is administered or is to be administered at a dose of 50 mg/m$^2$, or 60 mg/m$^2$, or at a dose for a AUC of 4 mg/mL*min, or at a dose for a AUC of 5 mg/mL*min. In an embodiment, cisplatin is administered or is to be administered at a dose of 50 mg/m$^2$ or 60 mg/m$^2$. In an embodiment, carboplatin is administered or is to be administered at a dose for an AUC of 4 mg/mL*min or at a dose for an AUC of 5 mg/mL*min.

Further provided herein is a FGFR inhibitor for use in combination with an anti-PD1 antibody or antigen binding fragment thereof for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 480 mg every four weeks, and wherein the combination is administered or is to be administered after evaluation of a biological sample from the patient for the presence of one or more FGFR2 or 3 gene alterations and if one or more FGFR2 or 3 gene alterations is present in the sample. In an embodiment, the anti-PD1 antibody or antigen binding fragment thereof is administered or is to be administered at a dose of about 480 mg every four weeks as of cycle 5 of treatment and beyond.

Further provided herein is an anti-PD1 antibody or antigen binding fragment thereof for use in combination with a FGFR inhibitor for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 240 mg every two weeks, and wherein the combination is administered or is to be administered after evaluation of a biological sample from the patient for the presence of one or more FGFR2 or 3 gene alterations and if one or more FGFR2 or 3 gene alterations is present in the sample. In an embodiment, the anti-PD1 antibody or antigen binding fragment thereof is administered or is to be administered at a dose of about 240 mg every two weeks in cycle 1 to 4 of treatment.

Further provided herein is an anti-PD1 antibody or antigen binding fragment thereof for use in combination with a FGFR inhibitor for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 360 mg every three weeks, and wherein the combination is administered or is to be administered after evaluation of a biological sample from the patient for the presence of one or more FGFR2 or 3 gene alterations and if one or more FGFR2 or 3 gene alterations is present in the sample. In an embodiment, the treatment further comprises a platinum chemotherapy, in particular cisplatin or carboplatin. In an embodiment the platinum chemotherapy is administered or is to be administered every three weeks. In an embodiment, the platinum chemotherapy is administered or is to be administered at a dose of 50 mg/m$^2$, or 60 mg/m$^2$, or at a dose for a AUC of 4 mg/mL*min, or at a dose for a AUC of 5 mg/mL*min. In an embodiment, cisplatin is administered or is to be administered at a dose of 50 mg/m$^2$ or 60 mg/m. In an embodiment, carboplatin is administered or is to be administered at a dose for an AUC of 4 mg/mL*min or at a dose for an AUC of 5 mg/mL*min.

Further provided herein is an anti-PD1 antibody or antigen binding fragment thereof for use in combination with a FGFR inhibitor for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 480 mg every four weeks, and wherein the combination is administered or is to be administered after evaluation of a biological sample from the patient for the presence of one or more FGFR2 or 3 gene alterations and if one or more FGFR2 or 3 gene alterations is present in the sample. In an embodiment, the anti-PD1 antibody or antigen binding fragment thereof is administered or is to be administered at a dose of about 480 mg every four weeks as of cycle 5 of treatment and beyond.

Further provided herein is the use of a FGFR inhibitor at a dose of about 8 mg per day for the manufacture of a medicament for the treatment of urothelial carcinoma in a patient who harbors at least one FGFR2 genetic alteration and/or FGFR3 genetic alteration wherein the FGFR inhibitor is used or is to be used in combination with an anti-PD1 antibody or antigen binding fragment thereof at a dose of about 240 mg every two weeks, and wherein the combination is administered or is to be administered after evaluation of a biological sample from the patient for the presence of one or more FGFR2 or 3 gene alterations and if one or more FGFR2 or 3 gene alterations is present in the sample. In an embodiment, the anti-PD1 antibody or antigen binding fragment thereof is administered or is to be administered at a dose of about 240 mg every two weeks in cycle 1 to 4 of treatment.

Further provided herein is the use of a FGFR inhibitor at a dose of about 8 mg per day for the manufacture of a medicament for the treatment of urothelial carcinoma in a patient who harbors at least one FGFR2 genetic alteration and/or FGFR3 genetic alteration wherein the FGFR inhibitor is used or is to be used in combination with an anti-PD1 antibody or antigen binding fragment thereof at a dose of about 360 mg every three weeks, and wherein the combination is administered or is to be administered after evaluation of a biological sample from the patient for the presence of one or more FGFR2 or 3 gene alterations and if one or more FGFR2 or 3 gene alterations is present in the sample. In an embodiment, the treatment further comprises a platinum chemotherapy, in particular cisplatin or carboplatin. In an embodiment the platinum chemotherapy is administered or is to be administered every three weeks. In an embodiment, the platinum chemotherapy is administered or is to be administered at a dose of 50 mg/m$^2$, or 60 mg/m$^2$, or at a dose for a AUC of 4 mg/mL*min, or at a dose for a AUC of 5 mg/mL*min. In an embodiment, cisplatin is administered or is to be administered at a dose of 50 mg/m$^2$ or 60 mg/m$^2$. In an embodiment, carboplatin is administered or is to be administered at a dose for an AUC of 4 mg/mL*min or at a dose for an AUC of 5 mg/mL*min.

Further provided herein is the use of a FGFR inhibitor at a dose of about 8 mg per day for the manufacture of a medicament for the treatment of urothelial carcinoma in a patient who harbors at least one FGFR2 genetic alteration and/or FGFR3 genetic alteration wherein the FGFR inhibitor is used or is to be used in combination with an anti-PD1 antibody or antigen binding fragment thereof at a dose of about 480 mg every four weeks, and wherein the combination is administered or is to be administered after evaluation of a biological sample from the patient for the presence of one or more FGFR2 or 3 gene alterations and if one or more FGFR2 or 3 gene alterations is present in the sample. In an embodiment, the anti-PD1 antibody or antigen binding fragment thereof is administered or is to be administered at a dose of about 480 mg every four weeks as of cycle 5 of treatment and beyond.

Further provided herein is the use of an anti-PD1 antibody or antigen binding fragment thereof at a dose of about 240 mg every two weeks for the manufacture of a medicament for the treatment of urothelial carcinoma in a patient who harbors at least one FGFR2 genetic alteration and/or FGFR3 genetic alteration wherein the anti-PD1 antibody or antigen binding fragment thereof is used or is to be used in combination with a FGFR inhibitor at a dose of about 8 mg per day, and wherein the combination is administered or is to be administered after evaluation of a biological sample from the patient for the presence of one or more FGFR2 or 3 gene alterations and if one or more FGFR2 or 3 gene alterations is present in the sample. Described herein are methods of treating urothelial carcinoma comprising, consisting of, or consisting essential of, administering a FGFR inhibitor at a dose of about 8 mg per day in combination with an anti-PD1 antibody or antigen binding fragment thereof at a dose of about 240 mg every two weeks in further combination with a platinum chemotherapy to a patient that has been diagnosed with urothelial carcinoma who harbors at least one FGFR2 genetic alteration and/or FGFR3 genetic alteration. According to particular embodiments, the dose of about 240 mg every two weeks of the anti-PD1 antibody or antigen binding fragment thereof refers to a single intravenous (IV) infusion once every two weeks. In an embodiment, the anti-PD1 antibody or antigen binding fragment thereof is administered or is to be administered at a dose of about 240 mg every two weeks in cycle 1 to 4 of treatment.

Further provided herein is the use of an anti-PD1 antibody or antigen binding fragment thereof at a dose of about 360 mg every three weeks for the manufacture of a medicament for the treatment of urothelial carcinoma in a patient who harbors at least one FGFR2 genetic alteration and/or FGFR3 genetic alteration wherein the anti-PD1 antibody or antigen binding fragment thereof is used or is to be used in combination with a FGFR inhibitor at a dose of about 8 mg per day, and wherein the combination is administered or is to be administered after evaluation of a biological sample from the patient for the presence of one or more FGFR2 or 3 gene alterations and if one or more FGFR2 or 3 gene alterations is present in the sample. Described herein are methods of treating urothelial carcinoma comprising, consisting of, or consisting essential of, administering a FGFR inhibitor at a dose of about 8 mg per day in combination with an anti-PD1 antibody or antigen binding fragment thereof at a dose of about 360 mg every three weeks in further combination with a platinum chemotherapy to a patient that has been diagnosed with urothelial carcinoma who harbors at least one FGFR2 genetic alteration and/or FGFR3 genetic alteration. According to particular embodiments, the dose of about 360 mg every three weeks of the anti-PD1 antibody or antigen binding fragment thereof refers to a single intravenous (IV) infusion once every three weeks. In an embodiment, the platinum chemotherapy is cisplatin or carboplatin. In an embodiment the platinum chemotherapy is administered or is to be administered every three weeks. In an embodiment, the platinum chemotherapy is administered or is to be administered at a dose of 50 $mg/m^2$, or 60 $mg/m^2$, or at a dose for a AUC of 4 mg/mL*min, or at a dose for a AUC of 5 mg/mL*min. In an embodiment, cisplatin is administered or is to be administered at a dose of 50 $mg/m^2$ or 60 $mg/m^2$. In an embodiment, carboplatin is administered or is to be administered at a dose for an AUC of 4 mg/mL*min or at a dose for an AUC of 5 mg/mL*min.

Further provided herein is the use of an anti-PD1 antibody or antigen binding fragment thereof at a dose of about 480 mg every four weeks for the manufacture of a medicament for the treatment of urothelial carcinoma in a patient who harbors at least one FGFR2 genetic alteration and/or FGFR3 genetic alteration wherein the anti-PD1 antibody or antigen binding fragment thereof is used or is to be used in combination with a FGFR inhibitor at a dose of about 8 mg per day, and wherein the combination is administered or is to be administered after evaluation of a biological sample from the patient for the presence of one or more FGFR2 or 3 gene alterations and if one or more FGFR2 or 3 gene alterations is present in the sample. Described herein are methods of treating urothelial carcinoma comprising, consisting of, or consisting essential of, administering a FGFR inhibitor at a dose of about 8 mg per day in combination with an anti-PD1 antibody or antigen binding fragment thereof at a dose of about 480 mg every four weeks in further combination with a platinum chemotherapy to a patient that has been diagnosed with urothelial carcinoma who harbors at least one FGFR2 genetic alteration and/or FGFR3 genetic alteration. According to particular embodiments, the dose of about 480 mg every four weeks of the anti-PD1 antibody or antigen binding fragment thereof refers to a single intravenous (IV) infusion once every four weeks. In an embodiment, the anti-PD1 antibody or antigen binding fragment thereof is administered or is to be administered at a dose of about 480 mg every four weeks as of cycle 5 of treatment and beyond.

According to particular embodiments, on days in which the FGFR inhibitor (e.g., erdafitinib), the anti-PD1 antibody (e.g., cetrelimab) and the platinum chemotherapy (e.g. cisplatin or carboplatin) are administered, the FGFR inhibitor is administered within about 60 minutes, or about 60 minutes±about 15 minutes before the start of the anti-PD1 antibody IV infusion, e.g., between about 45 minutes to about 75 minutes, before the start of the IV infusion. According to alternative embodiments, the FGFR inhibitor is administered within about 1 hour, or about 2 hours, or about 3 hours, or about 4 hours, or about 5 hours before or after the start of the anti-PD1 antibody IV infusion.

Described herein is a combination of a FGFR inhibitor at a dose of about 8 mg per day and an anti-PD1 antibody or antigen binding fragment thereof at a dose of about 240 mg every two weeks or at a dose of about 360 mg every three weeks or at a dose of about 480 mg every four weeks and in further combination with a platinum chemotherapy, in particular for use in the treatment of urothelial carcinoma in a patient who harbors at least one FGFR2 genetic alteration and/or FGFR3 genetic alteration. In certain embodiments, described herein is a combination of a FGFR inhibitor at a dose of about 8 mg per day and an anti-PD1 antibody or antigen binding fragment thereof at a dose of about 240 mg every two weeks or at a dose of about 360 mg every three weeks or at a dose of about 480 mg every four weeks and in further combination with a platinum chemotherapy, in particular for use in the treatment of urothelial carcinoma in a patient who does not harbor at least one FGFR2 genetic alteration and/or FGFR3 genetic alteration.

Described herein is a FGFR inhibitor for use in combination with an anti-PD1 antibody or antigen binding fragment thereof and in further combination with cisplatin for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day, wherein the anti-PD1 antibody or antigen binding fragment thereof is administered or is to be administered at a dose of about 240 mg every two weeks or at a dose of about 360 mg every three weeks or at a dose of about 480 mg every four weeks and wherein the cisplatin is administered at a dose of about 50 $mg/m^2$ every 3 weeks. Described herein is a FGFR inhibitor for use in combination with an anti-PD1 antibody or antigen binding fragment thereof and in further combination with cisplatin for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day, wherein the anti-PD1 antibody or antigen binding fragment thereof is administered or is to be administered at a dose of about 240 mg every two weeks or at a dose of about 360 mg every three weeks or at a dose of about 480 mg every four weeks and wherein the cisplatin is administered at a dose of about 60 $mg/m^2$ every 3 weeks.

Described herein is a FGFR inhibitor for use in combination with an anti-PD1 antibody or antigen binding fragment thereof and in further combination with carboplatin for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day, wherein the anti-PD1 antibody or antigen binding fragment thereof is administered or is to be administered at a dose of about 240 mg every two weeks or at a dose of about 360 mg every three weeks or at a dose of about 480 mg every four weeks and wherein the carboplatin is administered at a dose of about AUC of 4 mg/mL/min every 3 weeks. Described herein is a FGFR inhibitor for use in combination with an anti-PD1 antibody or antigen binding fragment thereof and in further combination with carboplatin for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day, wherein the anti-PD1 antibody or antigen binding fragment thereof is administered or is to be administered at a dose of about 240 mg every two weeks or at a dose of about 360 mg every three weeks or at a dose of about 480 mg every four weeks and wherein the carboplatin is administered at a dose of about AUC 5 mg/mL/min every 3 weeks.

Described herein is a FGFR inhibitor for use in combination with an anti-PD1 antibody or antigen binding fragment thereof and in further combination with cisplatin for use in the treatment of urothelial carcinoma in a patient who does not harbor at least one FGFR2 genetic alteration and/or FGFR3 genetic alteration, wherein the FGFR inhibitor is administered or is to be administered at a dose of about 8 mg per day, wherein the anti-PD1 antibody or antigen binding fragment thereof is administered or is to be administered at a dose of about 240 mg every two weeks or at a dose of about 360 mg every three weeks or at a dose of about 480 mg every four weeks and wherein the cisplatin is administered at a dose of about 50 mg/$m^2$ every 3 weeks. Described herein is a FGFR inhibitor for use in combination with an anti-PD1 antibody or antigen binding fragment thereof and in further combination with cisplatin for use in the treatment of urothelial carcinoma in a patient who does not harbor at least one FGFR2 genetic alteration and/or FGFR3 genetic alteration, wherein the FGFR inhibitor is administered or is to be administered at a dose of about 8 mg per day, wherein the anti-PD1 antibody or antigen binding fragment thereof is administered or is to be administered at a dose of about 240 mg every two weeks or at a dose of about 360 mg every three weeks or at a dose of about 480 mg every four weeks and wherein the cisplatin is administered at a dose of about 60 mg/$m^2$ every 3 weeks.

Described herein is a FGFR inhibitor for use in combination with an anti-PD1 antibody or antigen binding fragment thereof and in further combination with carboplatin for use in the treatment of urothelial carcinoma in a patient who does not harbor at least one FGFR2 genetic alteration and/or FGFR3 genetic alteration, wherein the FGFR inhibitor is administered or is to be administered at a dose of about 8 mg per day, wherein the anti-PD1 antibody or antigen binding fragment thereof is administered or is to be administered at a dose of about 240 mg every two weeks or at a dose of about 360 mg every three weeks or at a dose of about 480 mg every four weeks and wherein the carboplatin is administered at a dose of about AUC 4 mg/mL/min every 3 weeks. Described herein is a FGFR inhibitor for use in combination with an anti-PD1 antibody or antigen binding fragment thereof and in further combination with carboplatin for use in the treatment of urothelial carcinoma in a patient who does not harbor at least one FGFR2 genetic alteration and/or FGFR3 genetic alteration, wherein the FGFR inhibitor is administered or is to be administered at a dose of about 8 mg per day, wherein the anti-PD1 antibody or antigen binding fragment thereof is administered or is to be administered at a dose of about 240 mg every two weeks or at a dose of about 360 mg every three weeks or at a dose of about 480 mg every four weeks and wherein the carboplatin is administered at a dose of about AUC 5 mg/mL/min every 3 weeks.

Described herein is an anti-PD1 antibody or antigen binding fragment thereof for use in combination with a FGFR inhibitor and in further combination with cisplatin for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day, wherein the anti-PD1 antibody or antigen binding fragment thereof is administered or is to be administered at a dose of about 240 mg every two weeks or at a dose of about 360 mg every three weeks or at a dose of about 480 mg every four weeks, and wherein the cisplatin is administered at a dose of about 50 mg/m2 every 3 weeks. Described herein is an anti-PD1 antibody or antigen binding fragment thereof for use in combination with a FGFR inhibitor and in further combination with cisplatin for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day, wherein the anti-PD1 antibody or antigen binding fragment thereof is administered or is to be administered at a dose of about 240 mg every two weeks or at a dose of about 360 mg every three weeks or at a dose of about 480 mg every four weeks, and wherein the cisplatin is administered at a dose of about 60 mg/$m^2$ every 3 weeks.

Described herein is an anti-PD1 antibody or antigen binding fragment thereof for use in combination with a FGFR inhibitor and in further combination with carboplatin for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day, wherein the anti-PD1 antibody or antigen binding fragment thereof is administered or is to be administered at a dose of about 240 mg every two weeks or at a dose of about 360 mg every three weeks or at a dose of about 480 mg every four weeks, and wherein the carboplatin is administered at a dose of about AUC 4 mg/mL/min every 3 weeks. Described herein is an anti-PD1 antibody or antigen binding fragment thereof for use in combination with a FGFR inhibitor and in further combination with cisplatin for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day, wherein the anti-PD1 antibody or antigen binding fragment thereof is administered or is to be administered at a dose of about 240 mg every two weeks or at a dose of about 360 mg every three weeks or at a dose of about 480 mg every four weeks, and wherein the cisplatin is administered at a dose of about AUC 5 mg/mL/min every 3 weeks.

Described herein is an anti-PD1 antibody or antigen binding fragment thereof for use in combination with a FGFR inhibitor and in further combination with cisplatin for use in the treatment of urothelial carcinoma in a patient who does not harbor at least one FGFR2 genetic alteration and/or FGFR3 genetic alteration, wherein the FGFR inhibitor is administered or is to be administered at a dose of about 8 mg per day, wherein the anti-PD1 antibody or antigen binding fragment thereof is administered or is to be administered at a dose of about 240 mg every two weeks or at a dose of about 360 mg every three weeks or at a dose of about 480 mg every four weeks, and wherein the cisplatin is administered at a dose of about 50 $mg/m^2$ every 3 weeks. Described herein is an anti-PD1 antibody or antigen binding fragment thereof for use in combination with a FGFR inhibitor and in further combination with cisplatin for use in the treatment of urothelial carcinoma in a patient who does not harbor at least one FGFR2 genetic alteration and/or FGFR3 genetic alteration, wherein the FGFR inhibitor is administered or is to be administered at a dose of about 8 mg per day, wherein the anti-PD1 antibody or antigen binding fragment thereof is administered or is to be administered at a dose of about 240 mg every two weeks or at a dose of about 360 mg every three weeks or at a dose of about 480 mg every four weeks, and wherein the cisplatin is administered at a dose of about 60 $mg/m^2$ every 3 weeks.

Described herein is an anti-PD1 antibody or antigen binding fragment thereof for use in combination with a FGFR inhibitor and in further combination with carboplatin for use in the treatment of urothelial carcinoma in a patient who does not harbor at least one FGFR2 genetic alteration and/or FGFR3 genetic alteration, wherein the FGFR inhibitor is administered or is to be administered at a dose of about 8 mg per day, wherein the anti-PD1 antibody or antigen binding fragment thereof is administered or is to be administered at a dose of about 240 mg every two weeks or at a dose of about 360 mg every three weeks or at a dose of about 480 mg every four weeks, and wherein the carboplatin is administered at a dose of about AUC 4 mg/mL/min every 3 weeks. Described herein is an anti-PD1 antibody or antigen binding fragment thereof for use in combination with a FGFR inhibitor and in further combination with cisplatin for use in the treatment of urothelial carcinoma in a patient who does not harbor at least one FGFR2 genetic alteration and/or FGFR3 genetic alteration, wherein the FGFR inhibitor is administered or is to be administered at a dose of about 8 mg per day, wherein the anti-PD1 antibody or antigen binding fragment thereof is administered or is to be administered at a dose of about 240 mg every two weeks or at a dose of about 360 mg every three weeks or at a dose of about 480 mg every four weeks, and wherein the cisplatin is administered at a dose of about AUC 5 mg/mL/min every 3 weeks.

Described herein is the use of a FGFR inhibitor at a dose of about 8 mg per day for the manufacture of a medicament for the treatment of urothelial carcinoma in a patient who harbors at least one FGFR2 genetic alteration and/or FGFR3 genetic alteration wherein the FGFR inhibitor is used or is to be used in combination with an anti-PD1 antibody or antigen binding fragment thereof at a dose of about 240 mg every two weeks or at a dose of about 360 mg every three weeks or at a dose of about 480 mg every four weeks and wherein the FGFR inhibitor is used or to be used in further combination with cisplatin at a dose of 50 $mg/m^2$ every 3 weeks. Described herein is the use of a FGFR inhibitor at a dose of about 8 mg per day for the manufacture of a medicament for the treatment of urothelial carcinoma in a patient who harbors at least one FGFR2 genetic alteration and/or FGFR3 genetic alteration wherein the FGFR inhibitor is used or is to be used in combination with an anti-PD1 antibody or antigen binding fragment thereof at a dose of about 240 mg every two weeks or at a dose of about 360 mg every three weeks or at a dose of about 480 mg every four weeks and wherein the FGFR inhibitor is use or to be used in further combination with cisplatin at a dose of 60 $mg/m^2$ every 3 weeks.

Described herein is the use of a FGFR inhibitor at a dose of about 8 mg per day for the manufacture of a medicament for the treatment of urothelial carcinoma in a patient who harbors at least one FGFR2 genetic alteration and/or FGFR3 genetic alteration wherein the FGFR inhibitor is used or is to be used in combination with an anti-PD1 antibody or antigen binding fragment thereof at a dose of about 240 mg every two weeks or at a dose of about 360 mg every three weeks or at a dose of about 480 mg every four weeks and wherein the FGFR inhibitor is used or to be used in further combination with carboplatin at a dose of AUC 4 mg/mL/min every 3 weeks. Described herein is the use of a FGFR inhibitor at a dose of about 8 mg per day for the manufacture of a medicament for the treatment of urothelial carcinoma in a patient who harbors at least one FGFR2 genetic alteration and/or FGFR3 genetic alteration wherein the FGFR inhibitor is used or is to be used in combination with an anti-PD1 antibody or antigen binding fragment thereof at a dose of about 240 mg every two weeks or at a dose of about 360 mg every three weeks or at a dose of about 480 mg every four weeks and wherein the FGFR inhibitor is used or to be used in further combination with carboplatin at a dose of AUC 5 mg/mL/min every 3 weeks.

Described herein is the use of a FGFR inhibitor at a dose of about 8 mg per day for the manufacture of a medicament for the treatment of urothelial carcinoma in a patient does not harbor at least one FGFR2 genetic alteration and/or FGFR3 genetic alteration wherein the FGFR inhibitor is used or is to be used in combination with an anti-PD1 antibody or antigen binding fragment thereof at a dose of about 240 mg every two weeks or at a dose of about 360 mg every three weeks or at a dose of about 480 mg every four weeks and wherein the FGFR inhibitor is used or to be used in further combination with cisplatin at a dose of 50 $mg/m^2$ every 3 weeks. Described herein is the use of a FGFR inhibitor at a dose of about 8 mg per day for the manufacture of a medicament for the treatment of urothelial carcinoma in a patient who does not harbor at least one FGFR2 genetic alteration and/or FGFR3 genetic alteration wherein the FGFR inhibitor is used or is to be used in combination with an anti-PD1 antibody or antigen binding fragment thereof at a dose of about 240 mg every two weeks or at a dose of about 360 mg every three weeks or at a dose of about 480 mg every four weeks and wherein the FGFR inhibitor is used or to be used in further combination with cisplatin at a dose of 60 $mg/m^2$ every 3 weeks.

Described herein is the use of a FGFR inhibitor at a dose of about 8 mg per day for the manufacture of a medicament for the treatment of urothelial carcinoma in a patient who does not harbor at least one FGFR2 genetic alteration and/or FGFR3 genetic alteration wherein the FGFR inhibitor is used or is to be used in combination with an anti-PD1 antibody or antigen binding fragment thereof at a dose of about 240 mg every two weeks or at a dose of about 360 mg every three weeks or at a dose of about 480 mg every four weeks and wherein the FGFR inhibitor is used or to be used in further combination with carboplatin at a dose of AUC 4 mg/mL/min every 3 weeks. Described herein is the use of a FGFR inhibitor at a dose of about 8 mg per day for the manufacture of a medicament for the treatment of urothelial carcinoma in a patient who does not harbor at least one FGFR2 genetic alteration and/or FGFR3 genetic alteration wherein the FGFR inhibitor is used or is to be used in combination with an anti-PD1 antibody or antigen binding fragment thereof at a dose of about 240 mg every two weeks or at a dose of about 360 mg every three weeks or at a dose of about 480 mg every four weeks and wherein the FGFR inhibitor is used or to be used in further combination with carboplatin at a dose of AUC 5 mg/mL/min every 3 weeks.

Described herein is the use of an anti-PD1 antibody or antigen binding fragment thereof at a dose of about 240 mg every two weeks or at a dose of about 360 mg every three weeks or at a dose of about 480 mg every four weeks for the manufacture of a medicament for the treatment of urothelial carcinoma in a patient who harbors at least one FGFR2 genetic alteration and/or FGFR3 genetic alteration wherein the anti-PD1 antibody or antigen binding fragment thereof is used or is to be used in combination with a FGFR inhibitor at a dose of about 8 mg per day and a platinum chemotherapy. In certain embodiments, the platinum chemotherapy is cisplatin. In certain embodiments, the platinum chemotherapy is carboplatin. In certain embodiments, the cisplatin is to be used at a dose of 50 $mg/m^2$ every 3 weeks. In certain embodiments, the cisplatin is to be used at a dose of 60 $mg/m^2$ every 3 weeks. In certain embodiments, the carboplatin is to be used at a dose of AUC 4 mg/mL/min every 3 weeks. In certain embodiments, the carboplatin is to be used at a dose of AUC 5 mg/mL/min every 3 weeks.

Further provided herein is a combination of a FGFR inhibitor at a dose of about 8 mg per day and an anti-PD1 antibody or antigen binding fragment thereof at a dose of about 240 mg every two weeks or at a dose of about 360 mg every three weeks or at a dose of about 480 mg every four weeks and a platinum chemotherapy, in particular for use in the treatment of urothelial carcinoma in a patient who harbors at least one FGFR2 genetic alteration and/or FGFR3 genetic alteration, and wherein the combination is administered or is to be administered after evaluation of a biological sample from the patient for the presence of one or more FGFR2 or 3 gene alterations and if one or more FGFR2 or 3 gene alterations is present in the sample.

Further provided herein is a FGFR inhibitor for use in combination with an anti-PD1 antibody or antigen binding fragment thereof and a platinum chemotherapy for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 240 mg every two weeks or at a dose of about 360 mg every three weeks or at a dose of about 480 mg every four weeks, and wherein the combination is administered or is to be administered after evaluation of a biological sample from the patient for the presence of one or more FGFR2 or 3 gene alterations and if one or more FGFR2 or 3 gene alterations is present in the sample.

Further provided herein is an anti-PD1 antibody or antigen binding fragment thereof for use in combination with a FGFR inhibitor and a platinum chemotherapy for use in the treatment of urothelial carcinoma in a patient who harbors at least one FGFR2 genetic alteration and/or FGFR3 genetic alteration, wherein the FGFR inhibitor is administered or is to be administered at a dose of about 8 mg per day and wherein the anti-PD1 antibody or antigen binding fragment thereof is administered or is to be administered at a dose of about 240 mg every two weeks or at a dose of about 360 mg every three weeks or at a dose of about 480 mg every four weeks, and wherein the combination is administered or is to be administered after evaluation of a biological sample from the patient for the presence of one or more FGFR2 or 3 gene alterations and if one or more FGFR2 or 3 gene alterations is present in the sample.

Further provided herein is the use of a FGFR inhibitor at a dose of about 8 mg per day for the manufacture of a medicament for the treatment of urothelial carcinoma in a patient who harbors at least one FGFR2 genetic alteration and/or FGFR3 genetic alteration wherein the FGFR inhibitor is used or is to be used in combination with an anti-PD1 antibody or antigen binding fragment thereof at a dose of about 240 mg every two weeks or at a dose of about 360 mg every three weeks or at a dose of about 480 mg every four weeks and a platinum chemotherapy, and wherein the combination is administered or is to be administered after evaluation of a biological sample from the patient for the presence of one or more FGFR2 or 3 gene alterations and if one or more FGFR2 or 3 gene alterations is present in the sample.

Further provided herein is the use of an anti-PD1 antibody or antigen binding fragment thereof at a dose of about 240 mg every two weeks or at a dose of about 360 mg every three weeks or at a dose of about 480 mg every four weeks for the manufacture of a medicament for the treatment of urothelial carcinoma in a patient who harbors at least one FGFR2 genetic alteration and/or FGFR3 genetic alteration wherein the anti-PD1 antibody or antigen binding fragment thereof is used or is to be used in combination with a FGFR inhibitor at a dose of about 8 mg per day and a platinum chemotherapy, and wherein the combination is administered or is to be administered after evaluation of a biological sample from the patient for the presence of one or more FGFR2 or 3 gene alterations and if one or more FGFR2 or 3 gene alterations is present in the sample.

Said methods and uses also encompass administration of at least one, one, two, three or four FGFR inhibitors to a patient that has been diagnosed with urothelial carcinoma.

In certain embodiments, the urothelial carcinoma is locally advanced or metastatic.

In some embodiments, the subject has received one, two, three or more prior therapeutics to treat the urothelial carcinoma prior to said administration of said FGFR inhibitor and said anti-PD1 antibody or antigen binding fragment thereof. In certain embodiments, the patient received at least one systemic therapy for the treatment of urothelial carcinoma prior to administration of said FGFR inhibitor and said anti-PD1 antibody or antigen binding fragment thereof. In some embodiments, the at least one systemic therapy for the treatment of urothelial carcinoma is platinum-containing chemotherapy. Non-limiting examples of platinum-based chemotherapies include cisplatin, carboplatin, oxaliplatin and nedaplatin. In further embodiments, the urothelial carcinoma progressed during or following at least one line of the platinum-containing chemotherapy.

In still further embodiments, the platinum-containing chemotherapy is neoadjuvant platinum-containing chemotherapy or adjuvant platinum-containing chemotherapy. Neoadjuvant therapy, which is given as a first step to shrink a tumor, may be distinguished from adjuvant therapy, which is given after the primary treatment to lower the risk that the cancer will come back. In even further embodiments, the urothelial carcinoma progressed within 12 months following at least one line of the neoadjuvant platinum-containing chemotherapy or adjuvant platinum-containing chemotherapy.

In some embodiments, the subject has not received or is ineligible to receive at least one prior therapeutic to treat the urothelial carcinoma prior to said administration of said FGFR inhibitor and said anti-PD1 antibody or antigen binding fragment thereof. In some embodiments, the patient did not receive systemic therapy for the treatment of urothelial carcinoma prior to said administration of said FGFR inhibitor and said anti-PD1 antibody or antigen binding fragment thereof. In certain embodiments, the patient is cisplatin-ineligible. In certain embodiments, the patient is a first line cisplatin-ineligible mUC patient. The determination of eligibility may be made, for example, by a treating physician.

In certain embodiments, the patient is PD-1 axis naïve. "PD-1 axis naïve" refers to a subject who has not been treated with PD-1, PD-L1 or PD-L2 antagonists. Exemplary PD-1, PD-L1 or PD-L2 antagonists are nivolumab (OPDIVO®), pembrolizumab (KEYTRUDA®), cemiplimab (Libtayo®), sintilimab, tislelizumab, tripolibamab durvalumab (IMFINZI®), atezolizumab (TECENTRIQ®), avelumab (BAVENCIO®) or envafolimab, or any other PD-1, PD-L1 or PD-L2 antagonist. Additional such antagonists are known and include those listed for example at Citeline PharmaIntelligence website.

In further embodiments, the patient has an Eastern Cooperative Oncology Group (ECOG) performance status of less than or equal to 2. In certain embodiments, the patient has an ECOG performance status of 2. In certain embodiments, the patient has an ECOG performance status of 1. In certain embodiments, the patient has an ECOG performance status of 0.

In further embodiments, the combination of an FGFR inhibitor and an anti-PD1 antibody or antigen binding fragment thereof as described herein is indicated for adult patients with metastatic or locally advanced urothelial carcinoma that harbors at least one FGFR2 genetic alteration and/or FGFR3 genetic alteration and who have not received prior systemic therapy for metastatic disease. In an embodiment, the patients are ineligible for cisplatin chemotherapy.

In further embodiments, administration of the FGFR inhibitor in combination with the anti-PD1 antibody or antigen binding fragment thereof provides improved anti-tumor activity as measured by objective response rate or disease control rate relative to a patient that has been diagnosed with urothelial carcinoma that has not received treatment with an FGFR inhibitor and an anti-PD1 antibody or antigen binding fragment thereof. In certain embodiments, administration of the FGFR inhibitor in combination with the anti-PD1 antibody or antigen binding fragment thereof provides improved anti-tumor activity as measured by objective response rate relative to a patient that has been diagnosed with urothelial carcinoma that has not received treatment with an FGFR inhibitor and an anti-PD1 antibody or antigen binding fragment thereof. In further embodiments, administration of the FGFR inhibitor in combination with the anti-PD1 antibody or antigen binding fragment thereof provides improved anti-tumor activity as measured by disease control rate relative to a patient that has been diagnosed with urothelial carcinoma that has not received treatment with an FGFR inhibitor and an anti-PD1 antibody or antigen binding fragment thereof.

In certain embodiments, administration of the FGFR inhibitor in combination with the anti-PD1 antibody or antigen binding fragment thereof as described herein, in particular erdafitinib at a dose of 8 mg potentially with uptitration and cetrelimab at a dose of 240 mg as described herein, provides an objective response rate of at least 40%, or at least 44%, or at least 45%, or at least 50%. In an embodiment, erdafitinib is not uptitrated.

In certain embodiments, administration of the FGFR inhibitor in combination with the anti-PD1 antibody or antigen binding fragment thereof as described herein, in particular erdafitinib at a dose of 8 mg potentially with uptitration and cetrelimab at a dose of 240 mg as described herein, provides a disease control rate of at least 90%, or at least 95% or a disease control rate of 100%. In an embodiment, erdafitinib is not uptitrated.

In certain embodiments, the improvement in anti-tumor activity is relative to treatment with placebo. In certain embodiments, the improvement in anti-tumor activity is relative to no treatment. In certain embodiments, the improvement in anti-tumor activity is relative to standard of care. In certain embodiments, the improvement in anti-tumor activity is relative to a patient population without urothelial carcinoma.

In some embodiments, administration of the FGFR inhibitor in combination with the anti-PD1 antibody or antigen binding fragment thereof does not result in hematological toxicity, in particular does not result in hematological toxicity of Grade 3 or higher. In still further embodiments, administration of the FGFR inhibitor in combination with the anti-PD1 antibody or antigen binding fragment thereof does not result in non-hematological toxicity of Grade 3 or higher.

Also described herein are methods of improving objective response rate in a patient with urothelial carcinoma relative to a patient that has been diagnosed with urothelial carcinoma that has not received treatment with an FGFR inhibitor and an anti-PD1 antibody or antigen binding fragment thereof, said method comprising, consisting of, or consisting essential of, administering a FGFR inhibitor at a dose of about 8 mg per day in combination with an anti-PD1 antibody or antigen binding fragment thereof at a dose of about 240 mg every two weeks to a patient that has been diagnosed with urothelial carcinoma who harbors at least one FGFR2 genetic alteration and/or FGFR3 genetic alteration. Also described herein are methods of improving disease control rate in a patient with urothelial carcinoma relative to a patient that has been diagnosed with urothelial carcinoma that has not received treatment with an FGFR inhibitor and an anti-PD1 antibody or antigen binding fragment thereof, said method comprising, consisting of, or consisting essential of, administering a FGFR inhibitor at a dose of about 8 mg per day in combination with an anti-PD1 antibody or antigen binding fragment thereof at a dose of about 240 mg every two weeks to a patient that has been diagnosed with urothelial carcinoma who harbors at least one FGFR2 genetic alteration and/or FGFR3 genetic alteration. In an embodiment, the anti-PD1 antibody or antigen binding fragment thereof is administered or is to be administered at a dose of about 240 mg every two weeks in cycle 1 to 4 of treatment.

Also described herein are methods of improving objective response rate in a patient with urothelial carcinoma relative to a patient that has been diagnosed with urothelial carcinoma that has not received treatment with an FGFR inhibitor and an anti-PD1 antibody or antigen binding fragment thereof, said method comprising, consisting of, or consisting essential of, administering a FGFR inhibitor at a dose of about 8 mg per day in combination with an anti-PD1 antibody or antigen binding fragment thereof at a dose of about 360 mg every three weeks to a patient that has been diagnosed with urothelial carcinoma who harbors at least one FGFR2 genetic alteration and/or FGFR3 genetic alteration. Also described herein are methods of improving disease control rate in a patient with urothelial carcinoma relative to a patient that has been diagnosed with urothelial carcinoma that has not received treatment with an FGFR inhibitor and an anti-PD1 antibody or antigen binding fragment thereof, said method comprising, consisting of, or consisting essential of, administering a FGFR inhibitor at a dose of about 8 mg per day in combination with an anti-PD1 antibody or antigen binding fragment thereof at a dose of about 360 mg every three weeks to a patient that has been diagnosed with urothelial carcinoma who harbors at least one FGFR2 genetic alteration and/or FGFR3 genetic alteration. In an embodiment, the treatment further comprises a platinum chemotherapy, in particular cisplatin or carboplatin. In an embodiment the platinum chemotherapy is administered or is to be administered every three weeks. In an embodiment, the platinum chemotherapy is administered or is to be administered at a dose of 50 $mg/m^2$, or 60 $mg/m^2$, or at a dose for a AUC of 4 mg/mL*min, or at a dose for a AUC of 5 mg/mL*min. In an embodiment, cisplatin is administered or is to be administered at a dose of 50 $mg/m^2$ or 60 $mg/m^2$. In an embodiment, carboplatin is administered or is to be administered at a dose for an AUC of 4 mg/mL*min or at a dose for an AUC of 5 mg/mL*min.

Also described herein are methods of improving objective response rate in a patient with urothelial carcinoma relative to a patient that has been diagnosed with urothelial carcinoma that has not received treatment with an FGFR inhibitor and an anti-PD1 antibody or antigen binding fragment thereof, said method comprising, consisting of, or consisting essential of, administering a FGFR inhibitor at a dose of about 8 mg per day in combination with an anti-PD1 antibody or antigen binding fragment thereof at a dose of about 480 mg every four weeks to a patient that has been diagnosed with urothelial carcinoma who harbors at least one FGFR2 genetic alteration and/or FGFR3 genetic alteration. Also described herein are methods of improving disease control rate in a patient with urothelial carcinoma relative to a patient that has been diagnosed with urothelial carcinoma that has not received treatment with an FGFR inhibitor and an anti-PD1 antibody or antigen binding fragment thereof, said method comprising, consisting of, or consisting essential of, administering a FGFR inhibitor at a dose of about 8 mg per day in combination with an anti-PD1 antibody or antigen binding fragment thereof at a dose of about 480 mg every four weeks to a patient that has been diagnosed with urothelial carcinoma who harbors at least one FGFR2 genetic alteration and/or FGFR3 genetic alteration. In an embodiment, the anti-PD1 antibody or antigen binding fragment thereof is administered or is to be administered at a dose of about 480 mg every four weeks as of cycle 5 of treatment and beyond.

In certain embodiments, the improvement is relative to treatment with placebo. In certain embodiments, the improvement is relative to no treatment. In certain embodiments, the improvement is relative to standard of care.

Evaluating a Sample for the Presence of One or More FGFR Genetic Alterations

Also described herein are methods of treating urothelial carcinoma comprising, consisting of, or consisting essential of: (a) evaluating a biological sample from a patient with urothelial carcinoma for the presence of one or more FGFR gene alterations, in particular one or more FGFR2 or FGFR3 gene alterations; and (b) administering a FGFR inhibitor at a dose of about 8 mg per day in combination with an anti-PD1 antibody or antigen binding fragment thereof at a dose of about 240 mg every two weeks or at a dose of about 360 mg every three weeks or at a dose of about 480 mg every four weeks to the patient if one or more FGFR gene alterations, in particular one or more FGFR2 or FGFR3 gene alterations, is present in the sample.

The following methods for evaluating a biological sample for the presence of one or more FGFR genetic alterations apply equally to any of the above disclosed methods of treatment and uses.

The disclosed methods are suitable for treating urothelial carcinoma in a patient if one or more FGFR genetic alterations are present in a biological sample from the patient. In some embodiments, the FGFR genetic alteration can be one or more FGFR fusion genes. In some embodiments, the FGFR genetic alteration can be one or more FGFR mutations. In some embodiments, the FGFR genetic alteration can be one or more FGFR amplifications. In some embodiments, a combination of the one or more FGFR genetic alterations can be present in the biological sample from the patient. For example, in some embodiments, the FGFR genetic alterations can be one or more FGFR fusion genes and one or more FGFR mutations. In some embodiments, the FGFR genetic alterations can be one or more FGFR fusion genes and one or more FGFR amplifications. In some embodiments, the FGFR genetic alterations can be one or more FGFR mutations and one or more FGFR amplifications. In yet other embodiments, the FGFR genetic alterations can be one or more FGFR fusion genes, mutations, and amplifications. Exemplary FGFR fusion genes are provided in Table 4 and include but are not limited to: FGFR2-BICC1; FGFR2-CASP7; FGFR3-BAIAP2L1; FGFR3-TACC3 V1; FGFR3-TACC3 V3; or a combination thereof.

Suitable methods for evaluating a biological sample for the presence of one or more FGFR genetic alterations are described in the methods section herein and in WO 2016/048833 and U.S. patent application Ser. No. 16/723,975, which are incorporated herein in their entireties. For example, and without intent to be limiting, evaluating a biological sample for the presence of one or more FGFR genetic alterations can comprise any combination of the following steps: isolating RNA from the biological sample; synthesizing cDNA from the RNA; and amplifying the cDNA (preamplified or non-preamplified). In some embodiments, evaluating a biological sample for the presence of one or more FGFR genetic alterations can comprise: amplifying cDNA from the patient with a pair of primers that bind to and amplify one or more FGFR genetic alterations; and determining whether the one or more FGFR genetic alterations are present in the sample. In some aspects, the cDNA can be pre-amplified. In some aspects, the evaluating step can comprise isolating RNA from the sample, synthesizing cDNA from the isolated RNA, and pre-amplifying the cDNA.

Suitable primer pairs for performing an amplification step include, but are not limited to, those disclosed in WO 2016/048833, as exemplified below in Table 6:

TABLE 6

| Target | Forward Primer | Reverse Primer 5'-3' |
|---|---|---|
| FGFR3-TACC3 V1 | GACCTGGACC GTGTCCTTAC C (SEQ ID NO: 5) | CTTCCCCAGT TCCAGGTTCT T (SEQ ID NO: 6) |
| FGFR3-TACC3 V3 | AGGACCTGGA CCGTGTCCTT (SEQ ID NO: 7) | TATAGGTCCG GTGGACAGGG (SEQ ID NO: 8) |

TABLE 6-continued

| Target | Forward Primer | Reverse Primer 5'-3' |
|---|---|---|
| FGFR3-BAIAP2L1 | CTGGACCGTG TCCTTACCGT (SEQ ID NO: 9) | GCAGCCCAGG ATTGAACTGT (SEQ ID NO: 10) |
| FGFR2-BICC1 | TGGATCGAAT TCTCACTCTC ACA (SEQ ID NO: 11) | GCCAAGCAAT CTGCGTATTT G (SEQ ID NO: 12) |
| FGFR2-CASP7 | GCTCTTCAAT ACAGCCCTGA TCA (SEQ ID NO: 13) | ACTTGGATCG AATTCTCACT CTCA (SEQ ID NO: 14) |
| FGFR2-CCDC6 | TGGATCGAAT TCTCACTCTC ACA (SEQ ID NO: 15) | GCAAAGCCTG AATTTTCTTG AATAA (SEQ ID NO: 16) |
| FGFR3 R248C | GCATCCGGCA GACGTACA (SEQ ID NO: 17) | CCCCGCCTGC AGGAT (SEQ ID NO: 18) |
| FGFR3 S249C | GCATCCGGCA GACGTACA (SEQ ID NO: 19) | CCCCGCCTGC AGGAT (SEQ ID NO: 20) |
| FGFR3 G370C | AGGAGCTGGT GGAGGCTGA (SEQ ID NO: 21) | CCGTAGCTGA GGATGCCTG (SEQ ID NO: 22) |
| FGFR3 Y373C | CTGGTGGAGG CTGACGAG (SEQ ID NO: 23) | AGCCCACCCC GTAGCT (SEQ ID NO: 24) |
| FGFR3 R248C | GTCGTGGAGA ACAAGTTTGG C (SEQ ID NO: 25) | GTCTGGTTGG CCGGCAG (SEQ ID NO: 26) |
| FGFR3 S249C | GTCGTGGAGA ACAAGTTTGG C (SEQ ID NO: 27) | GTCTGGTTGG CCGGCAG (SEQ ID NO: 28) |
| FGFR3 G370C | AGGAGCTGGT GGAGGCTGA (SEQ ID NO: 29) | CCGTAGCTGA GGATGCCTG (SEQ ID NO: 30) |
| FGFR3 Y373C | GACGAGGCGG GCAGTG (SEQIDNO: 31) | GAAGAAGCCC ACCCCGTAG (SEQ ID NO: 32) |

The presence of one or more FGFR genetic alterations can be evaluated at any suitable time point including upon diagnosis, following tumor resection, following first-line therapy, during clinical treatment, or any combination thereof For example, a biological sample taken from a patient may be analyzed to determine whether a condition or disease, such as cancer, that the patient is or may be suffering from is one which is characterized by a genetic abnormality or abnormal protein expression which leads to up-regulation of the levels or activity of FGFR or to sensitization of a pathway to normal FGFR activity, or to upregulation of these growth factor signaling pathways such as growth factor ligand levels or growth factor ligand activity or to upregulation of a biochemical pathway downstream of FGFR activation.

Examples of such abnormalities that result in activation or sensitization of the FGFR signal include loss of, or inhibition of apoptotic pathways, up-regulation of the receptors or ligands, or presence of genetic alterations of the receptors or ligands e.g. PTK variants. Tumors with genetic alterations of FGFR1, FGFR2 or FGFR3 or FGFR4 or up-regulation, in particular over-expression of FGFR1, or gain-of-function genetic alterations of FGFR2 or FGFR3 may be particularly sensitive to FGFR inhibitors.

The methods, approved drug products, and uses can further comprise evaluating the presence of one or more FGFR genetic alterations in the biological sample before the administering step.

The diagnostic tests and screens are typically conducted on a biological sample selected from tumor biopsy samples, blood samples (isolation and enrichment of shed tumor cells), stool biopsies, sputum, chromosome analysis, pleural fluid, peritoneal fluid, buccal spears, biopsy, circulating DNA, or urine. In certain embodiments, the biological sample is blood, lymph fluid, bone marrow, a solid tumor sample, or any combination thereof. In certain embodiments, the biological sample is a solid tumor sample. In certain embodiments, the biological sample is a blood sample. In certain embodiments, the biological sample is a urine sample.

Methods of identification and analysis of genetic alterations and up-regulation of proteins are known to a person skilled in the art. Screening methods could include, but are not limited to, standard methods such as reverse-transcriptase polymerase chain reaction (RT PCR) or in-situ hybridization such as fluorescence in situ hybridization (FISH).

Identification of an individual carrying a genetic alteration in FGFR, in particular an FGFR genetic alteration as described herein, may mean that the patient would be particularly suitable for treatment with erdafitinib. Tumors may preferentially be screened for presence of a FGFR variant prior to treatment. The screening process will typically involve direct sequencing, oligonucleotide microarray analysis, or a mutant specific antibody. In addition, diagnosis of tumor with such genetic alteration could be performed using techniques known to a person skilled in the art and as described herein such as RT-PCR and FISH.

In addition, genetic alterations of, for example FGFR, can be identified by direct sequencing of, for example, tumor biopsies using PCR and methods to sequence PCR products directly as hereinbefore described. The skilled artisan will recognize that all such well-known techniques for detection of the over expression, activation or mutations of the aforementioned proteins could be applicable in the present case.

In screening by RT-PCR, the level of mRNA in the tumor is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), 3rd Ed, Molecular Cloning: A Laboratory Manual, Cold Spring Harbor Laboratory Press. Alternatively, a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridization technique for assessing mRNA expression would be fluorescence in-situ hybridization (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer,* 3:3). Briefly, the protocol is as follows: double-stranded cDNA is synthesized from total RNA Using a (dT)24 oligomer (SEQ ID NO: 38: ttttttttt ttttttttt tttt) for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, CA, USA), and then hybridized overnight on Human Genome Arrays.

Alternatively, the protein products expressed from the mRNAs may be assayed by immunohistochemistry of tumor samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site-specific antibodies. The skilled person will recognize that all such well-known techniques for detection of upregulation of FGFR or detection of FGFR variants or mutants could be applicable in the present case.

Abnormal levels of proteins such as FGFR can be measured using standard enzyme assays, for example, those assays described herein. Activation or overexpression could also be detected in a tissue sample, for example, a tumor tissue. By measuring the tyrosine kinase activity with an assay such as that from Chemicon International. The tyrosine kinase of interest would be immunoprecipitated from the sample lysate and its activity measured.

Alternative methods for the measurement of the over expression or activation of FGFR including the isoforms thereof, include the measurement of microvessel density. This can for example be measured using methods described by Orre and Rogers (Int J Cancer (1999), 84(2) 101-8). Assay methods also include the use of markers.

Therefore, all of these techniques could also be used to identify tumors particularly suitable for treatment with the compounds of the invention.

Erdafitinib is in particular useful in treatment of a patient having a genetic altered FGFR, in particular a mutated FGFR. In certain embodiments, the urothelial carcinoma is susceptible to an FGFR2 genetic alteration and/or an FGFR3 genetic alteration. In certain embodiments, the FGFR2 or FGFR3 genetic alteration is an FGFR3 gene mutation or an FGFR2 or FGFR3 gene fusion. In some embodiments, the FGFR3 gene mutation is R248C, S249C, G370C, Y373C, or any combination thereof. In further embodiments, the FGFR2 or FGFR3 gene fusion is FGFR3-TACC3, in particular FGFR3-TACC3 V1 or V3, FGFR3-BAIAP2L1, FGFR2-BICC1, FGFR2-CASP7, or any combination thereof.

According to certain embodiments, FGFR2 and/or FGFR3 genetic alterations can be identified using commercially available kits including, but not limiting to, a QIAGEN Therascreen® FGFR RGQ RT-PCR kit.

FGFR Inhibitor Pharmaceutical Compositions and Routes of Administration

In view of its useful pharmacological properties, the FGFR inhibitor generally, and erdafitinib more specifically, may be formulated into various pharmaceutical forms for administration purposes.

In one embodiment the pharmaceutical composition (e.g. formulation) comprises at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

To prepare the pharmaceutical compositions, an effective amount of the FGFR inhibitor generally, and erdafitinib more specifically, as the active ingredient is combined in intimate admixture with a pharmaceutically acceptable carrier, which carrier may take a wide variety of forms depending on the form of preparation desired for administration. The pharmaceutical compositions can be in any form suitable for oral, parenteral, topical, intranasal, ophthalmic, otic, rectal, intra-vaginal, or transdermal administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

The pharmaceutical compositions of the invention, in particular capsules and/or tablets, may include one or more pharmaceutically acceptable excipients (pharmaceutically acceptable carrier) such as disintegrants, diluents, fillers, binders, buffering agents, lubricants, glidants, thickening agents, sweetening agents, flavors, colorants, preservatives and the like. Some excipients can serve multiple purposes.

Suitable disintegrants are those that have a large coefficient of expansion. Examples thereof are hydrophilic, insoluble or poorly water-soluble crosslinked polymers such as crospovidone (crosslinked polyvinylpyrrolidone) and croscarmellose sodium (crosslinked sodium carboxymethylcellulose). The amount of disintegrant in the tablets according to the present invention may conveniently range from about 2.5 to about 15% w/w and preferably range from about 2.5 to 7% w/w, in particular range from about 2.5 to 5% w/w. Because disintegrants by their nature yield sustained release formulations when employed in bulk, it is advantageous to dilute them with an inert substance called a diluent or filler.

A variety of materials may be used as diluents or fillers. Examples are lactose monohydrate, anhydrous lactose, sucrose, dextrose, mannitol, sorbitol, starch, cellulose (e.g. micro-crystalline cellulose (Avicel™), silicified microcrystalline cellulose), dihydrated or anhydrous dibasic calcium phosphate, and others known in the art, and mixtures thereof (e.g. spray-dried mixture of lactose monohydrate (75%) with microcrystalline cellulose (25%) which is commercially available as Microcelac™). Preferred are microcrystalline cellulose and mannitol. The total amount of diluent or filler in the pharmaceutical compositions of the present invention may conveniently range from about 20% to about 95% w/w and preferably ranges from about 55% to about 95% w/w, or from about 70% to about 95% w/w, or from about 80% to about 95% w/w, or from about 85% to about 95%.

Lubricants and glidants can be employed in the manufacture of certain dosage forms and will usually be employed when producing tablets. Examples of lubricants and glidants are hydrogenated vegetable oils, e.g hydrogenated Cottonseed oil, magnesium stearate, stearic acid, sodium lauryl sulfate, magnesium lauryl sulfate, colloidal silica, colloidal anhydrous silica talc, mixtures thereof, and others known in the art. Interesting lubricants are magnesium stearate, and mixtures of magnesium stearate with colloidal silica, magnesium stearate being preferred. A preferred glidant is colloidal anhydrous silica.

If present, glidants generally comprise 0.2 to 7.0% w/w of the total composition weight, in particular 0.5 to 1.5% w/w, more in particular 1 to 1.5% w/w.

If present, lubricants generally comprise 0.2 to 7.0% w/w of the total composition weight, in particular 0.2 to 2% w/w, or 0.5 to 2% w/w, or 0.5 to 1.75% w/w, or 0.5 to 1.5% w/w.

Binders can optionally be employed in the pharmaceutical compositions of the present invention. Suitable binders are water-soluble polymers, such as alkylcelluloses such as methylcellulose; hydroxyalkylcelluloses such as hydroxymethylcellulose, hydroxyethylcellulose, hydroxypropylcellulose and hydroxybutylcellulose; hydroxyalkyl alkylcelluloses such as hydroxyethyl methylcellulose and hydroxypropyl methylcellulose; carboxyalkylcelluloses such as carboxymethylcellulose; alkali metal salts of carboxyalkylcelluloses such as sodium carboxymethylcellulose; carboxyalkylalkylcelluloses such as carboxymethylethylcellulose; carboxyalkylcellulose esters; starches; pectines such as sodium carboxymethylamylopectine; chitin derivates such as chitosan; di-, oligo- and polysaccharides such as trehalose, cyclodextrins and derivatives thereof, alginic acid, alkali metal and ammonium salts thereof, carrageenans, galactomannans, tragacanth, agar agar, gummi arabicum, guar gummi and xanthan gummi; polyacrylic acids and the salts thereof; polymethacrylic acids, the salts and esters thereof, methacrylate copolymers; polyvinylpyrrolidone (PVP), polyvinylalcohol (PVA) and copolymers thereof, e.g. PVP-VA. Preferably, the water-soluble polymer is a hydroxyalkyl alkylcelluloses, such as for example hydroxypropylmethyl cellulose, e.g. hydroxypropylmethyl cellulose 15 cps.

Other excipients such as coloring agents and pigments may also be added to the compositions of the invention. Coloring agents and pigments include titanium dioxide and dyes suitable for food. A coloring agent or a pigment is an optional ingredient in the formulation of the invention, but when used the coloring agent can be present in an amount up to 3.5% w/w based on the total composition weight.

Flavors are optional in the composition and may be chosen from synthetic flavor oils and flavoring aromatics or natural oils, extracts from plants leaves, flowers, fruits and so forth and combinations thereof. These may include cinnamon oil, oil of wintergreen, peppermint oils, bay oil, anise oil, eucalyptus, thyme oil. Also useful as flavors are vanilla, citrus oil, including lemon, orange, grape, lime and grapefruit, and fruit essences, including apple, banana, pear, peach, strawberry, raspberry, cherry, plum, pineapple, apricot and so forth, the amount of flavor may depend on a number of factors including the organoleptic effect desired. Generally, the flavor will be present in an amount from about 0% to about 3% (w/w).

Formaldehyde scavengers are compounds that are capable of absorbing formaldehyde. They include compounds comprising a nitrogen center that is reactive with formaldehyde, such as to form one or more reversible or irreversible bonds between the formaldehyde scavenger and formaldehyde. For example, the formaldehyde scavenger comprises one or more nitrogen atoms/centers that are reactive with formaldehyde to form a schiff base imine that is capable of subsequently binding with formaldehyde. For example, the formaldehyde scavenger comprises one or more nitrogen centers that are reactive with formaldehyde to form one or more 5-8 membered cyclic rings. The formaldehyde scavenger preferably comprises one or more amine or amide groups. For example, the formaldehyde scavenger can be an amino acid, an amino sugar, an alpha amine compound, or a conjugate or derivative thereof, or a mixture thereof. The formaldehyde scavenger may comprise two or more amines and/or amides.

Formaldehyde scavengers include, for example, glycine, alanine, serine, threonine, cysteine, valine, leucine, isoleucine, methionine, phenylalanine, tyrosine, aspartic acid, glutamic acid, arginine, lysine, ornithine, citrulline, taurine pyrrolysine, meglumine, histidine, aspartame, proline, tryptophan, citrulline, pyrrolysine, asparagine, glutamine, or a conjugate or mixture thereof; or, whenever possible, pharmaceutically acceptable salts thereof.

In an aspect of the invention, the formaldehyde scavenger is meglumine or a pharmaceutically acceptable salt thereof, in particular meglumine base.

In an embodiment, in the methods and uses as described herein, erdafitinib is administered or is to be administered as a pharmaceutical composition, in particular a tablet or capsule, comprising erdafitinib or a pharmaceutically acceptable salt thereof, in particular erdafitinib base; a formaldehyde scavenger, in particular meglumine or a pharmaceutically acceptable salt thereof, in particular meglumine base; and a pharmaceutically acceptable carrier.

It is another object of the invention to provide a process of preparing a pharmaceutical composition as described herein, in particular in the form of a tablet or a capsule, characterized by blending a formaldehyde scavenger, in particular meglumine, and erdafitinib, a pharmaceutically acceptable salt thereof or a solvate thereof, in particular erdafitinib base, with a pharmaceutically acceptable carrier and compressing said blend into tablets or filling said blend in capsules.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

It is especially advantageous to formulate the aforementioned pharmaceutical compositions in dosage unit form for ease of administration and uniformity of dosage. Dosage unit form as used herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof. Preferred forms are tablets and capsules.

In certain embodiments, the FGFR inhibitor is present in a solid unit dosage form, and a solid unit dosage form suitable for oral administration. The unit dosage form may contain about 1, 2, 3, 4, 5, 6, 7, 8, 9, or 10 mg of the FGFR inhibitor per unit dose form or an amount in a range bounded by two of these values, in particular 3, 4 or 5 mg per unit dose.

Depending on the mode of administration, the pharmaceutical composition will preferably comprise from 0.05 to 99% by weight, more preferably from 0.1 to 70% by weight, even more preferably from 0.1 to 50% by weight of the compound of the present invention, and, from 1 to 99.95% by weight, more preferably from 30 to 99.9% by weight, even more preferably from 50 to 99.9% by weight of a pharmaceutically acceptable carrier, all percentages being based on the total weight of the composition.

Tablets or capsules of the present invention may further be film-coated e.g. to improve taste, to provide ease of swallowing and an elegant appearance. Polymeric film-coating materials are known in the art. Preferred film coatings are water-based film coatings opposed to solvent based film coatings because the latter may contain more traces of aldehydes. A preferred film-coating material is Opadry® II aqueous film coating system, e.g. Opadry® II 85F, such as Opadry® II 85F92209. Further preferred film coatings are water-based film coatings that protects from environmental moisture, such as Readilycoat® (e.g. Readilycoat® D), AquaPolish® MS, Opadry® amb, Opadry® amb II, which are aqueous moisture barrier film coating systems. A preferred film-coating is Opadry® amb II, a high-performance moisture barrier film coating which is a PVA-based immediate release system, without polyethylene glycol.

In tablets according to the invention, the film coat in terms of weight preferably accounts for about 4% (w/w) or less of the total tablet weight.

For capsules according to the present invention, hypromellose (HPMC) capsules are preferred over gelatin capsules.

In an aspect of the invention, the pharmaceutical compositions as described herein, in particular in the form of a capsule or a tablet, comprise from 0.5 mg to 20 mg base equivalent, or from 2 mg to 20 mg base equivalent, or from 0.5 mg to 12 mg base equivalent, or from 2 mg to 12 mg base equivalent, or from 2 mg to 10 mg base equivalent, or from 2 mg to 6 mg base equivalent, or 2 mg base equivalent, 3 mg base equivalent, 4 mg base equivalent, 5 mg base equivalent, 6 mg base equivalent, 7 mg base equivalent, 8 mg base equivalent, 9 mg base equivalent, 10 mg base equivalent, 11 mg base equivalent or 12 mg base equivalent of erdafitinib, a pharmaceutically acceptable salt thereof or a solvate thereof. In particular, the pharmaceutical compositions as described herein comprise 3 mg base equivalent, 4 mg base equivalent or 5 mg base equivalent of erdafitinib, a pharmaceutically acceptable salt thereof or a solvate thereof, in particular 3 mg or 4 mg or 5 mg of erdafitinib base.

In an aspect of the invention, the pharmaceutical compositions as described herein, in particular in the form of a capsule or a tablet, comprise from 0.5 mg to 20 mg, or from 2 mg to 20 mg, or from 0.5 mg to 12 mg, or from 2 mg to 12 mg, or from 2 mg to 10 mg, or from 2 mg to 6 mg, or 2 mg, 3 mg, 4 mg, 5 mg, 6 mg, 7 mg, 8 mg, 9 mg, 10 mg, 11 mg or 12 mg of erdafitinib base. In particular, the pharmaceutical compositions as described herein comprise 3 mg, 4 mg or 5 mg of erdafitinib base. In particular, the pharmaceutical compositions as described herein comprise 3 mg, 4 mg or 5 mg of erdafitinib base and from about 0.5 to about 5% w/w, from about 0.5 to about 3% w/w, from about 0.5 to about 2% w/w, from about 0.5 to about 1.5% w/w, or from about 0.5 to about 1% w/w of a formaldehyde scavenger, in particular meglumine. In particular, the pharmaceutical compositions as described herein comprise 3 mg, 4 mg or 5 mg of erdafitinib base and from about 0.5 to about 1.5% w/w or from about 0.5 to about 1% w/w of a formaldehyde scavenger, in particular meglumine.

In an aspect of the invention, more than one, e.g. two, pharmaceutical compositions as described herein can be administered in order to obtain a desired dose, e.g. a daily dose. For example, for a daily dose of 8 mg base equivalent of erdafitinib, 2 tablets or capsules of 4 mg erdafitinib base equivalent each may be administered; or a tablet or a capsule of 3 mg erdafitinib base equivalent and a tablet or capsule of 5 mg base equivalent may be administered. For example, for a daily dose of 9 mg base equivalent of erdafitinib, 3 tablets or capsules of 3 mg erdafitinib base equivalent each may be administered; or a tablet or a capsule of 4 mg erdafitinib base equivalent and a tablet or capsule of 5 mg base equivalent may be administered.

The amount of formaldehyde scavenger, in particular meglumine, in the pharmaceutical compositions according to the present invention may range from about 0.1 to about 10% w/w, about 0.1 to about 5% w/w, from about 0.1 to about 3% w/w, from about 0.1 to about 2% w/w, from about 0.1 to about 1.5% w/w, from about 0.1 to about 1% w/w, from about 0.5 to about 5% w/w, from about 0.5 to about 3% w/w, from about 0.5 to about 2% w/w, from about 0.5 to about 1.5% w/w, from about 0.5 to about 1% w/w.

According to particular embodiments, erdafitinib is supplied as 3 mg, 4 mg or 5 mg film-coated tablets for oral administration and contains the following inactive ingredients or equivalents thereof: Tablet Core: croscarmellose sodium, magnesium stearate, mannitol, meglumine, and microcrystalline cellulose; and Film Coating: Opadry amb II: Glycerol monocaprylocaprate Type I, polyvinyl alcohol-partially hydrolyzed, sodium lauryl sulfate, talc, titanium dioxide, iron oxide yellow, iron oxide red (for orange and brown tablets), ferrosoferric oxide/iron oxide black (for brown tablets).

Studies that look at safety seek to identify any potential adverse effects that may result from exposure to the drug. Efficacy is often measured by determining whether an active pharmaceutical ingredient demonstrates a health benefit over a placebo or other intervention when tested in an appropriate situation, such as a tightly controlled clinical trial.

The term "acceptable" with respect to a formulation, composition or ingredient, as used herein, means that the beneficial effects of that formulation, composition or ingredient on the general health of the human being treated substantially outweigh its detrimental effects, to the extent any exist.

All formulations for oral administration are in dosage form suitable for such administration.

Anti-PD1 Antibody Pharmaceutical Compositions and Routes of Administration

In view of its useful pharmacological properties, the anti-PD1 antibody or antigen fragment thereof generally, and cetrelimab more specifically, may be formulated into various pharmaceutical forms for administration purposes.

In some embodiments, the anti-PD-1 antibody or the antigen binding fragment thereof is administered or provided for administration in a pharmaceutical composition comprising between about 10 mg/ml to about 30 mg/ml of the anti-PD-1 antibody or the antigen binding fragment thereof and one or more pharmaceutically acceptable excipients.

Exemplary buffers that may be used are acetic acid, citric acid, formic acid, succinic acid, phosphoric acid, carbonic acid, malic acid, aspartic acid, histidine, boric acid, Tris buffers, HEPPSO and HEPES.

Exemplary antioxidants that may be used are ascorbic acid, methionine, cysteine hydrochloride, sodium bisulfate, sodium metabisulfite, sodium sulfite, lecithin, citric acid, ethylenediamine tetraacetic acid (EDTA), sorbitol and tartaric acid.

Exemplary amino acids that may be used are histidine, isoleucine, methionine, glycine, arginine, lysine, L-leucine, tri-leucine, alanine, glutamic acid, L-threonine, and 2-phenylamine.

Exemplary surfactants that may be used are polysorbates (e.g., polysorbate-20 or polysorbate-80); polyoxamers (e.g., poloxamer 188); Triton; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUA™ series (Mona Industries, Inc., Paterson, N.J.), polyethyl glycol, polypropyl glycol, and copolymers of ethylene and propylene glycol (e.g., PLURONICS™, PF68, etc).

Exemplary preservatives that may be used are phenol, m-cresol, p-cresol, o-cresol, chlorocresol, benzyl alcohol, phenylmercuric nitrite, phenoxyethanol, formaldehyde, chlorobutanol, magnesium chloride, alkylparaben (methyl, ethyl, propyl, butyl and the like), benzalkonium chloride, benzethonium chloride, sodium dehydroacetate and thimerosal, or mixtures thereof.

Exemplary saccharides that may be used are monosaccharides, disaccharides, trisaccharides, polysaccharides, sugar alcohols, reducing sugars, nonreducing sugars such as glucose, sucrose, trehalose, lactose, fructose, maltose, dextran, glycerin, dextran, erythritol, glycerol, arabitol, sylitol, sorbitol, mannitol, mellibiose, melezitose, raffinose, mannotriose, stachyose, maltose, lactulose, maltulose, glucitol, maltitol, lactitol or iso-maltulose.

Exemplary salts that may be used are acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like. An exemplary salt is sodium chloride.

The amounts of pharmaceutically acceptable carrier(s) in the pharmaceutical compositions may be determined experimentally based on the activities of the carrier(s) and the desired characteristics of the formulation, such as stability and/or minimal oxidation.

In some embodiments, the pharmaceutical composition comprises histidine. In some embodiments, the pharmaceutical composition comprises histidine at a concentration of from about 1 mM to about 50 mM. In some embodiments, the pharmaceutical composition comprises histidine at a concentration of from about 5 mM to about 50 mM. In some embodiments, the pharmaceutical composition comprises histidine at a concentration of from about 5 mM to about 30 mM. In some embodiments, the pharmaceutical composition comprises histidine at a concentration of from about 5 mM to about 20 mM. In some embodiments, the pharmaceutical composition comprises histidine at a concentration of from about 5 mM to about 15 mM. In some embodiments, the pharmaceutical composition comprises histidine at a concentration of from about 5 mM to about 10 mM.

In some embodiments, the pharmaceutical composition comprises histidine at a concentration of about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM or about 50 mM.

In some embodiments, the pharmaceutical composition comprises histidine at a concentration of about 10 mM.

In some embodiments, the pharmaceutical composition comprises sucrose. In some embodiments, the pharmaceutical composition comprises sucrose at a concentration of from about 1% (w/v) to about 20% (w/v). In some embodiments, the pharmaceutical composition comprises sucrose at a concentration of from about 2% (w/v) to about 18% (w/v). In some embodiments, the pharmaceutical composition comprises sucrose at a concentration of from about 4% (w/v) to about 16% (w/v). In some embodiments, the pharmaceutical composition comprises sucrose at a concentration of from about 6% (w/v) to about 14% (w/v). In some embodiments, the pharmaceutical composition comprises sucrose at a concentration of from about 6% (w/v) to about 12% (w/v). In some embodiments, the pharmaceutical composition comprises sucrose at a concentration of from about 6% (w/v) to about 10% (w/v).

In some embodiments, the pharmaceutical composition comprises sucrose at a concentration of about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), about 11% (w/v), about 12% (w/v), about 13% (w/v), about 14% (w/v), about 150% (w/v), about 16% (w/v), about 17% (w/v), about 18% (w/v), about 19% (w/v) or about 20% (w/v), In some embodiments, the pharmaceutical composition comprises sucrose at a concentration of about 8% (w/v).

In some embodiments, the pharmaceutical composition comprises polysorbate-20. In some embodiments, the pharmaceutical composition comprises polysorbate-20 (PS-20) at a concentration of from about 0.01% (w/v) to about 0.1% (w/v). In some embodiments, the pharmaceutical composition comprises polysorbate-20 (PS-20) at a concentration of from about 0.01% (w/v) to about 0.08% (w/v). In some embodiments, the pharmaceutical composition comprises polysorbate-20 (PS-20) at a concentration of from about 0.02% (w/v) to about 0.06% (w/v).

In some embodiments, the pharmaceutical composition comprises polysorbate-20 (PS-20) at a concentration of about 0.01% (w/v), about 0.02% (w/v), about 0.03% (w/v), about 0.04% (w/v), about 0.05% (w/v), about 0.06% (w/v), about 0.07% (w/v), about 0.08% (w/v), about 0.09% (w/v) or about 0.1% (w/v).

In some embodiments, the pharmaceutical composition comprises polysorbate-20 (PS-20) at a concentration of about 0.04% (w/v).

In some embodiments, the pharmaceutical composition comprises EDTA. In some embodiments, the pharmaceutical composition comprises EDTA at a concentration of from about 1 μg/ml to about 50 μg/ml. In some embodiments, the pharmaceutical composition comprises EDTA at a concentration of from about 5 μg/ml to about 50 μg/ml. In some embodiments, the pharmaceutical composition comprises EDTA at a concentration of from about 5 μg/ml to about 30 μg/ml. In some embodiments, the pharmaceutical composition comprises EDTA at a concentration of from about 5 μg/ml to about 20 μg/ml. In some embodiments, the pharmaceutical composition comprises EDTA at a concentration of from about 5 μg/ml to about 15 μg/ml. In some embodiments, the pharmaceutical composition comprises EDTA at a concentration of from about 5 μg/ml to about 10 μg/ml.

In some embodiments, the pharmaceutical composition comprises EDTA at a concentration of about 1 μg/ml, about 2 μg/ml, about 3 μg/ml, about 4 μg/ml, about 5 μg/ml, about 6 μg/ml, about 7 μg/ml, about 8 μg/ml, about 9 μg/ml, about 10 μg/ml, about 11 μg/ml, about 12 μg/ml, about 13 μg/ml, about 14 μg/ml, about 15 μg/ml, about 16 μg/ml, about 17 μg/ml, about 18 μg/ml, about 19 μg/ml, about 20 μg/ml, about 21 μg/ml, about 22 μg/ml, about 23 μg/ml, about 24 μg/ml, about 25 μg/ml, about 26 μg/ml, about 27 μg/ml, about 28 μg/ml, about 29 μg/ml, about 30 μg/ml, about 31 μg/ml, about 32 μg/ml, about 33 μg/ml, about 34 μg/ml, about 35 μg/ml, about 36 μg/ml, about 37 μg/ml, about 38 μg/ml, about 39 μg/ml, about μg/ml, about 41 μg/ml, about 42 μg/ml, about 43 μg/ml, about 44 μg/ml, about 45 μg/ml, about 46 μg/ml, about 47 μg/ml, about 48 μg/ml, about 49 μg/ml or about 50 μg/ml.

In some embodiments, the pharmaceutical composition comprises EDTA at a concentration of about 20 μg/ml.

In some embodiments, the anti-PD-1 antibody or the antigen binding fragment thereof is administered or provided for administration in a pharmaceutical composition comprising between about 10 mg/ml to about 30 mg/ml of the antagonistic anti-PD-1 antibody or the antigen binding fragment thereof, histidine, sucrose, polysorbate-20 and EDTA.

In some embodiments, the anti-PD-1 antibody or the antigen binding fragment thereof is administered or provided for administration in a pharmaceutical composition comprising between about 10 mg/ml to about 30 mg/ml of the antagonistic anti-PD-1 antibody or the antigen binding fragment thereof, about 10 mM histidine, about 8.0% (w/v) sucrose, about 0.04% (w/v) polysorbate-20 and about 20 μg/ml EDTA at pH 6.5.

In some embodiments, the anti-PD-1 antibody or the antigen binding fragment thereof is administered or provided for administration in a pharmaceutical composition comprising about 10 mg/ml of the antagonistic anti-PD-1 antibody or the antigen binding fragment thereof, about 10 mM histidine, about 8.0% (w/v) sucrose, about 0.04% (w/v) polysorbate-20 and about 20 μg/ml EDTA at pH 6.5.

In some embodiments, the anti-PD-1 antibody or the antigen binding fragment thereof is administered or provided for administration in a pharmaceutical composition comprising about 30 mg/ml of the antagonistic anti-PD-1 antibody or the antigen binding fragment thereof, about 10 mM histidine, about 8.0% (w/v) sucrose, about 0.04% (w/v) polysorbate-20 and about 20 μg/ml EDTA at pH 6.5.

In some embodiments, the anti-PD-1 antibody or the antigen binding fragment thereof is provided for administration as a lyophilized formulation comprising between about 90 mg and about 240 mg of the antagonistic anti-PD-1 antibody or the antigen binding fragment thereof and one or more pharmaceutically acceptable excipients.

In some embodiments, the anti-PD-1 antibody or the antigen binding fragment thereof is provided for administration as a lyophilized formulation comprising about 90 mg of the antagonistic anti-PD-1 antibody or the antigen binding fragment thereof and one or more pharmaceutically acceptable excipients.

In some embodiments, the anti-PD-1 antibody or the antigen binding fragment thereof is provided for administration as a lyophilized formulation comprising about 240 mg of the antagonistic anti-PD-1 antibody or the antigen binding fragment thereof and one or more pharmaceutically acceptable excipients.

In some embodiments, the anti-PD-1 antibody or the antigen binding fragment thereof is provided for administration as a lyophilized formulation comprising about 360 mg of the antagonistic anti-PD-1 antibody or the antigen binding fragment thereof and one or more pharmaceutically acceptable excipients.

In some embodiments, the anti-PD-1 antibody or the antigen binding fragment thereof is provided for administration as a lyophilized formulation comprising about 480 mg of the antagonistic anti-PD-1 antibody or the antigen binding fragment thereof and one or more pharmaceutically acceptable excipients.

In some embodiments, the lyophilized formulation, once reconstituted, comprises about 30 mg/ml of the anti-PD-1 antibody or the antigen binding fragment thereof, about 10 mM histidine, about 8.0% (w/v) sucrose, about 0.04% (w/v) polysorbate-20 and about 20 μg/ml EDTA at pH 6.5.

In some embodiments, the pharmaceutical composition is a liquid. In some embodiments, the pharmaceutical composition is a frozen liquid. In some embodiments, the pharmaceutical composition is a lyophilized powder.

"Lyophilization," "lyophilized," and "freeze-dried" refer to a process by which the material to be dried is first frozen and then the ice or frozen solvent is removed by sublimation in a vacuum environment. An excipient may be included in pre-lyophilized formulations to enhance stability of the lyophilized product upon storage.

In some embodiments, the pharmaceutical composition is provided in a volume of between about 1 ml to about 20 ml. In some embodiments, the pharmaceutical composition is provided in a volume of about 1 ml, about 2 ml, about 3 ml, about 4 ml, about 5 ml, about 6 ml, about 7 ml, about 8 ml, about 9 ml, about 10 ml, about 11 ml, about 12 ml, about 13 ml, about 14 ml, about 15 ml, about 16 ml, about 17 ml, about 18 ml, about 19 ml or about 20 ml. In some embodiments, the pharmaceutical composition is provided or reconstituted in a volume of about 3 ml. In some embodiments, the pharmaceutical composition is provided or reconstituted in a volume of about 3.3 ml. In some embodiments, the pharmaceutical composition is provided or reconstituted in a volume of about 8 ml. In some embodiments, the pharmaceutical composition is provided or reconstituted in a volume of about 8.6 ml. In some embodiments, the pharmaceutical composition is provided or reconstituted in a volume of about 8.8 ml.

In some embodiments, the anti-PD-1 antibody or the antigen binding fragment thereof generally, or cetrelimab specifically, is administered or provided for administration in a pharmaceutical composition comprising about 10 mg/ml of the anti-PD-1 antibody or the antigen binding fragment thereof, about 10 mM histidine, about 8.0% (w/v) sucrose, about 0.04% (w/v) polysorbate-20 and about 20 μg/ml EDTA at pH 6.5 in a volume of about 3.3 ml.

In some embodiments, the antagonistic anti-PD-1 antibody or the antigen binding fragment thereof generally, or cetrelimab specifically, is administered or provided for administration as a lyophilized formulation comprising about 90 mg of the antagonistic anti-PD-1 antibody or the antigen binding fragment thereof and one or more pharmaceutically acceptable excipients that upon reconstitution into about 3.3 ml comprises about 30 mg/ml of the antagonistic anti-PD-1 antibody or the antigen binding fragment thereof, about 10 mM histidine, about 8.0% (w/v) sucrose, about 0.04% (w/v) polysorbate-20 and about 20 μg/ml EDTA at pH 6.5.

In some embodiments, the antagonistic anti-PD-1 antibody or the antigen binding fragment thereof generally, or cetrelimab specifically, is administered or provided for administration as a lyophilized formulation comprising about 240 mg of the antagonistic anti-PD-1 antibody or the antigen binding fragment thereof and one or more pharmaceutically acceptable excipients that upon reconstitution into about 8.6 ml comprises about 30 mg/ml of the antagonistic anti-PD-1 antibody or the antigen binding fragment thereof, about 10 mM histidine, about 8.0% (w/v) sucrose, about 0.04% (w/v) polysorbate-20 and about 20 μg/ml EDTA at pH 6.5.

In some embodiments, the lyophilized formulation is reconstituted into sterile water for injection (sWFI).

"Reconstitute", "reconstituted" or "reconstitution" refers to dissolving the lyophilized formulation in a diluent so that the protein in the lyophilized formulation is dispersed in the reconstituted formulation. The reconstituted formulation is suitable for administration, e.g. parenteral administration), and may optionally be suitable for subcutaneous administration. In some embodiments, the diluent is sterile water for injection (sWFI).

"Pharmaceutical composition", "pharmaceutical formulation" or "formulation" as used in this section refers to a combination of an active ingredient (e.g. the anti-PD-1 antibody) and one or more excipients in either liquid or solid (e.g. lyophilized) form.

All formulations for intravenous or subcutaneous administration are in dosage form suitable for such administration.

Methods of Dosing and Treatment Regimens

In one aspect, described herein are methods of treating urothelial carcinoma comprising, consisting of, or consisting essentially of administering a therapeutically effective amount of an FGFR inhibitor to a patient that has been diagnosed with urothelial carcinoma, wherein the FGFR inhibitor is administered orally. In some embodiments, the FGFR inhibitor generally, and erdafitinib specifically is administered daily, in particular once daily. In some embodiments, the FGFR inhibitor generally, and erdafitinib specifically is administered twice-a-day. In some embodiments, the FGFR inhibitor generally, and erdafitinib specifically is administered three times a day. In some embodiments, the FGFR inhibitor generally, and erdafitinib specifically is administered four times a day. In some embodiments, the FGFR inhibitor generally, and erdafitinib specifically is administered every other day. In some embodiments, the FGFR inhibitor generally, and erdafitinib specifically is administered weekly. In some embodiments, the FGFR inhibitor generally, and erdafitinib specifically is administered twice a week. In some embodiments, the FGFR inhibitor generally, and erdafitinib specifically is administered every other week. In some embodiments, the FGFR inhibitor generally, and erdafitinib specifically is administered orally on a continuous daily dosage schedule.

In general, doses of the FGFR inhibitor, and erdafitinib specifically, employed for treatment of the diseases or conditions described herein in humans are typically in the range of about 1 to 20 mg per day. In some embodiments, the FGFR inhibitor, and erdafitinib specifically, is administered orally to the human at a dose of about 1 mg per day, about 2 mg per day, about 3 mg per day, about 4 mg per day, about 5 mg per day, about 6 mg per day, about 7 mg per day, about 8 mg per day, about 9 mg per day, about 10 mg per day, about 11 mg per day, about 12 mg per day, about 13 mg per day, about 14 mg per day, about 15 mg per day, about 16 mg per day, about 17 mg per day, about 18 mg per day, about 19 mg per day or about 20 mg per day. In an embodiment, erdafitinib is administered at a dose of 8 mg per day.

In some embodiments, erdafitinib is administered orally. In certain embodiments, erdafitinib is administered orally at a dose of about 8 mg once daily. In further embodiments, the dose of erdafitinib is increased from 8 mg once daily to 9 mg once daily. In still further embodiments, the dose of erdafitinib is increased from 8 mg once daily to 9 mg once daily at 14 to 21 days after initiating treatment if. (a) the patient exhibits a serum phosphate ($PO_4$) level that is less than about 5.5 mg/dL at 14-21 days after initiating treatment and administration of erdafitinib at 8 mg once daily resulted in no ocular disorder; or (b) administration of erdafitinib at 8 mg once daily resulted in no Grade 2 or greater adverse reaction.

In certain embodiments, the dose of erdafitinib is increased from 8 mg once daily to 9 mg once daily at 14 days after initiating treatment. In certain embodiments, the dose of erdafitinib is increased from 8 mg once daily to 9 mg once daily at 15 days after initiating treatment. In certain embodiments, the dose of erdafitinib is increased from 8 mg once daily to 9 mg once daily at 16 days after initiating treatment. In certain embodiments, the dose of erdafitinib is increased from 8 mg once daily to 9 mg once daily at 17 days after initiating treatment. In certain embodiments, the dose of erdafitinib is increased from 8 mg once daily to 9 mg once daily at 18 days after initiating treatment. In certain embodiments, the dose of erdafitinib is increased from 8 mg once daily to 9 mg once daily at 19 days after initiating treatment. In certain embodiments, the dose of erdafitinib is increased from 8 mg once daily to 9 mg once daily at 20 days after initiating treatment. In certain embodiments, the dose of erdafitinib is increased from 8 mg once daily to 9 mg once daily at 21 days after initiating treatment In an embodiment, erdafitinib is administered at a dose of 8 mg, in particular 8 mg once daily. In an embodiment, erdafitinib is administered at a dose of 8 mg, in particular 8 mg once daily, with an option to uptitrate to 9 mg depending on serum phosphate levels (e.g. serum phosphate levels are $<5.5$ mg/dL, or are $<7$ mg/dL or range from and include 7 mg/dL to $\leq 9$ mg/dL or are $\leq 9$ mg/dL), and depending on treatment-related adverse events observed. In an embodiment, the levels of serum phosphate for determining whether or not to up-titrate are measured on a treatment day during the first cycle of erdafitinib treatment, in particular on day 14±2 days, more in particular on day 14, of erdafitinib administration.

In an embodiment, the treatment cycle as used herein is a 28-day cycle. In certain embodiments, the treatment cycle is a 28-day cycle for up to two years. In certain embodiments, the treatment cycle is four weeks.

In one embodiment, the desired dose is conveniently presented in a single dose or in divided doses administered simultaneously (or over a short period of time) or at appropriate intervals, for example as two, three, four or more sub-doses per day. In some embodiments, the FGFR inhibitor is conveniently presented in divided doses that are administered simultaneously (or over a short period of time) once a day. In some embodiments, the FGFR inhibitor generally, and erdafitinib specifically, is conveniently presented in divided doses that are administered in equal portions twice-a-day. In some embodiments, the FGFR inhibitor generally, and erdafitinib specifically, is conveniently presented in divided doses that are administered in equal portions three times a day. In some embodiments, the FGFR inhibitor is conveniently presented in divided doses that are administered in equal portions four times a day.

In certain embodiments, the desired dose may be delivered in 1, 2, 3, 4, 5, 6, 7, 8, 9, or 10 fractional unit dosages throughout the course of the day, such that the total amount of FGFR inhibitor generally, and erdafitinib specifically, delivered by the fractional unit dosages over the course of the day provides the total daily dosages.

In some embodiments, the amount of the FGFR inhibitor generally, and erdafitinib specifically, that is given to the human varies depending upon factors such as, but not limited to, condition and severity of the disease or condition, and the identity (e.g., weight) of the human, and the particular additional therapeutic agents that are administered (if applicable).

In further embodiments, the anti-PD1 antibody generally, and cetrelimab specifically, is administered by intravenous infusion. In some embodiments, the antagonistic anti-PD-1 antibody or the antigen binding fragment thereof is diluted into a volume of between about 100 ml and 1000 ml prior to administration. In some embodiments, duration of the intravenous infusion is between about 20 minutes and about 80 minutes. In some embodiments, duration of the intravenous infusion is about 20, about 30, about 40, about 50, about 60, about 70 or about 80 minutes.

In some embodiments, the anti-PD-1 antibody or the antigen binding fragment thereof is administered by one or more subcutaneous injections.

In some embodiments, the anti-PD1 antibody or the antigen binding fragment thereof is administered by an intravenous administration, by a subcutaneous administration, or a combination thereof.

In still further embodiments, the anti-PD1 antibody or the antigen binding fragment thereof generally, and cetrelimab specifically, is administered at a dose of about 240 mg once every two weeks, once every three weeks, once every four weeks, once every five weeks or once every six weeks. In some embodiments, the anti-PD-1 antibody or the antigen binding fragment thereof is administered at the dosage of about 240 mg once every two weeks. In some embodiments, the anti-PD-1 antibody or the antigen binding fragment thereof is administered at a dose of about 240 mg once every three weeks. In some embodiments, the anti-PD-1 antibody or the antigen binding fragment thereof is administered at a dose of about 240 mg once every four weeks. In some embodiments, the anti-PD-1 antibody or the antigen binding fragment thereof is administered at a dose of about 240 mg once every five weeks. In some embodiments, the anti-PD-1 antibody or the antigen binding fragment thereof is administered at a dose of about 240 mg once every six weeks. In some embodiments, the anti-PD-1 antibody or the antigen binding fragment thereof is administered at a dose of about 480 mg once every two weeks, once every three weeks, once every four weeks, once every five weeks or once every six weeks. In some embodiments, the anti-PD-1 antibody or the antigen binding fragment thereof is administered at a dose of about 480 mg once every two weeks. In some embodiments, the anti-PD-1 antibody or the antigen binding fragment thereof is administered at a dose of about 480 mg once every three weeks. In some embodiments, the anti-PD-1 antibody or the antigen binding fragment thereof is administered at a dose of about 480 mg once every four weeks. In some embodiments, the anti-PD-1 antibody or the antigen binding fragment thereof is administered at a dose of about 480 mg once every five weeks. In some embodiments, the anti-PD-1 antibody or the antigen binding fragment thereof is administered at a dose of about 480 mg once every six weeks.

In certain embodiments, the anti-PD1 antibody or the antigen binding fragment thereof generally, and cetrelimab specifically, is administered at a dose of about 240 mg to about 480 mg once every two weeks, once every three weeks, once every four weeks, once every five weeks or once every six weeks. In certain embodiments, the anti-PD1 antibody or the antigen binding fragment thereof generally, and cetrelimab specifically, is administered at a dose of about 80 mg to about 1000 mg once every two weeks, once every three weeks, once every four weeks, once every five weeks or once every six weeks.

In some embodiments, the anti-PD1 antibody or the antigen binding fragment thereof generally, and cetrelimab specifically, is administered at a dosage of about 240 mg once in two weeks; at a dosage of about 480 mg once in four weeks; or as an initial dose of about 240 mg followed by a second dose of about 480 mg six weeks after the initial dose, and thereafter about 480 mg once in four weeks; or as an initial dose of about 240 mg followed by a second dose of about 480 mg six weeks after the initial dose, and thereafter about 240 mg once in two weeks. In some embodiments, the anti-PD1 antibody or the antigen binding fragment thereof generally, and cetrelimab specifically, is administered at a dosage of about 240 mg once every two weeks in cycle 1 to 4 of treatment followed by a dose of about 480 mg every four weeks as of cycle 5 of treatment and beyond.

In one embodiment, erdafitinib is administered or is to be administered at a dose of 8 mg daily, and cetrelimab is administered or is to be administered at a dose of 240 mg every two weeks starting at cycle 1 day 1 (C1D1). In certain embodiments, erdafitinib is administered or is to be administered orally at a dose of 8 mg daily, and cetrelimab is administered or is to be administered intravenously at a dose of 240 mg every two weeks starting at cycle 1 day 1 (C1D1).

In one embodiment, erdafitinib is administered or is to be administered at a dose of 8 mg daily, and cetrelimab is administered or is to be administered at a dose of 480 mg every four weeks, in particular starting at cycle 1 day 1 (C1D1). In certain embodiments, erdafitinib is administered or is to be administered orally at a dose of 8 mg daily, and cetrelimab is administered or is to be administered intravenously at a dose of 480 mg every four weeks, in particular starting at cycle 1 day 1 (C1D1).

In one embodiment, erdafitinib is administered or is to be administered at a dose of 8 mg daily, and cetrelimab is administered or is to be administered at a dose of 240 mg every two weeks starting at cycle 1 day 1 (C1D1), and as of cycle 5 cetrelimab is administered or is to be administered at a dose of 480 mg every four weeks starting at cycle 5 day 1 (C5D1). In certain embodiments, erdafitinib is administered or is to be administered orally at a dose of 8 mg daily, and cetrelimab is administered or is to be administered at a dose of 240 mg every two weeks starting at cycle 1 day 1 (C1D1), and as of cycle 5 cetrelimab is administered or is to be administered at a dose of 480 mg every four weeks starting at cycle 5 day 1 (C5D1).

In one embodiment, erdafitinib is administered or is to be administered at a dose of 8 mg daily, and cetrelimab is administered or is to be administered at a dose of 360 mg every three weeks starting at cycle 1 day 1 (C1D1). In certain embodiments, erdafitinib is administered or is to be administered orally at a dose of 8 mg daily, and cetrelimab is administered or is to be administered at a dose of 360 mg every three weeks starting at cycle 1 day 1 (C1D1). In an embodiment, the treatment further comprises platinum chemotherapy, in particular cisplatin or carboplatin. In an embodiment, the platinum chemotherapy, in particular cisplatin or carboplatin, is administered or is to be administered every three weeks starting at cycle 1 day 1 (C1D1). In an embodiment, the platinum chemotherapy is administered or is to be administered at a dose of 50 mg/$m^2$, or 60 mg/$m^2$, or at a dose for a AUC of 4 mg/mL*min, or at a dose for a AUC of 5 mg/mL*min. In an embodiment, cisplatin is administered or is to be administered at a dose of 50 mg/$m^2$ or 60 mg/$m^2$. In an embodiment, carboplatin is administered or is to be administered at a dose for an AUC of 4 mg/mL*min or at a dose for an AUC of 5 mg/mL*min.

In one embodiment, erdafitinib is administered or is to be administered at a dose of 8 mg daily with an option to uptitrate to 9 mg depending on serum phosphate levels, in particular serum phosphate levels as described herein, at about day 14 of erdafitinib administration, and cetrelimab is administered or is to be administered at a dose of 240 mg every two weeks starting at cycle 1 day 1 (C1D1). In certain embodiments, erdafitinib is administered or is to be administered orally at a dose of 8 mg daily with an option to uptitrate to 9 mg depending on serum phosphate levels, in particular serum phosphate levels as described herein, at about day 14 of erdafitinib administration, and cetrelimab is administered or is to be administered intravenously at a dose of 240 mg every two weeks starting at cycle 1 day 1 (C1D1).

In one embodiment, erdafitinib is administered or is to be administered at a dose of 8 mg daily with an option to uptitrate to 9 mg depending on serum phosphate levels, in particular serum phosphate levels as described herein, at about day 14 of erdafitinib administration, and cetrelimab is administered or is to be administered at a dose of 480 mg every four weeks, in particular starting at cycle 1 day 1 (C1D1). In certain embodiments, erdafitinib is administered or is to be administered orally at a dose of 8 mg daily with an option to uptitrate to 9 mg depending on serum phosphate levels, in particular serum phosphate levels as described herein, at about day 14 of erdafitinib administration, and cetrelimab is administered or is to be administered intravenously at a dose of 480 mg every four weeks, in particular starting at cycle 1 day 1 (C1D1).

In one embodiment, erdafitinib is administered or is to be administered at a dose of 8 mg daily with an option to uptitrate to 9 mg depending on serum phosphate levels, in particular serum phosphate levels as described herein, at about day 14 of erdafitinib administration, and cetrelimab is administered or is to be administered at a dose of 240 mg every two weeks starting at cycle 1 day 1 (C1D1), and as of cycle 5 cetrelimab is administered or is to be administered at a dose of 480 mg every four weeks starting at cycle 5 day 1 (C5D1). In certain embodiments, erdafitinib is administered or is to be administered orally at a dose of 8 mg daily with an option to uptitrate to 9 mg depending on serum phosphate levels, in particular serum phosphate levels as described herein, at about day 14 of erdafitinib administration, and cetrelimab is administered or is to be administered at a dose of 240 mg every two weeks starting at cycle 1 day 1 (C1D1), and as of cycle 5 cetrelimab is administered or is to be administered at a dose of 480 mg every four weeks starting at cycle 5 day 1 (C5D1).

In one embodiment, erdafitinib is administered or is to be administered at a dose of 8 mg daily with an option to uptitrate to 9 mg depending on serum phosphate levels, in particular serum phosphate levels as described herein, at about day 14 of erdafitinib administration, and cetrelimab is administered or is to be administered at a dose of 360 mg every three weeks starting at cycle 1 day 1 (C1D1). In certain embodiments, erdafitinib is administered or is to be administered orally at a dose of 8 mg daily with an option to uptitrate to 9 mg depending on serum phosphate levels, in particular serum phosphate levels as described herein, at about day 14 of erdafitinib administration, and cetrelimab is administered or is to be administered at a dose of 360 mg every three weeks starting at cycle 1 day 1 (C1D1). In an embodiment, the treatment further comprises platinum chemotherapy, in particular cisplatin or carboplatin. In an embodiment, the platinum chemotherapy, in particular cisplatin or carboplatin, is administered or is to be administered every three weeks starting at cycle 1 day 1 (C1D1). In an embodiment, the platinum chemotherapy is administered or is to be administered at a dose of 50 mg/$m^2$, or 60 mg/$m^2$, or at a dose for a AUC of 4 mg/mL*min, or at a dose for a AUC of 5 mg/mL*min. In an embodiment, cisplatin is administered or is to be administered at a dose of 50 mg/$m^2$ or 60 mg/$m^2$. In an embodiment, carboplatin is administered or is to be administered at a dose for an AUC of 4 mg/mL*min or at a dose for an AUC of 5 mg/mL*min.

In one embodiment, erdafitinib is administered or is to be administered at a dose of 6 mg daily, and cetrelimab is administered or is to be administered at a dose of 240 mg every two weeks starting at cycle 1 day 1 (C1D1). In certain embodiments, erdafitinib is administered or is to be administered orally at a dose of 6 mg daily, and cetrelimab is administered or is to be administered intravenously at a dose of 240 mg every two weeks starting at cycle 1 day 1 (C1D1).

In one embodiment, erdafitinib is administered or is to be administered at a dose of 6 mg daily, and cetrelimab is administered or is to be administered at a dose of 480 mg every four weeks, in particular starting at cycle 1 day 1 (C1D1). In certain embodiments, erdafitinib is administered or is to be administered orally at a dose of 6 mg daily, and cetrelimab is administered or is to be administered intravenously at a dose of 480 mg every four weeks, in particular starting at cycle 1 day 1 (C1D1).

In one embodiment, erdafitinib is administered or is to be administered at a dose of 6 mg daily, and cetrelimab is administered or is to be administered at a dose of 240 mg every two weeks starting at cycle 1 day 1 (C1D1), and as of cycle 5 cetrelimab is administered or is to be administered at a dose of 480 mg every four weeks starting at cycle 5 day 1 (C5D1). In certain embodiments, erdafitinib is administered or is to be administered orally at a dose of 6 mg daily, and cetrelimab is administered or is to be administered at a dose of 240 mg every two weeks starting at cycle 1 day 1 (C1D1), and as of cycle 5 cetrelimab is administered or is to be administered at a dose of 480 mg every four weeks starting at cycle 5 day 1 (C5D1).

In one embodiment, erdafitinib is administered or is to be administered at a dose of 6 mg daily, and cetrelimab is administered or is to be administered at a dose of 360 mg every three weeks, in particular starting at cycle 1 day 1 (C1D1). In certain embodiments, erdafitinib is administered or is to be administered orally at a dose of 6 mg daily, and cetrelimab is administered or is to be administered intravenously at a dose of 360 mg every three weeks, in particular starting at cycle 1 day 1 (C1D1). In an embodiment, the treatment further comprises platinum chemotherapy, in particular cisplatin or carboplatin. In an embodiment, the platinum chemotherapy, in particular cisplatin or carboplatin, is administered or is to be administered every three weeks starting at cycle 1 day 1 (C1D1). In an embodiment, the platinum chemotherapy is administered or is to be administered at a dose of 50 mg/$m^2$, or 60 mg/$m^2$, or at a dose for a AUC of 4 mg/mL*min, or at a dose for a AUC of 5 mg/mL*min. In an embodiment, cisplatin is administered or is to be administered at a dose of 50 mg/$m^2$ or 60 mg/$m^2$. In an embodiment, carboplatin is administered or is to be administered at a dose for an AUC of 4 mg/mL*min or at a dose for an AUC of 5 mg/mL*min.

In further embodiments, the platinum chemotherapy generally, and cisplatin or carboplatin specifically, is administered by intravenous infusion.

In still further embodiments, the cisplatin is administered at a dose of about 50 mg/$m^2$ once every two weeks, once every three weeks, once every four weeks, once every five weeks or once every six weeks. In some embodiments the cisplatin is administered at the dosage of about 50 mg/$m^2$ once every two weeks. In some embodiments, the cisplatin is administered at a dose of about 50 mg/$m^2$ once every three weeks. In some embodiments, the cisplatin is administered at a dose of about 50 mg/$m^2$ once every four weeks. In some embodiments, the cisplatin is administered at a dose of about 50 mg/$m^2$ once every five weeks. In some embodiments, the cisplatin is administered at a dose of about 50 mg/$m^2$ once every six weeks. In some embodiments, the cisplatin is administered at a dose of about 60 mg/$m^2$ once every two weeks, once every three weeks, once every four weeks, once every five weeks or once every six weeks. In some embodiments, the cisplatin is administered at a dose of about 60 mg/$m^2$ once every two weeks. In some embodiments, the cisplatin is administered at a dose of about 60 mg/$m^2$ once every three weeks. In some embodiments, the cisplatin is administered at a dose of about 60 mg/$m^2$ once every four weeks. In some embodiments, the cisplatin is administered at a dose of about 60 mg/$m^2$ once every five weeks. In some embodiments, the cisplatin is administered at a dose of about 60 mg/$m^2$ once every six weeks.

In still further embodiments, the carboplatin is administered at a dose of about AUC 4 mg/mL/min once every two weeks, once every three weeks, once every four weeks, once every five weeks or once every six weeks. In some embodiments the carboplatin is administered at the dosage of about AUC 4 mg/mL/min once every two weeks. In some embodiments, the carboplatin is administered at a dose of about AUC 4 mg/mL/min once every three weeks. In some embodiments, the carboplatin is administered at a dose of about AUC 4 mg/mL/min once every four weeks. In some embodiments, the carboplatin is administered at a dose of about AUC 4 mg/mL/min once every five weeks. In some embodiments, the carboplatin is administered at a dose of about AUC 4 mg/mL/min once every six weeks. In some embodiments, the carboplatin is administered at a dose of about AUC 5 mg/mL/min once every two weeks, once every three weeks, once every four weeks, once every five weeks or once every six weeks. In some embodiments, the carboplatin is administered at a dose of about AUC 5 mg/mL/min once every two weeks. In some embodiments, the carboplatin is administered at a dose of about AUC 5 mg/mL/min once every three weeks. In some embodiments, the carboplatin is administered at a dose of about AUC 5 mg/mL/min once every four weeks. In some embodiments, the carboplatin is administered at a dose of about AUC 5 mg/mL/min once every five weeks. In some embodiments, the cisplatin is administered at a dose of about AUC 5 mg/mL/min once every six weeks.

In one embodiment, erdafitinib is administered or is to be administered at a dose of 8 mg daily, and cetrelimab is administered or is to be administered at a dose of 360 mg every three weeks starting at cycle 1 day 1 (C1D1), and cisplatin or carboplatin is administered or is to be administered every three weeks, in particular starting at cycle 1 day 1 (C1D1). In certain embodiments, erdafitinib is administered or is to be administered orally at a dose of 8 mg daily, and cetrelimab is administered or is to be administered intravenously at a dose of 360 mg every three weeks starting at cycle 1 day 1 (C1D1), and cisplatin or carboplatin is administered or is to be administered every three weeks, in particular starting at cycle 1 day 1 (C1D1). In an embodiment, cisplatin is administered or is to be administered every three weeks at a dose of 50 mg/$m^2$ Q3W, in particular starting at cycle 1 day 1 (C1D1). In an embodiment, cisplatin is administered or is to be administered every three weeks at a dose of 60 mg/$m^2$ Q3W, in particular starting at cycle 1 day 1 (C1D1). In an embodiment, carboplatin is administered or is to be administered every three weeks at a dose of AUC 4 mg/mL/min Q3W (not to exceed 600 mg), in particular starting at cycle 1 day 1 (C1D1). In an embodiment, carboplatin is administered or is to be administered every three weeks at a dose of AUC 5 mg/mL/min Q3W (not to exceed 750 mg), in particular starting at cycle 1 day 1 (C1D1).

In one embodiment, erdafitinib is administered or is to be administered at a dose of 8 mg daily with an option to uptitrate to 9 mg depending on serum phosphate levels, in particular serum phosphate levels as described herein, at about day 14 of erdafitinib administration, and cetrelimab is administered or is to be administered at a dose of 360 mg every three weeks starting at cycle 1 day 1 (C1D1), and cisplatin or carboplatin is administered or is to be administered every three weeks, in particular starting at cycle 1 day 1 (C1D1). In certain embodiments, erdafitinib is administered or is to be administered orally at a dose of 8 mg daily with an option to uptitrate to 9 mg depending on serum phosphate levels, in particular serum phosphate levels as described herein, at about day 14 of erdafitinib administration, and cetrelimab is administered or is to be administered intravenously at a dose of 360 mg every three weeks starting at cycle 1 day 1 (C1D1), and cisplatin or carboplatin is administered or is to be administered every three weeks, in particular starting at cycle 1 day 1 (C1D1). In an embodiment, cisplatin is administered or is to be administered every three weeks at a dose of 50 mg/m$^2$ Q3W, in particular starting at cycle 1 day 1 (C1D1). In an embodiment, cisplatin is administered or is to be administered every three weeks at a dose of 60 mg/m$^2$ Q3W, in particular starting at cycle 1 day 1 (C1D1). In an embodiment, carboplatin is administered or is to be administered every three weeks at a dose of AUC 4 mg/mL/min Q3W (not to exceed 600 mg), in particular starting at cycle 1 day 1 (C1D1). In an embodiment, carboplatin is administered or is to be administered every three weeks at a dose of AUC 5 mg/mL/min Q3W (not to exceed 750 mg), in particular starting at cycle 1 day 1 (C1D1).

In one embodiment, erdafitinib is administered or is to be administered at a dose of 6 mg daily, and cetrelimab is administered or is to be administered at a dose of 360 mg every three weeks starting at cycle 1 day 1 (C1D1), and cisplatin or carboplatin is administered or is to be administered every three weeks, in particular starting at cycle 1 day 1 (C1D1). In certain embodiments, erdafitinib is administered or is to be administered orally at a dose of 6 mg daily, and cetrelimab is administered or is to be administered intravenously at a dose of 360 mg every three weeks starting at cycle 1 day 1 (C1D1), and cisplatin or carboplatin is administered or is to be administered every three weeks, in particular starting at cycle 1 day 1 (C1D1). In an embodiment, cisplatin is administered or is to be administered every three weeks at a dose of 50 mg/m$^2$ Q3W, in particular starting at cycle 1 day 1 (C1D1). In an embodiment, cisplatin is administered or is to be administered every three weeks at a dose of 60 mg/m$^2$ Q3W, in particular starting at cycle 1 day 1 (C1D1). In an embodiment, carboplatin is administered or is to be administered every three weeks at a dose of AUC 4 mg/mL/min Q3W (not to exceed 600 mg), in particular starting at cycle 1 day 1 (C1D1). In an embodiment, carboplatin is administered or is to be administered every three weeks at a dose of AUC 5 mg/mL/min Q3W (not to exceed 750 mg), in particular starting at cycle 1 day 1 (C1D1).

In one specific embodiment, the FGFR inhibitor is administered in combination with the anti-PD-1 antibody or the antigen binding fragment thereof, wherein the FGFR inhibitor and the anti-PD-1 antibody or the antigen binding fragment thereof modulate different aspects of the urothelial carcinoma, thereby providing a greater overall benefit than administration of either therapeutic agent alone. Without wishing to be being bound by any theory, the FGFR inhibitor, in particular erdafitinib, in combination with the anti-PD1 antibody or the antigen binding fragment thereof, in particular cetrelimab, may demonstrate complementary mechanisms as neoantigen release by erdafitinib may prime the tumor microenvironment for response to the anti-PD1 antibody or the antigen binding fragment thereof. Given the potentially complementary mechanisms of action of erdafitinib and cetrelimab (PD-1 inhibitor), it is hypothesized that this combination will provide increased efficacy relative to either agent alone in patients with urothelial cancer. In certain embodiments, the FGFR inhibitor and anti-PD-1 antibody are further administered in combination with platinum chemotherapy generally, and cisplatin or carboplatin specifically.

The overall benefit experienced by the patient may simply be additive of the two therapeutic agents or the patient may experience a synergistic benefit.

The overall benefit experienced by the patient may simply be additive of the three therapeutic agents or the patient may experience a synergistic benefit.

In combination therapies, the multiple therapeutic agents (one of which is one of the compounds described herein) are administered in any order or even simultaneously. In one embodiment, the FGFR inhibitor is co-administered with the anti PD-1 antibody or antigen binding fragment thereof on day 1 of treatment, and thereafter only the FGFR inhibitor is administered on subsequent days of treatment. In another embodiment, the FGFR inhibitor is co-administered with the anti PD-1 antibody or antigen binding fragment thereof and the platinum chemotherapy on day 1 of treatment, and thereafter only the FGFR inhibitor is administered on subsequent days of treatment.

In an embodiment, on days that the FGFR inhibitor, the anti PD-1 antibody or antigen binding fragment thereof and platinum chemotherapy are administered or are to be administered, the sequence of administration is the FGFR inhibitor first, followed by the anti PD-1 antibody or antigen binding fragment thereof and then platinum chemotherapy.

In an embodiment, on days that erdafitinib, cetrelimab and cisplatin or carboplatin are administered or are to be administered, the sequence of administration is erdafitinib first, followed by cetrelimab and then cisplatin or carboplatin.

In an embodiment, on days that the FGFR inhibitor and the anti PD-1 antibody or antigen binding fragment thereof are administered or are to be administered, the sequence of administration is the FGFR inhibitor first, followed by the anti PD-1 antibody or antigen binding fragment thereof.

In an embodiment, on days that erdafitinib and cetrelimab are administered or are to be administered, the sequence of administration is erdafitinib first, followed by cetrelimab.

In an embodiment, the treatment with the FGFR inhibitor is started prior to the first administration of the anti PD-1 antibody or antigen binding fragment thereof. In an embodiment, the treatment with the FGFR inhibitor is started four weeks or 28 days prior to the first administration of the anti PD-1 antibody or antigen binding fragment thereof.

In an embodiment, the treatment with erdafitinib is started prior to the first administration of cetrelimab. In an embodiment, the treatment with erdafitinib is started four weeks or 28 days prior to the first administration of cetrelimab.

Kits/Articles of Manufacture

For use in the methods or uses described herein, kits and articles of manufacture are also described. Such kits include a package or container that is compartmentalized to receive one or more dosages of the pharmaceutical compositions disclosed herein. Suitable containers include, for example, bottles. In one embodiment, the containers are formed from a variety of materials such as glass or plastic.

The articles of manufacture provided herein contain packaging materials. Packaging materials for use in packaging pharmaceutical products include, e.g., U.S. Pat. Nos. 5,323,907, 5,052,558 and 5,033,252. Examples of pharmaceutical packaging materials include, but are not limited to, blister packs, bottles, tubes, bags, containers, bottles, and any packaging material suitable for a selected formulation and intended mode of administration and treatment.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself, a label is associated with a container when it is present within a receptacle or carrier that also holds the container, e.g., as a package insert.

In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack.

In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

Nucleotide Sequences of FGFR Fusion Genes

The nucleotide sequences for the FGFR fusion cDNA are provided in Table 7. The underlined sequences correspond to either FGFR3 or FGFR2, the sequences in black represent the fusion partners.

TABLE 7

| | |
|---|---|
| FGFR3-TACC3 VI<br>(2850 base pairs)<br>(SEQ ID NO: 33) | >ATGGGCGCCCCTGCCTGCGCCCTCGCGCTCTGCGTGGCCGTGGCCATCGTGGCC<br>GGCGCCTCCTCGGAGTCCTTGGGGACGGAGCAGCGCGTCGTGGGGCGAGCGGCA<br>GAAGTCCCGGGCCCAGAGCCCGGCCAGCAGGAGCAGTTGGTCTTCGGCAGCGGG<br>GATGCTGTGGAGCTGAGCTGTCCCCCGCCCGGGGGTGGTCCCATGGGGCCCACTG<br>TCTGGGTCAAGGATGGCACAGGGCTGGTGCCCTCGGAGCGTGTCCTGGTGGGGC<br>CCCAGCGGCTGCAGGTGCTGAATGCCTCCCACGAGGACTCCGGGGCCTACAGCT<br>GCCGGCAGCGGCTCACGCAGCGCGTACTGTGCCACTTCAGTGTGCGGGTGACAG<br>ACGCTCCATCCTCGGGAGATGACGAAGACGGGGAGGACGAGGCTGAGGACACA<br>GGTGTGGACACAGGGGCCCCTTACTGGACACGGCCCGAGCGGATGGACAAGAAG<br>CTGCTGGCCGTGCCGGCCGCCAACACCGTCCGCTTCCGCTGCCCAGCCGCTGGCA<br>ACCCCACTCCCTCCATCTCCTGGCTGAAGAACGGCAGGGAGTTCCGCGGCGAGC<br>ACCGCATTGGAGGCATCAAGCTGCGGCATCAGCAGTGGAGCCTGGTCATGGAAA<br>GCGTGGTGCCCTCGGACCGCGGCAACTACACCTGCGTCGTGGAGAACAAGTTTG<br>GCAGCATCCGGCAGACGTACACGCTGGACGTGCTGGAGCGCTCCCCGCACCGGC<br>CCATCCTGCAGGCGGGGCTGCCGGCCAACCAGACGGCGGTGCTGGGCAGCGACG<br>TGGAGTTCCACTGCAAGGTGTACAGTGACGCACAGCCCCACATCCAGTGGCTCA<br>AGCACGTGGAGGTGAATGGCAGCAAGGTGGGCCCGGACGGCACACCCTACGTTA<br>CCGTGCTCAAGACGGCGGGCGCTAACACCACCGACAAGGAGCTAGAGGTTCTCT<br>CCTTGCACAACGTCACCTTTGAGGACGCCGGGGAGTACACCTGCCTGGCGGGCA<br>ATTCTATTGGGTTTTCTCATCACTCTGCGTGGCTGGTGGTGCTGCCAGCCGAGGA<br>GGAGCTGGTGGAGGCTGACGAGGCGGGCAGTGTGTATGCAGGCATCCTCAGCTA<br>CGGGGTGGGCTTCTTCCTGTTCATCCTGGTGGTGGCGGCTGTGACGCTCTGCCGC<br>CTGCGCAGCCCCCCCAAGAAAGGCCTGGGCTCCCCCACCGTGCACAAGATCTCCC<br>GCTTCCCGCTCAAGCGACAGGTGTCCCTGGAGTCCAACGCGTCCATGAGCTCCAA<br>CACACCACTGGTGCGCATCGCAAGGCTGTCCTCAGGGGAGGGCCCCACGCTGGC<br>CAATGTCTCCGAGCTCGAGCTGCCTGCCGACCCCAAATGGGAGCTGTCTCGGGCC<br>CGGCTGACCCTGGGCAAGCCCCTTGGGGAGGGCTGCTTCGGCCAGGTGGTCATG<br>GCGGAGGCCATCGGCATTGACAAGGACCGGGCCGCCAAGCCTGTCACCGTAGCC<br>GTGAAGATGCTGAAAGACGATGCCACTGACAAGGACCTGTCGGACCTGGTGTCT<br>GAGATGGAGATGATGAAGATGATCGGGAAACACAAAAACATCATCAACCTGCTG<br>GGCGCCTGCACGCAGGGCGGGCCCCTGTACGTGCTGGTGGAGTACGCGGCCAAG<br>GGTAACCTGCGGGAGTTTCTGCGGGCGCGGCGGCCCCCGGGCCTGGACTACTCCT<br>TCGACACCTGCAAGCCGCCCGAGGAGCAGCTCACCTTCAAGGACCTGGTGTCCTG<br>TGCCTACCAGGTGGCCCGGGGCATGGAGTACTTGGCCTCCCAGAAGTGCATCCAC<br>AGGGACCTGGCTGCCCGCAATGTGCTGGTGACCGAGGACAACGTGATGAAGATC<br>GCAGACTTCGGGCTGGCCCGGGACGTGCACAACCTCGACTACTACAAGAAGACG<br>ACCAACGGCCGGCTGCCCGTGAAGTGGATGGCGCCTGAGGCCTTGTTTGACCGA<br>GTCTACACTCACCAGAGTGACGTCTGGTCCTTTGGGGTCCTGCTCTGGGAGATCT<br>TCACGCTGGGGGGCTCCCCGTACCCCGGCATCCCTGTGGAGGAGCTCTTCAAGCT<br>GCTGAAGGAGGGCCACCGCATGGACAAGCCCGCCAACTGCACACACGACCTGTA<br>CATGATCATGCGGGAGTGCTGGCATGCCGCGCCCTCCCAGAGGCCCACCTTCAAG<br>CAGCTGGTGGAGGACCTGGACCGTGTCCTTACCGTGACGTCCACCGACGTAAAG<br>GCGACACAGGAGGAGAACCGGGAGCTGAGGAGCAGGTGTGAGGAGCTCCACGG<br>GAAGAACCTGGAACTGGGGAAGATCATGGACAGGTTCGAAGAGGTTGTGTACCA<br>GGCCATGGAGGAAGTTCAGAAGCAGAAGGAACTTTCCAAAGCTGAAATCCAGAA<br>AGTTCTAAAAGAAAAAGACCAACTTACCACAGATCTGAACTCCATGGAGAAGTC<br>CTTCTCCGACCTCTTCAAGCGTTTTGAGAAACAGAAAGAGGTGATCGAGGGCTAC |

TABLE 7-continued

| | |
|---|---|
| | CGCAAGAACGAAGAGTCACTGAAGAAGTGCGTGGAGGATTACCTGGCAAGGATC<br>ACCCAGGAGGGCCAGAGGTACCAAGCCCTGAAGGCCCACGCGGAGGAGAAGCT<br>GCAGCTGGCAAACGAGGAGATCGCCCAGGTCCGGAGCAAGGCCCAGGCGGAAG<br>CGTTGGCCCTCCAGGCCAGCCTGAGGAAGGAGCAGATGCGCATCCAGTCGCTGG<br>AGAAGACAGTGGAGCAGAAGACTAAAGAGAACGAGGAGCTGACCAGGATCTGC<br>GACGACCTCATCTCCAAGATGGAGAAGATCTGA |
| FGFR3-TACC3 V3<br>(2955 base pairs)<br>(SEQ ID NO: 34 | >ATGGGCGCCCCTGCCTGCGCCCTCGCGCTCTGCGTGGCCGTGGCCATCGTGGCC<br>GGCGCCTCCTCGGAGTCCTTGGGGACGGAGCAGCGCGTCGTGGGGCGAGCGGCA<br>GAAGTCCCGGGCCCAGAGCCCGGCCAGCAGGAGCAGTTGGTCTTCGGCAGCGGG<br>GATGCTGTGGAGCTGAGCTGTCCCCCGCCCGGGGGTGGTCCCATGGGGCCCACTG<br>TCTGGGTCAAGGATGGCACAGGGCTGGTGCCCTCGGAGCGTGTCCTGGTGGGGC<br>CCCAGCGGCTGCAGGTGCTGAATGCCTCCCACGAGGACTCCGGGGCCTACAGCT<br>GCCGGCAGCGGCTCACGCAGCGCGTACTGTGCCACTTCAGTGTGCGGGTGACAG<br>ACGCTCCATCCTCGGGAGATGACGAAGACGGGGAGGACGAGGCTGAGGACACA<br>GGTGTGGACACAGGGGCCCCTTACTGGACACGGCCCGAGCGGATGGACAAGAAG<br>CTGCTGGCCGTGCCGGCCGCCAACACCGTCCGCTTCCGCTGCCCAGCCGCTGGCA<br>ACCCCACTCCCTCCATCTCCTGGCTGAAGAACGGCAGGGAGTTCCGCGGCGAGC<br>ACCGCATTGGAGGCATCAAGCTGCGGCATCAGCAGTGGAGCCTGGTCATGGAAA<br>GCGTGGTGCCCTCGGACCGCGGCAACTACACCTGCGTCGTGGAGAACAAGTTTG<br>GCAGCATCCGGCAGACGTACACGCTGGACGTGCTGGAGCGCTCCCCGCACCGGC<br>CCATCCTGCAGGCGGGGCTGCCGGCCAACCAGACGGCGGTGCTGGGCAGCGACG<br>TGGAGTTCCACTGCAAGGTGTACAGTGACGCACAGCCCCACATCCAGTGGCTCA<br>AGCACGTGGAGGTGAATGGCAGCAAGGTGGGCCCGGACGGCACACCCTACGTTA<br>CCGTGCTCAAGACGGCGGGCGCTAACACCACCGACAAGGAGCTAGAGGTTCTCT<br>CCTTGCACAACGTCACCTTTGAGGACGCCGGGGAGTACACCTGCCTGGCGGGCA<br>ATTCTATTGGGTTTTCTCATCACTCTGCGTGGCTGGTGGTGCTGCCAGCCGAGGA<br>GGAGCTGGTGGAGGCTGACGAGGCGGGCAGTGTGTATGCAGGCATCCTCAGCTA<br>CGGGGTGGGCTTCTTCCTGTTCATCCTGGTGGTGGCGGCTGTGACGCTCTGCCGC<br>CTGCGCAGCCCCCCCAAGAAAGGCCTGGGCTCCCCCACCGTGCACAAGATCTCCC<br>GCTTCCCGCTCAAGCGACAGGTGTCCCTGGAGTCCAACGCGTCCATGAGCTCCAA<br>CACACCACTGGTGCGCATCGCAAGGCTGTCCTCAGGGGAGGGCCCCACGCTGGC<br>CAATGTCTCCGAGCTCGAGCTGCCTGCCGACCCCAAATGGGAGCTGTCTCGGGCC<br>CGGCTGACCCTGGGCAAGCCCCTTGGGGAGGGCTGCTTCGGCCAGGTGGTCATG<br>GCGGAGGCCATCGGCATTGACAAGGACCGGGCCGCCAAGCCTGTCACCGTAGCC<br>GTGAAGATGCTGAAAGACGATGCCACTGACAAGGACCTGTCGGACCTGGTGTCT<br>GAGATGGAGATGATGAAGATGATCGGGAAACACAAAAACATCATCAACCTGCTG<br>GGCGCCTGCACGCAGGGCGGGCCCCTGTACGTGCTGGTGGAGTACGCGGCCAAG<br>GGTAACCTGCGGGAGTTTCTGCGGGCGCGGCGGCCCCCGGGCCTGGACTACTCCT<br>TCGACACCTGCAAGCCGCCCGAGGAGCAGCTCACCTTCAAGGACCTGGTGTCCTG<br>TGCCTACCAGGTGGCCCGGGGCATGGAGTACTTGGCCTCCCAGAAGTGCATCCAC<br>AGGGACCTGGCTGCCCGCAATGTGCTGGTGACCGAGGACAACGTGATGAAGATC<br>GCAGACTTCGGGCTGGCCCGGGACGTGCACAACCTCGACTACTACAAGAAGACG<br>ACCAACGGCCGGCTGCCCGTGAAGTGGATGGCGCCTGAGGCCTTGTTTGACCGA<br>GTCTACACTCACCAGAGTGACGTCTGGTCCTTTGGGGTCCTGCTCTGGGAGATCT<br>TCACGCTGGGGGGCTCCCCGTACCCCGGCATCCCTGTGGAGGAGCTCTTCAAGCT<br>GCTGAAGGAGGGCCACCGCATGGACAAGCCCGCCAACTGCACACACGACCTGTA<br>CATGATCATGCGGGAGTGCTGGCATGCCGCGCCCTCCCAGAGGCCCACCTTCAAG<br>CAGCTGGTGGAGGACCTGGACCGTGTCCTTACCGTGACGTCCACCGACGTGCCAG<br>GCCCACCCCCAGGTGTTCCCGCGCCTGGGGGCCCACCCCTGTCCACCGGACCTAT<br>AGTGGACCTGCTCCAGTACAGCCAGAAGGACCTGGATGCAGTGGTAAAGGCGAC<br>ACAGGAGGAGAACCGGGAGCTGAGGAGCAGGTGTGAGGAGCTCCACGGGAAGA<br>ACCTGGAACTGGGGAAGATCATGGACAGGTTCGAAGAGGTTGTGTACCAGGCCA<br>TGGAGGAAGTTCAGAAGCAGAAGGAACTTTCCAAAGCTGAAATCCAGAAAGTTC<br>TAAAAGAAAAAGACCAACTTACCACAGATCTGAACTCCATGGAGAAGTCCTTCT<br>CCGACCTCTTCAAGCGTTTTGAGAAACAGAAAGAGGTGATCGAGGGCTACCGCA<br>AGAACGAAGAGTCACTGAAGAAGTGCGTGGAGGATTACCTGGCAAGGATCACCC<br>AGGAGGGCCAGAGGTACCAAGCCCTGAAGGCCCACGCGGAGGAGAAGCTGCAG<br>CTGGCAAACGAGGAGATCGCCCAGGTCCGGAGCAAGGCCCAGGCGGAAGCGTTG<br>GCCCTCCAGGCCAGCCTGAGGAAGGAGCAGATGCGCATCCAGTCGCTGGAGAAG<br>ACAGTGGAGCAGAAGACTAAAGAGAACGAGGAGCTGACCAGGATCTGCGACGA<br>CCTCATCTCCAAGATGGAGAAGATCTGA |
| FGFR3-BAIAP2L1<br>(3765 base pairs)<br>(SEQ ID NO: 35) | >ATGGGCGCCCCTGCCTGCGCCCTCGCGCTCTGCGTGGCCGTGGCCATCGTGGCC<br>GGCGCCTCCTCGGAGTCCTTGGGGACGGAGCAGCGCGTCGTGGGGCGAGCGGCA<br>GAAGTCCCGGGCCCAGAGCCCGGCCAGCAGGAGCAGTTGGTCTTCGGCAGCGGG<br>GATGCTGTGGAGCTGAGCTGTCCCCCGCCCGGGGGTGGTCCCATGGGGCCCACTG<br>TCTGGGTCAAGGATGGCACAGGGCTGGTGCCCTCGGAGCGTGTCCTGGTGGGGC<br>CCCAGCGGCTGCAGGTGCTGAATGCCTCCCACGAGGACTCCGGGGCCTACAGCT<br>GCCGGCAGCGGCTCACGCAGCGCGTACTGTGCCACTTCAGTGTGCGGGTGACAG<br>ACGCTCCATCCTCGGGAGATGACGAAGACGGGGAGGACGAGGCTGAGGACACA<br>GGTGTGGACACAGGGGCCCCTTACTGGACACGGCCCGAGCGGATGGACAAGAAG<br>CTGCTGGCCGTGCCGGCCGCCAACACCGTCCGCTTCCGCTGCCCAGCCGCTGGCA<br>ACCCCACTCCCTCCATCTCCTGGCTGAAGAACGGCAGGGAGTTCCGCGGCGAGC<br>ACCGCATTGGAGGCATCAAGCTGCGGCATCAGCAGTGGAGCCTGGTCATGGAAA<br>GCGTGGTGCCCTCGGACCGCGGCAACTACACCTGCGTCGTGGAGAACAAGTTTG<br>GCAGCATCCGGCAGACGTACACGCTGGACGTGCTGGAGCGCTCCCCGCACCGGC<br>CCATCCTGCAGGCGGGGCTGCCGGCCAACCAGACGGCGGTGCTGGGCAGCGACG<br>TGGAGTTCCACTGCAAGGTGTACAGTGACGCACAGCCCCACATCCAGTGGCTCA<br>AGCACGTGGAGGTGAATGGCAGCAAGGTGGGCCCGGACGGCACACCCTACGTTA |

TABLE 7-continued

| | |
|---|---|
| | CCGTGCTCAAGTCCTGGATCAGTGAGAGTGTGGAGGCCGACGTGCGCCTCCGCCT<br>GGCCAATGTGTCGGAGCGGGACGGGGGCGAGTACCTCTGTCGAGCCACCAATTT<br>CATAGGCGTGGCCGAGAAGGCCTTTTGGCTGAGCGTTCACGGGCCCCGAGCAGC<br>CGAGGAGGAGCTGGTGGAGGCTGACGAGGCGGGCAGTGTGTATGCAGGCATCCT<br>CAGCTACGGGGTGGGCTTCTTCCTGTTCATCCTGGTGGTGGCGGCTGTGACGCTC<br>TGCCGCCTGCGCAGCCCCCCCAAGAAAGGCCTGGGCTCCCCCACCGTGCACAAG<br>ATCTCCCGCTTCCCGCTCAAGCGACAGGTGTCCCTGGAGTCCAACGCGTCCATGA<br>GCTCCAACACACCACTGGTGCGCATCGCAAGGCTGTCCTCAGGGGAGGGCCCCA<br>CGCTGGCCAATGTCTCCGAGCTCGAGCTGCCTGCCGACCCCAAATGGGAGCTGTC<br>TCGGGCCCGGCTGACCCTGGGCAAGCCCCTTGGGGAGGGCTGCTTCGGCCAGGT<br>GGTCATGGCGGAGGCCATCGGCATTGACAAGGACCGGGCCGCCAAGCCTGTCAC<br>CGTAGCCGTGAAGATGCTGAAAGACGATGCCACTGACAAGGACCTGTCGGACCT<br>GGTGTCTGAGATGGAGATGATGAAGATGATCGGGAAACACAAAAACATCATCAA<br>CCTGCTGGGCGCCTGCACGCAGGGCGGGCCCCTGTACGTGCTGGTGGAGTACGC<br>GGCCAAGGGTAACCTGCGGGAGTTTCTGCGGGCGCGGCGGCCCCCGGGCCTGGA<br>CTACTCCTTCGACACCTGCAAGCCGCCCGAGGAGCAGCTCACCTTCAAGGACCTG<br>GTGTCCTGTGCCTACCAGGTGGCCCGGGGCATGGAGTACTTGGCCTCCCAGAAGT<br>GCATCCACAGGGACCTGGCTGCCCGCAATGTGCTGGTGACCGAGGACAACGTGA<br>TGAAGATCGCAGACTTCGGGCTGGCCCGGGACGTGCACAACCTCGACTACTACA<br>AGAAGACGACCAACGGCCGGCTGCCCGTGAAGTGGATGGCGCCTGAGGCCTTGT<br>TTGACCGAGTCTACACTCACCAGAGTGACGTCTGGTCCTTTGGGGTCCTGCTCTG<br>GGAGATCTTCACGCTGGGGGGCTCCCCGTACCCCGGCATCCCTGTGGAGGAGCTC<br>TTCAAGCTGCTGAAGGAGGGCCACCGCATGGACAAGCCCGCCAACTGCACACAC<br>GACCTGTACATGATCATGCGGGAGTGCTGGCATGCCGCGCCCTCCCAGAGGCCC<br>ACCTTCAAGCAGCTGGTGGAGGACCTGGACCGTGTCCTTACCGTGACGTCCACCG<br>ACAATGTTATGGAACAGTTCAATCCTGGGCTGCGAAATTTAATAAACCTGGGGA<br>AAAATTATGAGAAAGCTGTAAACGCTATGATCCTGGCAGGAAAAGCCTACTACG<br>ATGGAGTGGCCAAGATCGGTGAGATTGCCACTGGGTCCCCCGTGTCAACTGAACT<br>GGGACATGTCCTCATAGAGATTTCAAGTACCCACAAGAAACTCAACGAGAGTCT<br>TGATGAAAATTTTAAAAAATTCCACAAAGAGATTATCCATGAGCTGGAGAAGAA<br>GATAGAACTTGACGTGAAATATATGAACGCAACTCTAAAAAGATACCAAACAGA<br>ACACAAGAATAAATTAGAGTCTTTGGAGAAATCCCAAGCTGAGTTGAAGAAGAT<br>CAGAAGGAAAAGCCAAGGAAGCCGAAACGCACTCAAATATGAACACAAAGAAA<br>TTGAGTATGTGGAGACCGTTACTTCTCGTCAGAGTGAAATCCAGAAATTCATTGC<br>AGATGGTTGCAAAGAGGCTCTGCTTGAAGAGAAGAGGCGCTTCTGCTTTCTGGTT<br>GATAAGCACTGTGGCTTTGCAAACCACATACATTATTATCACTTACAGTCTGCAG<br>AACTACTGAATTCCAAGCTGCCTCGGTGGCAGGAGACCTGTGTTGATGCCATCAA<br>AGTGCCAGAGAAAATCATGAATATGATCGAAGAAATAAAGACCCCAGCCTCTAC<br>CCCCGTGTCTGGAACTCCTCAGGCTTCACCCATGATCGAGAGAAGCAATGTGGTT<br>AGGAAAGATTACGACACCCTTTCTAAATGCTCACCAAAGATGCCCCCCGCTCCTT<br>CAGGCAGAGCATATACCAGTCCCTTGATCGATATGTTTAATAACCCAGCCACGGC<br>TGCCCCGAATTCACAAAGGGTAAATAATTCAACAGGTACTTCCGAAGATCCCAGT<br>TTACAGCGATCAGTTTCGGTTGCAACGGGACTGAACATGATGAAGAAGCAGAAA<br>GTGAAGACCATCTTCCCGCACACTGCGGGCTCCAACAAGACCTTACTCAGCTTTG<br>CACAGGGAGATGTCATCACGCTGCTCATCCCCGAGGAGAAGGATGGCTGGCTCT<br>ATGGAGAACACGACGTGTCCAAGGCGAGGGGTTGGTTCCCGTCGTCGTACACGA<br>AGTTGCTGGAAGAAAATGAGACAGAAGCAGTGACCGTGCCCACGCCAAGCCCCA<br>CACCAGTGAGAAGCATCAGCACCGTGAACTTGTCTGAGAATAGCAGTGTTGTCAT<br>CCCCCCACCCGACTACTTGGAATGCTTGTCCATGGGGGCAGCTGCCGACAGGAG<br>AGCAGATTCGGCCAGGACGACATCCACCTTTAAGGCCCCAGCGTCCAAGCCCGA<br>GACCGCGGCTCCTAACGATGCCAACGGGACTGCAAAGCCGCCTTTTCTCAGCGG<br>AGAAAACCCCTTTGCCACTGTGAAACTCCGCCCGACTGTGACGAATGATCGCTCG<br>GCACCCATCATTCGATGA |
| FGFR2-BICC1<br>(4989 base pairs)<br>(SEQ ID NO: 36) | >ATGGTCAGCTGGGGTCGTTTCATCTGCCTGGTCGTGGTCACCATGGCAACCTTGT<br>CCCTGGCCCGGCCCTCCTTCAGTTTAGTTGAGGATACCACATTAGAGCCAGAAGA<br>GCCACCAACCAAATACCAAATCTCTCAACCAGAAGTGTACGTGGCTGCGCCAGG<br>GGAGTCGCTAGAGGTGCGCTGCCTGTTGAAAGATGCCGCCGTGATCAGTTGGACT<br>AAGGATGGGGTGCACTTGGGGCCCAACAATAGGACAGTGCTTATTGGGGAGTAC<br>TTGCAGATAAAGGGCGCCACGCCTAGAGACTCCGGCCTCTATGCTTGTACTGCCA<br>GTAGGACTGTAGACAGTGAAACTTGGTACTTCATGGTGAATGTCACAGATGCCAT<br>CTCATCCGGAGATGATGAGGATGACACCGATGGTGCGGAAGATTTTGTCAGTGA<br>GAACAGTAACAACAAGAGAGCACCATACTGGACCAACACAGAAAAGATGGAAA<br>AGCGGCTCCATGCTGTGCCTGCGGCCAACACTGTCAAGTTTCGCTGCCCAGCCGG<br>GGGGAACCCAATGCCAACCATGCGGTGGCTGAAAAACGGGAAGGAGTTTAAGCA<br>GGAGCATCGCATTGGAGGCTACAAGGTACGAAACCAGCACTGGAGCCTCATTAT<br>GGAAAGTGTGGTCCCATCTGACAAGGGAAATTATACCTGTGTAGTGGAGAATGA<br>ATACGGGTCCATCAATCACACGTACCACCTGGATGTTGTGGAGCGATCGCCTCAC<br>CGGCCCATCCTCCAAGCCGGACTGCCGGCAAATGCCTCCACAGTGGTCGGAGGA<br>GACGTAGAGTTTGTCTGCAAGGTTTACAGTGATGCCCAGCCCCACATCCAGTGGA<br>TCAAGCACGTGGAAAAGAACGGCAGTAAATACGGGCCCGACGGGCTGCCCTACC<br>TCAAGGTTCTCAAGGCCGCCGGTGTTAACACCACGGACAAAGAGATTGAGGTTC<br>TCTATATTCGGAATGTAACTTTTGAGGACGCTGGGGAATATACGTGCTTGGCGGG<br>TAATTCTATTGGGATATCCTTTCACTCTGCATGGTTGACAGTTCTGCCAGCGCCTG<br>GAAGAGAAAAGGAGATTACAGCTTCCCCAGACTACCTGGAGATAGCCATTTACT<br>GCATAGGGGTCTTCTTAATCGCCTGTATGGTGGTAACAGTCATCCTGTGCCGAAT<br>GAAGAACACGACCAAGAAGCCAGACTTCAGCAGCCAGCCGGCTGTGCACAAGCT<br>GACCAAACGTATCCCCCTGCGGAGACAGGTAACAGTTTCGGCTGAGTCCAGCTCC<br>TCCATGAACTCCAACACCCCGCTGGTGAGGATAACAACACGCCTCTCTTCAACGG<br>CAGACACCCCCATGCTGGCAGGGGTCTCCGAGTATGAACTTCCAGAGGACCCAA |

TABLE 7-continued

AATGGGAGTTTCCAAGAGATAAGCTGACACTGGGCAAGCCCCTGGGAGAAGGTT
GCTTTGGGCAAGTGGTCATGGCGGAAGCAGTGGGAATTGACAAAGACAAGCCCA
AGGAGGCGGTCACCGTGGCCGTGAAGATGTTGAAAGATGATGCCACAGAGAAAG
ACCTTTCTGATCTGGTGTCAGAGATGGAGATGATGAAGATGATTGGGAAACACA
AGAATATCATAAATCTTCTTGGAGCCTGCACACAGGATGGGCCTCTCTATGTCAT
AGTTGAGTATGCCTCTAAAGGCAACCTCCGAGAATACCTCCGAGCCCGGAGGCC
ACCCGGGATGGAGTACTCCTATGACATTAACCGTGTTCCTGAGGAGCAGATGACC
TTCAAGGACTTGGTGTCATGCACCTACCAGCTGGCCAGAGGCATGGAGTACTTGG
CTTCCCAAAAATGTATTCATCGAGATTTAGCAGCCAGAAATGTTTTGGTAACAGA
AAACAATGTGATGAAAATAGCAGACTTTGGACTCGCCAGAGATATCAACAATAT
AGACTATTACAAAAAGACCACCAATGGGCGGCTTCCAGTCAAGTGGATGGCTCC
AGAAGCCCTGTTTGATAGAGTATACACTCATCAGAGTGATGTCTGGTCCTTCGGG
GTGTTAATGTGGGAGATCTTCACTTTAGGGGGCTCGCCCTACCCAGGGATTCCCG
TGGAGGAACTTTTTAAGCTGCTGAAGGAAGGACACAGAATGGATAAGCCAGCCA
ACTGCACCAACGAACTGTACATGATGATGAGGGACTGTTGGCATGCAGTGCCCTC
CCAGAGACCAACGTTCAAGCAGTTGGTAGAAGACTTGGATCGAATTCTCACTCTC
ACAACCAATGAGATCATGGAGGAAACAAATACGCAGATTGCTTGGCCATCAAAA
CTGAAGATCGGAGCCAAATCCAAGAAAGATCCCCATATTAAGGTTTCTGGAAAG
AAAGAAGATGTTAAAGAAGCCAAGGAAATGATCATGTCTGTCTTAGACACAAAA
AGCAATCGAGTCACACTGAAGATGGATGTTTCACATACAGAACATTCACATGTA
ATCGGCAAAGGTGGCAACAATATTAAAAAAGTGATGGAAGAAACCGGATGCCAT
ATCCACTTTCCAGATTCCAACAGGAATAACCAAGCAGAAAAAAGCAACCAGGTA
TCTATAGCGGGACAACCAGCAGGAGTAGAATCTGCCCGAGTTAGAATTCGGGAG
CTGCTTCCTTTGGTGCTGATGTTTGAGCTACCAATTGCTGGAATTCTTCAACCGGT
TCCTGATCCTAATTCCCCCTCTATTCAGCATATATCACAAACGTACAATATTTCAG
TATCATTTAAACAGCGTTCCCGAATGTATGGTGCTACTGTCATAGTACGAGGGTC
TCAGAATAACACTAGTGCTGTGAAGGAAGGAACTGCCATGCTGTTAGAACATCTT
GCTGGGAGCTTAGCATCAGCTATTCCTGTGAGCACACAACTAGATATTGCAGCTC
AACATCATCTCTTTATGATGGGTCGAAATGGGAGCAACATCAAACATATCATGCA
GAGAACAGGTGCTCAGATCCACTTTCCTGATCCCAGTAATCCACAAAAGAAATCT
ACCGTCTACCTCCAGGGCACCATTGAGTCTGTCTGTCTTGCAAGGCAATATCTCA
TGGGTTGTCTTCCTCTTGTGTTGATGTTTGATATGAAGGAAGAAATTGAAGTAGA
TCCACAATTCATTGCGCAGTTGATGGAACAGCTTGATGTCTTCATCAGTATTAAA
CCAAAGCCCAAACAGCCAAGCAAGTCTGTGATTGTGAAAAGTGTTGAGCGAAAT
GCCTTAAATATGTATGAAGCAAGGAAATGTCTCCTCGGACTTGAAAGCAGTGGG
GTTACCATAGCAACCAGTCCATCCCCAGCATCCTGCCCTGCCGGCCTGGCATGTC
CCAGCCTGGATATCTTAGCTTCAGCAGGCCTTGGACTCACTGGACTAGGTCTTTT
GGGACCCACCACCTTATCTCTGAACACTTCAACAACCCCAAACTCACTCTTGAAT
GCTCTTAATAGCTCAGTCAGTCCTTTGCAAAGTCCAAGTTCTGGTACACCCAGCC
CCACATTATGGGCACCCCCACTTGCTAATACTTCAAGTGCCACAGGTTTTTCTGCT
ATACCACACCTTATGATTCCATCTACTGCCCAAGCCACATTAACTAATATTTTGTT
GTCTGGAGTGCCCACCTATGGGCACACAGCTCCATCTCCCCCTCCTGGCTTGACT
CCTGTTGATGTCCATATCAACAGTATGCAGACCGAAGGCAAAAAAATCTCTGCTG
CTTTAAATGGACATGCACAGTCTCCAGATATAAAATATGGTGCAATATCCACTTC
ATCACTTGGAGAAAAAGTGCTGAGTGCAAATCACGGGGATCCGTCCATCCAGAC
AAGTGGGTCTGAGCAGACATCTCCCAAATCAAGCCCCACTGAAGGTTGTAATGA
TGCTTTTGTTGAAGTAGGCATGCCTCGAAGTCCTTCCCATTCTGGGAATGCTGGT
GACTTGAAACAGATGATGTGTCCCTCCAAGGTTTCCTGTGCCAAAAGGCAGACA
GTGGAACTATTGCAAGGCACGAAAAACTCACACTTACACAGCACTGACAGGTTG
CTCTCAGACCCTGAACTGAGTGCTACCGAAAGCCCTTTGGCTGACAAGAAGGCTC
CAGGGAGTGAGCGCGCTGCAGAGAGGGCAGCAGCTGCCCAGCAAAACTCCGAA
AGGGCCCACCTTGCTCCACGGTCATCATATGTCAACATGCAGGCATTTGACTATG
AACAGAAGAAGCTATTAGCCACCAAAGCTATGTTAAAGAAACCAGTGGTGACGG
AGGTCAGAACGCCCACAAATACCTGGAGTGGCCTGGGTTTTTCTAAATCCATGCC
AGCTGAAACTATCAAGGAGTTGAGAAGGGCCAATCATGTGTCCTATAAGCCCAC
AATGACAACCACTTATGAGGGCTCATCCATGTCCCTTTCACGGTCCAACAGTCGT
GAGCACTTGGGAGGTGGAAGCGAATCTGATAACTGGAGAGACCGAAATGGAATT
GGACCTGGAAGTCATAGTGAATTTGCAGCTTCTATTGGCAGCCCTAAGCGTAAAC
AAAACAAATCAACGGAACACTATCTCAGCAGTAGCAATTACATGGACTGCATTT
CCTCGCTGACAGGAAGCAATGGCTGTAACTTAAATAGCTCTTTCAAAGGTTCTGA
CCTCCCTGAGCTCTTCAGCAAACTGGGCCTGGGCAAATACACAGATGTTTTCCAG
CAACAAGAGATCGATCTTCAGACATTCCTCACTCTCACAGATCAGGATCTGAAGG
AGCTGGGAATAACTACTTTTGGTGCCAGGAGGAAAATGCTGCTTGCAATTTCAGA
ACTAAATAAAAACCGAAGAAAGCTTTTTGAATCGCCAAATGCACGCACCTCTTTC
CTGGAAGGTGGAGCGAGTGGAAGGCTACCCCGTCAGTATCACTCAGACATTGCT
AGTGTCAGTGGCCGCTGGTAG

FGFR2-CASP7
(3213 base pairs)
(SEQ ID NO: 37)

>ATGGTCAGCTGGGGTCGTTTCATCTGCCTGGTCGTGGTCACCATGGCAACCTTGT
CCCTGGCCCGGCCCTCCTTCAGTTTAGTTGAGGATACCACATTAGAGCCAGAAGA
GCCACCAACCAAATACCAAATCTCTCAACCAGAAGTGTACGTGGCTGCGCCAGG
GGAGTCGCTAGAGGTGCGCTGCCTGTTGAAAGATGCCGCCGTGATCAGTTGGACT
AAGGATGGGGTGCACTTGGGGCCCAACAATAGGACAGTGCTTATTGGGGAGTAC
TTGCAGATAAAGGGCGCCACGCCTAGAGACTCCGGCCTCTATGCTTGTACTGCCA
GTAGGACTGTAGACAGTGAAACTTGGTACTTCATGGTGAATGTCACAGATGCCAT
CTCATCCGGAGATGATGAGGATGACACCGATGGTGCGGAAGATTTTGTCAGTGA
GAACAGTAACAACAAGAGAGCACCATACTGGACCAACACAGAAAAGATGGAAA
AGCGGCTCCATGCTGTGCCTGCGGCCAACACTGTCAAGTTTCGCTGCCCAGCCGG
GGGGAACCCAATGCCAACCATGCGGTGGCTGAAAAACGGGAAGGAGTTTAAGCA
GGAGCATCGCATTGGAGGCTACAAGGTACGAAACCAGCACTGGAGCCTCATTAT
GGAAAGTGTGGTCCCATCTGACAAGGGAAATTATACCTGTGTAGTGGAGAATGA

TABLE 7-continued

| |
|---|
| ATACGGGTCCATCAATCACACGTACCACCTGGATGTTGTGGAGCGATCGCCTCAC |
| CGGCCCATCCTCCAAGCCGGACTGCCGGCAAATGCCTCCACAGTGGTCGGAGGA |
| GACGTAGAGTTTGTCTGCAAGGTTTACAGTGATGCCCAGCCCCACATCCAGTGGA |
| TCAAGCACGTGGAAAAGAACGGCAGTAAATACGGGCCCGACGGGCTGCCCTACC |
| TCAAGGTTCTCAAGGCCGCCGGTGTTAACACCACGGACAAAGAGATTGAGGTTC |
| TCTATATTCGGAATGTAACTTTTGAGGACGCTGGGGAATATACGTGCTTGGCGGG |
| TAATTCTATTGGGATATCCTTTCACTCTGCATGGTTGACAGTTCTGCCAGCGCCTG |
| GAAGAGAAAAGGAGATTACAGCTTCCCCAGACTACCTGGAGATAGCCATTTACT |
| GCATAGGGGTCTTCTTAATCGCCTGTATGGTGGTAACAGTCATCCTGTGCCGAAT |
| GAAGAACACGACCAAGAAGCCAGACTTCAGCAGCCAGCCGGCTGTGCACAAGCT |
| GACCAAACGTATCCCCCTGCGGAGACAGGTAACAGTTTCGGCTGAGTCCAGCTCC |
| TCCATGAACTCCAACACCCCGCTGGTGAGGATAACAACACGCCTCTCTTCAACGG |
| CAGACACCCCCATGCTGGCAGGGGTCTCCGAGTATGAACTTCCAGAGGACCCAA |
| AATGGGAGTTTCCAAGAGATAAGCTGACACTGGGCAAGCCCCTGGGAGAAGGTT |
| GCTTTGGGCAAGTGGTCATGGCGGAAGCAGTGGGAATTGACAAAGACAAGCCCA |
| AGGAGGCGGTCACCGTGGCCGTGAAGATGTTGAAAGATGATGCCACAGAGAAAG |
| ACCTTTCTGATCTGGTGTCAGAGATGGAGATGATGAAGATGATTGGGAAACACA |
| AGAATATCATAAATCTTCTTGGAGCCTGCACACAGGATGGGCCTCTCTATGTCAT |
| AGTTGAGTATGCCTCTAAAGGCAACCTCCGAGAATACCTCCGAGCCCGGAGGCC |
| ACCCGGGATGGAGTACTCCTATGACATTAACCGTGTTCCTGAGGAGCAGATGACC |
| TTCAAGGACTTGGTGTCATGCACCTACCAGCTGGCCAGAGGCATGGAGTACTTGG |
| CTTCCCAAAAATGTATTCATCGAGATTTAGCAGCCAGAAATGTTTTGGTAACAGA |
| AAACAATGTGATGAAAATAGCAGACTTTGGACTCGCCAGAGATATCAACAATAT |
| AGACTATTACAAAAAGACCACCAATGGGCGGCTTCCAGTCAAGTGGATGGCTCC |
| AGAAGCCCTGTTTGATAGAGTATACACTCATCAGAGTGATGTCTGGTCCTTCGGG |
| GTGTTAATGTGGGAGATCTTCACTTTAGGGGGCTCGCCCTACCCAGGGATTCCCG |
| TGGAGGAACTTTTTAAGCTGCTGAAGGAAGGACACAGAATGGATAAGCCAGCCA |
| ACTGCACCAACGAACTGTACATGATGATGAGGGACTGTTGGCATGCAGTGCCCTC |
| CCAGAGACCAACGTTCAAGCAGTTGGTAGAAGACTTGGATCGAATTCTCACTCTC |
| ACAACCAATGAGATGGCAGATGATCAGGGCTGTATTGAAGAGCAGGGGGTTGAG |
| GATTCAGCAAATGAAGATTCAGTGGATGCTAAGCCAGACCGGTCCTCGTTTGTAC |
| CGTCCCTCTTCAGTAAGAAGAAGAAAAATGTCACCATGCGATCCATCAAGACCA |
| CCCGGGACCGAGTGCCTACATATCAGTACAACATGAATTTTGAAAAGCTGGGCA |
| AATGCATCATAATAAACAACAAGAACTTTGATAAAGTGACAGGTATGGGCGTTC |
| GAAACGGAACAGACAAAGATGCCGAGGCGCTCTTCAAGTGCTTCCGAAGCCTGG |
| GTTTTGACGTGATTGTCTATAATGACTGCTCTTGTGCCAAGATGCAAGATCTGCTT |
| AAAAAAGCTTCTGAAGAGGACCATACAAATGCCGCCTGCTTCGCCTGCATCCTCT |
| TAAGCCATGGAGAAGAAAATGTAATTTATGGGAAAGATGGTGTCACACCAATAA |
| AGGATTTGACAGCCCACTTTAGGGGGGATAGATGCAAAACCCTTTTAGAGAAAC |
| CCAAACTCTTCTTCATTCAGGCTTGCCGAGGGACCGAGCTTGATGATGGCATCCA |
| GGCCGACTCGGGGCCCATCAATGACACAGATGCTAATCCTCGATACAAGATCCC |
| AGTGGAAGCTGACTTCCTCTTCGCCTATTCCACGGTTCCAGGCTATTACTCGTGG |
| AGGAGCCCAGGAAGAGGCTCCTGGTTTGTGCAAGCCCTCTGCTCCATCCTGGAGG |
| AGCACGGAAAAGACCTGGAAATCATGCAGATCCTCACCAGGGTGAATGACAGAG |
| TTGCCAGGCACTTTGAGTCTCAGTCTGATGACCCACACTTCCATGAGAAGAAGCA |
| GATCCCCTGTGTGGTCTCCATGCTCACCAAGGAACTCTACTTCAGTCAATAG |

Amino Acid Sequences of Anti-PD1 Antibody

The amino acid sequences for the anti-PD1 antibody cetrelimab are provided in Table 8.

TABLE 8

| | |
|---|---|
| HCDR1 (SEQ ID NO: 40) | SYAIS |
| HCDR2 (SEQ ID NO: 41) | GIIPIFDTANYAQKFQG |
| HCDR3 (SEQ ID NO: 42) | PGLAAAYDTGSLDY |
| LCDR1 (SEQ ID NO: 43) | RASQSVRSYLA |
| LCDR2 (SEQ ID NO: 44) | DASNRAT |
| LCDR3 (SEQ ID NO: 45) | QQRNYWPLT |
| VH (SEQ ID NO: 46) | QVQLVQSGAEVKKPGSSVKVSCKAS GGTFSSYAISWVRQAPGQGLEWMGG IIPIFDATNYAQKFQGRVTITADES TSTAYMELSSLRSEDTAVYYCARPG LAAAYDTGSLDYGQWGTLVTVSS |

TABLE 8-continued

| | |
|---|---|
| VL (SEQ ID NO: 47) | EIVLTQSPATLSLSPGERATLSCRA SQSVRSYLAWYQQKPGQAPRLLIYD ASNRATGIPARFSGSGSGTDFTLTI SSLEPEDFAVYYCQQRNYWPLTFGQ GTKVEIK |
| HC (SEQ ID NO: 48) | QVQLVQSGAEVKKPGSSVKVSCKAS GGTFSSYAISWVRQAPGQGLEWMGG IIPIFDTANYAQKFQGRVTITADES TSTAYMELSSLRSEDTAVYYCARPG LAAAYDTGSLDYWGQGTLVTVSSAS TKGPSVFPLAPCSRSTSESTAALGC LVKDYFPEPVTVSWNSGALTSGVHT FPAVLQSSGLYSLSSVVTVPSSSLG TKTYTCNVDHKPSNTKVDKRVESKY GPPCPPCPAPEFLGGPSVFLFPPKP KDTLMISRTPEVTCVVVDVSQEDPE VQFNWYVDGVEVHNAKTKPREEQFN STYRVVSVLTVLHQDWLNGKEYKCK VSNKGLPSSIEKTISKAKGQPREPQ VYTLPPSQEEMTKNQVSLTCLVKGF YPSDIAVEWESNGQPENNYKTTPPV LDSDGSFFLYSRLTVDKSRWQEGNV FSCSVMHEALHNHYTQKSLSLSLGK |
| LC (SEQ ID NO: 49) | EIVLTQSPATLSLSPGERATLSCRA SQSVRSYLAWYQQKPGQAPRLLIYD ASNRATGIPARFSGSGSGTDFTLTI |

TABLE 8-continued

| |
|---|
| SSLEPEDFAVYYCQQRNYWPLTFGQ<br>GTKVEIKRTVAAPSVFIFPPSDEQL<br>KSGTASVVCLLNNFYPREAKVQWKV<br>DNALQSGNSQESVTEQDSKDSTYSL<br>SSTLTLSKADYEKHKVYACEVTHQG<br>LSSPVTKSFNRGEC |

EXAMPLES

These examples are provided for illustrative purposes only and not to limit the scope of the claims provided herein.

Example 1: Phase 1b/2, Multicenter, Open-Label Study, Erdafitinib Plus Cetrelimab Cohort (NCT03473743)

A non-limiting example of a phase 1b/2, multicenter, open-label dose-escalation study to evaluate erdafitinib plus cetrelimab is described below.

Objective

The primary objective of the study is to assess safety, characterize PK and identify the recommended phase 2 dose (RP2D) and schedule of erdafitinib in combination with cetrelimab.

Methods

Study Overview

Subjects with metastatic or locally advanced urothelial cancer with select FGFR gene alterations with any number of prior lines of systemic therapy are eligible for enrollment in this part of the study. Subjects must have select FGFR gene alterations in tumor or blood. Subjects must be 18 years or older and have ECOG performance status (PS) Grade of 0-2

Three dosing levels (DL1, DL2 or DL2A) of erdafitinib were explored in phase 1b (as defined in FIG. 1), while CET intravenous (IV) dose was fixed at 240 mg every two weeks. In DL1, DL2 and DL2A, concurrent daily dosing of oral erdafitinib plus the fixed IV dose of CET were started at Cycle 1 Day 1 (C1D1) (240 mg IV every 2 weeks). Dose-limiting toxicity (DLT) evaluation period is 1 cycle (4 weeks). The starting dose was DL1 (6 mg erdafitinib+240 mg CET). Dose escalation was permitted if no patient in a dose cohort experienced a DLT and continued until RP2D was identified.

Alternative dosing regimens (DL1B and DL2B) are currently under exploration. Without wishing to be bound by any theory, it is hypothesized that sequential administration (starting with the FGFR inhibitor erdafitinib for 1 cycle of 4 weeks [28 days] prior to first administration of anti-PD-1 cetrelimab) might mitigate potential toxicities or lead to increased clinical benefit compared with concurrent administration. The Alternative Dose Level regime starts with a 4-week run-in of erdafitinib with subsequent concurrent dosing of erdafitinib and cetrelimab. Dose Level 1B (DL1B) will receive erdafitinib (6 mg) and cetrelimab 240 mg administered intravenously on Day 1 and Day 15 of a 4-week cycle. Dose Level 2B (DL2B) will receive erdafitinib (8 mg with up-titration to 9 mg after RP2D) and cetrelimab 240 mg administered intravenously on Day 1 and Day 15 of a 4-week cycle. At Cycle 5, the dose regimen for cetrelimab for all Alternative Dose Levels changes to 480 mg every 4 weeks. The Alternative Dose Levels will have a DLT period of 2 cycles (8 weeks). In these Alternative dose levels, the administration of cetrelimab is initiated on Cycle 2 Day 1 (C2D1), while the dose and schedule of erdafitinib is unchanged.

Inclusion and Exclusion Criteria

Inclusion criteria

Adult mUC patients aged 18 years or older with specific FGFR alterations (FGFRa) (see Table 9) based on evaluation of tumor tissue and blood; ECOG performance status of less than or equal to 2, and who have progressed on or after one or more prior line of systemic therapy.

Exclusion Criteria

Prior FGFR or PD-1/PD(L)-1 inhibitor treatment;

Adequate bone marrow liver and renal (CrC greater than or equal to 40 ml/min) function;

Uncontrolled cardiovascular disease, symptomatic brain metastases, active autoimmune disease, known hepatitis B or C, or known HIV;

Chemotherapy within 3 weeks of cycle 1, day 1 (C1D1).

TABLE 9

| Molecular Eligibility Based Upon the Following FGFR Alterations | | | | |
|---|---|---|---|---|
| 1 of the following fusions: | | OR | 1 of the following FGFR3 gene mutations: | |
| FGFR2-BICC1 | FGFR2-CASP7 | | R248C | S249C |
| FGFR3-TACC3 | FGFR3-BAIAP2L1 | | G370C | Y373C |

Outcome Measures

The outcome measures were: incidences of DLT; safety (adverse events (AEs) were monitored throughout the study); and pharmacokinetic (PK) parameters and metrics of systemic exposure of erdafitinib.

Assessments

Safety was assessed continuously by the investigator according to the NCI CTCAE v4.03 and based on medical review of AE reports and the results of vital sign measurements, physical examinations, clinical laboratory tests, ophthalmology examinations, and other safety evaluations. Patients were assessed for efficacy using radiographic imaging performed during screening, once every 6 weeks for the first 12 months, then every 12 weeks until disease progression. Tumor responses were assessed by investigators according to RECIST 1.1 criteria.

Dose-Limiting Toxicity

The DLTs were based on drug-related AEs. DLT evaluation period is 1 full cycle (4 weeks) of erdafitinib and cetrelimab. Patients were evaluable, if they received more than 75% of any of the study drugs in the DLT evaluation period. Patients receiving <75% of each assigned dose due to reasons other than toxicities were replaced with a new patient. Only toxicities that occurred during the DLT evaluation period were considered as DLTs for dose escalation decisions, but toxicities that occurred during the entire treatment period were considered in decisions regarding the RP2D.

Pharmacokinetics (PK)

The PK of erdafitinib and cetrelimab in combination was assessed at different timepoints, following the administration of each compound. Pre- and post-dose plasma samples (C1D1 [pre- and post-dose], C1D15 [pre- and post-dose], C2D1 [pre-dose], C3D1 [pre-dose]) were collected for erdafitinib. Serum samples were also analyzed for cetrelimab concentrations 24 hours before infusion and at end of infusion on C1D1 and C1D15.

Statistical Assessments

A modified toxicity probability interval method (mTPI)-2 guided the dose escalation and RP2D recommendation. In the mTPI-2 method, a decision theoretical framework links the dose-finding decisions of "Stay", "De-escalation", and "Escalation" with the equivalence interval, over-dosing interval(s), and under-dosing interval(s), respectively.

Results

Patients

At the time of data cut off, 22 patients were enrolled in the dose-escalation (phase 1b) study. Baseline disease characteristics and demographics are provided in Table 10.

TABLE 10

Baseline disease characteristics and demographics

| n (%) | ERDA 6 mg + CET 240 mg (n = 4) | ERDA 8 mg no Upt + CET 240 mg (n = 3) | ERDA 8 mg with Upt + CET 240 mg at C2D1 (n = 3) | ERDA 8 mg with Upt + CET 240 mg (n = 12) | Total (N = 22) |
|---|---|---|---|---|---|
| Treatment exposure, mos, median (range) | 5.3 (3-7) | 8.3 (0-9) | 5.1 (5-5) | 5.5 (0-9) | 5.5 (0-9) |
| Age, yrs, median (range) | 74 (64-79) | 68 (57-75) | 58 (51-65) | 67 (31-73) | 67 (31-79) |
| Sex, n (%) | | | | | |
| Men | 4 (100) | 2 (67) | 3 (100) | 7 (58) | 16 (73) |
| Female | 0 | 1 (33) | 0 | 5 (42) | 6 (27) |
| ECOG, n (%) | | | | | |
| 0 | 2 (50) | 1 (33) | 3 (100) | 8 (67) | 14 (64) |
| 1 | 2 (50) | 2 (67) | 0 | 4 (33) | 8 (36) |
| Presence of visceral metastases[a] | 2 (50) | 3 (100) | 2 (67) | 5 (2) | 12 (55) |
| No. of prior therapy lines[b] | | | | | |
| 0 | 0 | 0 | 0 | 1 (8) | 1 (5) |
| 1 | 4 (100) | 2 (67) | 3 (100) | 7 (58) | 16 (73) |
| 2 | 0 | 1 (33) | 0 | 4 (33) | 5 (23) |
| Primary tumor location | | | | | |
| Lower tract | 3 (75) | 3 (100) | 2 (67) | 6 (50) | 14 (64) |
| Upper tract | 1 (25) | 0 | 1 (33) | 6 (50) | 8 (36) |
| PD-L1 positive status[c] | | | | | |
| Yes | 0 | 0 | 0 | 4 (33) | 4 (18) |
| No | 1 (25) | 1 (33) | 0 | 2 (17) | 4 (18) |
| Not available | 3 (75) | 2 (67) | 3 (100) | 6 (50) | 14 (64) |
| Any FGFR alteration[d] | 4 (100) | | 1 (33) | 10 (83) | 17 (77) |
| Mutations (excluding fusions)*, n (%) | 3 (75) | 2 (67) | 1 (33) | 9 (75) | 15 (68) |
| Fusions (excluding mutations)*, n (%) | 1 (25) | 0 | 0 | 1 (8) | 2 (9) |

Values are n (%) unless otherwise noted.

[a]Lung, liver, bone.

[b]In phase 2, prior lines were for neo/adjuvant therapy.

[c]PD-L1 expression level was assessed by immunohistochemistry in tumor tissue provided at screening (PD-L1 positivity if Tumor Proportion Score ≥ 1%).

[d]Based on central laboratory tissue testing, FGFR alteration status was not available for 3 patients at the time of this analysis; 2 patients enrolled using local and blood-based testing, respectively, but did not have FGFR alterations according to central laboratory tissue testing.

DLT and Safety

RP2D was established as 8 mg UpT+240 mg CET (DL2). At data cutoff, 13 of 22 patients were currently on active treatment; all 4 patients treated with DL1 have discontinued the study. Overall (across all dose cohorts), treatment-emergent AEs (TEAEs) and treatment-related AEs (TRAEs) were reported in most patients (91% each; Table 11)

TABLE 11

| Patients with AEs, n (%) | Erda 6 mg + CET 240 mg (n = 4) | Erda 8 mg No-Upt + CET 240 mg (n = 3) | Erda 8 mg with Upt + CET 240 mg at C2D1 (n = 3) | Erda 8 mg with Upt + CET 240 mg (n = 12) | Total (N = 22) |
|---|---|---|---|---|---|
| Any TEAEs | 4 (100) | 3 (100) | 2 (67) | 11 (92) | 20 (91) |
| Any TRAEs[a] | 4 (100) | 3 (100) | 2 (67) | 11 (92) | 20 (91) |
| Grade 3-4 TEAs | 3 (75) | 2 (67) | 1 (33) | 5 (42) | 11 (50) |
| Grade 3-4 TRAEs[a] | 1 (25) | 2 (67) | 1 (33) | 5 (42) | 9 (41) |

TABLE 11-continued

| Patients with AEs, n (%) | Erda 6 mg + CET 240 mg (n = 4) | Erda 8 mg No-Upt + CET 240 mg (n = 3) | Erda 8 mg with Upt + CET 240 mg at C2D1 (n = 3) | Erda 8 mg with Upt + CET 240 mg (n = 12) | Total (N = 22) |
|---|---|---|---|---|---|
| Serious TEAs | 3 (75) | 0 | 0 | 4 (33) | 7 (32) |
| Serious TRAEs[a] | 0 | 0 | 0 | 3 (25) | 3 (14) |
| TRAEs leading to discontinuation | 0 | 1 (33) | 0 | 3 (25) | 4 (18) |
| Most common grade 3-4 TRAE, i.e. stomatitis[b] | 1 (25) | 0 | 0 | 2 (17) | 3 (14) |
| TEAE of special interest, i.e. CSR[b] | 0 | 1 (33) | 0 | 2 (17) | 3 (14) |

[a]An AE was categorized as related if assessed by the investigator as possibly, probably, or very likely related to study agent.
[b]AEs were coded using MedDRA v22.1
CSR stands for central serous retinopathy.

Grade 3-4 TRAEs occurred in 41% of patients overall and in 42% of patients at the RP2D (Table 11). Only 1 (25%) grade 4 TEAE occurred.

TABLE 12

Most Common TEAEs (Occurring in >20% of Patients Overall)

| Patients with TEAs, n (%) | Erda 6 mg + CET 240 mg (n = 4) | Erda 8 mg No-Upt + CET 240 mg (n = 3) | Erda 8 mg with Upt + CET 240 mg at C2D1 (n = 3) | Erda 8 mg with Upt + CET 240 mg (n = 12) | Total (N = 22) |
|---|---|---|---|---|---|
| Stomatitis | 3 (75) | 3 (100) | 1 (33) | 9 (75) | 16 (73) |
| Diarrhea | 1 (25) | 1 (33) | 1 (33) | 9 (75) | 12 (55) |
| Dry mouth | 2 (50) | 2 (67) | 1 (33) | 7 (58) | 12 (55) |
| Hyperphophataemia | 1 (25) | 2 (67) | 0 | 7 (58) | 10 (46) |
| Dysgeusia | 2 (50) | 2 (67) | 0 | 4 (33) | 8 (36) |
| Dry skin | 1 (25) | 2 (67) | 0 | 4 (33) | 7 (32) |
| Alopecia | 0 | 2 (67) | 0 | 4 (33) | 6 (27) |
| Asthenia | 0 | 1 (33) | 0 | 7 (58) | 8 (36) |
| Decreased appetite | 2 (50) | 0 | 0 | 5 (33) | 6 (27) |
| Palmar-plantar erythrodysesthesia syndrome | 0 | 2 (67) | 1 (33) | 2 (17) | 5 (23) |
| Pyrexia | 2 (50) | 0 | 0 | 3 (25) | 5 (23) |
| Pruritus | 1 (25) | 1 (33) | 0 | 3 (25) | 5 (23) |
| Onycholysis | 0 | 1 (33) | 1 (33) | 3 (25) | 5 (23) |

Abbreviations:
CET = cetrelimab,
ERDA = erdafitinib;
Upt = uptitration

Overall, serious TRAEs occurred in 3 patients (Table 11): pneumonia and diarrhea in 1, serous retinal detachment in 1, and herpetic keratitis in 1 patient.

Overall, stomatitis was the most common TEAE, occurring in 73% of patients; grade 3 treatment-related stomatitis occurred in 14% of patients overall and in 17% of patients at the RP2D (Tables 12 and 13). A summary of the most common TEAs (occurring in >20% of patients overall), is provided in Table 12.

Two patients died due to TEAEs: 1 patient due to large intestinal obstruction and 1 patient due to urinary tract infection (both in the DL1 cohort). Overall, 3 patients had central serous retinopathy (CSR) events (a known class effect of FGFR inhibitors) (Table 11); 1 patient had a grade 3 CSR event and 2 patients had grade 2 CSR events; all events improved to grade 1 or resolved. There were no grade 4/5 TRAEs.

Table 13 provides the most common grade≥3 TRAE (treatment related adverse event).

TABLE 13

| Grade ≥3 TRAEs[a] | | | | | |
|---|---|---|---|---|---|
| Patients with TRAEs, n (%) | ERDA 6 mg + CET 240 mg (n = 4) | ERDA 8 mg No UpT + CET 240 mg (n = 3) | ERDA 8 mg UpT + CET 240 mg at C2D1 (n = 3) | ERDA 8 mg UpT + CET 240 mg (n = 12) | Total (n = 22) |
| Stomatitis | 1 (25) | 0 | 0 | 2 (17) | 3 (14) |
| Nail discoloration | 0 | 0 | 1 (33) | 0 | 1 (5) |
| Nail dystrophy | 0 | 1 (33) | 0 | 0 | 1 (5) |
| Onycholysis | 0 | 1 (33) | 0 | 0 | 1 (5) |
| Hypothyroidism | 0 | 0 | 0 | 1 (8) | 1 (5) |
| Serious retinal detachment | 0 | 0 | 0 | 1 (8) | 1 (5) |
| Autoimmune hepatitis | 0 | 0 | 0 | 1 (8) | 1 (5) |
| Pneumonia | 0 | 0 | 0 | 1 (8) | 1 (5) |
| GGT increased | 0 | 0 | 0 | 1 (8) | 1 (5) |
| Hyperophosphatemia | 0 | 1 (33) | 0 | 0 | 1 (5) |

[a]No grade 4 or 5 TRAEs were reported. GGT stands for gamma-glutamyltrasferase.

Efficacy

Figure 2:
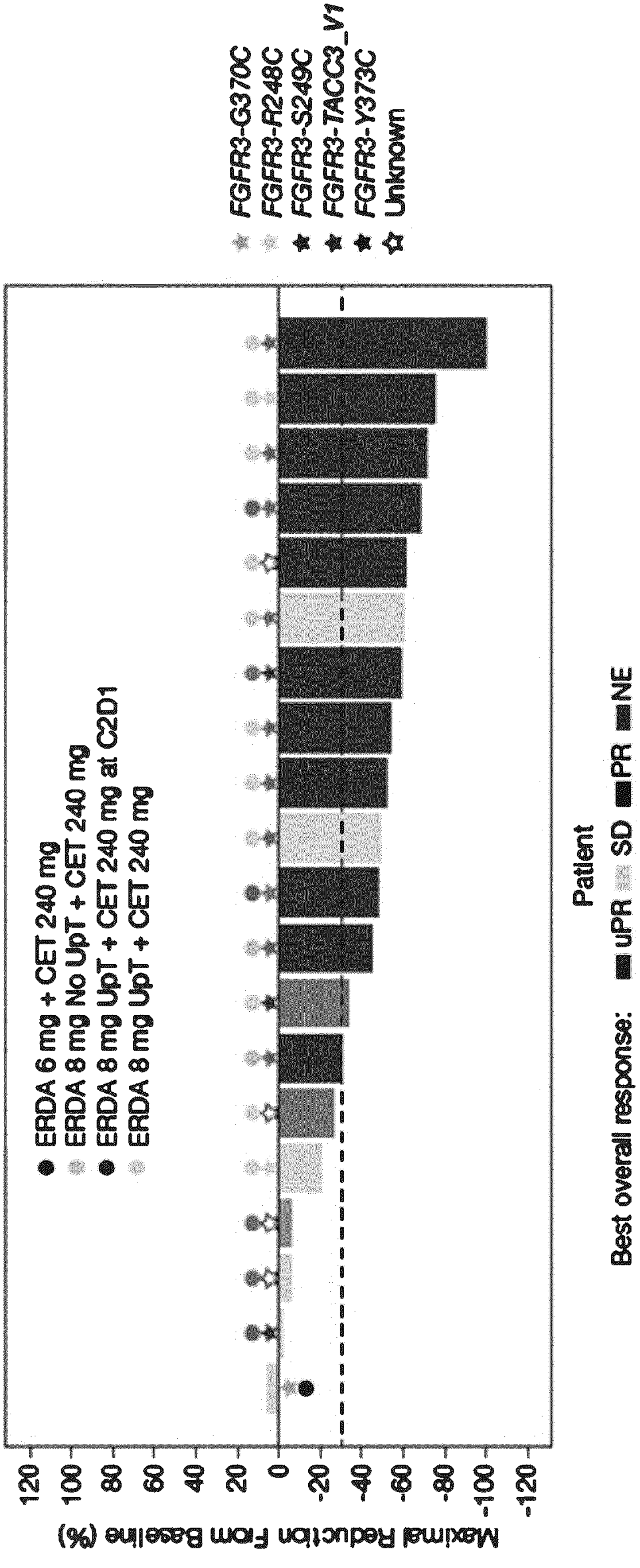
FIG. 2 is a graph showing maximal percentage reduction of sum of target lesion diameters from baseline for the safety analysis population. The y-axis is maximal reduction from baseline (%) and the x-axis is patient. For a response to qualify as stable disease (SD), follow-up measurements must have met the stable disease criteria at least once at a minimum interval not less than 6 weeks after first dose of study drug. One patient was not response evaluable as they did not have measurable disease at baseline, and therefore this patient was excluded from the analysis for response. As of the time of data cutoff, 1 other patient did not have a subsequent on-study tumor assessment. To be counted as a PR, a second scan to confirm response was required. Bars are designated uPR (unconfirmed PR), SD (stable disease), PR (partial response) and NE (not evaluable).
Figure 3:
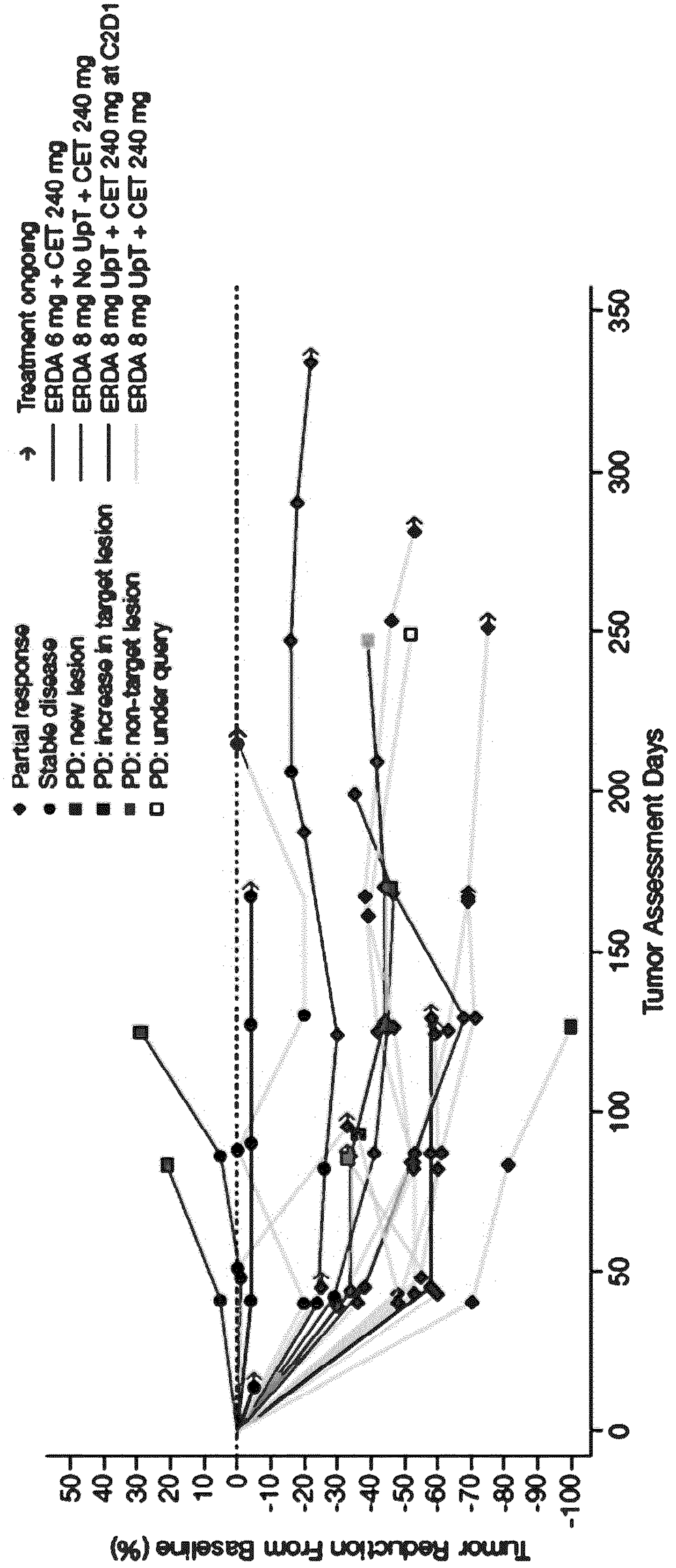
FIG. 3 is a graph of percent change of tumor reduction (target lesion) over time from baseline for the safety analysis population. The y-axis is percent tumor reduction from baseline (%), and the x-axis is tumor assessment in days.

In all response-evaluable patients (n=21), confirmed ORR was 52%; confirmed ORR in 11 evaluable patients treated at the RP2D was 55% (Table 14, FIG. 2 and FIG. 3). The disease control rate, which included unconfirmed complete responses (CRs) and partial responses (PRs), and stable disease (SD), was 91% overall and 100% at the RP2D.

TABLE 14

| Summary of Best Overall Response for the Response-Evaluable Set[a] | | | | | |
|---|---|---|---|---|---|
| Patients with response, n (%) | ERDA 6 mg + CET 240 mg (n = 4) | ERDA 8 mg No UpT + CET 240 mg (n = 3) | ERDA 8 mg UpT + CET 240 mg at C2D1 (n = 3) | ERDA 8 mg UpT + CET 240 mg (n = 11) | Total (n = 21) |
| ORR[b] | 2 (50) | 2 (67) | 1 (33) | 6 (55) | 11 (52) |
| Disease control rate[c] | 4 (100) | 2 (67) | 2 (67) | 11 (100) | 19 (91) |
| Best overall response | | | | | |
| PR (confirmed) | 2 (50) | 2 (67) | 1 (33) | 6 (55) | 11 (52) |
| uPR | 0 | 0 | 0 | 2 (18) | 2 (10) |
| SD | 2 (50) | 0 | 1 (33) | 3 (27) | 6 (29) |
| PD | 0 | 1 (33) | 0 | 0 | 1 (5) |
| Not evaluable | 0 | 0 | 1 (33) | 0 | 1 (5) |

[a]Includes all patients in the safety analysis set who have had a baseline and ≥1 adequate post-treatment disease evaluation, have had clinical signs or symptoms of disease progression, or died before the first post-treatment disease evaluation; 1 patient was not response evaluable as they did not have measurable disease at baseline, and therefore this patient was excluded from the analysis for response.
[b]Includes only confirmed responses (CR + PR).
[c]CR + PR + uCR + uPR + SD.
CI, confidence interval; PD, progressive disease; uCR, unconfirmed CR; uPR, unconfirmed PR.

The maximal percentage reduction of sum of target lesion diameters from baseline is presented in FIG. 2. FIG. 3 provides data showing percent change of tumor reduction (target lesions) over time from baseline.

CONCLUSIONS

Erdafitinib plus cetrelimab is an active and tolerable combination in patients with mUC and specific FGFR alterations. The randomized phase 2 portion of this study is ongoing and continuing to explore erdafitinib plus cetrelimab versus erdafitinib monotherapy as first-line treatment for cisplatin-ineligible patients with mUC. A safety cohort of patients receiving a combination treatment regimen of erdafitinib, cetrelimab, and platinum-based chemotherapy in phase 1 of the NCT03473743 study is being developed.

Example 2: Phase 1b, Multicenter, Open-Label Study, Erdafitinib Plus Cetrelimab Plus Platinum (Cisplatin or Carboplatin) Chemotherapy Cohort (NCT03473743)

A non-limiting example of an ongoing phase 1b, multicenter, open-label dose-escalation study to evaluate erdafitinib plus cetrelimab plus platinum (cisplatin or carboplatin) chemotherapy is described below.

Objective

The primary objective of the study is to characterize the safety and tolerability of erdafitinib in combination with cetrelimab and platinum (cisplatin or carboplatin) chemotherapy, and to identify the recommended Phase 2 dose(s) (RP2D) and schedule for erdafitinib with cetrelimab and platinum (cisplatin or carboplatin) chemotherapy. The secondary objective is to characterize the PK of erdafitinib in combination with cetrelimab, and platinum (cisplatin or carboplatin) chemotherapy and to assess the immunogenicity of cetrelimab.

Endpoint

The primary endpoint is frequency and type of dose-limiting toxicity (DLT). The secondary endpoints are concentration and PK parameters of erdafitinib, cetrelimab, and platinum (cisplatin or carboplatin) chemotherapy and detection of antibodies to cetrelimab and effects on serum cetrelimab levels.

Methods

Study Overview

The expected number of subjects to be treated in the Phase 1b erdafitinib plus cetrelimab plus platinum chemotherapy cohort is approximately 40. Three wild-type subjects will be enrolled in the initial erdafitinib plus cetrelimab plus cisplatin dose level (50 mg/m$^2$). If the starting dose is safe, 3 additional wild-type subjects and 3 additional subjects with select FGFR gene alterations will be enrolled into the escalated dose of cisplatin (60 mg/m$^2$). Wild-type is defined as subjects without FGFR gene alteration and subjects with FGFR gene alterations other than the select FGFR alterations (see Table 9). Approximately 10 additional subjects with select FGFR gene alterations will be enrolled at the MTD for erdafitinib plus cetrelimab plus cisplatin.

Three wild-type subjects will be enrolled in the initial erdafitinib plus cetrelimab plus carboplatin dose level (AUC 4 mg/mL/min). If the starting dose is safe, 3 additional wild-type subjects and 3 additional subjects with select FGFR gene alterations will be enrolled into the escalated dose of carboplatin (AUC 5 mg/mL/min). Approximately 10 additional subjects with select FGFR gene alterations will be enrolled at the MTD for erdafitinib plus cetrelimab plus carboplatin.

The dose levels within the platinum chemotherapy cohort are:

Erdafitinib+cetrelimab+cisplatin (DL2C, DL2C1, or DL2C2)

Erdafitinib, cetrelimab and cisplatin start concurrently on C1D1. A maximum of 4 cycles of cisplatin will be administered. The DLT period is 2 cycles (6 weeks).

Erdafitinib+cetrelimab+carboplatin (DL2D or DL2D1)

Erdafitinib, cetrelimab and carboplatin start concurrently on C1D1. A maximum of 4 cycles of carboplatin will be administered. The DLT period is 2 cycles (6 weeks).

Dose-Limiting Toxicity

The DLTs will be based on drug-related AEs. DLT evaluation period is 1 full cycle (4 weeks) of erdafitinib and cetrelimab. Patients are evaluable, if they receive more than 75% of any of the study drugs in the DLT evaluation period. Patients receiving <75% of each assigned dose due to reasons other than toxicities are replaced with a new patient. All available safety data from subjects will be taken into consideration.

Dosage and Administration

Erdafitinib (8 mg) will be given once daily at approximately the same time of the day with or without food. Cetrelimab and platinum chemotherapy intravenous infusions will be administered on Day 1 of a 3-week cycle. Erdafitinib oral dose will be given first, followed by cetrelimab and then platinum chemotherapy. A maximum of 4 cycles of platinum chemotherapy will be administered. If platinum chemotherapy is discontinued, the subject can continue to receive erdafitinib and cetrelimab.

Table 15 provides an overview of the dose levels (in which Q3W refers to once every three weeks and AUC refers to area under the concentration curve).

TABLE 15

Erdafitinib, Cetrelimab, and Platinum Chemotherapy Administration; Dose Levels

| Phase | Dosing Level [a, e] | Cisplatin or Carboplatin (IV infusion) [c, d] | Erdafitinib (oral administration) [c] | Cetrelimab (IV infusion)[b, c] |
|---|---|---|---|---|
| 1b | DL2C | Cisplatin 50 mg/m$^2$ Q3W | 8 mg (no up-titration) once daily | 360 mg Q3W |
| 1b | DL2C1 | Cisplatin 60 mg/m$^2$ Q3W | | |
| 1b | DL2D | Carboplatin AUC 4 mg/mL/min Q3W (Not to Exceed 600 mg) | | |
| 1b | DL2D1 | Carboplatin AUC 5 mg/mL/min Q3W (Not to Exceed 750 mg) | | |

[a] Additional dosing schedules may be explored if recommended and agreed upon by the sponsor.
[b]The cetrelimab dosing schedule can be adjusted if recommended and agreed upon by the sponsor.
[c] On days that all study drugs will be administered, the sequence of administration will be erdafitinib first, followed by cetrelimab and then platinum chemotherapy
[d] Erdafitinib + cetrelimab can continue every 3 weeks after a maximum of 4 cycles of platinum chemotherapy.
[e] Subject to dose escalation criteria The starting dose is 8 mg erdafitinib (no up titration); 360 mg Q3W cetrelimab, and either 50 mg/m$^2$ Q3W for cisplatin (DL2C) or AUC 4 mg/mL/min Q3W for carboplatin (DL2D).

If based on the rules below, dose escalation for cisplatin is DL2C to DL2C1. If based on the rules below, dose escalation for carboplatin is DL2D to DL2D1.

The following rules for escalation apply:

At least 3 subjects may be dosed in each dose level that will be explored.

A staggered enrollment strategy will be applied to the first 3 subjects in a dose level. A minimal interval of 24 hours between a subject's first dose will be required.

At least 3 subjects per dose level are required to complete the DLT evaluation period or be discontinued for DLT before determination of the dose and schedule for the next dose cohort.

All available data will be evaluated including, but not limited to, PK, PD, safety, and preliminary anti-tumor activity, and a decision will be made about whether to escalate, stay at the current dose, or de-escalate the dose level based on modified toxicity probability interval (mTPI-2) guidelines.

Dose escalation may continue until the RP2D is identified.

The identification of the RP2D will be based on the totality of data from all dose cohorts tested.

Determination as to whether to modify or terminate dose levels, include additional dose levels, change doses or schedules of either drug, modify the study conduct if deemed necessary, and select the RP2D regimen for Phase 2 based on emerging data.

Intra-subject dose escalation is not allowed and subjects in Phase 1b erdafitinib+cetrelimab+platinum chemotherapy dose levels will not be entered into Phase 2.

Subject Population

Adult subjects age 18 years and older with metastatic or locally advanced urothelial cancer who meet the molecular eligibility and full-study eligibility are eligible for the study. Screening assessments will be performed as indicated in the Phase 1b erdafitinib+cetrelimab cohort. Molecular eligibility assessment may occur ≥28 days prior to administration of the study drugs.

Inclusion and Exclusion Criteria

Inclusion Criteria

≥18 years of age;

Histologic demonstration of transitional cell carcinoma of the urothelium. Variant urothelial carcinoma histologies such as glandular or squamous differentiation, or evolution to more aggressive phenotypes such as sarcomatoid or micropapillary change are acceptable;

Metastatic or locally advanced urothelial cancer (Stage IV disease per AJCC Staging Guidelines)

Approximately 6 subjects will be wild-type. Wild-type is defined as subjects without FGFR gene alteration and subjects with FGFR gene alterations other than the select FGFR alterations described in Table 9. All other subjects must have at least one select FGFR alteration as defined in Table 9;

Must have measurable disease by radiological imaging according to the Response Evaluation Criteria in Solid Tumors (RECIST, version 1.1) at baseline;

No prior systemic therapy for metastatic disease. Note: Subjects who received neoadjuvant or adjuvant chemotherapy and showed disease progression, within 12 months of the last dose are considered to have received systemic chemotherapy in the metastatic setting;

Renal function for subjects must have a creatinine clearance (CrCl)>50 mL/min as calculated by Cockcroft Gault;

ECOG 0-1 for cisplatin and ECOG 0-2 for carboplatin;

Adequate organ function at screening;

Before the first does of study drug, women of childbearing potential and fertile men who are sexually active must agree to use a highly effective method of contraception (<1%/year failure rate) during the study and for 6 months after the last dose of study drug;

Women of childbearing potential must have a negative pregnancy test at Screening within ≤7 days of C1D1 (first dose of study drug) using a highly sensitive pregnancy test (serum Phuman chorionic gonadotropin [β-hCG]);

Exclusion Criteria

Treatment with any other investigational agent or participation in another clinical study with therapeutic intent within 30 days prior to C1D1 and subjects who have received the following nitrosoureas and mitomycin C within 6 weeks;

Prior neoadjuvant/adjuvant chemotherapy is allowed if the last dose was given >12 months prior to recurrent disease progression and did not result in drug-related toxicity leading to treatment discontinuation;

Prior anti-PD-1, anti-PD-L1, or anti-PD-L2 therapy. Prior neoadjuvant/adjuvant checkpoint inhibitor therapy is allowed if the last dose was given >12 months prior to recurrent disease progression and did not result in drug-related toxicity leading to treatment discontinuation. PD-1 for non-muscle invasive bladder cancer is also allowed;

Active malignancies requiring concurrent therapy other than urothelial cancer;

Symptomatic central nervous system metastases;

Prior FGFR inhibitor treatment;

Radiation therapy 30 days prior to planned C1D1;

History of uncontrolled cardiovascular disease including: Unstable angina, myocardial infarction, ventricular fibrillation, Torsades de Pointes, cardiac arrest, or known congestive heart failure Class III-V within the preceding 3 months; cerebrovascular accident or transient ischemic attack within the preceding 3 months;

Known to be seropositive for human immunodeficiency virus or acquired immune deficiency syndrome;

Any of the following:

- Evidence of serious active viral, bacterial, or uncontrolled systemic fungal infection.
- Active autoimmune disease or a documented history of autoimmune disease that requires systemic steroids or immunosuppressive agents. Note: Subjects with vitiligo or resolved childhood asthma/atopy would be an exception to this rule.
- Grade 3 or higher toxicity effects from previous treatment with immunotherapy.
- Psychiatric conditions (e.g., alcohol or drug abuse), dementia, or altered mental status.
- Any other issue that would impair the ability of the subject to receive or tolerate the planned treatment at the investigational site, to understand informed consent or any condition for which, in the opinion of the investigator, participation would not be in the best interest of the subject (eg, compromise the well-being) or that could prevent, limit, or confound the protocol-specified assessments.

Pulmonary compromise requiring supplemental oxygen use to maintain adequate oxygenation.

Active or chronic hepatitis B or hepatitis C disease as determined by hepatitis B surface antigen (HBsAg), hepatitis B core antibody, or hepatitis C antibody (anti-HCV) positivity at Screening. If positive, further testing of quantitative levels to rule out active infection is required (see Attachment 2).

Not recovered from reversible toxicity of prior anticancer therapy (except toxicities which are considered by the investigator as not clinically significant, such as alopecia, skin discoloration, or Grade 1 hearing loss or neuropathy).

Impaired wound healing capacity defined as skin/decubitus ulcers, chronic leg ulcers, known gastric ulcers, or unhealed incisions;

Allergies, hypersensitivity, or intolerance to protein-based therapies or with a history of any significant drug allergy (such as anaphylaxis, hepatotoxicity, or immune-mediated thrombocytopenia or anemia), or to excipients of erdafitinib or cetrelimab (see the Investigator's Brochures for a list of excipients);

Current central serous retinopathy (CSR) or retinal pigment epithelial detachment (RPED) of any Grade;

Use of immunosuppressant agents, including, but not limited to systemic corticosteroids at doses exceeding 10 mg/day of prednisone or its equivalent, methotrexate, cyclosporine, azathioprine, and tumor necrosis factor α (TNF-α) blockers, within 2 weeks before the planned first dose of study drug;

Vaccinated with a live attenuated vaccine within 28 days prior to the first dose of study drug and for 3 months after receiving the last dose of study drug. Annual inactivated influenza vaccine is permitted;

Pregnant or breast-feeding, or planning to become pregnant while enrolled in this study or within 6 months after receiving the last dose of study drug;

Plans to father a child while enrolled in this study or within 6 months after receiving the last dose of study drug;

Major surgery within 4 weeks of enrollment, or inadequate recovery from the toxicity and/or complications from the intervention prior to starting therapy;

Known sensitivity to any component of cisplatin or carboplatin.

Evaluations

The safety of erdafitinib plus cetrelimab plus platinum chemotherapy will be assessed based on medical review of safety parameters including but not limited to AEs, vital signs, physical examination, ECOG PS, laboratory tests, and electrocardiograms. Corneal or retinal abnormalities for subjects receiving erdafitinib will be considered as AEs of special interest. These occurrences should be reported as AEs or as serious AEs if the severity is a Grade 3 or higher and require enhanced reporting and data collection. Blood samples will be collected to assess the plasma pharmacokinetics (PK) of erdafitinib, platinum (cisplatin or carboplatin) chemotherapy and serum PK and immunogenicity of cetrelimab. Blood and tumor samples will also be assessed for biomarkers that could correlate with response or resistance to erdafitinib alone or in combination with cetrelimab. The evaluation of response will be according to RECIST 1.1.

Example 3: Phase 2 (Dose Expansion) (NCT03473743)

A non-limiting example of an ongoing phase 2 dose expansion study is described below.

Objective

The primary objective is to o evaluate the safety and clinical activity of erdafitinib alone and in combination with cetrelimab in cisplatin-ineligible subjects with metastatic or locally advanced urothelial cancer with select FGFR gene alterations and no prior systemic therapy for metastatic disease. The secondary objectives are to characterize the PK of erdafitinib and cetrelimab, assess the immunogenicity of cetrelimab, further assess safety at the R2PD of erdafitinib alone and in combination with cetrelimab, and further characterize the clinical activity of erdafitinib alone and in combination with cetrelimab.

Endpoints

The primary endpoint is overall response rate (ORR) (partial response [PR] or better) per Response Evaluation Criteria in Solid Tumors (RECIST) 1.1 by investigator assessment and incidence of adverse events (AEs). The secondary endpoints are plasma erdafitinib and serum cetrelimab concentrations, detection of antibodies to cetrelimab and effects on serum cetrelimab levels, incidence of AEs, serious adverse events (SAEs) and laboratory values, duration of response (DoR), time to response (TTR), progression-free survival (PFS) and OS.

Methods

Study Overview

Subjects with metastatic or locally advanced urothelial cancer with select FGFR gene alterations who have had no prior systemic therapy for metastatic disease and are ineligible for cisplatin are eligible for enrollment in this part of the study. Subjects must have select FGFR gene alterations in tumor or blood. Subjects must be 18 years or older and have ECOG PS Grade of 0-2.

Two dosing arms may be explored: Arm A and Arm B.

Subjects who have not received prior systemic therapy for metastatic disease will be stratified by the Eastern Cooperative Oncology Group (ECOG) PS (0-1 versus 2) and assigned randomly (1:1 ratio) to either the erdafitinib monotherapy treatment at the starting oral dose of 8 mg (Arm A), or the combination treatment of erdafitinib and cetrelimab (Arm B). To further characterize safety and clinical activity of the erdafitinib and cetrelimab (Arm B) combination, the dose of erdafitinib and cetrelimab will be administered at 8 mg (no up-titration) and 240 mg Q2W, respectively for Cycles 1 through 4. At Cycle 5, the dosing regimen of cetrelimab is changed from 240 mg Q2W to 480 mg Q4W. Subjects in the Phase 2 dose expansion cohort of the study are cisplatin-ineligible. See FIG. 1 for study design of the phase 2 dose expansion.

Cisplatin-ineligible subjects are defined as meeting at least one of the following criteria:

Impaired renal function defined as calculated by Cockcroft-Gault (Galsky M D, et al. *Lancetrelimab Oncol.* 2011 March; 12(3):211-4).

Grade 2 or higher peripheral neuropathy per National Cancer Institute Common Terminology Criteria for Adverse Events (NCI-CTCAE version 5.0.)

Grade 2 or higher hearing loss per NCI-CTCAE version 5.0.

ECOG Performance Status 2.

Dosage and Administration

Arm A: erdafitinib monotherapy (8 mg up-titrated to 9 mg) will be given once daily at approximately the same time of the day with or without food.

Arm B: erdafitinib 8 mg will be given once daily at approximately the same time of the day with or without food. Cetrelimab will be administered at doses of 240 mg every 2 weeks (Cycles 1-4) or 480 mg every 4 weeks (starting at Cycle 5). When both drugs are administered on the same day, erdafitinib will be administered before cetrelimab.

All subjects will continue to receive study treatment until disease progression, unacceptable toxicity, or any other treatment discontinuation criteria are met.

Statistical Methods

Approximately 90 subjects will be assigned randomly in a 1:1 ratio to receive either erdafitinib monotherapy (Arm A) or erdafitinib and cetrelimab combination therapy (Arm B).

With approximately 45 subjects on Arm A and assuming a true ORR of 45%, the study is designed such that the resulting 95% confidence interval for estimating ORR excludes those less or equal to 30%. Similarly, assuming a true ORR of 55% in Arm B, 45 subjects results in a 95% confidence interval that excludes ORR less or equal to 40%. The objective response rate will be calculated with a 95% confidence interval by each arm in the treated population according to the RECIST 1.1 criteria. Safety data will be summarized descriptively.

Example 4. Clinical Study: Analysis of T Cell Populations

As described above, BLC2002 (NCT03473743) is a Phase 1b-2 Study to Evaluate Safety, Efficacy, Pharmacokinetics, and Pharmacodynamics of Erdafitinib plus Cetrelimab, an Anti-PD-1 Monoclonal Antibody, in Subjects with Metastatic or Locally Advanced Urothelial Cancer with Selected FGFR Gene Alterations. Phase 1b is the dose escalation part of the study wherein two dosing cohorts (Standard Cohorts and Alternative Cohorts) of erdafitinib were explored, while cetrelimab intravenous (IV) dose was fixed. In the Standard Cohorts (DL1, DL2 or DL2A), erdafitinib and cetrelimab start concurrently from Cycle 1 Day 1 (C1D1). In the Alternative Cohorts (DL1B or DL2B), administration of erdafitinib starts on C1D1 but cetrelimab is initiated 1 cycle (4 weeks) later, on Cycle 2 Day 1 (C2D1) (also referred to as a 28-day run-in of erdafitinib). In Phase 2, two dosing arms are explored: the erdafitinib monotherapy treatment at the starting oral dose of 8 mg (Arm A), or the combination treatment of erdafitinib and cetrelimab (Arm B).

For phase 1b, blood for immune cell profiling were collected at four time points (C1D1, C1D15, C2D1 and C3D1). For phase 2, blood was collected at six time points (C1D1, C1D15, C2D1, C2D15, C3D1 and C3D15). Blood samples were subjected to flow cytometry analysis on a real time basis. T cell activation is quantified as fold increase in the proportions of 1) CD38+CD3, CD38+CD4, or CD38+ CD8 T cells out of lymphocytes or CD3 T cell populations, and 2) CD38+ cells out of CD4+ or CD8+ T cell populations, compared to the baseline proportion levels at C1D1.

Longitudinal blood samples were analyzed from DL2A (E8J cohort: Erda 8 mg+cetrelimab 240 mg), DL2B (E8RJ cohort: Erda 8 mg 28 days run-in +cetrelimab 240 mg), and DL2 (EJ cohort: Erda 8 mg with the potential dose adjustments to 9 mg depending on phosphate levels measured on C1D15+cetrelimab 240 mg) of phase 1b, and blood samples from Arm A and Arm B of phase 2.

Figure 4A:
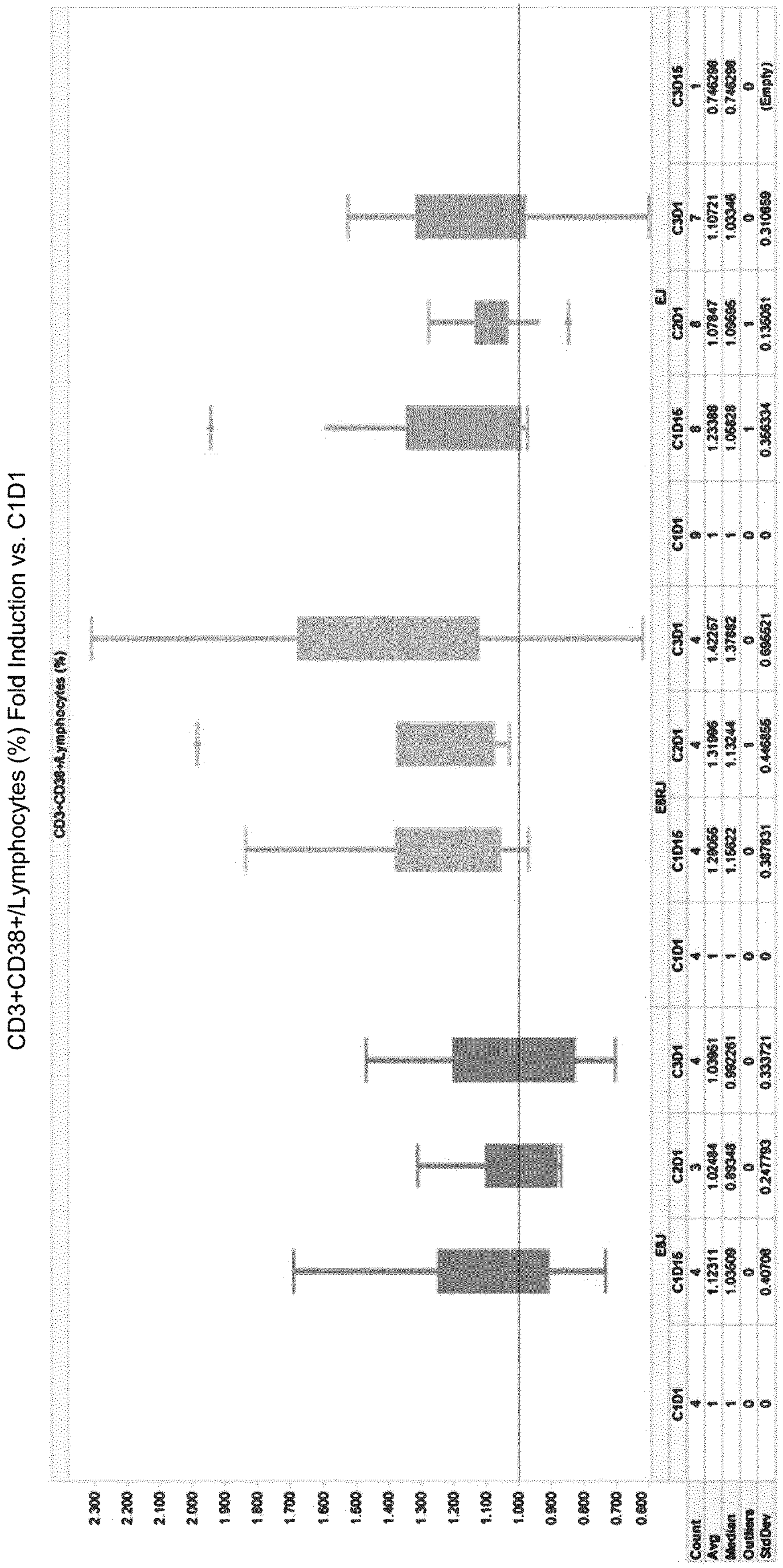
FIG. 4A, FIG. 4B and FIG. 4C illustrate proportions of T cells compared to baseline in a Phase 1b study to evaluate safety, efficacy, pharmacokinetics, and pharmacodynamics of erdafitinib plus cetrelimab.
Figure 4B:
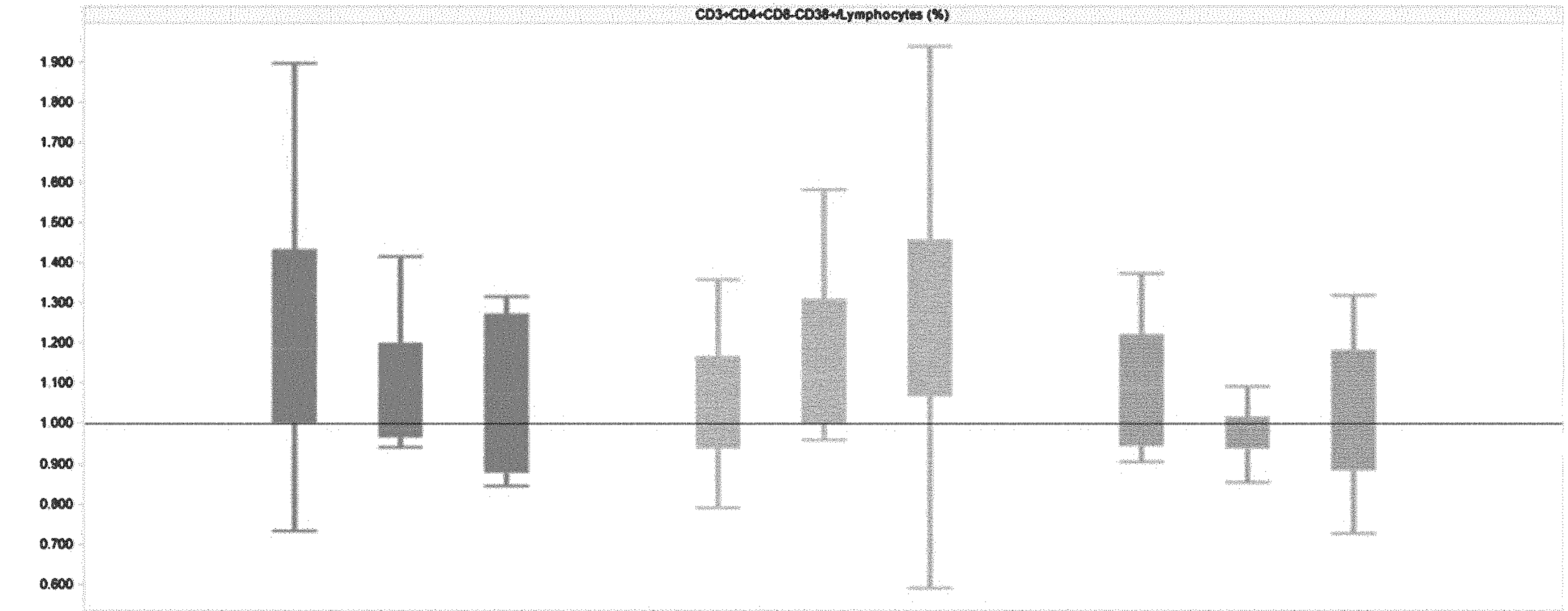
Figure 4C:
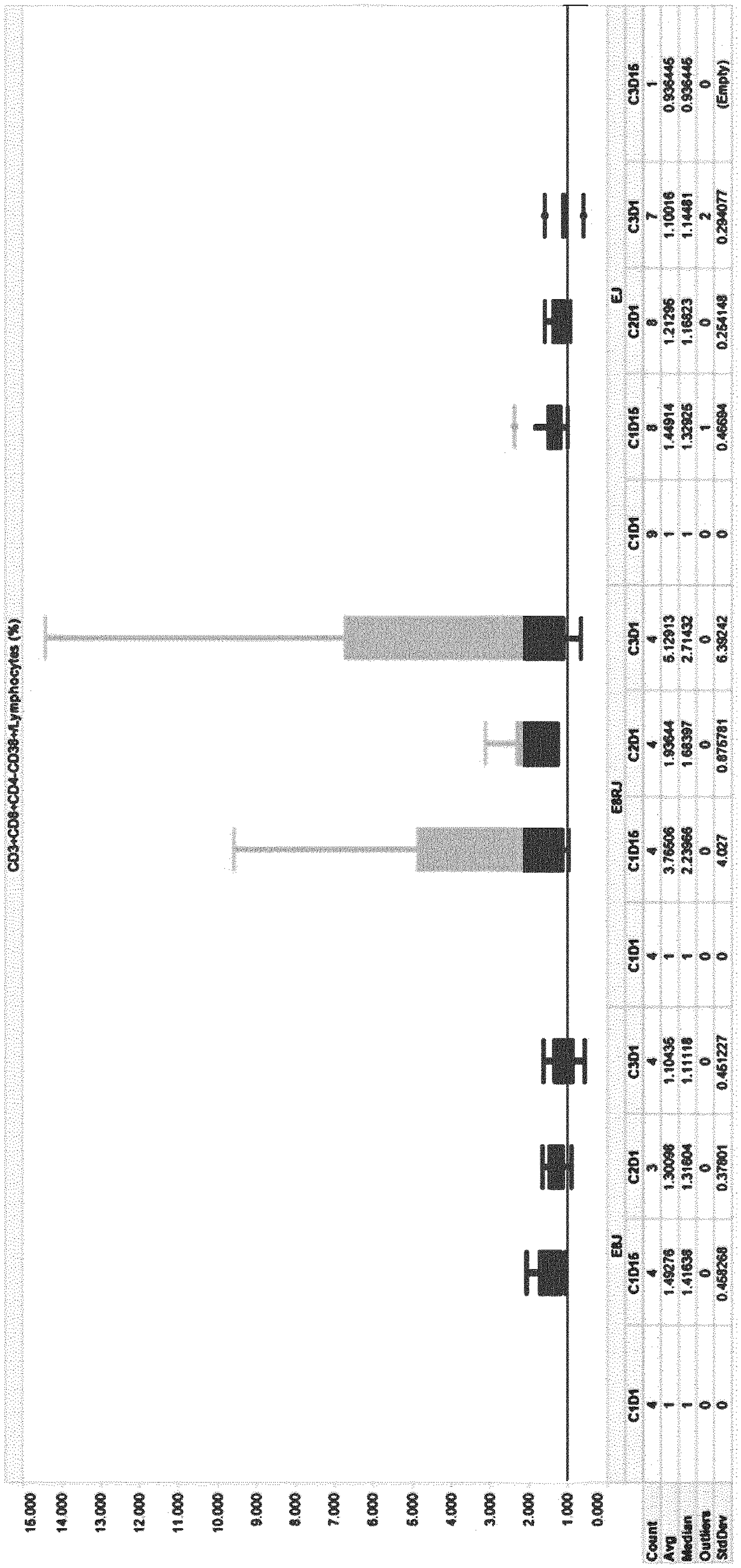
Figure 5A:
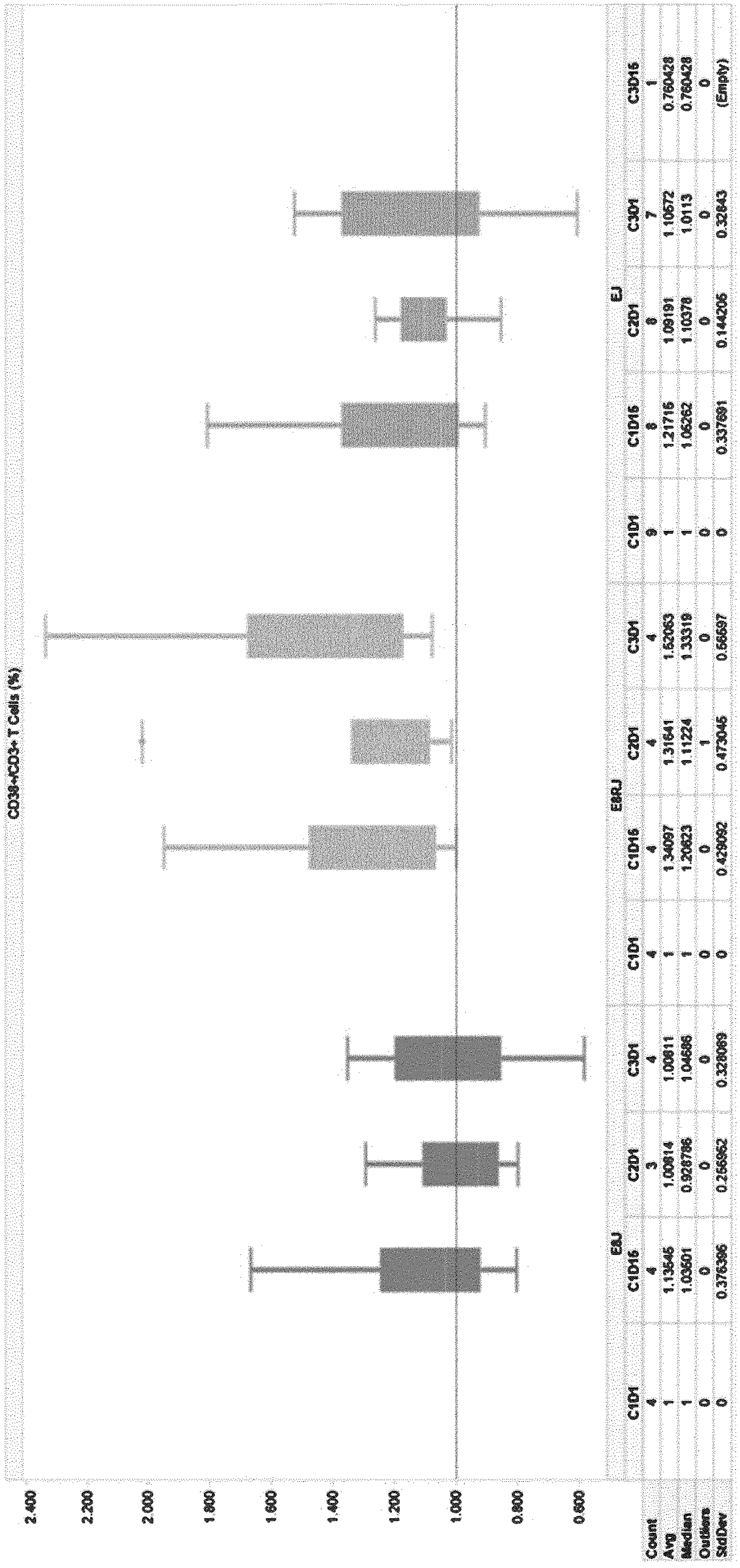
FIG. 5A, FIG. 5B and FIG. 5C illustrate proportions of T cells compared to baseline in a Phase 1b study to evaluate safety, efficacy, pharmacokinetics, and pharmacodynamics of erdafitinib plus cetrelimab.
Figure 5B:
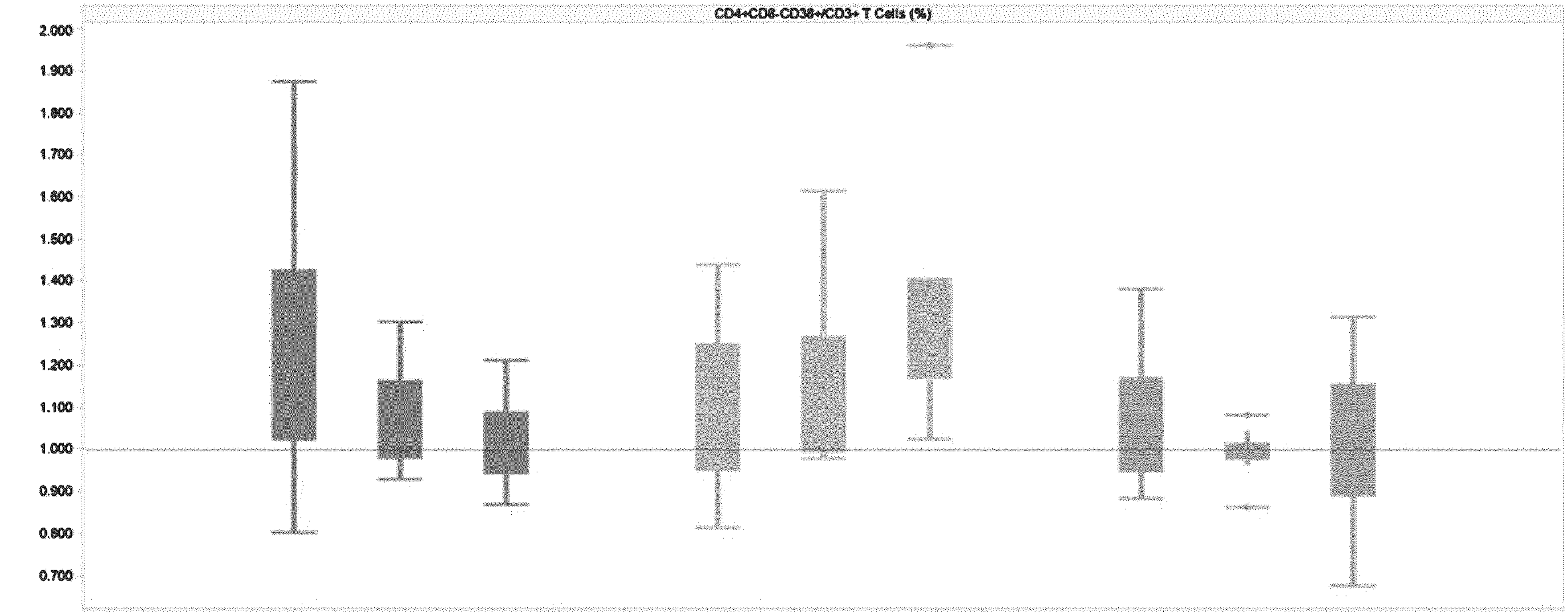
Figure 5C:
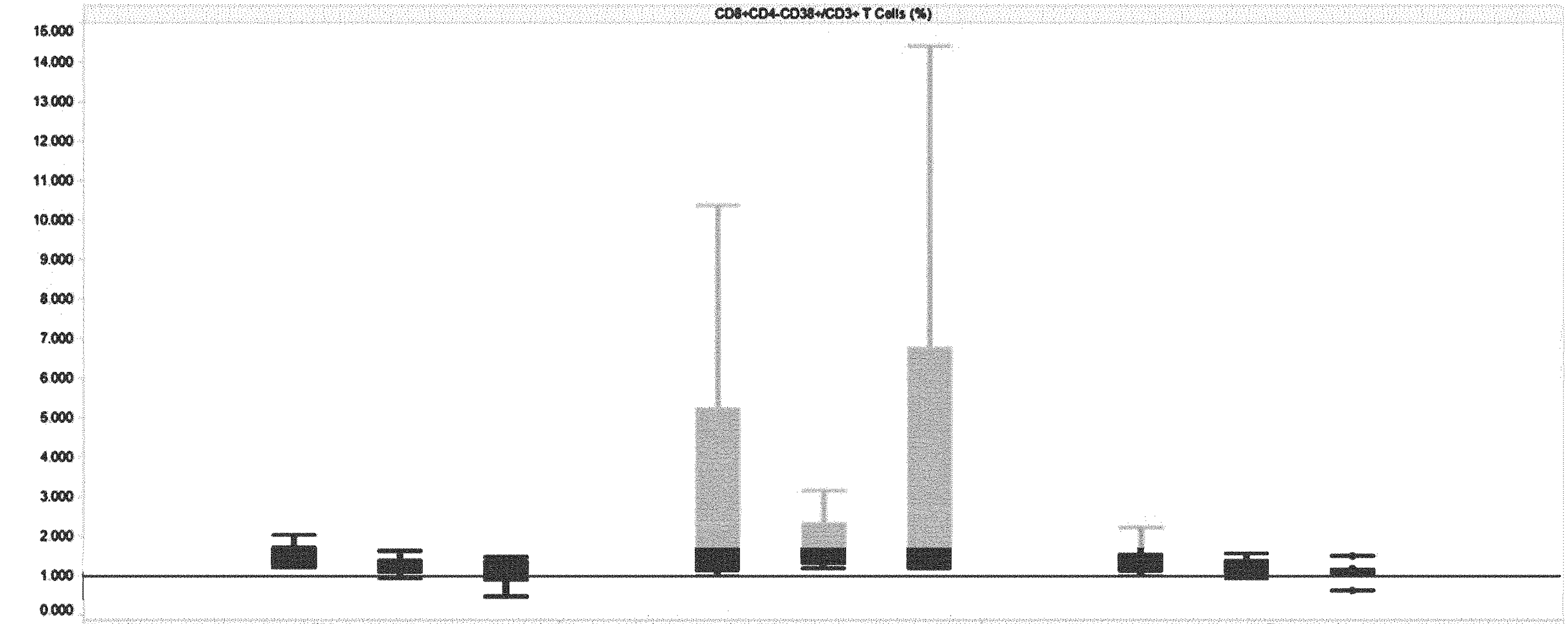
Figure 6A:
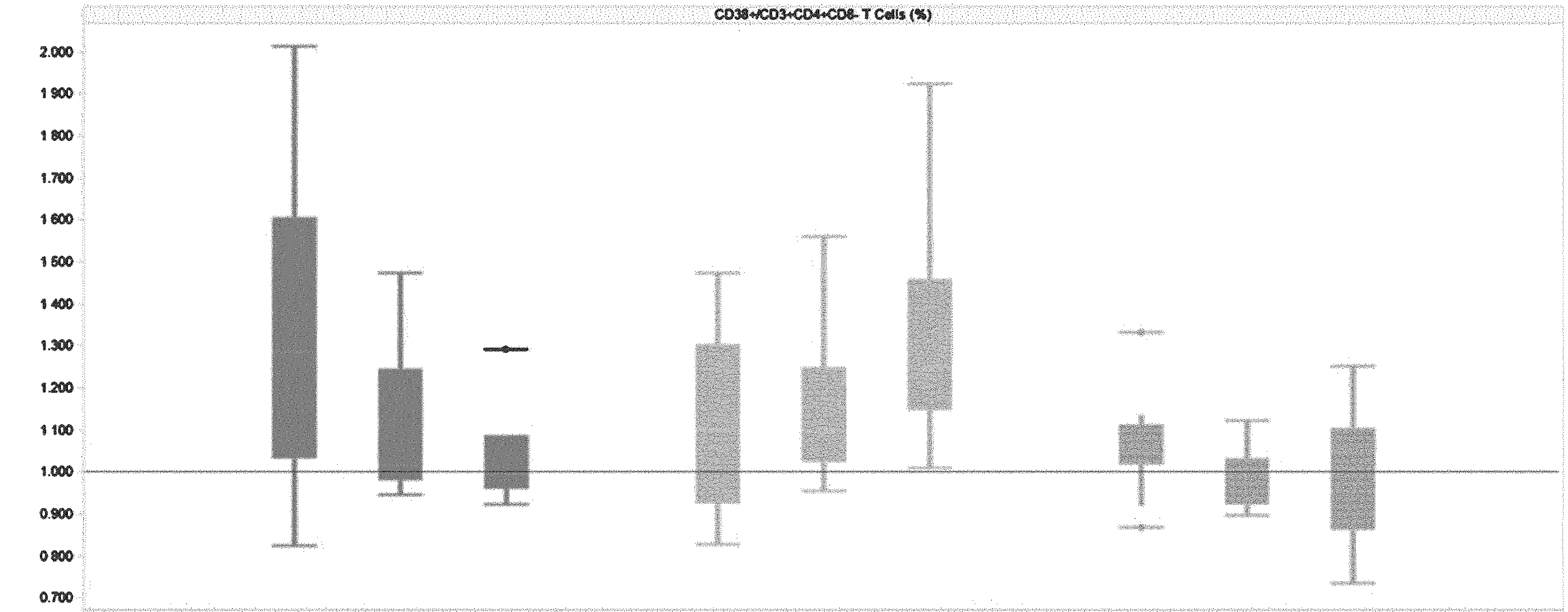
FIG. 6A and FIG. 6B illustrate proportions of T cells compared to baseline in a Phase 1b study to evaluate safety, efficacy, pharmacokinetics, and pharmacodynamics of erdafitinib plus cetrelimab.
Figure 6B:
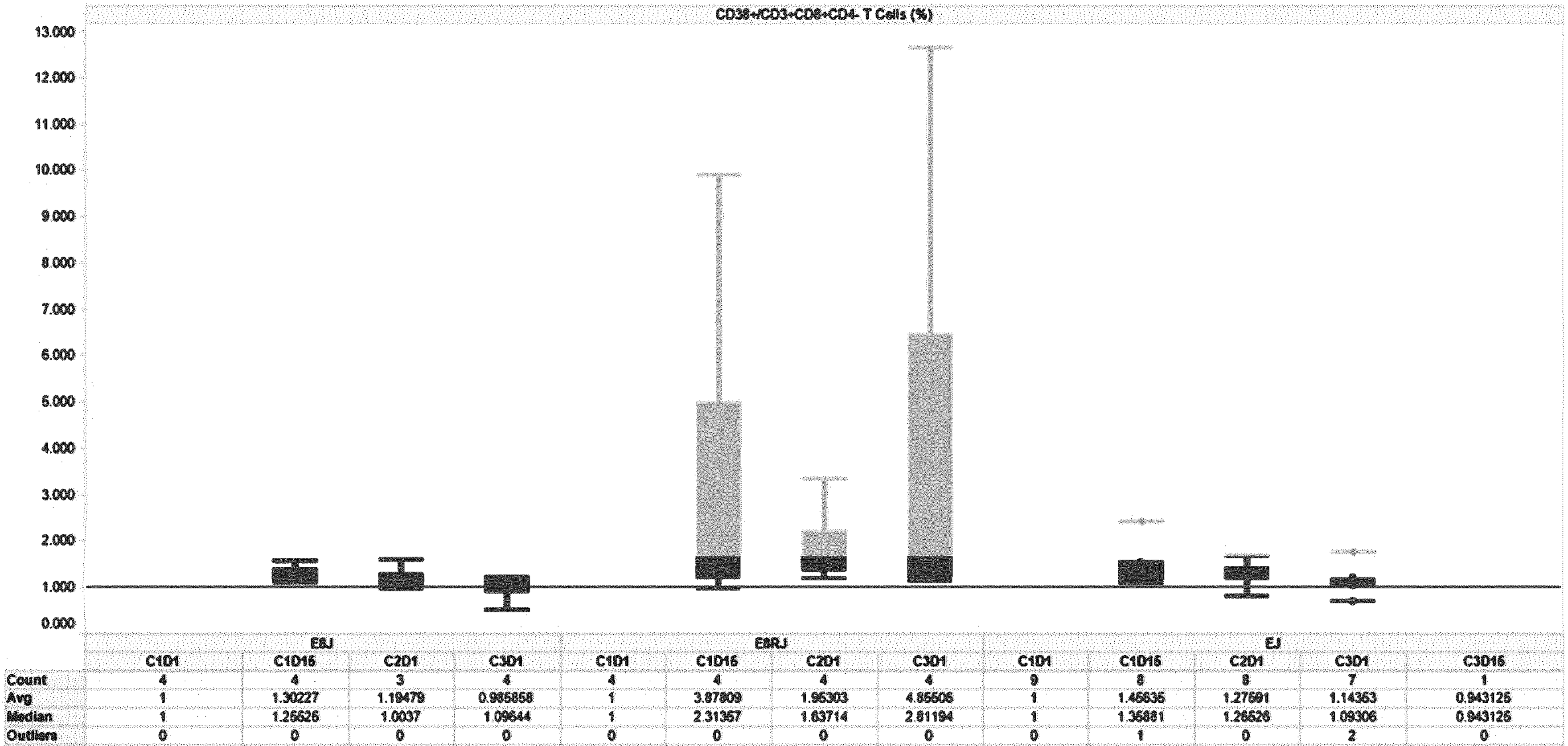

For phase 1b, for E8RJ cohort, a sustained increase was detected in the proportion of CD38+CD3 T cell (FIG. 4A) and CD38+CD4 T cell subset (FIG. 4B) in the lymphocytes population. Interestingly, the proportion of CD38+CD8 T cells for E8RJ dramatically increased at C1D15 in response to erdafitinib treatment alone, and was further increased at C3D1 when cetrelimab was applied at C2D1 (FIG. 4C). Similar findings were observed in the proportion of CD38+ CD3 T cell (FIG. 5A), CD38+CD4 T cell subset (FIG. 5B), and CD38+CD8 T cell subset (FIG. 5C) out of CD3 T cell population, as well as in the proportion of CD38+ cells out of CD4+(FIG. 6A) and CD38+ cells out of CD8+(FIG. 6B) T cell population. In contrast, the proportion of CD38+ T cells for E8J and EJ only showed peak increase at C1D15 and then dropped down to the level similar to that of C1D1 at later time points. These findings indicate that sequential administration of erdafitinib followed by cetrelimab could boost and prolong the T cell activation in the peripheral blood. The C3D15 in Phase 1b figures (cohort EJ) is not part of the scheduled visits based on the protocol dated before June 2020.

Figure 7A:
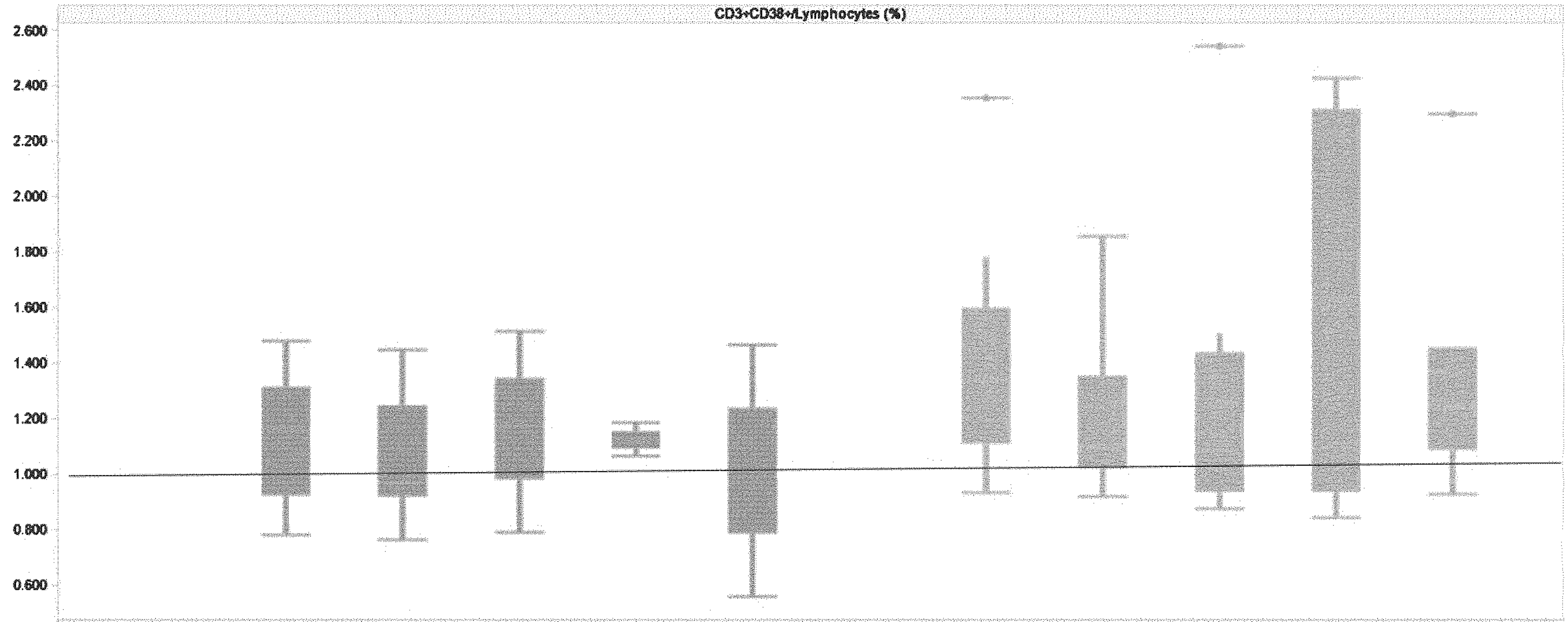
FIG. 7A, FIG. 7B and FIG. 7C illustrate proportions of T cells compared to baseline in a Phase 2 study to evaluate safety, efficacy, pharmacokinetics, and pharmacodynamics of erdafitinib plus cetrelimab.
Figure 7B:
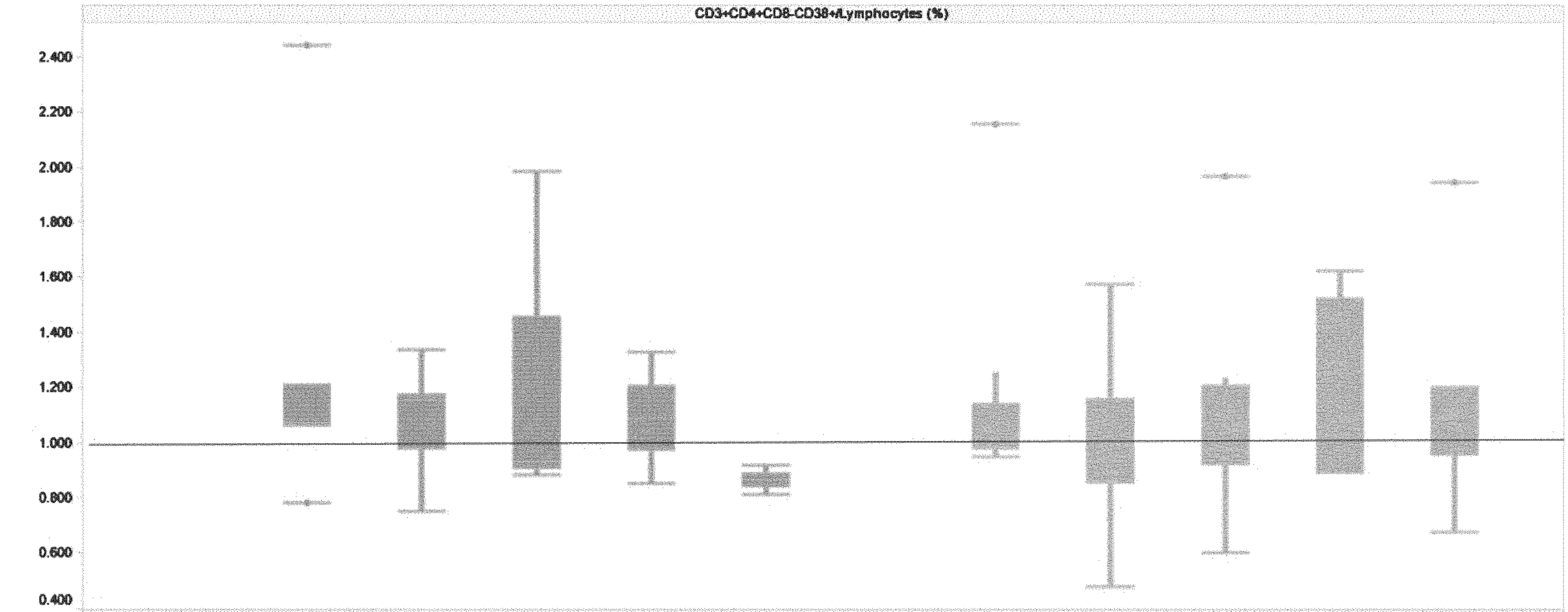
Figure 7C:
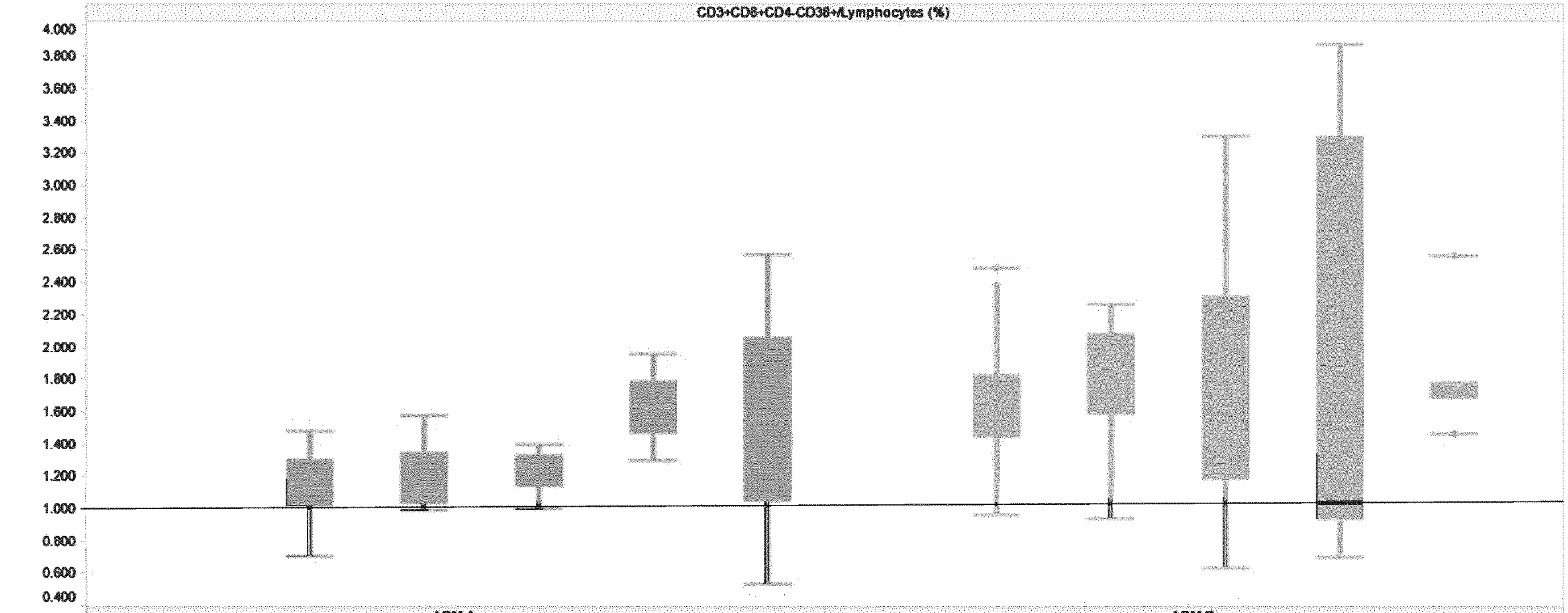
Figure 8A:
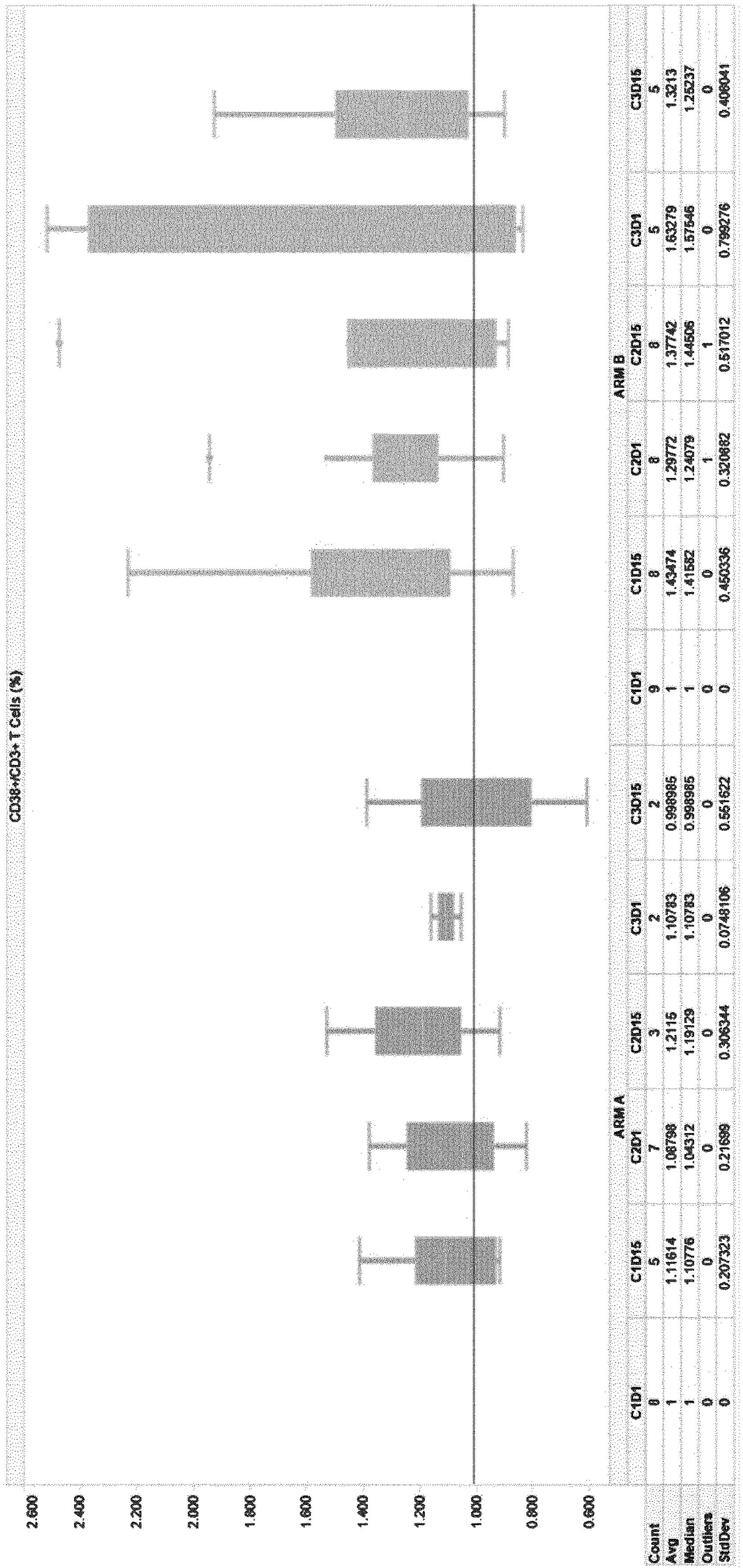
FIG. 8A, FIG. 8B and FIG. 8C illustrate proportions of T cells compared to baseline in a Phase 2 study to evaluate safety, efficacy, pharmacokinetics, and pharmacodynamics of erdafitinib plus cetrelimab.
Figure 8B:
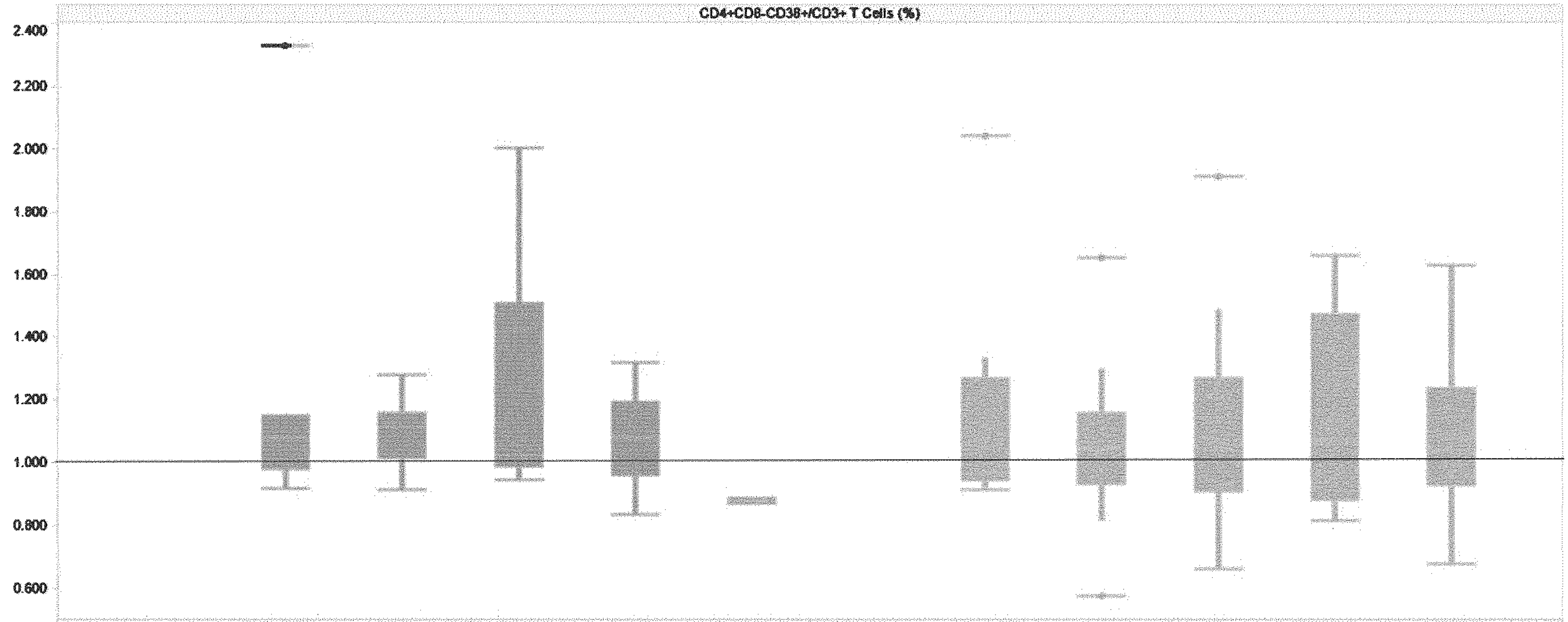
Figure 8C:
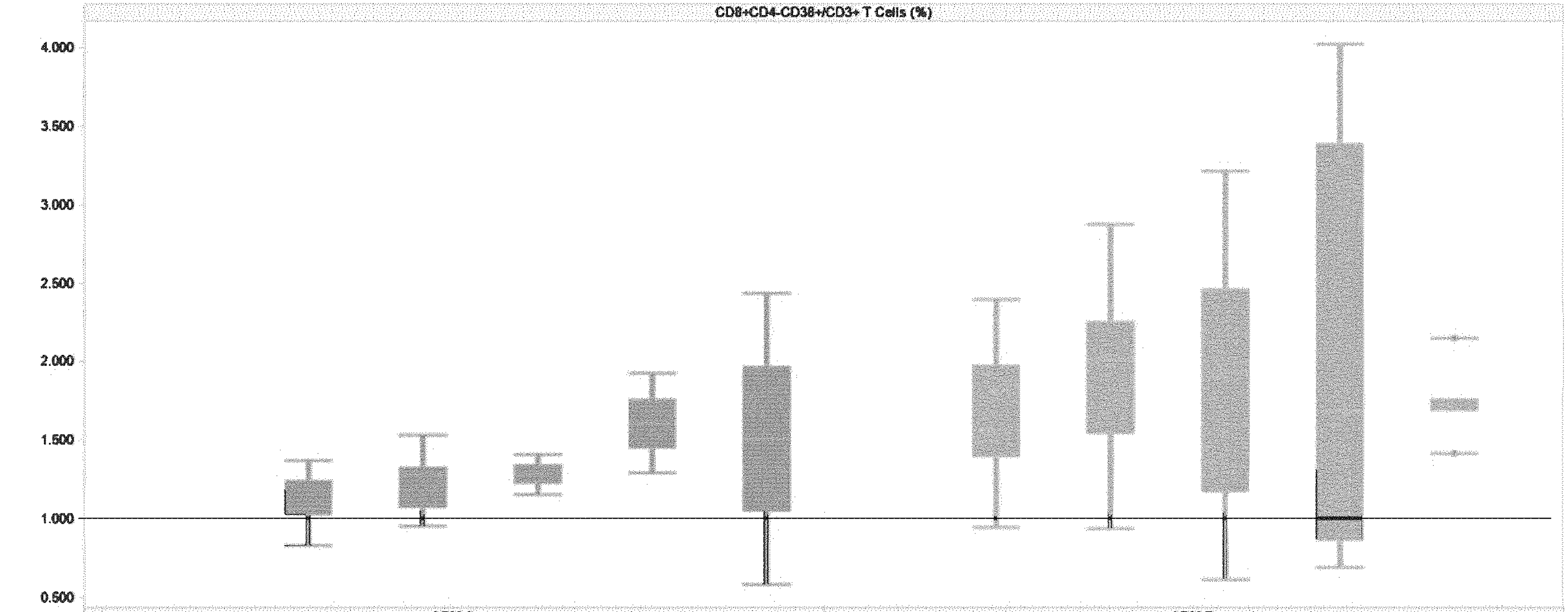
Figure 9A:
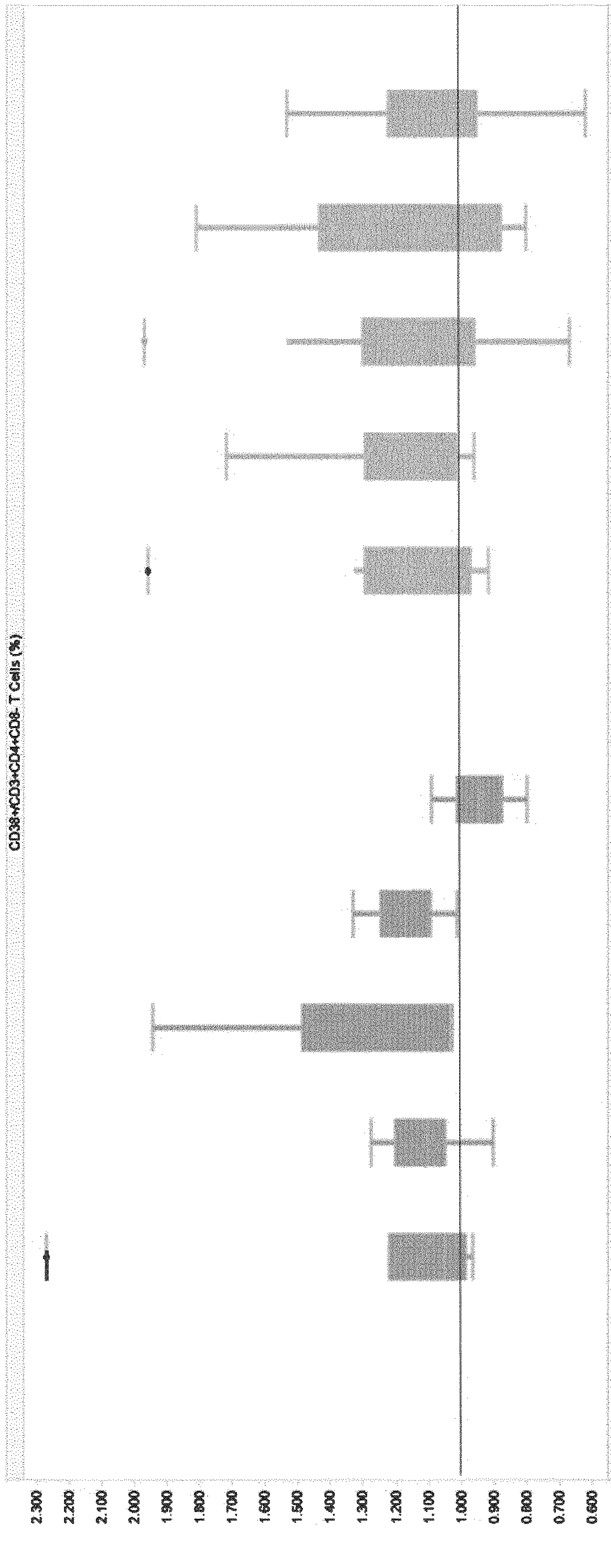
FIG. 9A and FIG. 9B illustrate proportions of T cells compared to baseline in a Phase 2 study to evaluate safety, efficacy, pharmacokinetics, and pharmacodynamics of erdafitinib plus cetrelimab.
Figure 9B:
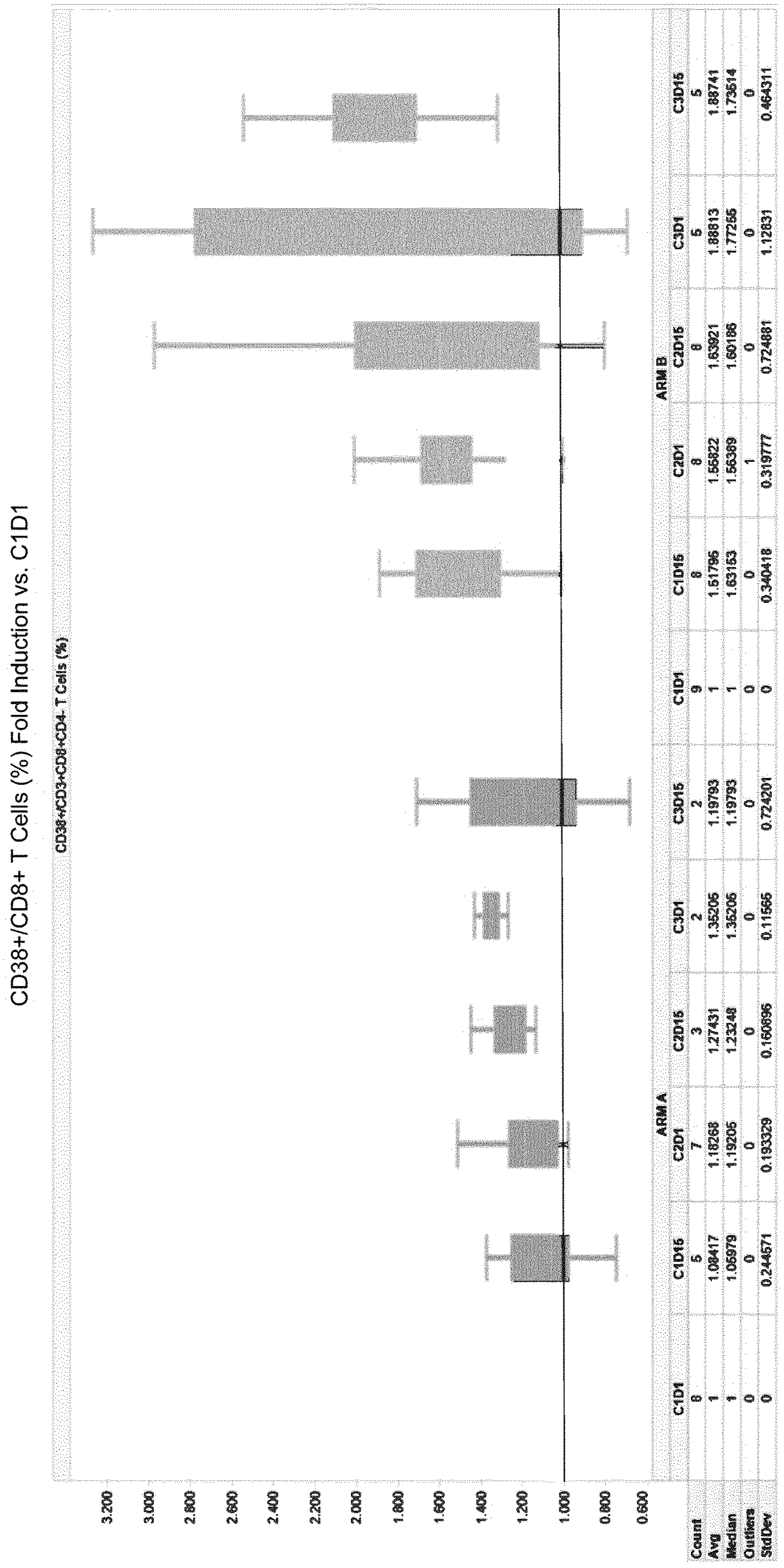

For phase 2, for Arm B, a sustained increase was detected in the proportion of CD38+CD3 T cell (FIG. 7*a*) out of the lymphocytes population. The proportion of CD38+CD8 T cells (FIG. 7*c*), but not CD38+CD4 T cells (FIG. 7*b*), dramatically increased at C1D15 in response to erdafitinib and cetrilimab combination treatment, and peaked at C3D1 (FIG. 7*c*). The proportion of CD38+CD8 T cells also increased with time for Arm A of erdafitinib monotherapy, but the extent of increase was less than that observed in Arm B (FIG. 7*c*). Similar findings were observed in the proportion of CD38+CD3 T cell (FIG. 8*a*) and CD38+CD8 T cell subset (FIG. 8*c*) out of CD3 T cell population, as well as in the proportion of CD38+ cells out of CD8+(FIG. 9*b*) T cell population. These findings indicate that the concurrent combination administration of erdafitinib and cetrelimab could have more and prolonged activation of T cells in the peripheral blood than erdafitinib monotherapy does.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

What is claimed:

1. A method of treating urothelial carcinoma harboring at least one FGFR2 genetic alteration and/or at least one FGFR3 genetic alteration in a patient, the method comprising administering to the patient:

a dose of 8 mg of erdafitinib base per day or 8 mg base equivalent of a pharmaceutically acceptable salt of erdafitinib per day; and a dose of about 240 mg, about 360 mg, or about 480 mg of cetrelimab, wherein the dose of erdafitinib base or the base equivalent of the pharmaceutically acceptable salt thereof is increased from 8 mg erdafitinib base per day or 8 mg base equivalent of the pharmaceutically acceptable salt of erdafitinib per day to 9 mg erdafitinib base per day or 9 mg base equivalent of the pharmaceutically acceptable salt of erdafitinib per day after initiating treatment if:

the patient exhibits a serum phosphate ($PO_4$) level that is less than about 5.5 mg/dL at 14-21 days after initiating treatment and administration of 8 mg erdafitinib base per day or 8 mg base equivalent of the pharmaceutically acceptable salt of erdafitinib per day resulted in no ocular disorder; or administration of 8 mg erdafitinib base per day or 8 mg base equivalent of the pharmaceutically acceptable salt of erdafitinib per day resulted in no Grade 2 or greater adverse reaction.

2. The method of claim 1, further comprising administering a platinum chemotherapy.

3. The method of claim 1, wherein the urothelial carcinoma is locally advanced or metastatic.

4. The method of claim 1, wherein administration of erdafitinib base or the pharmaceutically acceptable salt of erdafitinib and cetrelimab provides improved anti-tumor activity as measured by objective response rate relative to a patient that has been diagnosed with the urothelial carcinoma that has not received treatment with erdafitinib base or the pharmaceutically acceptable salt of erdafitinib and cetrelimab.

5. The method of claim 1, wherein administration of erdafitinib base or the pharmaceutically acceptable salt of erdafitinib and cetrelimab does not result in hematological toxicity of Grade 3 or higher.

6. The method of claim 1, wherein the patient received at least one systemic therapy for the treatment of the urothelial carcinoma prior to administration of the erdafitinib base or the pharmaceutically acceptable salt of erdafitinib and cetrelimab.

7. The method of claim 6, wherein the at least one systemic therapy for the treatment of the urothelial carcinoma is platinum-containing chemotherapy.

8. The method of claim 7, wherein the urothelial carcinoma progressed during or following at least one line of the platinum-containing chemotherapy.

9. The method of claim 8, wherein the platinum-containing chemotherapy is neoadjuvant platinum-containing chemotherapy or adjuvant platinum-containing chemotherapy.

10. The method of claim 9, wherein the urothelial carcinoma progressed within 12 months following at least one line of the neoadjuvant platinum-containing chemotherapy or the adjuvant platinum-containing chemotherapy.

11. The method of claim 1, wherein the patient did not receive systemic therapy for the treatment of the urothelial carcinoma prior to the administration of erdafitinib base or the pharmaceutically acceptable salt of erdafitinib and cetrelimab.

12. The method of claim 11, wherein the patient is cisplatin-ineligible.

13. The method of claim 1, wherein the patient has an ECOG performance status of less than or equal to 2.

14. The method of claim 1, wherein the FGFR2 genetic alteration and/or the FGFR3 genetic alteration is an FGFR3 gene mutation, FGFR2 gene fusion, or FGFR3 gene fusion.

15. The method of claim 14, wherein the FGFR3 gene mutation is R248C, S249C, G370C, Y373C, or any combination thereof.

16. The method of claim 14, wherein the FGFR2 or the FGFR3 gene fusion is FGFR3-TACC3, FGFR3-BAIAP2L1, FGFR2-BICC1, FGFR2-CASP7, or any combination thereof.

17. The method of claim 1, further comprising evaluating a biological sample from the patient for the presence of one or more FGFR2 genetic alterations and/or one or more FGFR3 genetic alterations prior to administration of erdafitinib base or the pharmaceutically acceptable salt of erdafitinib and cetrelimab.

18. The method of claim 17, wherein the biological sample is blood, lymph fluid, bone marrow, a solid tumor sample, or any combination thereof.

19. The method of claim 1, wherein erdafitinib base or the pharmaceutically acceptable salt of erdafitinib is administered orally.

20. The method of claim 1, wherein erdafitinib base or the pharmaceutically acceptable salt of erdafitinib is administered orally on a continuous daily dosing schedule.

21. The method of claim 1, wherein erdafitinib base or the pharmaceutically acceptable salt of erdafitinib is administered in a solid dosage form.

22. The method of claim 21, wherein the solid dosage form is a tablet.

23. The method of claim 1, wherein cetrelimab is administered at a dose of about 240 mg once every two weeks, at a dose of about 360 mg once every two weeks, or at a dose of about 480 mg once every four weeks.

24. The method of claim 1, wherein the cetrelimab is administered by intravenous infusion.

25. The method of claim 2, wherein the platinum chemotherapy is cisplatin.

26. The method of claim 25, wherein the cisplatin is administered at a dose of about 50 $mg/m^2$ or at a dose of about 60 $mg/m^2$.

27. The method of claim 2, wherein the platinum chemotherapy is carboplatin.

28. The method of claim 27, wherein the carboplatin is administered at a dose of about AUC 4 mg/mL/min or at a dose of about AUC 5 mg/mL/min.

29. A method of improving objective response rate in a patient that has been diagnosed with urothelial carcinoma harboring at least one FGFR2 genetic alteration and/or at least one FGFR3 genetic alteration relative to a patient that has been diagnosed with the urothelial carcinoma that has not received treatment with erdafitinib base, a pharmaceutically acceptable salt of erdafitinib, or cetrelimab, the method comprising administering to the patient:

a dose of 8 mg of erdafitinib base per day or 8 mg base equivalent of a pharmaceutically acceptable salt of erdafitinib per day; and a dose of about 240 mg, about 360 mg, or about 480 mg of cetrelimab, wherein the dose of erdafitinib base or the base equivalent of the pharmaceutically acceptable salt thereof is increased from 8 mg erdafitinib base per day or 8 mg base equivalent of the pharmaceutically acceptable salt of erdafitinib per day to 9 mg erdafitinib base per day or 9 mg base equivalent of the pharmaceutically acceptable salt of erdafitinib per day after initiating treatment if:

the patient exhibits a serum phosphate ($PO_4$) level that is less than about 5.5 mg/dL at 14-21 days after initiating treatment and administration of 8 mg erdafitinib base per day or 8 mg base equivalent of the pharmaceutically acceptable salt of erdafitinib per day resulted in no ocular disorder; or administration of 8 mg erdafitinib base per day or 8 mg base equivalent of the pharmaceutically acceptable salt of erdafitinib per day resulted in no Grade 2 or greater adverse reaction.

30. A method of treating urothelial carcinoma, the method comprising:

(a) evaluating a biological sample from a patient that has been diagnosed with the urothelial carcinoma for the presence of at least one FGFR2 genetic alteration and/or at least one FGFR3 genetic alteration; and (b) administering a dose of 8 mg erdafitinib base per day or 8 mg base equivalent of a pharmaceutically acceptable salt of erdafitinib per day, and a dose of about 240 mg, about 360 mg, or about 480 mg of cetrelimab to the patient if at least one FGFR2 genetic alteration and/or at least one FGFR3 genetic alteration is present in the sample, wherein the dose of erdafitinib base or the base equivalent of the pharmaceutically acceptable salt thereof is increased from 8 mg erdafitinib base per day or 8 mg base equivalent of the pharmaceutically acceptable salt of erdafitinib per day to 9 mg erdafitinib base per day or 9 mg base equivalent of the pharmaceutically acceptable salt of erdafitinib per day after initiating treatment if:

the patient exhibits a serum phosphate ($PO_4$) level that is less than about 5.5 mg/dL at 14-21 days after initiating treatment and administration of 8 mg erdafitinib base per day or 8 mg base equivalent of the pharmaceutically acceptable salt of erdafitinib per day resulted in no ocular disorder; or administration of 8 mg erdafitinib base per day or 8 mg base equivalent of the pharmaceutically acceptable salt of erdafitinib per day resulted in no Grade 2 or greater adverse reaction.

31. The method of claim 18, wherein the biological sample is a solid tumor sample.

32. The method of claim 1, wherein erdafitinib base or the pharmaceutically acceptable salt thereof is erdafitinib base.

33. The method of claim 23, wherein cetrelimab is administered at a dose of 240 mg once every two weeks.

34. The method of claim 23, wherein cetrelimab is administered at a dose of 360 mg once every three weeks.

35. The method of claim 23, wherein cetrelimab is administered at a dose of 480 mg once every four weeks.

36. The method of claim 2, wherein cetrelimab is administered at a dose of 240 mg.

* * * * *